(12) United States Patent
Bongartz et al.

(10) Patent No.: US 8,981,094 B2
(45) Date of Patent: Mar. 17, 2015

(54) PIPERIDINE/PIPERAZINE DERIVATIVES

(75) Inventors: Jean-Pierre André Marc Bongartz, Turnhout (BE); Joannes Theodorus Maria Linders, Eindhoven (NL); Lieven Meerpoel, Beerse (BE); Guy Rosalia Eugeen Van Lommen, Berlaar (BE); Erwin Coesemans, Nijlen (BE); Mirielle Braeken, Wechelderzande (BE); Christophe Francis Robert Nestor Buyck, Hamme (BE); Monique Jenny Marie Berwaer, Manhay (BE); Katharina Antonia Germania J. M. De Waepenaert, Vosselaar (BE); Peter Walter Maria Roevens, Malle (BE); Gustaaf Maria Boeckx, Oud-Turnhout (BE); Petr Vladimirivich Davidenko, Moscow (RU)

(73) Assignee: Janssen Pharmaceutica N.V., Beerse (BE)

( * ) Notice: Subject to any disclaimer, the term of this patent is extended or adjusted under 35 U.S.C. 154(b) by 48 days.

(21) Appl. No.: 12/663,013
(22) PCT Filed: Jun. 6, 2008
(86) PCT No.: PCT/EP2008/057060
§ 371 (c)(1),
(2), (4) Date: Dec. 4, 2009
(87) PCT Pub. No.: WO2008/148868
PCT Pub. Date: Dec. 11, 2008

(65) Prior Publication Data
US 2010/0190789 A1  Jul. 29, 2010

(30) Foreign Application Priority Data

Jun. 8, 2007 (EP) .................................. 07109868
Sep. 6, 2007 (EP) .................................. 07115805

(51) Int. Cl.
*C07D 211/00* (2006.01)
*C07D 241/04* (2006.01)
(Continued)

(52) U.S. Cl.
CPC .......... *C07D 295/205* (2013.01); *C07D 207/09* (2013.01); *C07D 211/26* (2013.01);
(Continued)

(58) Field of Classification Search
CPC . A61K 31/495; A61K 31/496; A61K 31/451; C07D 241/04; C07D 401/12; C07D 211/34
USPC ............. 514/252.13, 253.01, 254.01, 255.01, 514/330; 544/359, 360, 372, 390; 546/189
See application file for complete search history.

(56) References Cited

U.S. PATENT DOCUMENTS 4,698,352 A  10/1987 Narita et al.
5,429,770 A  7/1995 Closs et al.
(Continued)

FOREIGN PATENT DOCUMENTS

CN  1749256 A  3/2006
EP  030371 A  6/1981
(Continued)

OTHER PUBLICATIONS

Watt, Storing Up Trouble: Does Accumulation of Intramyocellular Triglyceride Protect Skeletal Muscle from Insulin Resistance?, Clinical and Experimental Pharmacology and Physiology, 36, 5-11 (2009).*
(Continued)

*Primary Examiner* — Erich A Leeser

(57) ABSTRACT

The invention relates to a DGAT inhibitor of formula (I): including any stereochemically isomeric form thereof, wherein A represents CH or N; the dotted line represents an optional bond in case A represents a carbon atom; X represents —C(=O)—; —O—C(=O)—; C(=O)—C(=O)—; —NR$^x$—C(=O)—; —Z$^1$—C(O)—; —Z$^1$—NR$^x$—C(=O)—; —C(=O)—Z$^1$—; —NR$^x$—C(=O)—Z$^1$—; —S(=O)p-; —C(=S)—; —NR$^x$—C(=S)—; —Z$^1$—C(=S)—; —Z$^1$—NR$^x$—C(=S)—; —C(=S)—Z1-; —NR$^x$—C(=S)—Z—; Y represents NR$^x$—C(=0)-Z$^2$—; —NR$^x$—C(=0)-Z$^2$—NR$^y$—; —NR$^x$—C(=0)-Z$^2$—NR$^y$—C(=0)-; —NR$^x$—C(=0)-Z$^2$—NR$^y$—C(=0)-O—; —NR$^x$—C(=0)-Z$^2$-O-; —NR$^x$—C(=0)-Z$^2$-0-C(=0)-; —NR$^x$—C(=0)-Z$^2$—C(=0)-; —NR$^x$—C(=0)-Z$^2$—C(=0)-; —NR$^x$—C(=0)-0-Z$^2$—C(=0)-; —NR$^x$—C(=0)-0-Z$^2$—C(=0)-0-; —NR$^x$—C(=O)—O—Z$^2$—O—C(=O)—; —NR$^x$—C(=O)—Z$^2$—C(=O)—NR$^y$—; —NR$^x$—C(=O)—Z$^2$—NR$^y$—C(=0)-NR$^y$—; —C(=O)—Z$^2$—; —C(=O)—Z$^2$—O—; —C(=0)-NR$^x$—Z$^2$—; —C(=0)-NR$^x$—Z$^2$-O-; —C(=0)-NR$^x$—Z$^2$—C(=0)-O-; —C(=0)-NR$^x$—Z$^2$-0-C(=0)-; —C(=0)-NR$^x$—Z$^2$—NR$^y$—; —C(=0)-NR$^x$—Z$^2$—NR$^y$—C(=0)-; —C(=0)-NR$^x$—Z$^2$—NR$^y$—C(=0)-0-; R$^1$ represents C$_{1-12}$alkyl optionally substituted with cyano, C$_{1-4}$alkyloxy, C$_{1-4}$alkyl-oxyC$_{1-4}$alkyloxy, C$_{3-6}$Cycloalkyl or aryl; C$_{2-6}$alkenyl; C$_{2-6}$alkynyl; C$_{3-6}$cycloalkyl; adamantanyl; aryl$^1$; aryl$^1$C$_{1-6}$alkyl; Het$^1$; or Het$^1$C$_{1-6}$alkyl; provided that when Y represents —NR$^x$—C(=O)—Z$^2$—; —NR$^x$—C(=0)-Z$^2$—NR$^y$; —NR$^x$—C(=O)—Z$^2$—C(=O)—NR$^y$—; —C(=O)—Z$^2$—; —NR$^x$—C(=0)-Z$^2$—NR$^y$—C(=0)-NR$^y$—; —C(=O)—NR$^x$—Z$^2$—; —C(=O)—NR$^x$—O—Z$^2$—; or —C(=0)-NR$^x$—Z$^2$—NR$^y$—; then R$^1$ may also represent hydrogen; R$^2$ represents hydrogen, C$_{1-12}$alkyl, C$_{2-6}$alkenyl or R$^3$; provided that if X represents —O—C(=O)—; the R$^2$ represents R$^3$; and provided that (A) is excluded; a N-oxide thereof, a pharmaceutically acceptable salt thereof or a solvate thereof. The invention further relates to methods for preparing such compounds, pharmaceutical compositions comprising said compounds as well as the use as a medicine of said compounds.

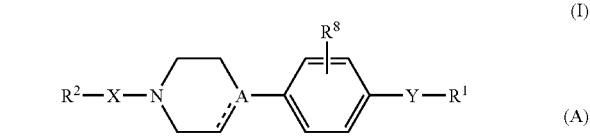

(I)

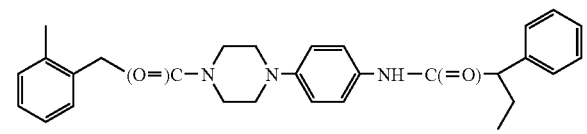

(A)

28 Claims, 1 Drawing Sheet

(51) Int. Cl.
*C07D 295/00* (2006.01)
*C07D 401/00* (2006.01)
*C07D 403/00* (2006.01)
*C07D 295/205* (2006.01)
*C07D 207/09* (2006.01)
*C07D 211/26* (2006.01)
*C07D 211/38* (2006.01)
*C07D 213/40* (2006.01)
*C07D 213/56* (2006.01)
*C07D 213/61* (2006.01)
*C07D 213/75* (2006.01)
*C07D 233/18* (2006.01)
*C07D 295/192* (2006.01)
*C07D 295/21* (2006.01)
*C07D 295/215* (2006.01)
*C07D 295/24* (2006.01)
*C07D 295/26* (2006.01)
*C07D 307/52* (2006.01)
*C07D 307/79* (2006.01)
*C07D 309/04* (2006.01)
*C07D 317/58* (2006.01)
*C07D 333/24* (2006.01)

(52) U.S. Cl.
CPC ............ *C07D211/38* (2013.01); *C07D 213/40* (2013.01); *C07D 213/56* (2013.01); *C07D 213/61* (2013.01); *C07D 213/75* (2013.01); *C07D 233/18* (2013.01); *C07D 295/192* (2013.01); *C07D 295/21* (2013.01); *C07D 295/215* (2013.01); *C07D 295/24* (2013.01); *C07D 295/26* (2013.01); *C07D 307/52* (2013.01); *C07D 307/79* (2013.01); *C07D 309/04* (2013.01); *C07D 317/58* (2013.01); *C07D 333/24* (2013.01)
USPC ............ 544/360; 544/372; 544/390; 546/189

(56) References Cited

U.S. PATENT DOCUMENTS

| 5,574,055 | A | 11/1996 | Borgulya et al. |
| 5,789,412 | A | 8/1998 | Halazy et al. |
| 6,492,368 | B1 | 12/2002 | Dorsch et al. |
| 6,884,868 | B1 | 4/2005 | Tojo et al. |
| 7,186,683 | B2 | 3/2007 | Henriksen et al. |
| 2003/0055055 | A1 | 3/2003 | Teuber et al. |
| 2003/0060472 | A1 | 3/2003 | Learmonth et al. |
| 2004/0038858 | A1 | 2/2004 | Dorsch et al. |
| 2004/0162282 | A1 | 8/2004 | Pennell et al. |
| 2004/0220191 | A1 | 11/2004 | Schwink et al. |
| 2005/0059650 | A1 | 3/2005 | Jones et al. |
| 2005/0209241 | A1 | 9/2005 | Jolidon |
| 2006/0030612 | A1 | 2/2006 | Steffan |
| 2007/0021339 | A1 | 1/2007 | Alloza Miravete et al. |
| 2007/0207999 | A1 | 9/2007 | Stadtmueller et al. |
| 2007/0249620 | A1 | 10/2007 | Kutura et al. |

FOREIGN PATENT DOCUMENTS

| EP | 321131 A | 6/1989 |
| EP | 378207 A | 7/1990 |
| EP | 630954 A | 12/1994 |
| EP | 657440 A | 6/1995 |
| EP | 1764360 A | 3/2007 |
| GB | 1383906 A | 2/1974 |
| JP | 11139969 | 5/1999 |
| JP | 2005/206492 | 8/2005 |
| JP | 2005-330266 A | 12/2005 |
| JP | 2007131584 A | 5/2007 |
| WO | WO 96/01820 A | 1/1996 |
| WO | WO 96/01822 A | 1/1996 |
| WO | 96/21648 A1 | 7/1996 |
| WO | WO 97/05877 A | 2/1997 |
| WO | WO 97/05878 A | 2/1997 |
| WO | 97/30995 A1 | 3/1997 |
| WO | WO 98/24766 A | 6/1998 |
| WO | WO 99/16751 A | 8/1999 |
| WO | 00/05225 A1 | 2/2000 |
| WO | WO 00/32582 A1 | 6/2000 |
| WO | WO 00/71107 | 11/2000 |
| WO | WO 01/58885 A | 8/2001 |
| WO | 01/95856 A1 | 12/2001 |
| WO | 01/98251 A1 | 12/2001 |
| WO | WO 01/97810 A2 | 12/2001 |
| WO | WO 02/20501 A2 | 3/2002 |
| WO | WO 02/20501 A3 | 3/2002 |
| WO | 02/48117 A1 | 6/2002 |
| WO | 02/055012 A1 | 7/2002 |
| WO | WO 02/081460 A1 | 10/2002 |
| WO | WO 03/064386 A | 8/2003 |
| WO | 03/076421 A1 | 9/2003 |
| WO | 03/076422 A1 | 9/2003 |
| WO | 03/087057 A1 | 10/2003 |
| WO | WO 03/082864 A | 10/2003 |
| WO | 2004/018439 A1 | 3/2004 |
| WO | WO 2004/047755 A2 | 6/2004 |
| WO | 2004/069792 A2 | 8/2004 |
| WO | WO 2004/072025 A | 8/2004 |
| WO | WO 2004/100881 A2 | 11/2004 |
| WO | WO 2004/110375 A2 | 12/2004 |
| WO | WO 2005/072740 A3 | 8/2005 |
| WO | WO 2006/004200 A1 | 1/2006 |
| WO | WO 2006/034441 A1 | 3/2006 |
| WO | 2006/038039 A1 | 4/2006 |
| WO | WO 2006/038039 A | 4/2006 |
| WO | WO 2006/044775 A | 4/2006 |
| WO | 2006/047277 A1 | 5/2006 |
| WO | 2006/064189 A1 | 6/2006 |
| WO | WO 2006/067071 A1 | 6/2006 |
| WO | WO 2006/086445 A3 | 8/2006 |
| WO | WO 2006/094842 A | 9/2006 |
| WO | 2006/105127 A2 | 10/2006 |
| WO | WO 2006/106326 A | 10/2006 |
| WO | WO 2006/113919 A2 | 10/2006 |
| WO | WO 2006/113919 A3 | 10/2006 |
| WO | WO 2006/134317 | * 12/2006 |
| WO | WO 2006/134317 A | 12/2006 |
| WO | 2007/071023 A1 | 6/2007 |
| WO | 2007/071966 A1 | 6/2007 |
| WO | 2007/096351 A1 | 8/2007 |
| WO | WO 2007/100990 A | 9/2007 |
| WO | 2008/003766 A2 | 1/2008 |
| WO | 2008/052638 A1 | 5/2008 |
| WO | 2008/122787 A1 | 10/2008 |
| WO | WO 2008/141976 A1 | 11/2008 |
| WO | WO 2008/148840 A1 | 12/2008 |
| WO | WO 2008/148849 A2 | 12/2008 |
| WO | WO 2008/148851 A1 | 12/2008 |
| WO | WO 2008/148868 A1 | 12/2008 |
| WO | 2009/147170 A2 | 12/2009 |

OTHER PUBLICATIONS

Extended EP Search Report relating to EP Application No. 07109868.5.

Glass et al., "4-(4-Guanidinobenzoyl)-2-Imidazolones and Related Compounds: Phosphodiesterase Inhibitors and Novel Cardiotonics With Combined Histamine H2 Receptor Agonist and PDE III Inhibitor Activity.", Archiv. Der Pharmazie, 1995, vol. 328 (10), pp. 709-719, XP009002222.

Griffett et al., "Effects of 6-[p(4-phenylacetylpiperazine-1-yl)phenyl1]-4, 5-dihydro-3(2 H)pyridazinone (CCI 17810) and aspirin on platelet aggregation and adhesiveness.", Database Medline, British J. of Pharmacology, Apr. 1981, vol. 72(4), pp. 697-705, XP002459094.

Jiang et al., "Synthesis and platelet aggregation inhibitory activity of 6-(4-substituted phenyl)-4,5-dihydro-3(2H)-pyridazinones.", Database CA, Chemical Abstracts Service, XP002459098.

Smith et al., "Obesity resistance and multiple mechanisms of

(56) References Cited

OTHER PUBLICATIONS triglyceride synthesis in mice lacking Dgat.", Nature Genetics May, 2000, vol. 25(1), pp. 87-90.
Wu et al., "Synthesis and platelet aggregation inhibitory activities of 6-[4(4-substituted-piperazine-1-yl)phenyl]-5-methyl-4,5-dihydro-3(2H)-pyridazinone derivatives.", Database CA, Chemical Abstracts Service, XP002459096.
Zhao et al., "Synthesis of 6-[4(4-substituted piperazyl)phenyl]-4,5-dihydro-3(2H)-pyridazinone derivatives by phase-transfer catalysis.", Database CA, Chemical Abstracts Service, XP002459095.
Chen, H., "Enhancing energy and glucose metabolism by disruption triglyceride synthesis: Lessons from mice lacking DGAT1", *Nutrition & Metabolism*, 2006, pp. 1-4, vol. 3(10).
Matsuda and Tomoda, "DGAT inhibitors for obesity", *Current Opinion in Investigational Drugs*, 2007, pp. 836-841, vol. 8(10).
Chen and Farese, "Inhibition of Triglyceride Synthesis as a Treatment Strategy for Obesity, Lessons from DGAT1-Deficient Mice", *Arterioscler Thromb Vasc Biol.*, 2005, pp. 482-486.
Birch et al., "DGAT1 inhibitors as anti-obesity and anti-diabetic agents", *Current Opinion in Drug Discovery & Development*, 2010, pp. 489-496, vol. 13(4).
Okawa et al., "Role of MGAT2 and DGAT1 in the release of gut peptides after triglyceride ingestion", *Biochemical and Biophysical Research Communications*, 2009, pp. 377-381, vol. 390.
Shandala et al., "Reactions of Acetylenic Esters with Cyclic Ketones and Substituted Acetophenones.", Journal f. prakt. Chemic. Band, 1979, pp. 899-904, vol. 321(6).
Aarmadaka et al., "Synthesis and Evaluation of Urea and Thiourea Derivatives of Oxazolidinones as Antibacterial Agents.", Chem. Pharm. Bull., Feb. 1, 2007, pp. 236-240, vol. 55.
Phillips et al., "Structure-antibacterial activity of arylcarbonyl- and arylsulfonyl-piperazine 5-Triazolylmethyl oxazolidinones.", Eur.J. Med. Chem., Nov. 29, 2006, pp. 214-225, vol. 42.
Chinese J. Med. Chem., 1994, pp. 162-170, vol. 4.
Lee et al., "Inhibition of Diacyglycerol Acyltransferase by Alkamides Isolated from the Fruits of Piper longum and Piper nigrum.", J. Agric. Food Chem., 2006, pp. 9759-9763, vol. 54.
Farese et al., "Lipopenia and Skin Barrier Abnormalities in DGAT2-deficient Mice.", J. Biol. Chem., Mar. 19, 2004, pp. 11767-1176, vol. 279(12).
Abstract RN854989-58-5, Jul. 13, 2005.
Abstract RN859099-41-5, Aug. 9, 2005.
Abstract RN859135-44-7, Aug. 9, 2005.
Abstract RN859646-88-1, Aug. 11, 2005.
Abstract RN860081-71-6, Aug. 12, 2005.
Abstract RN860458-98-6, Aug. 15, 2005.
Abstract RN861994-10-7, Aug. 29, 2005.
Abstract RN884476-57-7, May 16, 2006.
Abstract RN892188-37-3, Jul. 12, 2006.
Abstract RN892208-87-6, Jul. 12, 2006.
Abstract RN892693-34-4, Jul. 16, 2006.
Abstract RN897172-00-8, Jul. 28, 2006.
Abstract RN897548-47-9, Jul. 31, 2006.
Abstract RN898117-91-4, Aug. 2, 2006.
International Search Report, International Application No. PCT/EP2008/057060, Date of Mailing of International Search Report, Nov. 11, 2008.
International Preliminary Report on Patentability, relating to International Application No. PCT/EP2008/057060, Date of Mailing of IPER, Sep. 14, 2009.
Extended EP Search Report relating to EP Application No. 07109868.5, Apr. 11, 2008.
Bose et al., "Glucagon-like Peptide 1 Can Directly Protect the Heart Against Ischemia/Reperfusion Injury.", Diabetes, Jan. 2005, vol. 54, pp. 146-151.
Buhman et al., "DGAT1 Is Not Essential for Intestinal Triacylglycerol Absorption or Chylomicron Synthesis.", J. Biol. Chem. Jul. 12, 2002, vol. 277(28), pp. 25474-25479.
Cases et al., "Cloning of DGAT2, a Second Mammalian Diacylglycerol Acyltransferase, and Related Family Members.", J. Biol. Chem., Oct. 19, 2001, vol. 276(42), pp. 38870-38876.
Cases et al., "Identification of a gene encoding an acyl CoA:diacylglycerol acyltransferase, a key enzyme in triacylglycerol synthesis.", Proc. Natl. Acad. Sci., Oct. 1998, vol. 95, pp. 13018-13023.
Chen et al., "DGAT and Triglyceride Synthesis: A New Target for Obesity Treatment?", Trends Cardiovasc. Med., 2000, vol. 10(5), pp. 188-192.
Chen et al., "Increased insulin and leptin sensitivity in mice lacking acyl CoA:diacylglycerol acyltransferase 1.", J. Clin. Invest., 2002, vol. 109(8), pp. 1049-1055.
Database Registry, Aug. 3, 2005, XP002501332.
Database Registry, Aug. 5, 2005, XP002501333.
Database Registry, Aug. 8, 2005, XP002501334.
Database Registry, Aug. 8, 2005, XP002501335.
Database Registry, Mar. 22, 2004, XP002459101.
Database Registry, Mar. 22, 2004, XP002459102.
Database Registry, Mar. 22, 2004, XP002459103.
Database Registry, Nov. 3, 2004, XP002459099.
Farese et al., "Triglyceride synthesis: insights from the cloning of diacylglycerol acytransferase.", Curr. Opin. Lipidol. 2000, vol. 11, pp. 229-234.
Glass et al., "4-(4-Guanidinobenzoyl)-2-Imidazolones And Related Compounds: Phosphodiesterase Inhibitors and Novel Cardiotonics With Combined Histamine H2 Receptor Agonist and PDE III Inhibitor Activity.", Archiv. Der Pharmazie, 1995, vol. 328 (10), pp. 709-719, XP009002222.
Griffett et al., "Effects of 6-[p(4-phenylacetylpiperazine-1-yl)pheny11]-4,5-dihydro-3(2 H)pyridazinone (CCI 17810) and aspirin on platelet aggregation and adhesiveness.", Database Medline, British J. of Pharmacology, Apr. 1981, vol. 72(4), pp. 697-705, XP002459094.
Jiang et al., "Synthesis and platelet aggregation inhibitory activity of 6-(4-substituted phenyl)-4,5-dihydro-3(2H)-pyridazinones.", Database CA, Chemical Abstracts Service, XP002459098. 1990.
Khalaj et al., "Synthesis and antibacterial activity of 2-(4-substituted phenyl)-3(2H)-isothiazolones.", European Journal of Med. Chem., Aug. 2004, vol. 39(8), pp. 699-705, Paris, France, XP004523234.
Lewis et al., "Disordered fat storage and mobilization in the pathogenesis of insulin resistance and type 2 diabetes.", Endocrine Reviews, 2002, vol. 23(1), pp. 201-229.
Malloy and Kane, Pathogenesis and treatment in cardiomyopathy., Adv. Intern. Med., 2001, vol. 47, pp. 111-136.
Nikolaidis et al., "Glucagon-Like Peptide-1 Limits Myocardial Stunning following Brief Coronary Occlusion and Reperfusion in Conscious Canines.", Journal of Pharm. and Experimental Therapeutics, 2005, vol. 312(1), pp. 303-308.
Oelkers et al., "Characterizations of Two Human Genes Encoding Acyl Coenzyme A: Cholesterol Acyltransferase-related Enzymes.", J. Biol. Chem., Oct. 8, 1998, vol. 273(41), pp. 26765-26771, U.S.A.
Pearson et al., "Preparation of Functionalized P-Phenylenediamine Derivatives using Arene-Iron Chemistry.", J. of Org. Chem., 1996, vol. 61(4), pp. 1297-1305, Easton, US, XP002938137.
Perry et al., "Evidence of GLP-1-mediated neuroprotection in an animal model of pyridoxine-induced peripheral sensory neuropathy.", Experimental Neurology, 2007, vol. 203(2), pp. 293-301.
Smith et al., "Obesity resistance and multiple mechanisms of triglyceride synthesis in mice lacking Dgat.", Nature Genetics May 2000, vol. 25(1), pp. 87-90.
Stone et al., "Lipopenia and Skin Barrier Abnormalities in DGAT2-deficient Mice.", J. Biol. Chem., Mar. 19, 2004, vol. 279(12), pp. 11767-11776.
Wu et al., "Synthesis and platelet aggregation inhibitory activities of 6-[4(4-substituted-piperazine-1-yl)phenyl]-5-methyl-4,5-dihydro-3(2H)-pyridazinone derivatives.", Database CA, Chemical Abstracts Service, XP002459096. 2000.
Zhang et al., "Synthesis and platelet aggregation inhibitory activity of pyridazinones.", Database CA, Chemical Abstracts Service, XP002459097.
Zhao et al., "Synthesis of 6-[4(4-substituted piperazyl)phenyl]-4,5-dihydro-3(2H)-pyridazinone derivatives by phase-transfer catalysis.", Database CA, Chemical Abstracts Service, XP002459095. 2002.

(56) References Cited

OTHER PUBLICATIONS

Database Registry, Apr. 17, 2007, XP002458843.
Vippagunta et al., "Crystalline Solids.", *Advanced Drug Delivery Reviews*, 2001, pp. 3-26, vol. 48.
Kuwabara et al., "A Nove Novel Selective Peroxisome Proliferator-Activated Receptor Agonist, 2-Methyl-c-5-[4-[5-methyl-2-(4-methylpheny1)-4-oxazolyl]butyl]-1,3-dioxane-r-2-carboxylic acid (NS-220),Potently Decreases Plasma Triglyceride and Glucose Levels and Modifies Lipoprotein Profiles in KK-Ay Mice.", *J. Pharmacol. Exp. Ther.*, 2004, pp. 970-977, vol. 309(3).
Cao et al., "Targeting Acyl-CoA:Diacylglycerol Acyltransferase 1 (DGAT1) With Small Molecule Inhibitors for the Treatment of Metabolic Diseases.", *J. Biol. Chem.*, 2011, pp. 41838-41851, vol. 286.

\* cited by examiner

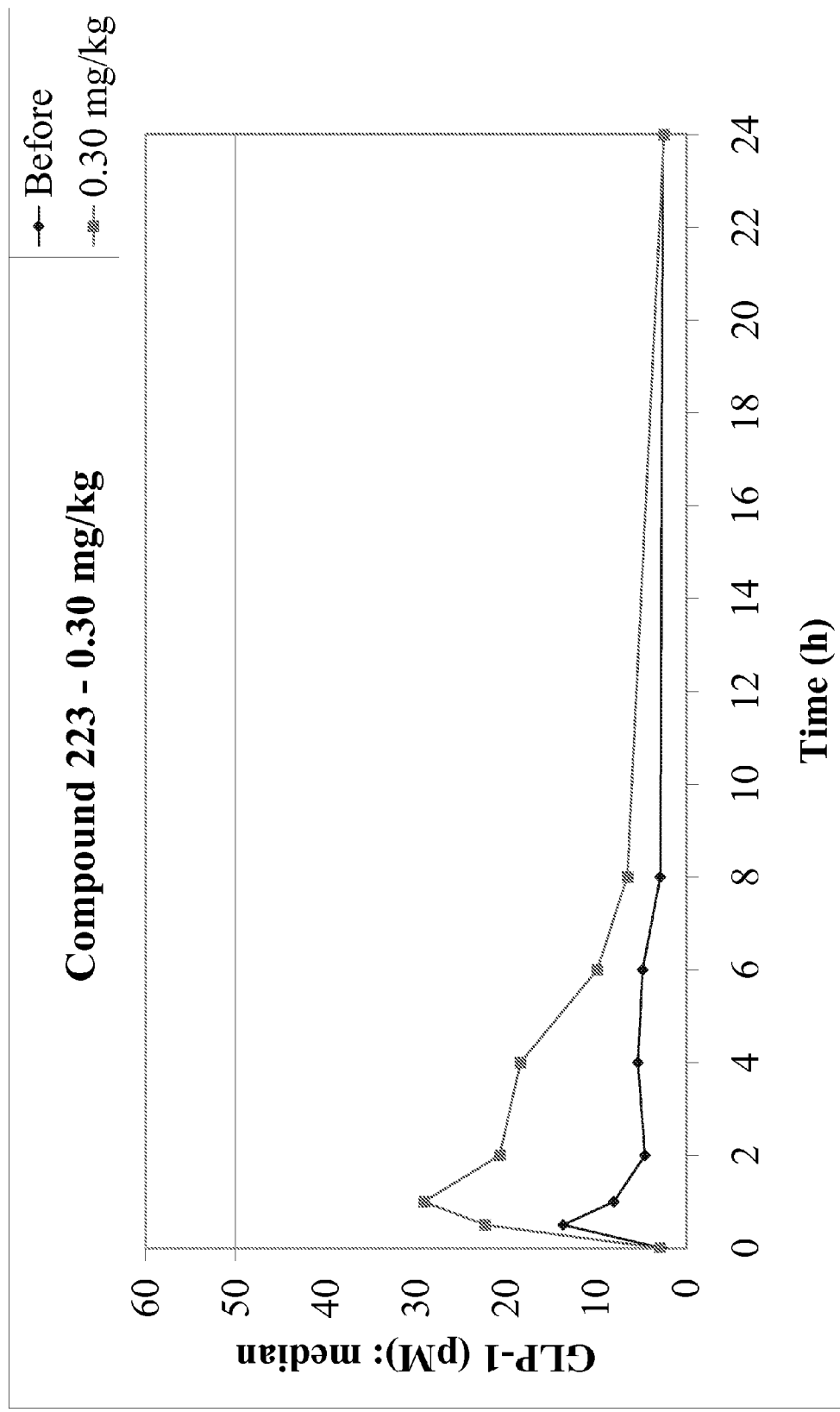

PIPERIDINE/PIPERAZINE DERIVATIVES

CROSS REFERENCE TO RELATED APPLICATIONS

This application is the US national stage of Application No. PCT/EP2008/057060, filed Jun. 6, 2008, which application claims priority from EP 07109868.5, filed Jun. 8, 2007 and EP 07115805.9, filed Sep. 6, 2007.

FIELD OF THE INVENTION

The present invention relates to the use of a DGAT inhibitor, in particular a DGAT1 inhibitor, for the manufacture of a medicament for the prevention or the treatment of a disease by elevating the levels of one or more satiety hormones, in particular GLP-1. The present invention also concerns piperidine/piperazine derivatives having DGAT inhibitory activity, in particular DGAT1 inhibitory activity. The invention further relates to methods for their preparation and pharmaceutical compositions comprising them. The invention also relates to the use of said compounds for the manufacture of a medicament for the prevention or the treatment of a disease mediated by DGAT, in particular DGAT 1.

BACKGROUND TO THE INVENTION

Triglycerides represent the major form of energy stored in eukaryotes. Disorders or imbalances in triglyceride metabolism are implicated in the pathogenesis of and increased risk for obesity, insulin resistance syndrome and type II diabetes, nonalcoholic fatty liver disease and coronary heart disease (see, Lewis, et al, *Endocrine Reviews* (2002) 23:201 and Malloy and Kane, *Adv. Intern. Med.* (2001) 47:11 1). Additionally, hypertriglyceridemia is often an adverse consequence of cancer therapy (see, Bast, et al. *Cancer Medicine*, 5th Ed., (2000) B. C. Decker, Hamilton, Ontario, CA).

A key enzyme in the synthesis of triglycerides is acyl CoA:diacylglycerol acyltransferase, or DGAT. DGAT is a microsomal enzyme that is widely expressed in mammalian tissues and that catalyzes the joining of 1,2-diacylglycerol (DAG) and fatty acyl CoA to form triglycerides (TG) at the endoplasmic reticulum (reviewed in Chen and Farese, *Trends Cardiovasc. Med.* (2000) 10: 188 and Farese, et al, *Curr. Opin. Lipidol.* (2000) 11:229). It was originally thought that DGAT uniquely controlled the catalysis of the final step of acylation of diacylglycerol to triglyceride in the two major pathways for triglyceride synthesis, the glycerol phosphate and monoacylglycerol pathways. Because triglycerides are considered essential for survival, and their synthesis was thought to occur through a single mechanism, inhibition of triglyceride synthesis through inhibiting the activity of DGAT has been largely unexplored.

Genes encoding mouse DGAT1 and the related human homologs ARGP1 (human DGAT1) and ARGP2 (human ACAT2) now have been cloned and characterized (Cases, et al, *Pro.c Nat.l Acad. Sci.* (1998) 95:13018; Oelkers, et al, *J. Biol. Chem.* (1998) 273:26765). The gene for mouse DGAT1 has been used to create DGAT knock-out mice to better elucidate the function of the DGAT gene.

Unexpectedly, mice unable to express a functional DGAT1 enzyme (Dgat1−/− mice) are viable and still able to synthesize triglycerides, indicating that multiple catalytic mechanisms contribute to triglyceride synthesis (Smith, et al, Nature Genetics (2000) 25:87). Other enzymes that catalyze triglyceride synthesis, for example, DGAT2 and diacylglycerol transacylase, also have been identified (Cases, et al, *J. Biol. Chem.* (2001) 276:38870). Gene knockout studies in mice have revealed that DGAT2 plays a fundamental role in mammalian triglyceride synthesis and is required for survival. DGAT2 deficient mice are lipopenic and die soon after birth, apparently from profound reductions in substrates for energy metabolism and from impaired permeability barrier function in the skin. (Farese, et al., *J. Biol. Chem.* (2004) 279: 11767).

Significantly, Dgat1−/− mice are resistant to diet-induced obesity and remain lean. Even when fed a high fat diet (21% fat) Dgat1−/− mice maintain weights comparable to mice fed a regular diet (4% fat) and have lower total body triglyceride levels. The obesity resistance in Dgat1−/− mice is not due to decreased caloric intake, but the result of increased energy expenditure and decreased resistance to insulin and leptin (Smith, et al, Nature Genetics (2000) 25:87; Chen and Farese, *Trends Cardiovasc. Med.* (2000) 10: 188; and Chen, et al, *J. Clin. Invest.* (2002) 109:1049). Additionally, Dgat1−/− mice have reduced rates of triglyceride absorption (Buhman, et al, *J. Biol. Chem.* (2002) 277:25474). In addition to improved triglyceride metabolism, Dgat1−/− mice also have improved glucose metabolism, with lower glucose and insulin levels following a glucose load, in comparison to wild-type mice (Chen and Farese, *Trends Cardiovasc. Med.* (2000) 10: 188).

The finding that multiple enzymes contribute to catalyzing the synthesis of triglyceride from diacylglycerol is significant, because it presents the opportunity to modulate one catalytic mechanism of this biochemical reaction to achieve therapeutic results in an individual with minimal adverse side effects. Compounds that inhibit the conversion of diacylglycerol to triglyceride, for instance by specifically inhibiting the activity of DGAT1, will find use in lowering corporeal concentrations and absorption of triglycerides to therapeutically counteract the pathogenic effects caused by abnormal metabolism of triglycerides in obesity, insulin resistance syndrome and overt type II diabetes, congestive heart failure and atherosclerosis, and as a consequence of cancer therapy.

Because of the ever increasing prevalence of obesity, type II diabetes, heart disease and cancer in societies throughout the world, there is a pressing need in developing new therapies to effectively treat and prevent these diseases. Therefore there is an interest in developing compounds that can potently and specifically inhibit the catalytic activity of DGAT, in particular DGAT1.

We have now unexpectedly found that the compounds of the present invention exhibit DGAT inhibitory activity, in particular DGAT1 inhibitory activity, and can therefore be used to prevent or treat a disease associated with or mediated by DGAT, such as for example obesity, type II diabetes, heart disease and cancer. The compounds of the invention differ from the prior art compounds in structure, in their pharmacological activity, pharmacological potency, and/or pharmacological profile.

We have also unexpectedly found that DGAT inhibitors can be used to elevate the levels of one or more satiety hormones, in particular glucagon-like-peptide-1 (GLP-1) and therefore DGAT inhibitors, in particular DGAT1 inhibitors, can also be used to prevent or treat a disease which can benefit from elevated levels of a satiety hormone, in particular GLP-1. Glucagon-like peptide 1 (GLP-1) is an intestinal hormone which generally stimulates insulin secretion during hyperglycemia, suppresses glucagon secretion, stimulates (pro) insulin biosynthesis and decelerates gastric emptying and acid secretion. GLP-1 is secreted from L cells in the small and large bowel following the ingestion of fat and proteins. GLP-1 has been suggested, among other indications, as a possible therapeutic agent for the management of type 2 non-insulin-dependent diabetes mellitus as well as related metabolic disorders, such as obesity.

Thus, by the present finding, a disease which can benefit from elevated levels of GLP-1 can be treated with small molecules (compared to large molecules such as proteins or protein-like compounds, e.g. GLP-1 analogues).

BACKGROUND PRIOR ART

WO 2006/034441 discloses heterocyclic derivatives and their use as stearoyl CoA desaturase inhibitors (SCD-1 inhibitors).

WO 2006/086445 relates to a combination therapy of a SCD-1 inhibitor and another drug to treat adverse weight gain.

WO 2006/004200 and JP2007131584 relate to urea and amino derivatives having DGAT inhibitory activity.

WO 2004/047755 relates to fused bicyclic nitrogen-containing heterocycles having DGAT inhibitory activity.

WO2005/072740 relates to an anorectic action of a compound having DGAT inhibitory activity.

DESCRIPTION OF THE FIGURES

FIG. 1 describes the postprandial GLP-1 plasma profile for compound 223 (dose of 0.3 mg/kg), determined according to the protocol described in pharmacological example D.B) hereinafter.

DESCRIPTION OF THE INVENTION

The present invention relates to the use of a DGAT inhibitor for the manufacture of a medicament for the prevention or the treatment, in particular for the treatment, of a disease which can benefit from elevated levels of one or more satiety hormones, in particular GLP-1.

The present invention further relates to a compound of formula

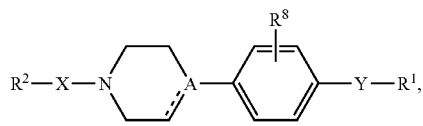

(I)

including any stereochemically isomeric form thereof, wherein
A represents CH or N;
the dotted line represents an optional bond in case A represents a carbon atom;
X represents —C(=O)—; —O—C(=O)—; —C(=O)—C(=O)—; —NR$^x$—C(=O)—; —Z$^1$—C(=O)—; —Z$^1$—NR$^x$—C(=O)—; —C(=O)—Z$^1$—; —NR$^x$—C(=O)—Z$^1$—; —S(=O)p-; —C(=S)—; —NR$^x$—C(=S)—; —Z$^1$—C(=S)—; —Z$^1$—NR$^x$—C(=S)—; —C(=S)—Z$^1$—; —NR$^x$—C(=S)—Z$^1$—;
Z$^1$ represents a bivalent radical selected from C$_{1-6}$alkanediyl, C$_{2-6}$alkenediyl or C$_{2-6}$alkynediyl; wherein each of said C$_{1-6}$alkanediyl, C$_{2-6}$alkenediyl or C$_{2-6}$alkynediyl may optionally be substituted with hydroxyl or amino; and wherein two hydrogen atoms attached to the same carbon atom in C$_{1-6}$alkanediyl may optionally be replaced by C$_{1-6}$alkanediyl;
Y represents NR$^x$—C(=O)—Z$^2$—; —NR$^x$—C(=O)—Z$^2$—NR$^y$—; —NR$^x$—C(=O)—Z$^2$—NR$^y$—C(=O)—; NR$^x$—C(=O)—Z$^2$—NR$^y$—C(=O)—O—; —NR$^x$—C(=O)—Z$^2$—O—; —NR$^x$—C(=O)—Z$^2$—O—C(=O)—; —NR$^x$—C(=O)—Z$^2$—C(=O)—; —NR$^x$—C(=O)—Z$^2$—C(=O)—O—; —NR$^x$—C(=O)—O—Z$^2$—C(=O)—; —NR$^x$—C(=O)—O—Z$^2$—C(=O)—O—; —NR$^x$—C(=O)—O—Z$^2$—O—C(=O)—; —NR$^x$—C(=O)—Z$^2$—C(=O)—NR$^y$—; —NR$^x$—C(=O)—Z$^2$—NR$^y$—C(=O)—NR$^y$—; —C(=O)—Z$^2$—; —C(=O)—Z$^2$—O—; —C(=O)—NR$^x$—Z$^2$—; —C(=O)—NR$^x$—Z$^2$—O—; —C(=O)—NR$^x$—Z$^2$—C(=O)—O—; —C(=O)—NR$^x$—Z$^2$—O—C(=O)—; —C(=O)—NR$^x$—O—Z$^2$—; —C(=O)—NR$^x$—Z$^2$—NR$^y$—; —C(=O)—NR$^x$—Z$^2$—NR$^y$—C(=O)—; —C(=O)—NR$^x$—Z$^2$—NR$^y$—C(=O)—O—;
Z$^2$ represents a bivalent radical selected from C$_{1-6}$alkanediyl, C$_{2-6}$alkenediyl or C$_{2-6}$alkynediyl; wherein each of said C$_{1-6}$alkanediyl, C$_{2-6}$alkenediyl or C$_{2-6}$alkynediyl may optionally be substituted with C$_{1-4}$alkyloxy, C$_{1-4}$alkylthio, hydroxyl, cyano or aryl; and wherein two hydrogen atoms attached to the same carbon atom in the definition of Z$^2$ may optionally be replaced by C$_{1-6}$alkanediyl;
R$^x$ represents hydrogen or C$_{1-4}$alkyl;
R$^y$ represents hydrogen; C$_{1-4}$alkyl optionally substituted with C$_{3-6}$cycloalkyl or aryl or Het; C$_{2-4}$alkenyl; or —S(=O)$_p$-aryl;
R$^1$ represents C$_{1-12}$alkyl optionally substituted with cyano, C$_{1-4}$alkyloxy, C$_{1-4}$alkyl-oxyC$_{1-4}$alkyloxy, C$_{3-6}$cycloalkyl or aryl; C$_{2-6}$alkenyl; C$_{2-6}$alkynyl; C$_{3-6}$cycloalkyl; adamantanyl; aryl$^1$; aryl$^1$C$_{1-6}$alkyl; Het$^1$; or Het$^1$C$_{1-6}$alkyl; provided that when Y represents —NR$^x$—C(=O)—Z$^2$—; —NR$^x$—C(=O)—Z$^2$—NR$^y$—; —NR$^x$—C(=O)—Z$^2$—C(=O)—NR$^y$—; —C(=O)—Z$^2$—; —NR$^x$—C(=O)—Z$^2$—NR$^y$—C(=O)—NR$^y$—; —C(=O)—NR$^x$—Z$^2$—; —C(=O)—NR$^x$—O—Z$^2$—; or —C(=O)—NR$^x$—Z$^2$—NR$^y$—; then R$^1$ may also represent hydrogen;
R$^2$ represents hydrogen, C$_{1-12}$alkyl, C$_{2-6}$alkenyl or R$^3$;
R$^3$ represents C$_{3-6}$cycloalkyl, phenyl, naphtalenyl, 2,3-dihydro-1,4-benzodioxinyl, 1,3-benzodioxolyl, 2,3-dihydrobenzo furanyl or a 6-membered aromatic heterocycle containing 1 or 2 N atoms, wherein said C$_{3-6}$cycloalkyl, phenyl, naphtalenyl, 2,3-dihydro-1,4-benzodioxinyl, 1,3-benzodioxolyl or heterocycle may optionally be substituted with at least one substituent, in particular one, two, three, four or five substituents, each substituent independently selected from hydroxyl; carboxyl; halo; C$_{1-6}$alkyl optionally substituted with hydroxy; polyhaloC$_{1-6}$alkyl; C$_{1-6}$alkyloxy optionally substituted with C$_{1-4}$alkyloxy; C$_{1-6}$alkylthio; polyhalo-C$_{1-6}$alkyloxy; C$_{1-6}$alkyloxycarbonyl wherein C$_{1-6}$alkyl may optionally be substituted with aryl; cyano; C$_{1-6}$alkylcarbonyl; nitro; amino; mono- or di(C$_{1-4}$alkyl)amino; C$_{1-4}$alkylcarbonylamino; —S(=O)$_p$—C$_{1-4}$alkyl; R$^5$R$^4$N—C(=O)—; R$^5$R$^4$N—C$_{1-6}$alkyl; C$_{3-6}$cycloalkyl; C$_{3-6}$cycloalkylC$_{1-4}$alkyl; C$_{3-6}$cycloalkyl-C(=O)—; aryl; aryloxy; arylC$_{1-4}$alkyl; aryl-C(=O)—C$_{1-4}$ alkyl; aryl-C(=O)—; Het; HetC$_{1-4}$alkyl; Het-C(=O)—C$_{1-4}$alkyl; Het-C(=O)—; Het-O—;
R$^4$ represents hydrogen; C$_{1-4}$alkyl optionally substituted with hydroxyl or C$_{1-4}$alkyloxy; R$^7$R$^6$N—C$_{1-4}$alkyl; C$_{1-4}$alkyloxy; Het; Het-C$_{1-4}$alkyl; aryl; R$^7$R$^6$N—C(=O)—C$_{1-4}$ alkyl;
R$^5$ represents hydrogen or C$_{1-4}$alkyl;
R$^6$ represents hydrogen; C$_{1-4}$alkyl; C$_{1-4}$alkylcarbonyl;
R$^7$ represents hydrogen or C$_{1-4}$alkyl; or
R$^6$ and R$^7$ may be taken together with the nitrogen to which they are attached to form a saturated monocyclic 5, 6 or 7-membered heterocycle which may further contain one or more heteroatoms each independently selected from O, S, $S(=O)_p$ or N; and which heterocycle may optionally be substituted with $C_{1-4}$alkyl;

$R^8$ represents hydrogen, halo, $C_{1-4}$alkyl, $C_{1-4}$alkyl substituted with hydroxyl;

aryl represents phenyl or phenyl substituted with at least one substituent, in particular one, two, three, four or five substituents, each substituent independently being selected from hydroxyl; carboxyl; halo; $C_{1-6}$alkyl optionally substituted with $C_{1-4}$alkyloxy, amino or mono- or di($C_{1-4}$alkyl)amino; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxycarbonyl; cyano; amino carbonyl; mono- or di($C_{1-4}$alkyl)aminocarbonyl; $C_{1-6}$alkylcarbonyl; nitro; amino; mono- or di($C_{1-4}$alkyl)amino; —$S(=O)_p$—$C_{1-4}$alkyl;

aryl$^1$ represents phenyl, naphthalenyl or fluorenyl; each of said phenyl, naphthalenyl or fluorenyl optionally substituted with at least one substituent, in particular one, two, three, four or five substituents, each substituent independently being selected from hydroxyl; oxo; carboxyl; halo; $C_{1-6}$alkyl optionally substituted with carboxyl, $C_{1-4}$alkyloxycarbonyl or aryl-C(=O)—; hydroxy$C_{1-6}$alkyl optionally substituted with aryl or aryl-C(=O)—; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxycarbonyl wherein $C_{1-6}$alkyl may optionally be substituted with aryl; cyano; aminocarbonyl; mono- or di($C_{1-4}$alkyl)aminocarbonyl; $C_{1-6}$alkylcarbonyl; nitro; amino; mono- or di($C_{1-6}$alkyl)amino; $R^5R^4N$—$C_{1-6}$alkyl; $C_{3-6}$cycloalkyl-NR$^x$—; aryl-NR$^x$—; Het-NR$^x$—; $C_{3-6}$cycloalkyl$C_{1-4}$alkyl-NR$^x$—; aryl$C_{1-4}$alkyl-NR$^x$—; HetC$_{1-4}$alkyl-NR$^x$—; —$S(=O)_p$—$C_{1-4}$alkyl; $C_{3-6}$cycloalkyl; $C_{3-6}$cycloalkyl$C_{1-4}$ alkyl; $C_{3-6}$cycloalkyl-C(=O)—; aryl; aryloxy; aryl$C_{1-4}$ alkyl; aryl-C(=O)—$C_{1-4}$alkyl; aryl-C(=O)—; Het; HetC$_{1-4}$alkyl; Het-C(=O)—$C_{1-4}$alkyl; Het-C(=O)—; Het-O—;

Het represents a monocyclic non-aromatic or aromatic heterocycle containing at least one heteroatom each independently selected from O, S, $S(=O)_p$ or N; or a bicyclic or tricyclic non-aromatic or aromatic heterocycle containing at least one heteroatom each independently selected from O, S, $S(=O)_p$ or N; said monocyclic heterocycle or said bi- or tricyclic heterocycle optionally being substituted with at least one substituent, in particular one, two, three, four or five substituents, each substituent independently being selected from hydroxyl; oxo; carboxyl; halo; $C_{1-6}$alkyl optionally substituted with $C_{1-4}$alkyloxy, amino or mono- or di($C_{1-4}$alkyl)amino; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyl-oxycarbonyl; cyano; aminocarbonyl; mono- or di($C_{1-4}$alkyl)aminocarbonyl; $C_{1-6}$alkylcarbonyl; nitro; amino; mono- or di($C_{1-4}$alkyl)amino; —$S(=O)_p$—$C_{1-4}$alkyl;

Het$^1$ represents a monocyclic non-aromatic or aromatic heterocycle containing at least one heteroatom each independently selected from O, S, $S(=O)_p$ or N; or a bicyclic or tricyclic non-aromatic or aromatic heterocycle containing at least one heteroatom each independently selected from O, S, $S(=O)_p$ or N; said monocyclic heterocycle or said bi- or tricyclic heterocycle optionally being substituted with at least one substituent, in particular one, two, three, four or five substituents, each substituent independently being selected from hydroxyl; oxo; carboxyl; halo; $C_{1-6}$alkyl optionally substituted with carboxyl, $C_{1-4}$alkyloxycarbonyl or aryl-C(=O)—; hydroxy$C_{1-6}$alkyl optionally substituted with aryl or aryl-C(=O)—; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxy-carbonyl wherein $C_{1-6}$alkyl may optionally be substituted with aryl; cyano; aminocarbonyl; mono- or di($C_{1-4}$alkyl)aminocarbonyl; $C_{1-6}$alkylcarbonyl; nitro; amino; mono- or di($C_{1-6}$alkyl)amino; $R^5R^4N$—$C_{1-6}$alkyl; $C_{3-6}$cycloalkyl-NR$^x$—; aryl-NR$^x$—; Het-NR$^x$—; $C_{3-6}$cycloalkyl$C_{1-4}$alkyl-NR$^x$—; aryl$C_{1-4}$alkyl-NR$^x$—; HetC$_{1-4}$alkyl-NR$^x$—; —$S(=O)_p$—$C_{1-4}$alkyl; $C_{3-6}$cycloalkyl; $C_{3-6}$cycloalkyl$C_{1-4}$ alkyl; $C_{3-6}$cycloalkyl-C(=O)—; aryl; aryloxy; aryl$C_{1-4}$ alkyl; aryl-C(=O)—$C_{1-4}$alkyl; aryl-C(=O)—; Het; HetC$_{1-4}$alkyl; Het-C(=O)—$C_{1-4}$alkyl; Het-C(=O)—; Het-O—;

p represents 1 or 2;

provided that if X represents —O—C(=O)—, then $R^2$ represents $R^3$; and provided that

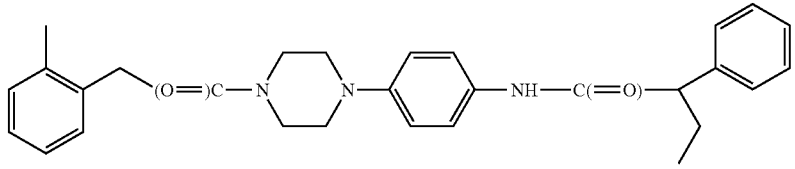

is excluded; a N-oxide thereof, a pharmaceutically acceptable salt thereof or a solvate thereof.

The present invention also relates to the use of a compound of formula (I) for the manufacture of a medicament for the prevention or the treatment of a disease which can benefit from elevated levels of one or more satiety hormones, in particular GLP-1, in particular the present invention relates to the use of a compound of formula (I) for the manufacture of a medicament for the treatment of a disease which can benefit from elevated levels of GLP-1.

The present invention further relates to the use of a compound of formula (I) for the manufacture of a medicament for the prevention or the treatment of a disease mediated by DGAT, in particular the present invention relates to the use of a compound of formula (I) for the manufacture of a medicament for the prevention or the treatment of a disease which can benefit from inhibition of DGAT, in particular for the treatment of a disease which can benefit from inhibition of DGAT, in particular DGAT1, wherein the compound of formula (I) is a compound of formula

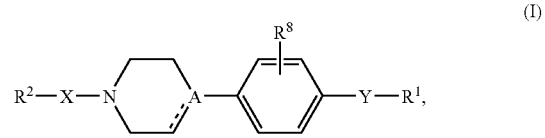

(I)

including any stereochemically isomeric form thereof, wherein

A represents CH or N;

the dotted line represents an optional bond in case A represents a carbon atom;

X represents —C(=O)—; —O—C(=O)—; —C(=O)—C(=O)—; —NR$^x$—C(=O)—; —Z$^1$—C(=O)—; —Z$^1$—NR$^x$—C(=O)—; —C(=O)—Z$^1$—; —NR$^x$—C(=O)—Z$^1$—; —S(=O)p-; —C(=S)—; —NR$^x$—C(=S)—; —Z$^1$—C(=S)—; —Z$^1$—NR$^x$—C(=S)—; —C(=S)—Z$^1$—; —NR$^x$—C(=S)—Z$^1$—;

Z$^1$ represents a bivalent radical selected from C$_{1-6}$alkanediyl, C$_{2-6}$alkenediyl or C$_{2-6}$alkynediyl; wherein each of said C$_{1-6}$alkanediyl, C$_{2-6}$alkenediyl or C$_{2-6}$alkynediyl may optionally be substituted with hydroxyl or amino; and wherein two hydrogen atoms attached to the same carbon atom in C$_{1-6}$alkanediyl may optionally be replaced by C$_{1-6}$alkanediyl;

Y represents NR$^x$—C(=O)—Z$^2$—; —NR$^x$—C(=O)—Z$^2$—NR$^y$—; —NR$^x$—C(=O)—Z$^2$—NR$^y$—C(=O)—; —NR$^x$—C(=O)—Z$^2$—NR$^y$—C(=O)—O—; —NR$^x$—C(=O)—Z$^2$—O—; —NR$^x$—C(=O)—Z$^2$—O—C(=O)—; —NR$^x$—C(=O)—Z$^2$—C(=O)—; —NR$^x$—C(=O)—Z$^2$—C(=O)—O—; —NR$^x$—C(=O)—O—Z$^2$—C(=O)—O—; —NR$^x$—C(=O)—O—Z$^2$—C(=O)—O—; —NR$^x$—C(=O)—O—Z$^2$—O—C(=O)—; —NR$^x$—C(=O)—Z$^2$—C(=O)—NR$^y$—; —NR$^x$—C(=O)—Z$^2$—NR$^y$—C(=O)—NR$^y$—; —C(=O)—Z$^2$—; —C(=O)—Z$^2$—O—; —C(=O)—NR$^x$—Z$^2$—; —C(=O)—NR$^x$—Z$^2$—O—; —C(=O)—NR$^x$—Z$^2$—C(=O)—O—; —C(=O)—NR$^x$—Z$^2$—O—C(=O)—; —C(=O)—NR$^x$—O—Z$^2$—; —C(=O)—NR$^x$—Z$^2$—NR$^y$—; —C(=O)—NR$^x$—Z$^2$—NR$^y$—C(=O)—; —C(=O)—NR$^x$—Z$^2$—NR$^y$—C(=O)—O—;

Z$^2$ represents a bivalent radical selected from C$_{1-6}$alkanediyl, C$_{2-6}$alkenediyl or C$_{2-6}$alkynediyl; wherein each of said C$_{1-6}$alkanediyl, C$_{2-6}$alkenediyl or C$_{2-6}$alkynediyl may optionally be substituted with C$_{1-4}$alkyloxy, C$_{1-4}$alkylthio, hydroxyl, cyano or aryl; and wherein two hydrogen atoms attached to the same carbon atom in the definition of Z$^2$ may optionally be replaced by C$_{1-6}$alkanediyl;

R$^x$ represents hydrogen or C$_{1-4}$alkyl;

R$^y$ represents hydrogen; C$_{1-4}$alkyl optionally substituted with C$_{3-6}$cycloalkyl or aryl or Het; C$_{2-4}$alkenyl; or —S(=O)$_p$-aryl;

R$^1$ represents C$_{1-12}$alkyl optionally substituted with cyano, C$_{1-4}$alkyloxy, C$_{1-4}$alkyl-oxyC$_{1-4}$alkyloxy, C$_{3-6}$cycloalkyl or aryl; C$_{2-6}$alkenyl; C$_{2-6}$alkynyl; C$_{3-6}$cycloalkyl; adamantanyl; aryl$^1$; aryl$^1$C$_{1-6}$alkyl; Het$^1$; or Het$^1$C$_{1-6}$alkyl; provided that when Y represents —NR$^x$—C(=O)—Z$^2$—; —NR$^x$—C(=O)—Z$^2$—NR$^y$—; —NR$^x$—C(=O)—Z$^2$—C(=O)—NR$^y$—; —C(=O)—Z$^2$—; —NR$^x$—C(=O)—Z$^2$—NR$^y$—C(=O)—NR$^y$—; —C(=O)—NR$^x$—Z$^2$—; —C(=O)—NR$^x$—O—Z$^2$—; or —C(=O)—NR$^x$—Z$^2$—NR$^y$—; then R$^1$ may also represent hydrogen;

R$^2$ represents hydrogen, C$_{1-12}$alkyl, C$_{2-6}$alkenyl or R$^3$;

R$^3$ represents C$_{3-6}$cycloalkyl, phenyl, naphtalenyl, 2,3-dihydro-1,4-benzodioxinyl, 1,3-benzodioxolyl, 2,3-dihydrobenzo furanyl or a 6-membered aromatic heterocycle containing 1 or 2 N atoms, wherein said C$_{3-6}$cycloalkyl, phenyl, naphtalenyl, 2,3-dihydro-1,4-benzodioxinyl, 1,3-benzodioxolyl or 6-membered aromatic heterocycle containing 1 or 2 N atoms may optionally be substituted with at least one substituent, in particular one, two, three, four or five substituents, each substituent independently selected from hydroxyl; carboxyl; halo; C$_{1-6}$alkyl optionally substituted with hydroxy; polyhaloC$_{1-6}$alkyl; C$_{1-6}$alkyloxy optionally substituted with C$_{1-4}$alkyloxy; C$_{1-6}$alkylthio; polyhalo-C$_{1-6}$alkyloxy; C$_{1-6}$alkyloxycarbonyl wherein C$_{1-6}$alkyl may optionally be substituted with aryl; cyano; C$_{1-6}$alkylcarbonyl; nitro; amino; mono- or di(C$_{1-4}$alkyl)amino; C$_{1-4}$alkylcarbonylamino; —S(=O)$_p$—C$_{1-4}$alkyl; R$^5$R$^4$N—C(=O)—; R$^5$R$^4$N—C$_{1-6}$alkyl; C$_{3-6}$cycloalkyl; C$_{3-6}$cycloalkylC$_{1-4}$alkyl; C$_{3-6}$cycloalkyl-C(=O)—; aryl; aryloxy; arylC$_{1-4}$alkyl; aryl-C(=O)—C$_{1-4}$alkyl; aryl-C(=O)—; Het; HetC$_{1-4}$alkyl; Het-C(=O)—C$_{1-4}$alkyl; Het-C(=O)—; Het-O—;

R$^4$ represents hydrogen; C$_{1-4}$alkyl optionally substituted with hydroxyl or C$_{1-4}$alkyloxy; R$^7$R$^6$N—C$_{1-4}$alkyl; C$_{1-4}$alkyloxy; Het; Het-C$_{1-4}$alkyl; aryl; R$^7$R$^6$N—C(=O)—C$_{1-4}$alkyl;

R$^5$ represents hydrogen or C$_{1-4}$alkyl;

R$^6$ represents hydrogen; C$_{1-4}$alkyl; C$_{1-4}$alkylcarbonyl;

R$^7$ represents hydrogen or C$_{1-4}$alkyl; or

R$^6$ and R$^7$ may be taken together with the nitrogen to which they are attached to form a saturated monocyclic 5, 6 or 7-membered heterocycle which may further contain one or more heteroatoms each independently selected from O, S, S(=O)$_p$ or N; and which heterocycle may optionally be substituted with C$_{1-4}$alkyl;

R$^8$ represents hydrogen, halo, C$_{1-4}$alkyl, C$_{1-4}$alkyl substituted with hydroxyl;

aryl represents phenyl or phenyl substituted with at least one substituent, in particular one, two, three, four or five substituents, each substituent independently being selected from hydroxyl; carboxyl; halo; C$_{1-6}$alkyl optionally substituted with C$_{1-4}$alkyloxy, amino or mono- or di(C$_{1-4}$alkyl)amino; polyhaloC$_{1-6}$alkyl; C$_{1-6}$alkyloxy optionally substituted with C$_{1-4}$alkyloxy; C$_{1-6}$alkylthio; polyhaloC$_{1-6}$alkyloxy; C$_{1-6}$alkyloxycarbonyl; cyano; amino carbonyl; mono- or di(C$_{1-4}$alkyl)aminocarbonyl; C$_{1-6}$alkylcarbonyl; nitro; amino; mono- or di(C$_{1-4}$alkyl)amino; —S(=O)$_p$—C$_{1-4}$alkyl;

aryl$^1$ represents phenyl, naphthalenyl or fluorenyl; each of said phenyl, naphthalenyl or fluorenyl optionally substituted with at least one substituent, in particular one, two, three, four or five substituents, each substituent independently being selected from hydroxyl; oxo; carboxyl; halo; C$_{1-6}$alkyl optionally substituted with carboxyl, C$_{1-4}$alkyloxycarbonyl or aryl-C(=O)—; hydroxyC$_{1-6}$alkyl optionally substituted with aryl or aryl-C(=O)—; polyhaloC$_{1-6}$alkyl; C$_{1-6}$alkyloxy optionally substituted with C$_{1-4}$alkyloxy; C$_{1-6}$alkylthio; polyhaloC$_{1-6}$alkyloxy; C$_{1-6}$alkyloxycarbonyl wherein C$_{1-6}$alkyl may optionally be substituted with aryl; cyano; aminocarbonyl; mono- or di(C$_{1-4}$alkyl)aminocarbonyl; C$_{1-6}$alkylcarbonyl; nitro; amino; mono- or di(C$_{1-6}$alkyl)amino; R$^5$R$^4$N—C$_{1-4}$alkyl; C$_{3-6}$cycloalkyl-NR$^x$—; aryl-NR$^x$—; Het-NR$^x$—; C$_{3-6}$cycloalkylC$_{1-4}$alkyl-NR$^x$—; arylC$_{1-4}$alkyl-NR$^x$—; HetC$_{1-4}$ alkyl-NR$^x$—; —S(=O)$_p$—C$_{1-4}$alkyl; C$_{3-6}$cycloalkyl; C$_{3-6}$cycloalkylC$_{1-4}$ alkyl; C$_{3-6}$cycloalkyl-C(=O)—; aryl; aryloxy; arylC$_{1-4}$ alkyl; aryl-C(=O)—C$_{1-4}$alkyl; aryl-C(=O)—; Het; HetC$_{1-4}$alkyl; Het-C(=O)—C$_{1-4}$alkyl; Het-C(=O)—; Het-O—;

Het represents a monocyclic non-aromatic or aromatic heterocycle containing at least one heteroatom each independently selected from O, S, S(=O)$_p$ or N; or a bicyclic or tricyclic non-aromatic or aromatic heterocycle containing at least one heteroatom each independently selected from O, S, S(=O)$_p$ or N; said monocyclic heterocycle or said bi- or tricyclic heterocycle optionally being substituted with at least one substituent, in particular one, two, three, four or five substituents, each substituent independently being selected from hydroxyl; oxo; carboxyl; halo; C$_{1-6}$alkyl optionally substituted with $C_{1-4}$alkyloxy, amino or mono- or di($C_{1-4}$alkyl)amino; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxycarbonyl; cyano; aminocarbonyl; mono- or di($C_{1-4}$alkyl)aminocarbonyl; $C_{1-6}$alkylcarbonyl; nitro; amino; mono- or di($C_{1-4}$alkyl) amino; —S(=O)$_p$—$C_{1-4}$alkyl;

Het$^1$ represents a monocyclic non-aromatic or aromatic heterocycle containing at least one heteroatom each independently selected from O, S, S(=O)$_p$ or N; or a bicyclic or tricyclic non-aromatic or aromatic heterocycle containing at least one heteroatom each independently selected from O, S, S(=O)$_p$ or N; said monocyclic heterocycle or said bi- or tricyclic heterocycle optionally being substituted with at least one substituent, in particular one, two, three, four or five substituents, each substituent independently being selected from hydroxyl; oxo; carboxyl; halo; $C_{1-6}$alkyl optionally substituted with carboxyl, $C_{1-4}$alkyloxycarbonyl or aryl-C(=O)—; hydroxy$C_{1-6}$alkyl optionally substituted with aryl or aryl-C(=O)—; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxy-carbonyl wherein $C_{1-6}$alkyl may optionally be substituted with aryl; cyano; aminocarbonyl; mono- or di($C_{1-4}$alkyl)aminocarbonyl; $C_{1-6}$alkylcarbonyl; nitro; amino; mono- or di($C_{1-6}$alkyl)amino; $R^5R^4N$—$C_{1-6}$alkyl; $C_{3-6}$cycloalkyl-NR$^x$—; aryl-NR$^x$—; Het-NR$^x$—; $C_{3-6}$cycloalkyl$C_{1-4}$ alkyl-NR$^x$—; aryl$C_{1-4}$alkyl-NR$^x$—; Het$C_{1-4}$alkyl-NR$^x$—; —S(=O)$_p$—$C_{1-4}$alkyl; $C_{3-6}$cycloalkyl; $C_{3-6}$cycloalkyl$C_{1-4}$ alkyl; $C_{3-6}$cycloalkyl-C(=O)—; aryl; aryloxy; aryl$C_{1-4}$ alkyl; aryl-C(=O)—$C_{1-4}$alkyl; aryl-C(=O)—; Het; Het$C_{1-4}$alkyl; Het-C(=O)—$C_{1-4}$alkyl; Het-C(=O)—; Het-O—;

p represents 1 or 2;

provided that if X represents —O—C(=O)—, then $R^2$ represents $R^3$;

a N-oxide thereof, a pharmaceutically acceptable salt thereof or a solvate thereof As used hereinbefore or hereinafter $C_{0-3}$alkyl as a group or part of a group defines straight or branched chain saturated hydrocarbon radicals having from 0 (then it represents a direct bond) to 3 carbon atoms such as methyl, ethyl, propyl, 1-methyl-ethyl; $C_{1-2}$alkyl as a group or part of a group defines straight or branched chain saturated hydrocarbon radicals having 1 or 2 carbon atoms such as methyl, ethyl; $C_{1-4}$alkyl as a group or part of a group defines straight or branched chain saturated hydrocarbon radicals having from 1 to 4 carbon atoms such as methyl, ethyl, propyl, 1-methylethyl, butyl; $C_{1-5}$alkyl as a group or part of a group defines straight or branched chain saturated hydrocarbon radicals having from 1 to 5 carbon atoms such as the group defined for $C_{1-4}$alkyl and pentyl, 2-methylbutyl and the like; $C_{1-6}$alkyl as a group or part of a group defines straight or branched chain saturated hydrocarbon radicals having from 1 to 6 carbon atoms such as the group defined for $C_{1-4}$alkyl and for $C_{1-5}$alkyl and hexyl, 2-methylpentyl and the like; $C_{1-12}$alkyl as a group or part of a group defines straight or branched chain saturated hydrocarbon radicals having from 1 to 12 carbon atoms such as the group defined for $C_{1-6}$alkyl and heptyl, 2-methylheptyl and the like; $C_{1-6}$alkanediyl defines straight or branched chain saturated bivalent hydro-carbon radicals having from 1 to 6 carbon atoms such as methylene, 1,2-ethanediyl or 1,2-ethylidene, 1,3-propanediyl or 1,3-propylidene, 1,4-butanediyl or 1,4-butylidene, 1,5-pentanediyl and the like; $C_{2-4}$alkenyl as a group or part of a group defines straight or branched chain hydrocarbon radicals having from 2 to 4 carbon atoms and having a double bond such as ethenyl, propenyl, butenyl and the like; $C_{2-6}$alkenyl as a group or part of a group defines straight or branched chain hydrocarbon radicals having from 2 to 6 carbon atoms and having a double bond such as the group defined for $C_{2-4}$alkenyl and pentenyl, hexenyl, 3-methylbutenyl and the like; $C_{2-6}$alkenediyl defines straight or branched chain bivalent hydrocarbon radicals having from 2 to 6 carbon atoms and having a double bond such as 1,2-ethenediyl, 1,3-propenediyl, 1,4-butenediyl, 1,5-pentenediyl and the like;

$C_{2-6}$alkynediyl as a group or part of a group defines straight or branched chain bivalent hydrocarbon radicals having from 2 to 6 carbon atoms and having a triple bond such as 1,2-ethynediyl, 1,3-propynediyl, 1,4-butynediyl, 1,5-pentynediyl and the like; $C_{3-6}$cycloalkyl is generic to cyclopropyl, cyclobutyl, cyclopentyl and cyclohexyl.

The term halo is generic to fluoro, chloro, bromo and iodo. As used hereinbefore or hereinafter, polyhalo$C_{1-6}$alkyl as a group or part of a group is defined as $C_{1-6}$alkyl substituted with one or more, such as for example 2, 3, 4 or 5 halo atoms, for example methyl substituted with one or more fluoro atoms, for example, difluoromethyl or trifluoromethyl, 1,1-difluoro-ethyl, 1,1-difluoro-2,2,2-trifluoro-ethyl and the like. In case more than one halogen atoms are attached to a $C_{1-6}$alkyl group within the definition of polyhalo$C_{1-6}$alkyl, they may be the same or different.

As used herein before, the term (=O) forms a carbonyl moiety when attached to a carbon atom, a sulfoxide moiety when attached to a sulfur atom and a sulfonyl moiety when two of said terms are attached to a sulfur atom. Oxo means =O.

The radical Het or Het$^1$ as defined hereinabove may be an optionally substituted monocyclic non-aromatic or aromatic heterocycle containing at least one heteroatom, in particular 1, 2 or 3 heteroatoms, each independently selected from O, S, S(=O)$_p$ or N; or an optionally substituted bi- or tricyclic non-aromatic or aromatic heterocycle containing at least one heteroatom, in particular 1, 2, 3, 4 or 5 heteroatoms, each independently selected from O, S, S(=O)$_p$ or N. Examples of such unsubstituted monocyclic heterocycles comprise, but are not limited to, non-aromatic (fully saturated or partially saturated) or aromatic 4-, 5-, 6- or 7-membered monocyclic heterocycles such as for example azetidinyl, tetrahydrofuranyl, pyrrolidinyl, dioxolanyl, imidazolidinyl, thiazolidinyl, tetrahydrothienyl, dihydrooxazolyl, isothiazolidinyl, isoxazolidinyl, oxadiazolidinyl, triazolidinyl, thiadiazolidinyl, pyrazolidinyl, piperidinyl, hexahydropyrimidinyl, hexahydropyrazinyl, dioxanyl, morpholinyl, dithianyl, thiomorpholinyl, piperazinyl, trithianyl, hexahydrodiazepinyl, pyrrolinyl, imidazolinyl, pyrazolinyl, pyrrolyl, furyl, thienyl, imidazolyl, oxazolyl, isoxazolyl, thiazolyl, isothiazolyl, pyrazolyl, triazolyl, thiadiazolyl, oxadiazolyl, tetrazolyl, pyridyl, pyrimidinyl, pyrazinyl, pyridazinyl, triazinyl, pyranyl and the like. Examples of such unsubstituted bicyclic or tricyclic heterocycles comprise, but are not limited to, non-aromatic (fully saturated or partially saturated) or aromatic 8- to 17-membered bicyclic or tricyclic heterocycles such as for example decahydroquinolinyl, octahydroindolyl, 2,3-dihydrobenzo furanyl, 1,3-benzodioxolyl, 2,3-dihydro-1,4-benzodioxinyl, indolinyl, benzofuryl, isobenzofuryl, benzothienyl, isobenzothienyl, indolizinyl, indolyl, isoindolyl, benzoxazolyl, benzimidazolyl, indazolyl, benzisoxazolyl, benzisothiazolyl, benzopyrazolyl, benzoxadiazolyl, benzothiadiazolyl, benzotriazolyl, purinyl, quinolinyl, isoquinolinyl, cinnolinyl, quinolizinyl, phthalazinyl, quinoxalinyl, quinazolinyl, naphthiridinyl, pteridinyl, benzopyranyl, pyrrolopyridyl, thienopyridyl, furopyridyl, isothiazolopyridyl, thiazolopyridyl, isoxazolopyridyl, oxazolopyridyl, pyrazolopyridyl, imidazopyridyl, pyrrolopyrazinyl, thienopyrazinyl, furopyrazinyl, isothiazolopyrazinyl, thiazolopyrazinyl, isoxazolopyrazinyl, oxazolopyrazinyl, pyrazolopyrazinyl, imidazopyrazinyl, pyrrolopyrimidinyl, thienopyrimidinyl, furopyrimidinyl, isothiazolopyrimidinyl, thiazolopyrimidinyl, isoxazolopyrimidinyl, oxazolopyrimidinyl, pyrazolopyrimidinyl, imidazopyrimidinyl, pyrrolopyridazinyl, thienopyridazinyl, furopyridazinyl, isothiazolopyridazinyl, thiazolopyridazinyl, isoxazolopyridazinyl, oxazolopyridazinyl, pyrazolopyridazinyl, imidazopyridazinyl, oxadiazolopyridyl, thiadiazolopyridyl, triazolopyridyl, oxadiazolopyrazinyl, thiadiazolopyrazinyl, triazolopyrazinyl, oxadiazolopyrimidinyl, thiadiazolopyrimidinyl, triazolopyrimidinyl, oxadiazolopyridazinyl, thiadiazolopyridazinyl, triazolopyridazinyl, imidazooxazolyl, imidazothiazolyl, imidazoimidazolyl, imidazopyrazolyl; isoxazolotriazinyl, isothiazolotriazinyl, pyrazolotriazinyl, oxazolotriazinyl, thiazolotriazinyl, imidazotriazinyl, oxadiazolotriazinyl, thiadiazolotriazinyl, triazolotriazinyl, carbazolyl, acridinyl, phenazinyl, phenothiazinyl, phenoxazinyl and the like. Optional substituents for Het heterocycles are hydroxyl; oxo; carboxyl; halo; $C_{1-6}$alkyl optionally substituted with $C_{1-4}$alkyloxy, amino or mono- or di($C_{1-4}$alkyl)amino; polyhalo$C_{1-6}$alkyl; $C_{1-6}$alkyloxy optionally substituted with $C_{1-4}$alkyloxy; $C_{1-6}$alkylthio; polyhalo $C_{1-6}$alkyloxy; $C_{1-6}$alkyl-oxycarbonyl; cyano; aminocarbonyl; mono- or di($C_{1-4}$alkyl)aminocarbonyl; $C_{1-6}$alkylcarbonyl; nitro; amino; mono- or di($C_{1-4}$alkyl)amino; —S(=O)$_p$—$C_{1-4}$alkyl. Optional substituents for Het$^1$ substituents are hydroxyl; oxo; carboxyl; halo; $C_{1-6}$alkyl optionally substituted with carboxyl, $C_{1-4}$alkyloxycarbonyl or aryl-C(=O)—; hydroxy$C_{1-6}$alkyl optionally substituted with aryl or aryl-C(=O)—; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxy-carbonyl wherein $C_{1-6}$alkyl may optionally be substituted with aryl; cyano; aminocarbonyl; mono- or di($C_{1-4}$alkyl)aminocarbonyl; $C_{1-6}$alkylcarbonyl; nitro; amino; mono- or di($C_{1-6}$alkyl)amino; $R^5R^4N$—$C_{1-6}$alkyl; $C_{3-6}$cycloalkyl-NR$^x$—; aryl-NR$^x$—; Het-NR$^x$—; $C_{3-6}$cycloalkyl$C_{1-4}$alkyl-NR$^x$—; aryl$C_{1-4}$alkyl-NR$^x$—; Het$C_{1-4}$alkyl-NR$^x$—; —S(=O)$_p$—$C_{1-4}$alkyl; $C_{3-6}$cycloalkyl; $C_{3-6}$cycloalkyl$C_{1-4}$alkyl; $C_{3-6}$cycloalkyl-C(=O)—; aryl; aryloxy; aryl$C_{1-4}$alkyl; aryl-C(=O)—$C_{1-4}$alkyl; aryl-C(=O)—; Het; Het$C_{1-4}$alkyl; Het-C(=O)—$C_{1-4}$alkyl; Het-C(=O)—; Het-O—.

Examples of a 6-membered aromatic heterocycle containing 1 or 2 N atoms in the definition of $R^3$ are pyridyl, pyrimidinyl, pyridazinyl, pyrazinyl.

When any variable occurs more than one time in any constituent (e.g. aryl, Het), each definition is independent.

The term Het or Het$^1$ is meant to include all the possible isomeric forms of the heterocycles, for instance, pyrrolyl comprises 1H-pyrrolyl and 2H-pyrrolyl.

The carbocycles or heterocycles covered by for instance the terms aryl, aryl$^1$, Het, Het$^1$ or $R^3$ may be attached to the remainder of the molecule of formula (I) through any ring carbon or heteroatom as appropriate, if not otherwise specified. Thus, for example, when the heterocycle is imidazolyl, it may be 1-imidazolyl, 2-imidazolyl, 4-imidazolyl and the like, or when the carbocycle is naphthalenyl, it may be 1-Naphthalenyl, 2-naphthalenyl and the like.

Lines drawn from substituents into ring systems indicate that the bond may be attached to any of the suitable ring atoms.

When X is defined as for instance —NR$^x$—C(=O)—, this means that the nitrogen of NR$^x$ is linked to the R$^2$ substituent and the carbon atom of C(=O) is linked to the nitrogen of the ring

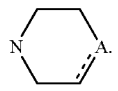

Thus the left part of the bivalent radical in the definition of X is linked to the R$^2$ substituent and the right part of the bivalent radical in the definition of X is linked to the ring moiety

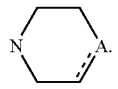

When Y is defined as for instance —NR$^x$—C(=O)—Z$^2$—, this means that the nitrogen of NR$^x$ is linked to the phenyl ring and the Z$^2$ is linked to the R$^1$ substituent. Thus the left part of the bivalent radical in the definition of Y is linked to the phenyl ring and the right part of the bivalent radical in the definition of Y is linked to R$^1$ substituent.

Some of the compounds of formula (I) may also exist in their tautomeric form. Such forms although not explicitly indicated in the above formula are intended to be included within the scope of the present invention.

Whenever used hereinbefore or hereinafter that substituents can be selected each independently out of a list of numerous definitions, such as for example for R$^4$ and R$^5$, all possible combinations are intended which are chemically possible.

For therapeutic use, salts of the compounds of formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable salts as mentioned hereinbefore or hereinafter are meant to comprise the therapeutically active non-toxic acid addition salt forms which the compounds of formula (I) are able to form. The latter can conveniently be obtained by treating the base form with such appropriate acids as inorganic acids, for example, hydrohalic acids, e.g. hydrochloric, hydrobromic and the like; sulfuric acid; nitric acid; phosphoric acid and the like; or organic acids, for example, acetic, propanoic, hydroxy-acetic, 2-hydroxypropanoic, 2-oxopropanoic, oxalic, malonic, succinic, maleic, fumaric, malic, tartaric, 2-hydroxy-1,2,3-propanetricarboxylic, methanesulfonic, ethanesulfonic, benzenesulfonic, 4-methylbenzenesulfonic, cyclohexanesulfonic, 2-hydroxybenzoic, 4-amino-2-hydroxybenzoic and the like acids. Conversely the salt form can be converted by treatment with alkali into the free base form.

The compounds of formula (I) containing acidic protons may be converted into their therapeutically active non-toxic metal or amine addition salt forms by treatment with appropriate organic and inorganic bases. The pharmaceutically acceptable salts as mentioned hereinbefore or hereinafter are meant to also comprise the therapeutically active non-toxic metal or amine addition salt forms (base addition salt forms) which the compounds of formula (I) are able to form. Appropriate base addition salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline, the benzathine, N-methyl-D-glucamine, 2-amino-2-(hydroxymethyl)-1,3-propanediol, hydrabamine salts, and salts with amino acids such as, for example, arginine, lysine and the like.

Conversely the salt form can be converted by treatment with acid into the free acid form.

The term salt also comprises the quaternary ammonium salts (quaternary amines) which the compounds of formula (I) are able to form by reaction between a basic nitrogen of a compound of formula (I) and an appropriate quaternizing agent, such as, for example, an optionally substituted $C_{1-6}$alkylhalide, arylhalide, $C_{1-6}$alkyl-carbonylhalide, arylcarbonylhalide, or aryl$C_{1-6}$alkylhalide, e.g. methyliodide or benzyliodide. Other reactants with good leaving groups may also be used, such as for example $C_{1-6}$alkyl trifluoromethanesulfonates, $C_{1-6}$alkyl methanesulfonates, and $C_{1-6}$alkyl p-toluenesulfonates. A quaternary amine has a positively charged nitrogen. Pharmaceutically acceptable counterions include chloro, bromo, iodo, trifluoroacetate, acetate, triflate, sulfate, sulfonate. The counterion of choice can be introduced using ion exchange resins.

The term solvate comprises the hydrates and solvent addition forms which the compounds of formula (I) are able to form, as well as the salts thereof. Examples of such forms are e.g. hydrates, alcoholates and the like.

The N-oxide forms of the present compounds are meant to comprise the compounds of formula (I) wherein one or several tertiary nitrogen atoms are oxidized to the so-called N-oxide.

It will be appreciated that some of the compounds of formula (I) and their N-oxides, salts, and solvates may contain one or more centers of chirality and exist as stereochemically isomeric forms.

The term "stereochemically isomeric forms" as used hereinbefore or hereinafter defines all the possible stereoisomeric forms which the compounds of formula (I), and their N-oxides, salts, or solvates may possess. Unless otherwise mentioned or indicated, the chemical designation of compounds denotes the mixture of all possible stereochemically isomeric forms, said mixtures containing all diastereomers and enantiomers of the basic molecular structure as well as each of the individual isomeric forms of formula (I) and their N-oxides, salts or solvates, substantially free, i.e. associated with less than 10%, preferably less than 5%, in particular less than 2% and most preferably less than 1% of the other isomers. Thus, when a compound of formula (I) is for instance specified as (E), this means that the compound is substantially free of the (Z) isomer.

In particular, stereogenic centers may have the R- or S-configuration; substituents on bivalent cyclic (partially) saturated radicals may have either the cis- or trans-configuration. Compounds encompassing double bonds can have an E (entgegen) or Z (zusammen)-stereochemistry at said double bond. The terms cis, trans, R, S, E and Z are well known to a person skilled in the art.

Stereochemically isomeric forms of the compounds of formula (I) are obviously intended to be embraced within the scope of this invention.

Following CAS-nomenclature conventions, when two stereogenic centers of known absolute configuration are present in a molecule, an R or S descriptor is assigned (based on Cahn-Ingold-Prelog sequence rule) to the lowest-numbered chiral center, the reference center. The configuration of the second stereogenic center is indicated using relative descriptors [R*,R*] or [R*,S*], where the first R* is always specified as the reference center and [R*,R*] indicates centers with the same chirality and [R*,S*] indicates centers of unlike chirality. For example, if the lowest-numbered chiral center in the molecule has an S configuration and the second center is R, the stereo descriptor would be specified as S—[R*,S*]. If "α" and "β" are used: the position of the highest priority substituent on the asymmetric carbon atom in the ring system having the lowest ring number, is arbitrarily always in the "α" position of the mean plane determined by the ring system. The position of the highest priority substituent on the other asymmetric carbon atom in the ring system relative to the position of the highest priority substituent on the reference atom is denominated "α", if it is on the same side of the mean plane determined by the ring system, or "β", if it is on the other side of the mean plane determined by the ring system.

The compounds of (I) may be synthesized in the form of racemic mixtures of enantiomers which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

Whenever used hereinafter, the term "compounds of formula (I)" or any subgroup thereof, is meant to also include their N-oxide forms, their salts, their stereochemically isomeric forms and their solvates. Of special interest are those compounds of formula (I) which are stereochemically pure.

A first embodiment of the present invention are those compounds of formula (I) having the following formula

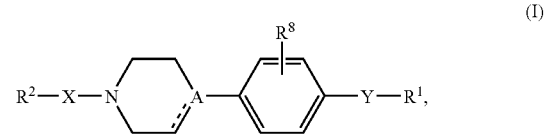

(I)

including any stereochemically isomeric form thereof, wherein

A represents CH or N;

the dotted line represents an optional bond in case A represents a carbon atom;

X represents —C(=O)—; —NR$^x$—C(=O)—; —Z$^1$—C(=O)—; —Z$^1$—NR$^x$—C(=O)—; —C(=O)—Z$^1$—; —NR$^x$—C(=O)—Z$^1$—; —S(=O)p-; —C(=S)—; —NR$^x$—C(=S)—; —Z$^1$—C(=S)—; —Z$^1$—NR$^x$—C(=S)—; —C(=S)—Z$^1$—; —NR$^x$—C(=S)—Z$^1$—;

Z$^1$ represents a bivalent radical selected from C$_{1-6}$alkanediyl, C$_{2-6}$alkenediyl or C$_{2-6}$alkynediyl; wherein each of said C$_{1-6}$alkanediyl, C$_{2-6}$alkenediyl or C$_{2-6}$alkynediyl may optionally be substituted with hydroxyl;

Y represents $-NR^x-C(=O)-Z^2-$; $-NR^x-C(=O)-Z^2-NR^y-$; $-NR^x-C(=O)-Z^2-NR^y-C(=O)-$; $-NR^x-C(=O)-Z^2-NR^y-C(=O)-O-$; $-NR^x-C(=O)-Z^2-O-$; $-NR^x-C(=O)-Z^2-O-C(=O)-$; $-NR^x-C(=O)-Z^2-C(=O)-$; $-NR^x-C(=O)-Z^2-C(=O)-O-$; $-NR^x-C(=O)-O-Z^2-C(=O)-$; $-NR^x-C(=O)-O-Z^2-C(=O)-O-$; $-NR^x-C(=O)-O-Z^2-O-C(=O)-$; $-NR^x-C(=O)-Z^2-C(=O)-NR^y-$; $-NR^x-C(=O)-Z^2-NR^y-C(=O)-NR^y-$; $-C(=O)-Z^2-$; $-C(=O)-Z^2-O-$; $-C(=O)-NR^x-Z^2-$; $-C(=O)-NR^x-Z^2-O-$; $-C(=O)-NR^x-Z^2-C(=O)-O-$; $-C(=O)-NR^x-Z^2-O-C(=O)-$; $-C(=O)-NR^x-O-Z^2-$; $-C(=O)-NR^x-Z^2-NR^y-$; $-C(=O)-NR^x-Z^2-NR^y-C(=O)-$; $-C(=O)-NR^x-Z^2-NR^y-C(=O)-O-$;

$Z^2$ represents a bivalent radical selected from $C_{1-6}$alkanediyl, $C_{2-6}$alkenediyl or $C_{2-6}$alkynediyl; wherein each of said $C_{1-6}$alkanediyl, $C_{2-6}$alkenediyl or $C_{2-6}$alkynediyl may optionally be substituted with $C_{1-4}$alkyloxy, $C_{1-4}$alkylthio, hydroxyl, cyano or aryl; and wherein two hydrogen atoms attached to the same carbon atom in the definition of $Z^2$ may optionally be replaced by $C_{1-6}$alkanediyl;

$R^x$ represents hydrogen or $C_{1-4}$alkyl;

$R^y$ represents hydrogen; $C_{1-4}$alkyl optionally substituted with $C_{3-6}$cycloalkyl or aryl or Het; $C_{2-4}$alkenyl; or $-S(=O)_p$-aryl;

$R^1$ represents $C_{1-12}$alkyl optionally substituted with cyano, $C_{1-4}$alkyloxy, $C_{1-4}$alkyl-oxy$C_{1-4}$alkyloxy, $C_{3-6}$cycloalkyl or aryl; $C_{2-6}$alkenyl; $C_{2-6}$alkynyl; $C_{3-6}$cycloalkyl; aryl$^1$; aryl$^1C_{1-6}$alkyl; Het$^1$; or Het$^1C_{1-6}$alkyl; provided that when Y represents $-NR^x-C(=O)-Z^2-$; $-NR^x-C(=O)-Z^2-NR^y-$; $-NR^x-C(=O)-Z^2-C(=O)-NR^y-$; $-C(=O)-Z^2-$; $-NR^x-C(=O)-Z^2-NR^y-C(=O)-NR^y-$; $-C(=O)-NR^x-Z^2-$; $-C(=O)-NR^x-O-Z^2-$; or $-C(=O)-NR^x-Z^2-NR^y-$; then $R^1$ may also represent hydrogen;

$R^2$ represents hydrogen, $C_{1-6}$alkyl, $C_{2-6}$alkenyl or $R^3$;

$R^3$ represents $C_{3-6}$cycloalkyl, phenyl, naphtalenyl, 2,3-dihydro-1,4-benzodioxinyl, 1,3-benzodioxolyl, wherein said $C_{3-6}$cycloalkyl, phenyl, naphtalenyl, 2,3-dihydro-1,4-benzodioxinyl, 1,3-benzodioxolyl may optionally be substituted with at least one substituent, in particular one, two, three, four or five substituents, each substituent independently selected from hydroxyl; carboxyl; halo; $C_{1-6}$alkyl optionally substituted with hydroxy; polyhalo$C_{1-6}$alkyl; $C_{1-6}$alkyloxy optionally substituted with $C_{1-4}$alkyloxy; $C_{1-6}$alkylthio; polyhalo-$C_{1-6}$alkyloxy; $C_{1-6}$alkyloxycarbonyl wherein $C_{1-6}$alkyl may optionally be substituted with aryl; cyano; $C_{1-6}$alkylcarbonyl; nitro; amino; mono- or di($C_{1-4}$alkyl)amino; $-S(=O)_p-C_{1-4}$alkyl; $R^5R^4N-C(=O)-$; $R^5R^4N-C_{1-6}$alkyl; $C_{3-6}$cycloalkyl; $C_{3-6}$cycloalkyl$C_{1-4}$alkyl; $C_{3-6}$cycloalkyl-C(=O)—; aryl; aryloxy; aryl$C_{1-4}$alkyl; aryl-C(=O)—; Het; Het$C_{1-4}$alkyl; Het-C(=O)—; Het-O—;

$R^4$ represents hydrogen; $C_{1-4}$alkyl optionally substituted with hydroxyl or $C_{1-4}$alkyloxy; $R^7R^6N-C_{1-4}$alkyl; $C_{1-4}$alkyloxy; Het; aryl; $R^7R^6N-C(=O)-C_{1-4}$alkyl;

$R^5$ represents hydrogen or $C_{1-4}$alkyl;

$R^6$ represents hydrogen; $C_{1-4}$alkyl; $C_{1-4}$alkylcarbonyl;

$R^7$ represents hydrogen or $C_{1-4}$alkyl; or $R^6$ and $R^7$ may be taken together with the nitrogen to which they are attached to form a saturated monocyclic 5, 6 or 7-membered heterocycle which may further contain one or more heteroatoms selected from O, S, $S(=O)_p$ or N; and which heterocycle may optionally be substituted with $C_{1-4}$alkyl;

aryl represents phenyl or phenyl substituted with at least one substituent, in particular one, two, three, four or five substituents, each substituent independently being selected from hydroxyl; carboxyl; halo; $C_{1-6}$alkyl optionally substituted with $C_{1-4}$alkyloxy, amino or mono- or di($C_{1-4}$alkyl)amino; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxycarbonyl; cyano; amino carbonyl; mono- or di($C_{1-4}$alkyl)aminocarbonyl; $C_{1-6}$alkylcarbonyl; nitro; amino; mono- or di($C_{1-4}$alkyl)amino; $-S(=O)_p-C_{1-4}$alkyl;

aryl$^1$ represents phenyl, naphthalenyl or fluorenyl; each of said phenyl, naphthalenyl or fluorenyl optionally substituted with at least one substituent, in particular one, two, three, four or five substituents, each substituent independently being selected from hydroxyl; oxo; carboxyl; halo; $C_{1-6}$alkyl optionally substituted with aryl-C(=O)—; hydroxy$C_{1-6}$alkyl optionally substituted with aryl or aryl-C(=O)—; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxy-carbonyl wherein $C_{1-6}$alkyl may optionally be substituted with aryl; cyano; aminocarbonyl; mono- or di($C_{1-4}$alkyl)aminocarbonyl; $C_{1-6}$alkylcarbonyl; nitro; amino; mono- or di($C_{1-4}$alkyl)amino; $C_{3-6}$cycloalkyl-NR$^x$—; aryl-NR$^x$—; Het-NR$^x$—; $C_{3-6}$cycloalkyl$C_{1-4}$alkyl-NR$^x$—; aryl$C_{1-4}$alkyl-NR$^x$—; Het$C_{1-4}$alkyl-NR$^x$—; $-S(=O)_p-C_{1-4}$alkyl; $C_{3-6}$cycloalkyl; $C_{3-6}$cycloalkyl$C_{1-4}$alkyl; $C_{3-6}$cycloalkyl-C(=O)—; aryl; aryloxy; aryl$C_{1-4}$alkyl; aryl-C(=O)—; Het; Het$C_{1-4}$alkyl; Het-C(=O)—; Het-O—;

Het represents a monocyclic non-aromatic or aromatic heterocycle containing at least one heteroatom selected from O, S, $S(=O)_p$ or N; or a bicyclic or tricyclic non-aromatic or aromatic heterocycle containing at least one heteroatom selected from O, S, $S(=O)_p$ or N; said monocyclic heterocycle or said bi- or tricyclic heterocycle optionally being substituted with at least one substituent, in particular one, two, three, four or five substituents, each substituent independently being selected from hydroxyl; oxo; carboxyl; halo; $C_{1-6}$alkyl optionally substituted with $C_{1-4}$alkyloxy, amino or mono- or di($C_{1-4}$alkyl)amino; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyl-oxycarbonyl; cyano; aminocarbonyl; mono- or di($C_{1-4}$alkyl)aminocarbonyl; $C_{1-6}$alkylcarbonyl; nitro; amino; mono- or di($C_{1-4}$alkyl)amino; $-S(=O)_p-C_{1-4}$alkyl;

Het$^1$ represents a monocyclic non-aromatic or aromatic heterocycle containing at least one heteroatom selected from O, S, $S(=O)_p$ or N; or a bicyclic or tricyclic non-aromatic or aromatic heterocycle containing at least one heteroatom selected from O, S, $S(=O)_p$ or N; said monocyclic heterocycle or said bi- or tricyclic heterocycle optionally being substituted with at least one substituent, in particular one, two, three, four or five substituents, each substituent independently being selected from hydroxyl; oxo; carboxyl; halo; $C_{1-6}$alkyl optionally substituted with aryl-C(=O)—; hydroxy$C_{1-6}$alkyl optionally substituted with aryl or aryl-C(=O)—; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxy-carbonyl wherein $C_{1-6}$alkyl may optionally be substituted with aryl; cyano; aminocarbonyl; mono- or di($C_{1-4}$alkyl)aminocarbonyl; $C_{1-6}$alkylcarbonyl; nitro; amino; mono- or di($C_{1-4}$alkyl)amino; $C_{3-6}$cycloalkyl-NR$^x$—; aryl-NR$^x$—; Het-NR$^x$—; $C_{3-6}$cycloalkyl$C_{1-4}$alkyl-NR$^x$—; aryl$C_{1-4}$alkyl-NR$^x$—; Het$C_{1-4}$alkyl-NR$^x$—; $-S(=O)_p-C_{1-4}$alkyl; $C_{3-6}$cycloalkyl;

$C_{3-6}$cycloalkyl$C_{1-4}$alkyl; $C_{3-6}$cycloalkyl-C(=O)—; aryl; aryloxy; aryl$C_{1-4}$alkyl; aryl-C(=O)—; Het; Het$C_{1-4}$alkyl; Het-C(=O)—; Het-O—;
p represents 1 or 2;
provided that

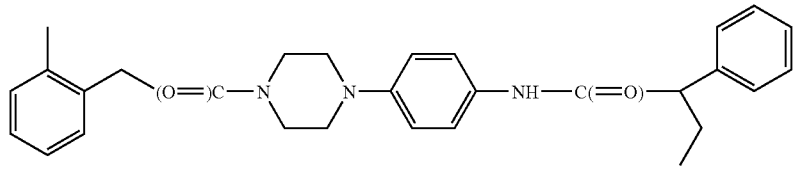

is excluded;
a N-oxide thereof, a pharmaceutically acceptable salt thereof or a solvate thereof.

A second embodiment of the present invention are those compounds of formula (I) or any subgroup thereof as mentioned hereinbefore as embodiment wherein X represents —C(=O)—C(=O)—; —O—C(=O)—; —NR$^x$—C(=O)—; —Z$^1$—C(=O)—; —Z$^1$—NR$^x$—C(=O)—; —C(=O)—Z$^1$—; —NR$^x$—C(=O)—Z$^1$—; —S(=O)p-; —NR$^x$—C(=S)—; in particular X represents —NR$^x$—C(=O)—; —Z$^1$—C(=O)—; —Z$^1$—NR$^x$—C(=O)—; —C(=O)—Z$^1$—; —NR$^x$—C(=O)—Z$^1$—; —S(=O)p-; —NR$^x$—C(=S)—; more in particular X represents —NR$^x$—C(=O)—; —Z$^1$—C(=O)—; —C(=O)—Z$^1$—; —Z$^1$—NR$^x$—C(=O)—; —NR$^x$—C(=S)— or —S(=O)p-; even more in particular X represents —NR$^x$—C(=O)— or —Z$^1$—NR$^x$—C(=O)—; even more in particular —NR$^x$—C(=O)—.

A third embodiment of the present invention are those compounds of formula (I) or any subgroup thereof as mentioned hereinbefore as embodiment wherein A represents N.

A fourth embodiment of the present invention are those compounds of formula (I) or any subgroup thereof as mentioned hereinbefore as embodiment wherein A represents CH, in particular wherein A represents CH and the dotted line does not represent a bond.

A fifth embodiment of the present invention are those compounds of formula (I) or any subgroup thereof as mentioned hereinbefore as embodiment wherein R$^1$ represents $C_{3-6}$cycloalkyl; adamantanyl; aryl$^1$; aryl$^1$$C_{1-6}$alkyl; Het$^1$; or Het$^1$$C_{1-6}$ alkyl; aryl$^1$; in particular aryl$^1$$C_{1-6}$alkyl; Het$^1$; or Het$^1$$C_{1-6}$ alkyl; more in particular aryl$^1$; aryl$^1$$C_{1-6}$alkyl; Het$^1$; or Het$^1$$C_{1-6}$alkyl, wherein said aryl$^1$ or Het$^1$ represent phenyl, naphthalenyl, morpholinyl, piperidinyl, piperazinyl, pyrrolidinyl, furanyl, imidazolyl, thienyl, pyridyl; each of said cycles representing aryl$^1$ or Het$^1$ being optionally substituted with one or two substituents; in particular with aryl, $C_{1-6}$alkyl, aryl$C_{1-4}$alkyl, hydroxyl, halo, polyhalo$C_{1-6}$alkyl, $C_{1-6}$alkyloxy, nitro, $C_{1-6}$alkyloxycarbonyl, —S(=O)$_2$—$C_{1-4}$ alkyl; more in particular with aryl, $C_{1-6}$alkyl, aryl$C_{1-4}$alkyl, halo, $C_{1-6}$alkyloxy, $C_{1-6}$alkyloxycarbonyl, —S(=O)$_2$—$C_{1-4}$ alkyl. More in particular R$^1$ represents aryl$^1$ wherein aryl$^1$ represents preferably optionally substituted phenyl. Even more in particular R$^1$ represents phenyl substituted with $C_{1-6}$alkyloxy, e.g. methoxy.

A sixth embodiment of the present invention are those compounds of formula (I) or any subgroup thereof as mentioned hereinbefore as embodiment wherein R$^1$ represents $C_{1-12}$alkyl optionally substituted with cyano, $C_{1-4}$alkyloxy, $C_{1-4}$alkyl-oxy$C_{1-4}$alkyloxy, $C_{3-6}$cycloalkyl or aryl; $C_{2-6}$alkenyl; $C_{2-6}$alkynyl; provided that when Y represents —NR$^x$—C(=O)—Z$^2$—; —NR$^x$—C(=O)—Z$^2$—NR$^y$; —NR$^x$—C(=O)—Z$^2$—C(=O)—NR$^y$—; —C(=O)—Z$^2$—; —NR$^x$—C(=O)—Z$^2$—NR$^y$—C(=O)—NR$^y$—; —C(=O)—NR$^x$—Z$^2$—; —C(=O)—NR$^x$—O—Z$^2$—; or —C(=O)—NR$^x$—Z$^2$—NR$^y$—; then R$^1$ may also represent hydrogen.

A seventh embodiment of the present invention are those compounds of formula (I) or any subgroup thereof as mentioned hereinbefore as embodiment wherein R$^2$ represents $C_{1-12}$alkyl; in particular $C_{1-6}$alkyl.

An eighth embodiment of the present invention are those compounds of formula (I) or any subgroup thereof as mentioned hereinbefore as embodiment wherein R$^2$ represents $C_{1-6}$alkyl or R$^3$; in particular wherein R$^2$ represents R$^3$ and said R$^3$ represents phenyl, naphthalenyl, 2,3-dihydrobenzofuranyl or 6-membered aromatic heterocycle containing 1 or 2 N atoms, each of said cycles, in particular phenyl, being optionally substituted with one to five substituents, said substituents being in particular halo, $C_{1-6}$alkyl optionally substituted with hydroxy, polyhalo$C_{1-6}$alkyl, $C_{1-6}$alkylthio, polyhalo$C_{1-6}$alkyloxy, carboxyl, hydroxyl, $C_{1-6}$alkylcarbonyl, $C_{1-6}$alkyloxy, $C_{1-6}$alkyloxycarbonyl, nitro, R$^5$R$^4$N—C(=O)—, R$^5$R$^4$N—$C_{1-6}$alkyl, Het$C_{1-4}$alkyl, Het-C(=O)—$C_{1-4}$alkyl, Het-C(=O)—; said substituents being more in particular halo, $C_{1-6}$alkyl optionally substituted with hydroxy, polyhalo$C_{1-6}$alkyl, polyhalo$C_{1-6}$alkyloxy, carboxyl, hydroxyl, $C_{1-6}$alkylcarbonyl, $C_{1-6}$alkyloxy, $C_{1-6}$alkylthio, $C_{1-6}$alkyloxycarbonyl, nitro, R$^5$R$^4$N—$C_{1-6}$alkyl, Het$C_{1-4}$alkyl; more in particular wherein R$^2$ represents phenyl substituted with one, two or three substituents, preferably three substituents, each substituent being selected from halo, e.g. chloro, or Het$C_{1-4}$alkyl, e.g. pyrrolidinylmethyl.

A ninth embodiment of the present invention are those compounds of formula (I) or any subgroup thereof as mentioned hereinbefore as embodiment wherein the compound of formula (I) is a compound of formula (I')

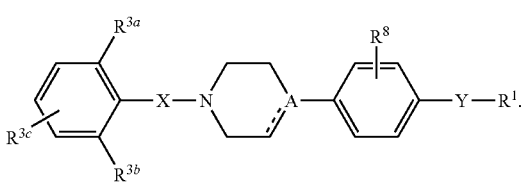

wherein R$^{3a}$ and R$^{3a}$ each independently represent hydrogen; hydroxyl; carboxyl; halo; $C_{1-6}$alkyl; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxycarbonyl; cyano; aminocarbonyl; mono- or di($C_{1-4}$alkyl)aminocarbonyl; $C_{1-6}$alkylcarbonyl; nitro; amino; mono- or di($C_{1-4}$alkyl)amino; —S(=O)$_p$—$C_{1-4}$alkyl; and wherein R$^{3c}$ represents hydrogen; hydroxyl; carboxyl; halo; $C_{1-6}$alkyl; polyhalo$C_{1-6}$ alkyl; $C_{1-6}$alkyloxy optionally substituted with $C_{1-4}$alkyloxy; $C_{1-6}$alkylthio; polyhalo-$C_{1-6}$alkyloxy; $C_{1-6}$alkyloxycarbonyl wherein C$_{1-6}$alkyl may optionally be substituted with aryl; cyano; C$_{1-6}$alkylcarbonyl; nitro; amino; mono- or di(C$_{1-4}$alkyl)amino; —S(=O)$_p$—C$_{1-4}$alkyl; R$^5$R$^4$N—C(=O)—; R$^5$R$^4$N—C$_{1-6}$alkyl; C$_{3-6}$cycloalkyl; aryl; aryloxy; arylC$_{1-4}$alkyl; aryl-C(=O)—C$_{1-4}$alkyl; aryl-C(=O)—; Het; HetC$_{1-4}$alkyl; Het-C(=O)—C$_{1-4}$alkyl; Het-C(=O)—; Het-O—.

A tenth embodiment of the present invention are those compounds of formula (I) or any subgroup thereof as mentioned hereinbefore as embodiment wherein the compound of formula (I) is a compound of formula (I″)

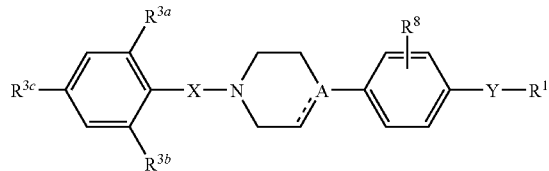

wherein R$^{3a}$ and R$^{3a}$ each independently represent hydrogen; hydroxyl; carboxyl; halo; C$_{1-6}$alkyl; polyhaloC$_{1-6}$alkyl; C$_{1-6}$alkyloxy optionally substituted with C$_{1-4}$alkyloxy; C$_{1-6}$alkylthio; polyhaloC$_{1-6}$alkyloxy; C$_{1-6}$alkyloxycarbonyl; cyano; aminocarbonyl; mono- or di(C$_{1-4}$alkyl)aminocarbonyl; C$_{1-6}$alkylcarbonyl; nitro; amino; mono- or di(C$_{1-4}$alkyl)amino; —S(=O)$_p$—C$_{1-4}$alkyl; and wherein R$^{3c}$ represents hydrogen; hydroxyl; carboxyl; halo; C$_{1-6}$alkyl; polyhaloC$_{1-6}$alkyl; C$_{1-6}$alkyloxy optionally substituted with C$_{1-4}$alkyloxy; C$_{1-6}$alkylthio; polyhalo-C$_{1-6}$alkyloxy; C$_{1-6}$alkyloxycarbonyl wherein C$_{1-6}$alkyl may optionally be substituted with aryl; cyano; C$_{1-6}$alkylcarbonyl; nitro; amino; mono- or di(C$_{1-4}$alkyl)amino; —S(=O)$_p$—C$_{1-4}$alkyl; R$^5$R$^4$N—C(=O)—; R$^5$R$^4$N—C$_{1-6}$alkyl; C$_{3-6}$cycloalkyl; aryl; aryloxy; aryl-C(=O)—C$_{1-4}$alkyl; arylC$_{1-4}$alkyl; aryl-C(=O)—; Het; HetC$_{1-4}$alkyl; Het-C(=O)—C$_{1-4}$alkyl; Het-C(=O)—; Het-O—.

A eleventh embodiment of the present invention are those compounds of formula (I) or any subgroup thereof as mentioned hereinbefore as embodiment wherein the compound of formula (I) is a compound of formula (I′) or (I″) and wherein R$^{3a}$ and R$^{3b}$ each independently represent halo, C$_{1-6}$alkyl or C$_{1-6}$alkyloxy; in particular halo or C$_{1-6}$alkyl; more in particular both R$^{3a}$ and R$^{3b}$ represent halo, more in particular both R$^{3a}$ and R$^{3b}$ represent chloro.

A twelfth embodiment of the present invention are those compounds of formula (I) or any subgroup thereof as mentioned hereinbefore as embodiment wherein the compound of formula (I) is a compound of formula (I′) or (I″) and wherein R$^{3c}$ represents amino; mono- or di(C$_{1-4}$alkyl)amino; R$^5$R$^4$N—C(=O)—; R$^5$R$^4$N—C$_{1-6}$alkyl; Het-C(=O)—; Het-C(=O)—C$_{1-4}$alkyl or HetC$_{1-4}$alkyl; or R$^{3c}$ represents hydrogen; more in particular wherein R$^{3c}$ represents amino; mono- or di(C$_{1-4}$alkyl)amino; R$^5$R$^4$N—C(=O)—; R$^5$R$^4$N—C$_{1-6}$alkyl; Het-C(=O)— or HetC$_{1-4}$alkyl; or R$^{3c}$ represents hydrogen; even more in particular wherein R$^{3c}$ represents HetC$_{1-4}$alkyl, e.g. pyrrolidinylmethyl.

A thirteenth embodiment of the present invention are those compounds of formula (I) or any subgroup thereof as mentioned hereinbefore as embodiment wherein p represents 2.

A fourteenth embodiment of the present invention are those compounds of formula (I) or any subgroup thereof as mentioned hereinbefore as embodiment wherein Y represents —NR$^x$—C(=O)—Z$^2$—; —NR$^x$—C(=O)—Z$^2$—NR$^y$; —NR$^x$—C(=O)—Z$^2$—NR$^y$—C(=O)—O—; —NR$^x$—C(=O)—Z$^2$—O—C(=O)—; —NR$^x$—C(=O)—Z$^2$—C(=O)—O—; —NR$^x$—C(=O)—O—Z$^2$—C(=O)—O—; —NR$^x$—C(=O)—O—Z$^2$—O—C(=O)—; —NR$^x$—C(=O)—Z$^2$—C(=O)—NR$^y$—; —NR$^x$—C(=O)—Z$^2$—NR$^y$—C(=O)—NR$^y$—; —C(=O)—NR$^x$—Z$^2$—; —C(=O)—NR$^x$—Z$^2$—O—; —C(=O)—NR$^x$—Z$^2$—C(=O)—O—; —C(=O)—NR$^x$—Z$^2$—O—C(=O)—; —C(=O)—NR$^x$—O—Z$^2$—; —C(=O)—NR$^x$—Z$^2$—NR$^y$—; —C(=O)—NR$^x$—Z$^2$—NR$^y$—C(=O)—; —C(=O)—NR$^x$—Z$^2$—NR$^y$—C(=O)—O—; or wherein Y represents NR$^x$—C(=O)—Z$^2$—; —NR$^x$—C(=O)—Z$^2$—NR$^y$; —NR$^x$—C(=O)—Z$^2$—NR$^y$—C(=O)—; —NR$^x$—C(=O)—Z$^2$—NR$^y$—C(=O)—O—; —NR$^x$—C(=O)—Z$^2$—O—; —NR$^x$—C(=O)—Z$^2$—C(=O)—O—; —NR$^x$—C(=O)—Z$^2$—C(=O)—NR$^y$—; —NR$^x$—C(=O)—Z$^2$—NR$^y$—C(=O)—NR$^y$—; —C(=O)—Z$^2$—; or wherein Y represents NR$^x$—C(=O)—Z$^2$— or —NR$^x$—C(=O)—Z$^2$—NR$^y$; or wherein Y represents —NR$^x$—C(=O)—Z$^2$—NR$^y$—C(=O)—O— or —NR$^x$—C(=O)—Z$^2$—C(=O)—O—. More in particular Y represents —NR$^x$—C(=O)—Z$^2$—.

A fifteenth embodiment of the present invention are those compounds of formula (I) or any subgroup thereof as mentioned hereinbefore as embodiment wherein Y represents NR$^x$—C(=O)—Z$^2$—; —NR$^x$—C(=O)—Z$^2$—NR$^y$—; —NR$^x$—C(=O)—Z$^2$—NR$^y$—C(=O)—; —NR$^x$—C(=O)—Z$^2$—NR$^y$—C(=O)—O—; —NR$^x$—C(=O)—Z$^2$—O—; —NR$^x$—C(=O)—Z$^2$—O—C(=O)—; —NR$^x$—C(=O)—Z$^2$—C(=O)—O—; —NR$^x$—C(=O)—Z$^2$—C(=O)—NR$^y$—; —NR$^x$—C(=O)—Z$^2$—NR$^y$—C(=O)—NR$^y$—; —C(=O)—Z$^2$—; —C(=O)—NR$^x$—Z$^2$—; —C(=O)—NR$^x$—Z$^2$—O—.

A sixteenth embodiment of the present invention are those compounds of formula (I) or any subgroup thereof as mentioned hereinbefore as embodiment wherein Z$^2$ represents C$_{1-6}$alkanediyl or C$_{2-6}$alkenediyl; in particular C$_{1-6}$alkanediyl; more in particular methylene.

A seventeenth embodiment of the present invention are those compounds of formula (I) or any subgroup thereof as mentioned hereinbefore as embodiment wherein Z$^1$ represents C$_{1-6}$alkanediyl, optionally substituted with hydroxyl or amino, or wherein two hydrogen atoms attached to the same carbon atom in C$_{1-6}$alkanediyl may optionally be replaced by C$_{1-6}$alkanediyl; in particular wherein Z$^1$ represents C$_{1-6}$alkanediyl.

An eighteenth embodiment of the present invention are those compounds of formula (I) or any subgroup thereof as mentioned hereinbefore as embodiment wherein R$^x$ represents hydrogen.

A nineteenth embodiment of the present invention are those compounds of formula (I) or any subgroup thereof as mentioned hereinbefore as embodiment wherein R$^y$ represents hydrogen or C$_{1-4}$alkyl or C$_{2-4}$alkenyl or —S(=O)$_p$-aryl.

A twentieth embodiment of the present invention are those compounds of formula (I) or any subgroup thereof as mentioned hereinbefore as embodiment wherein R$^8$ represents hydrogen.

A twenty first embodiment of the present invention are those compounds of formula (I) or any subgroup thereof as mentioned hereinbefore as embodiment wherein R$^8$ represents halo, C$_{1-4}$alkyl or C$_{1-4}$alkyl substituted with hydroxyl.

A twenty second embodiment of the present invention are those compounds of formula (I) or any subgroup thereof as mentioned hereinbefore as embodiment wherein aryl represents phenyl or phenyl substituted with one or two substituents, preferably each substituent independently selected from halo, $C_{1-6}$alkyl, polyhalo$C_{1-6}$alkyl, $C_{1-6}$alkyloxy, $C_{1-6}$alkyloxycarbonyl or nitro.

A twenty third embodiment of the present invention are those compounds of formula (I) or any subgroup thereof as mentioned hereinbefore as embodiment wherein Het¹ represents a monocyclic non-aromatic or aromatic heterocycle or a bicyclic non-aromatic heterocycle, each of said cycles may optionally be substituted. In particular Het¹ represents morpholinyl, pyrrolidinyl, piperazinyl, homopiperazinyl, piperidinyl, furanyl, imidazolyl, thienyl, pyridyl, 1,3-benzodioxolyl, tetrahydropyranyl, each of said heterocycles optionally being substituted with one or two substituents, preferably each substituent independently being selected from halo, $C_{1-6}$alkyl, $C_{1-6}$alkyloxycarbonyl, —S(=O)$_p$—$C_{1-4}$alkyl, aryl, aryl$C_{1-4}$alkyl, polyhalo$C_{1-6}$alkyl, $C_{1-6}$alkyloxy, nitro; more preferably each substituent independently being selected from halo, $C_{1-6}$alkyl, $C_{1-6}$alkyloxycarbonyl, —S(=O)$_p$—$C_{1-4}$alkyl, aryl, aryl$C_{1-4}$alkyl.

A twenty fourth embodiment of the present invention are those compounds of formula (I) or any subgroup thereof as mentioned hereinbefore as embodiment wherein aryl¹ represents phenyl, naphthalenyl or phenyl substituted with one or two substituents, preferably each substituent independently being selected from hydroxyl, halo, $C_{1-6}$alkyl, $C_{1-6}$alkyloxy, $C_{1-6}$alkyloxycarbonyl or Het.

A twenty fifth embodiment of the present invention are those compounds of formula (I) or any subgroup thereof as mentioned hereinbefore as embodiment wherein Het is a monocyclic non-aromatic or aromatic heterocycle, each of said heterocycles may optionally be substituted. In particular, Het is piperidinyl, pyrrolidinyl, piperazinyl, pyridyl, morpholinyl, each of said heterocycles optionally being substituted with one substituent, preferably the substituent is selected from $C_{1-6}$alkyl, $C_{1-6}$alkyl substituted with $C_{1-4}$alkyloxy, —S(=O)$_p$—$C_{1-4}$alkyl, $C_{1-6}$alkylcarbonyl.

A twenty sixth embodiment of the present invention are those compounds of formula (I) or any subgroup thereof as mentioned hereinbefore as embodiment wherein one or more, preferably all, of the following restrictions apply:
a) X represents —NR$^x$—C(=O)—; —Z¹—C(=O)—; —Z¹—NR$^x$—C(=O)—; —C(=O)—Z¹—; —S(=O)p-; —NR$^x$—C(=S)—;
b) R² represents $C_{1-6}$alkyl or R³, with R³ representing phenyl, naphthalenyl or 1,3-benzodioxolyl, each of said cycles being optionally substituted with one to five substituents, said substituents being in particular halo, $C_{1-6}$alkyl optionally substituted with hydroxy, polyhalo$C_{1-6}$alkyl, polyhalo$C_{1-6}$alkyloxy, carboxyl, hydroxyl, $C_{1-6}$alkylcarbonyl, $C_{1-6}$alkyloxy, $C_{1-6}$alkylthio, $C_{1-6}$alkyloxycarbonyl, nitro, R⁵R⁴N—$C_{1-6}$alkyl, Het$C_{1-4}$alkyl.
c) A represents N;
d) A represents CH;
e) Y represents NR$^x$—C(=O)—Z²—; —NR$^x$—C(=O)—Z²—NR$^y$—; —NR$^x$—C(=O)—Z²—NR$^y$—C(=O)—; —NR$^x$—C(=O)—Z²—NR$^y$—C(=O)—O—; —NR$^x$—C(=O)—Z²—O—; —NR$^x$—C(=O)—Z²—C(=O)—O—; —NR$^x$—C(=O)—Z²—C(=O)—NR$^y$—; —NR$^x$—C(=O)—Z²—NR$^y$—C(=O)—NR$^y$—; —C(=O)—Z²—;
f) Z¹ represents $C_{1-6}$alkanediyl optionally substituted with hydroxy;
g) R$^y$ represents hydrogen; $C_{1-4}$alkyl optionally substituted with $C_{3-6}$cycloalkyl or aryl; $C_{2-4}$alkenyl; or —S(=O)$_p$-aryl;

h) aryl¹ represents phenyl, said phenyl optionally substituted with $C_{1-6}$alkyl, halo, polyhalo$C_{1-6}$alkyl, $C_{1-6}$alkyloxy, nitro, $C_{1-6}$alkyloxycarbonyl;
i) Het¹ represents a 5- or 6-membered non-aromatic or aromatic heterocycle, such as for example morpholinyl, piperidinyl, piperazinyl, pyrrolidinyl, furanyl, imidazolyl, thienyl, pyridyl, said 5- or 6-membered heterocycle optionally substituted with aryl, $C_{1-6}$alkyl, aryl$C_{1-6}$alkyl, halo, polyhalo$C_{1-6}$alkyl, $C_{1-6}$alkyloxycarbonyl, —S(=O)$_2$—$C_{1-4}$alkyl.

A twenty seventh embodiment of the present invention are those compounds of formula (I) having the following formula

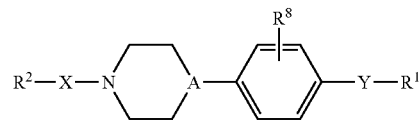

wherein one or more, preferably all, of the following restrictions apply:
a) A represents CH or N;
b) X represents —O—C(=O)—; —C(=O)—C(=O)—; —NR$^x$—C(=O)—; —Z'—C(=O)—; —Z¹—NR$^x$—C(=O)—; —C(=O)—Z¹—; —S(=O)p—; —NR$^x$—C(=S)—;
c) Z¹ represents $C_{1-6}$alkanediyl; wherein said $C_{1-6}$alkanediyl may optionally be substituted with hydroxyl or amino; and wherein two hydrogen atoms attached to the same carbon atom in $C_{1-6}$alkanediyl may optionally be replaced by $C_{1-6}$alkanediyl;
d) Y represents NR$^x$—C(=O)—Z²—; —NR$^x$—C(=O)—Z²—NR$^y$—; —NR$^x$—C(=O)—Z²—NR$^y$—C(=O)—; —NR$^x$—C(=O)—Z²—NR$^y$—C(=O)—O—; —NR$^x$—C(=O)—Z²—O—; —NR$^x$—C(=O)—Z²—O—C(=O)—; —NR$^x$—C(=O)—Z²—C(=O)—O—; —NR$^x$—C(=O)—Z²—C(=O)—NR$^y$—; —NR$^x$—C(=O)—Z²—NR$^y$—C(=O)—NR$^y$—; —C(=O)—Z²—; —C(=O)—NR$^x$—Z²—; —C(=O)—NR$^x$—Z²—O—;
e) Z² represents a bivalent radical selected from $C_{1-6}$alkanediyl, $C_{2-6}$alkenediyl or $C_{2-6}$alkynediyl; wherein each of said $C_{1-6}$alkanediyl, $C_{2-6}$alkenediyl or $C_{2-6}$alkynediyl may optionally be substituted with $C_{1-4}$alkyloxy, $C_{1-4}$alkylthio, hydroxyl, cyano or aryl; and wherein two hydrogen atoms attached to the same carbon atom in the definition of Z² may optionally be replaced by $C_{1-6}$alkanediyl;
f) R$^x$ represents hydrogen or $C_{1-4}$alkyl;
g) R$^y$ represents hydrogen; $C_{1-4}$alkyl; $C_{2-4}$alkenyl; or —S(=O)$_p$-aryl;
h) R¹ represents $C_{1-12}$alkyl optionally substituted with cyano, $C_{1-4}$alkyloxy, $C_{1-4}$alkyl-oxy$C_{1-4}$alkyloxy, $C_{3-6}$cycloalkyl or aryl; $C_{2-6}$alkenyl; $C_{2-6}$alkynyl; $C_{3-6}$cycloalkyl; adamantanyl; aryl¹; Het¹; or Het¹$C_{1-6}$alkyl; provided that when Y represents —NR$^x$—C(=O)—Z²—; —NR$^x$—C(=O)—Z²—NR$^y$; —NR$^x$—C(=O)—Z²—C(=O)—NR$^y$—; —C(=O)—Z²—; —NR$^x$—C(=O)—Z²—NR$^y$—C(=O)—NR$^y$—; —C(=O)—NR$^x$—Z²—; —C(=O)—NR$^x$—O—Z²—; or —C(=O)—NR$^x$—Z²—NR$^y$—; then R¹ may also represent hydrogen;
i) R² represents $C_{1-12}$alkyl or R³;
j) R³ represents phenyl, naphtalenyl, 2,3-dihydrobenzofuranyl or a 6-membered aromatic heterocycle containing 1 or 2 N atoms, wherein said phenyl, naphtalenyl, 2,3-dihydrobenzofuranyl or 6-membered aromatic heterocycle containing 1 or 2 N atoms may optionally be substituted with at least one substituent, in particular one, two, three, four or five substituents, each substituent independently selected from hydroxyl; carboxyl; halo; $C_{1-6}$alkyl optionally substituted with hydroxy; polyhalo$C_{1-6}$alkyl; $C_{1-6}$alkyloxy; $C_{1-6}$alkylthio; polyhalo-$C_{1-6}$alkyloxy; $C_{1-6}$alkyloxycarbonyl; $C_{1-6}$alkylcarbonyl; nitro; $R^5R^4N$—C(=O)—; $R^5R^4N$—$C_{1-6}$alkyl; Het$C_{1-4}$alkyl; Het-C(=O)—$C_{1-4}$alkyl; Het-C(=O)—;

k) $R^4$ represents hydrogen; $C_{1-4}$alkyl optionally substituted with hydroxyl or $C_{1-4}$alkyloxy; $R^7R^6N$—$C_{1-4}$alkyl; Het-$C_{1-4}$alkyl; $R^7R^6N$—C(=O)—$C_{1-4}$alkyl;

l) $R^5$ represents hydrogen or $C_{1-4}$alkyl;

m) $R^6$ represents $C_{1-4}$alkyl or $C_{1-4}$alkylcarbonyl;

n) $R^7$ represents hydrogen or $C_{1-4}$alkyl; or o) $R^6$ and $R^7$ may be taken together with the nitrogen to which they are attached to form a saturated monocyclic 5, 6 or 7-membered heterocycle which may further contain one or more heteroatoms each independently selected from O or N;

p) $R^8$ represents hydrogen, halo, $C_{1-4}$alkyl substituted with hydroxyl;

q) aryl represents phenyl or phenyl substituted with at least one substituent, in particular one or two substituents, each substituent independently being selected from halo; $C_{1-6}$alkyl; polyhalo$C_{1-6}$alkyl; $C_{1-6}$alkyloxy; nitro;

r) aryl$^1$ represents phenyl or naphthalenyl; wherein phenyl may optionally be substituted with one or two substituents, each substituent independently being selected from hydroxyl; halo; $C_{1-6}$alkyl; $C_{1-6}$alkyloxy; $C_{1-6}$alkyloxy-carbonyl or Het;

s) Het represents a monocyclic non-aromatic or aromatic heterocycle containing at least one heteroatom each independently selected from O, S, S(=O)$_p$ or N, in particular N; said monocyclic heterocycle optionally being substituted with one substituent, said substituent being selected from $C_{1-6}$alkyl optionally substituted with $C_{1-4}$alkyloxy; $C_{1-6}$alkylcarbonyl or —S(=O)$_p$—$C_{1-4}$alkyl;

t) Het$^1$ represents a monocyclic non-aromatic or aromatic heterocycle containing at least one heteroatom each independently selected from O, S, S(=O)$_p$ or N, in particular N, O or S; or a bicyclic non-aromatic heterocycle containing at least one heteroatom each independently selected from O, S, S(=O)$_p$ or N, in particular O; said monocyclic heterocycle or said bicyclic heterocycle optionally being substituted with one or two substituents, each substituent independently being selected from halo; $C_{1-6}$alkyl; $C_{1-6}$alkyloxy-carbonyl; —S(=O)$_p$—$C_{1-4}$alkyl; aryl; or aryl$C_{1-4}$alkyl;

u) p represents 2.

Preferred compounds of formula (I) are selected from

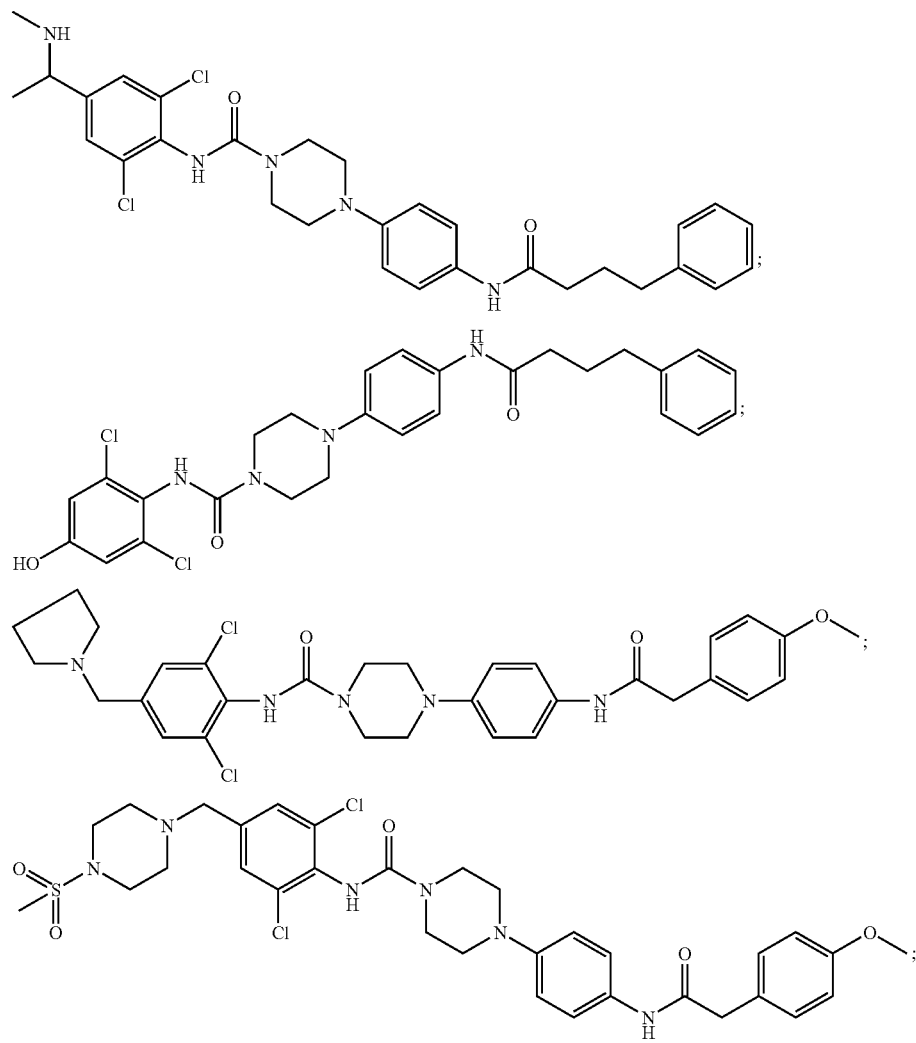

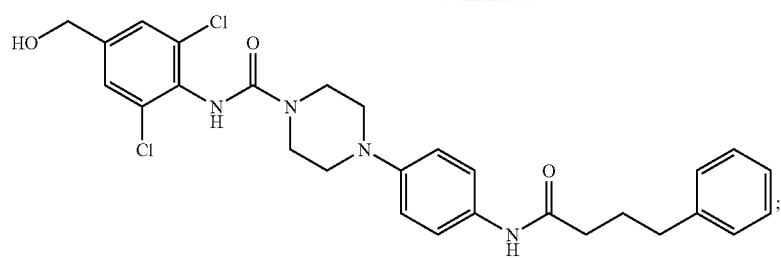
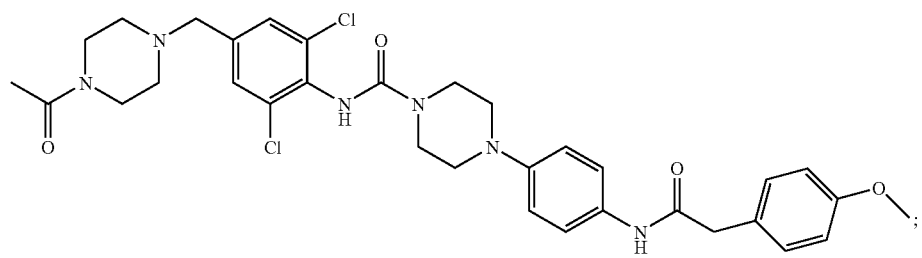
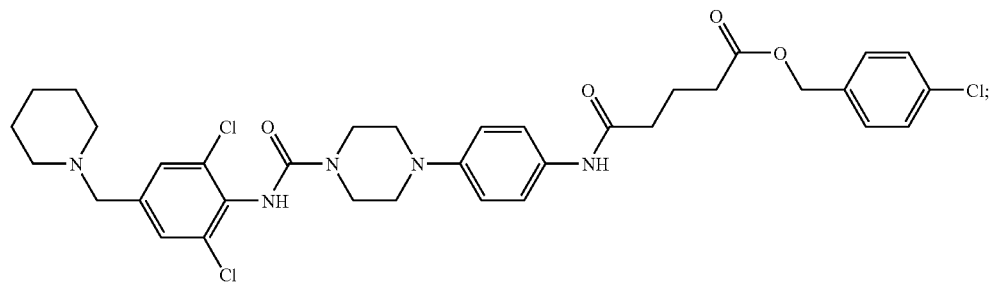
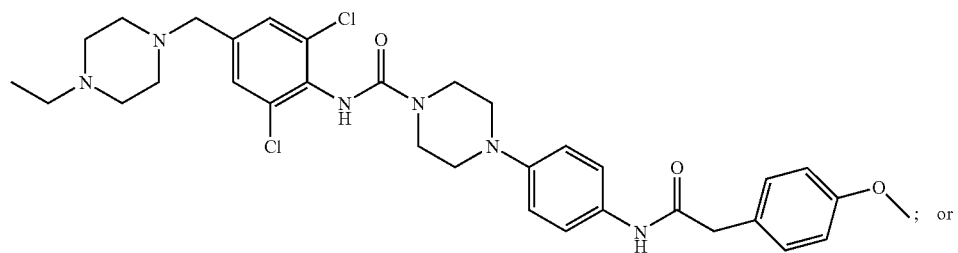
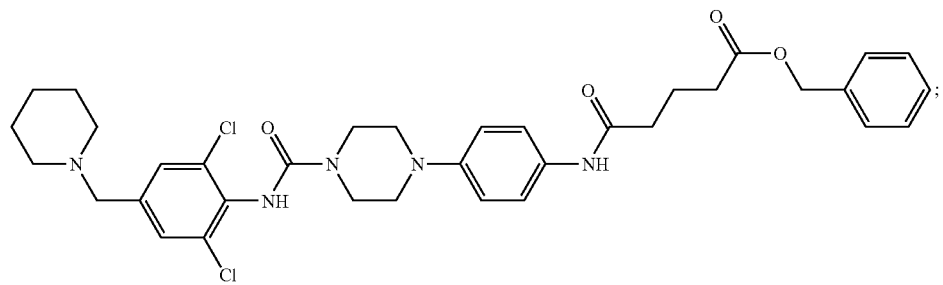

a N-oxide thereof, a pharmaceutically acceptable salt thereof or a solvate thereof
Preferably, preferred compounds of formula (I) are selected from
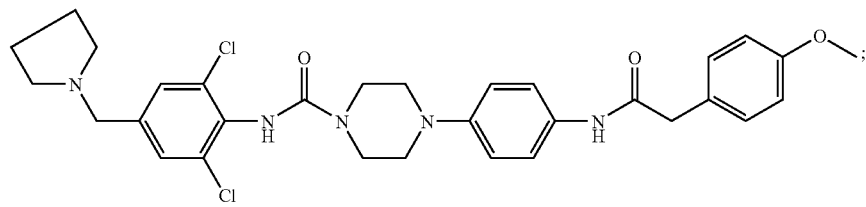
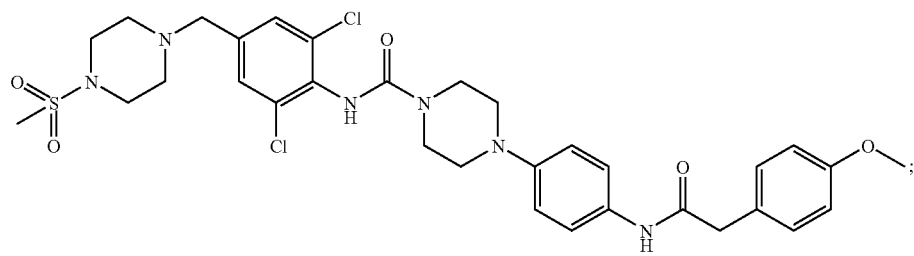
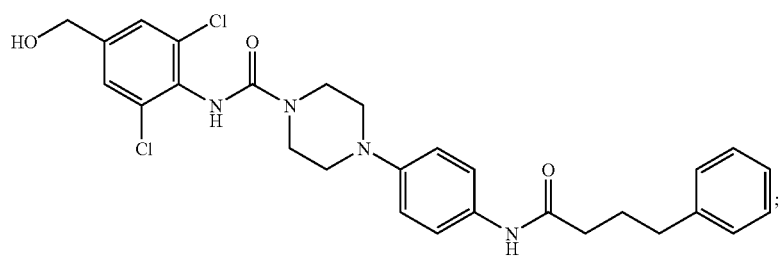
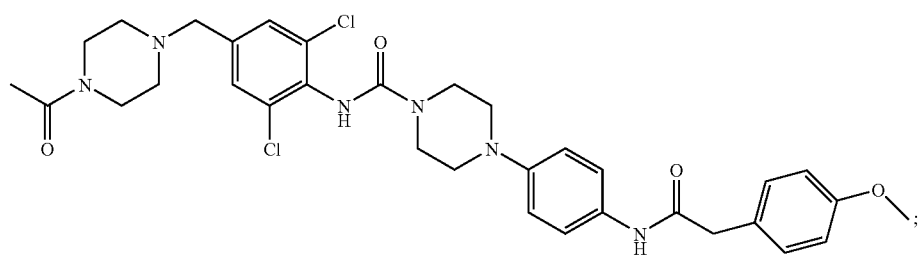
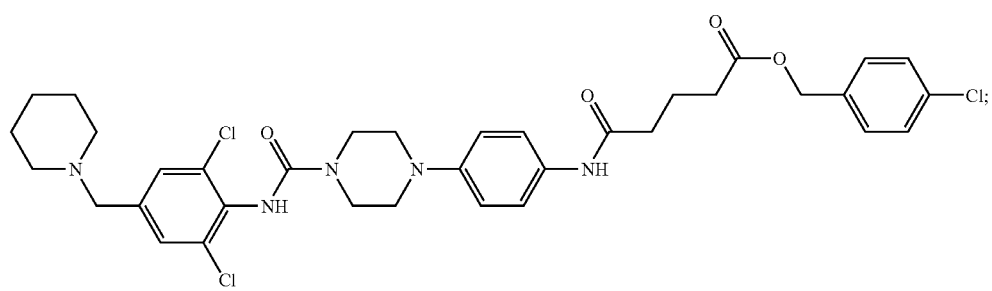
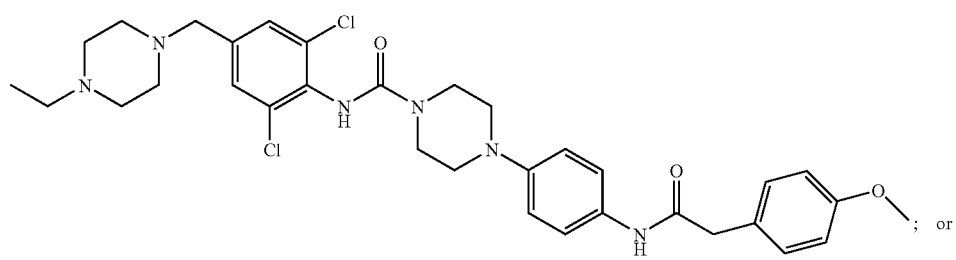

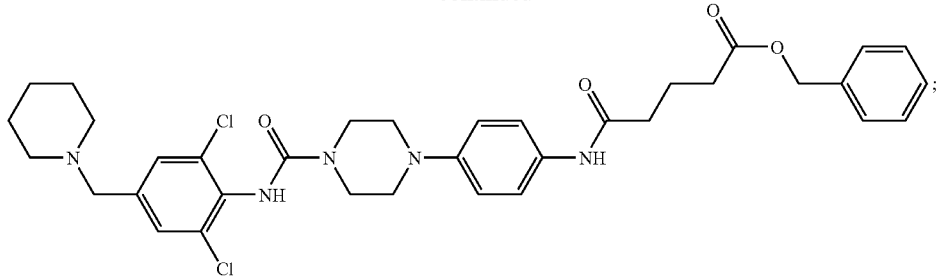

a N-oxide thereof, a pharmaceutically acceptable salt thereof or a solvate thereof The compounds of formula (I) can be prepared according to the following procedures. If not indicated, the skilled man will recognize in the below procedures when $R^2$ represents hydrogen, $C_{1-12}$alkyl, $C_{2-6}$alkenyl, or $R^2$ represents $R^3$, or $R^2$ represents hydrogen, $C_{1-12}$alkyl, $C_{2-6}$alkenyl or $R^3$.

In general, compounds of formula (I) wherein Y comprises $NR^x$—C(=O)—$Z^2$—, said compounds being represented by formula (I-a), wherein $Y^1$ represents the remainder of the linker Y including a direct bond, can be prepared by reacting an intermediate of formula (II) with an intermediate of formula (III) in the presence of a suitable dehydrating (coupling) agent, such as for example N-(ethylcarbonimidoyl)-N,N-dimethyl-1,3-propanediamine monohydrochloride (EDCI), dicyclohexylcarbodiimide (DCC), carbonyl diimidazole (CDI), 1-[bis(di-methylamino)methylene]-1H-benzotriazoliumhexafluorophosphate(1-)3-Oxide (HBTU), 1-[bis(dimethyl-amino)methylene]-5-chloro-1H-benzotriazolium-hexafluorophosphate(1-)3-Oxide (HCTU), O-benzotriazolyl tetramethylisouronium tetrafluoroborate (TBTU) or diethyl cyanophosphonate (DECP), optionally combined with hydroxy benzotriazole or chloro hydroxybenzotriazole, in the presence of a suitable solvent, such as for example N,N-dimethylformamide, dichloromethane, acetonitrile or tetrahydrofuran, and optionally in the presence of a suitable base, such as for example N,N-diisopropyl-ethanamine or N,N-diethyl-ethanamine. This reaction of an intermediate of formula (II) with an intermediate of formula (III) can also be performed in the presence of a suitable activating agent, such as for example Cl—C(=O)—C(=O)—Cl, a suitable base, such as for example N,N-diethyl-ethanamine, and a suitable solvent, such as for example N,N-dimethylformamide.

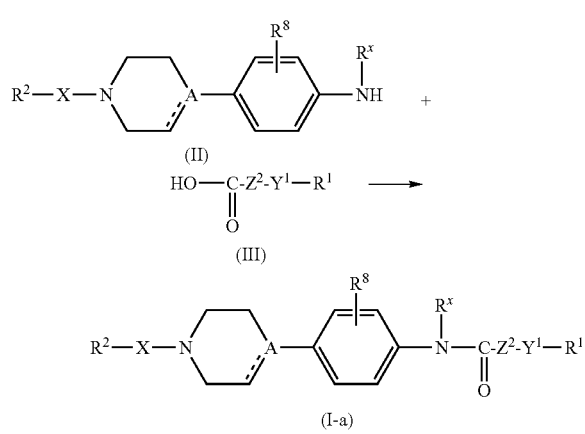

The above reaction can be performed as a fast synthesis reaction thereby using appropriate reagents well-known for fast synthesis, such as for example dicyclohexylcarbodiimide (DCC) linked to an appropriate carrier, e.g. polystyrene. Also for the purification of the reaction mixture, appropriate fast-synthesis reagents can be used, such as for example 1-ethenyl-4-(isocyanatomethyl)-benzene polymer with ethenylbenzene.

Compounds of formula (I-a) can also be prepared by reacting an intermediate of formula (II) with an intermediate of formula (IV) wherein $W_1$ represents a suitable leaving group, such as for example halo, e.g. chloro and the like, in the presence of a suitable base, such as for example sodium hydride, sodium bicarbonate, N,N-diisopropyl-ethanamine or N,N-diethyl-ethanamine, and a suitable solvent, such as for example N,N-dimethylformamide, dichloromethane, acetonitrile or tetrahydrofuran

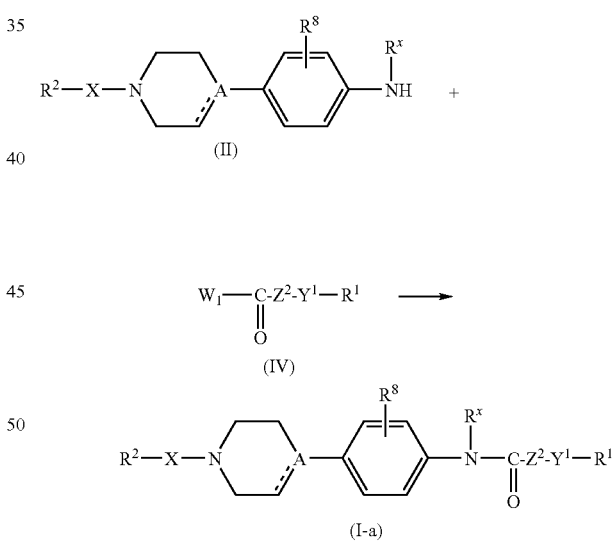

Compounds of formula (I) wherein Y represents —$NR^x$—C(=O)—$Z^2$—$NR^y$—, said compounds being represented by formula (I-a-1), can be prepared by reacting an intermediate of formula (V) wherein $W_2$ represents a suitable leaving group, such as for example halo, e.g. chloro, bromo and the like, with an intermediate of formula (VI) in the presence of a suitable base, such as for example $Na_2CO_3$, $K_2CO_3$, and a suitable solvent, such as for example N,N-dimethylformamide.

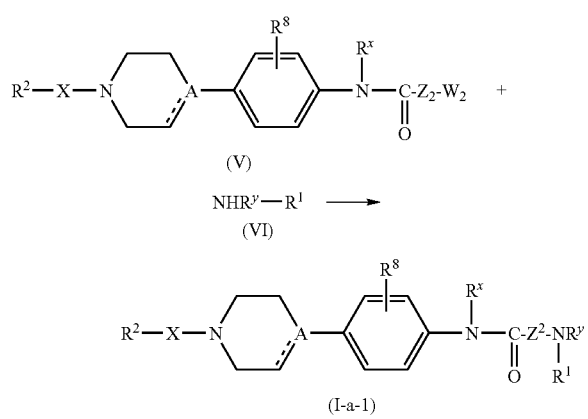

(V)

NHR$^y$—R$^1$ →
(VI)

(I-a-1)

Compounds of formula (I) wherein Y represents —NR$^x$—C(=O)—Z$^2$— and R$^1$ represents an optionally substituted monocyclic saturated heterocycle linked with a nitrogen atom to Z$^2$, said R$^1$ being represented by R$^{1a}$, and said compounds being represented by formula (I-a-2), can be prepared by reacting an intermediate of formula (V) with an intermediate of formula (VII) in the presence of a suitable base, such as for example N,N-diisopropyl-ethanamine or N,N-diethyl-ethanamine, and a suitable solvent, such as for example acetonitrile or tetrahydrofuran.

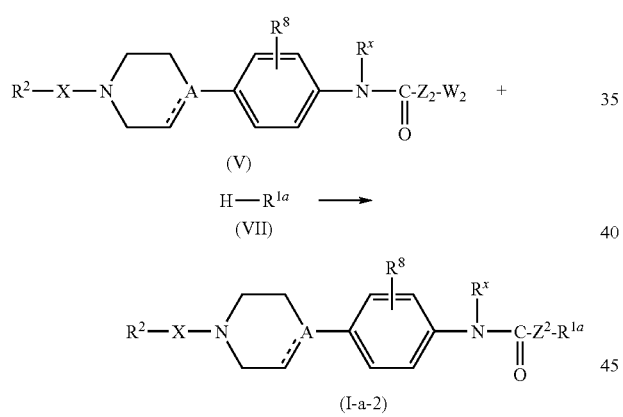

(V)

H—R$^{1a}$ →
(VII)

(I-a-2)

Compounds of formula (I) wherein R$^1$ is substituted with NH$_2$, said R$^1$ being represented by R$^{1'}$—NH$_2$, and said compounds being represented by formula (I-b), can be prepared by deprotecting an intermediate of formula (VIII) wherein P represents a suitable protecting group, such as for example tertiair butyloxycarbonyl, in the presence of a suitable acid, such as for example trifluoroacteic acid, and in the presence of a suitable solvent, such as for example dichloromethane. The intermediate of formula (VIII) can be prepared according to one of the above reactions.

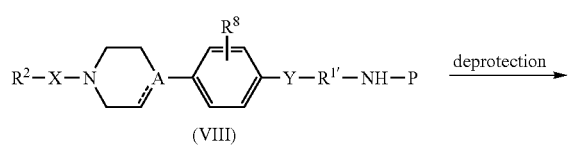

(VIII)  deprotection →

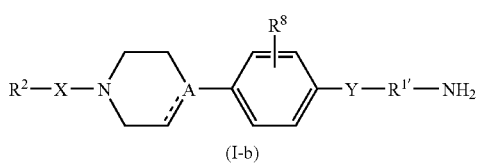

(I-b)

Compounds of formula (I) wherein X represents —X$_1$—NH—C(=O)— with X$_1$ representing a direct bond or Z$^1$, said compounds being represented by formula (I-c), can be prepared by reacting an intermediate of formula (IX) with an intermediate of formula (X) in the presence of a suitable solvent, such as for example acetonitrile, N,N-dimethylformamide or dichloromethane, optionally in the presence of a suitable base, such as for example N,N-diethyl-ethanamine. Intermediates of formula (IX) are commercially available or can be prepared by reacting R$^2$—X$_1$—NH$_2$ with phosgene in the presence of a suitable solvent, such as for example toluene or acetonitrile, optionally in the presence of a suitable acid, such as for example hydrochloric acid.

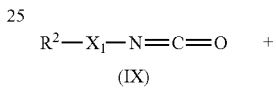

(IX)

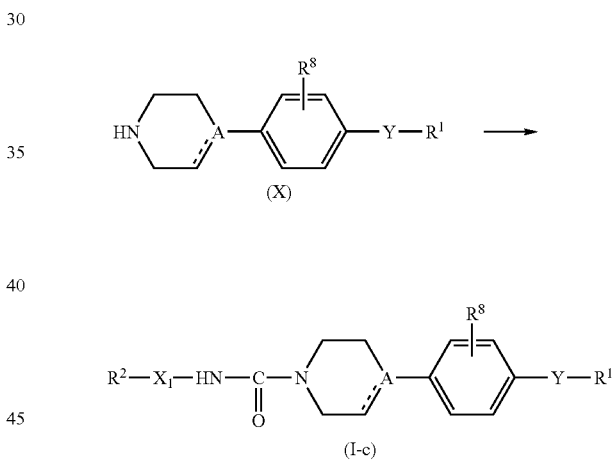

The above reaction can also be performed as a fast synthesis reaction thereby using appropriate reagents well-known for fast synthesis, such as for example for the purification of the reaction mixture 1-ethenyl-4-(isocyanatomethyl)-benzene polymer with ethenylbenzene and tris-2-aminoethylamine linked to polystyrene can be used.

Compounds of formula (I-c) wherein X$_1$ represents a direct bond, said compounds being represented by formula (I-c-1), can be prepared by reacting an intermediate of formula (XXI) with Cl$_3$COC(=O)—Cl or C(=O)Cl$_2$ optionally in the presence of HCl in diethylether, and in the presence of a suitable solvent, such as for example acetonitrile or toluene, followed by reaction with an intermediate of formula (X) in the presence of a suitable solvent, such as for example acetonitrile, N,N-dimethylformamide or dichloromethane, optionally in the presence of a suitable base, such as for example N,N-diethyl-ethanamine or N,N-diisopropyl-ethanamine.

$R^2$—$NH_2$
(XXI)

+

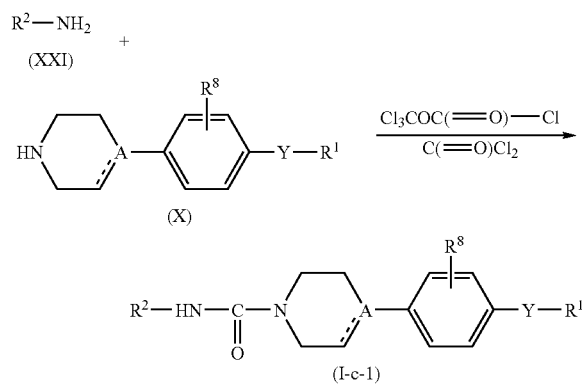

Compounds of formula (I) wherein X represents —$X_1$—C(=O)— with $X_1$ representing a direct bond or $Z^1$, said compounds being represented by formula (I-d), can be prepared by reacting an intermediate of formula (XI) with an intermediate of formula (X) in the presence of a suitable dehydrating (coupling) agent, such as for example N'-(ethyl-carbonimidoyl)-N,N-dimethyl-1,3-propanediamine monohydrochloride (EDCI), dicyclohexylcarbodiimide (DCC), carbonyl diimidazole (CDI), 1-[bis(di-methylamino)methylene]-1H-benzotriazoliumhexafluorophosphate(1-)3-oxide (HBTU), 1-[bis(dimethyl-amino)methylene]-5-chloro-1H-benzotriazolium-hexafluorophosphate(1-)3-oxide (HCTU), O-benzotriazolyl tetramethylisouronium tetrafluoroborate (TBTU) or diethyl cyanophosphonate (DECP), optionally combined with hydroxy benzotriazole or chloro hydroxybenzotriazole, in the presence of a suitable solvent, such as for example N,N-dimethylformamide, dichloromethane, acetonitrile or tetrahydrofuran, and optionally in the presence of a suitable base, such as for example N,N-diisopropyl-ethanamine or N,N-diethyl-ethanamine. This reaction of an intermediate of formula (XI) with an intermediate of formula (X) can also be performed in the presence of a suitable activating agent, such as for example Cl—C(=O)—C(=O)—Cl, a suitable base, such as for example N,N-diethyl-ethanamine, and a suitable solvent, such as for example N,N-dimethylformamide.

$R^2$—$X_1$—COOH + 
(XI)

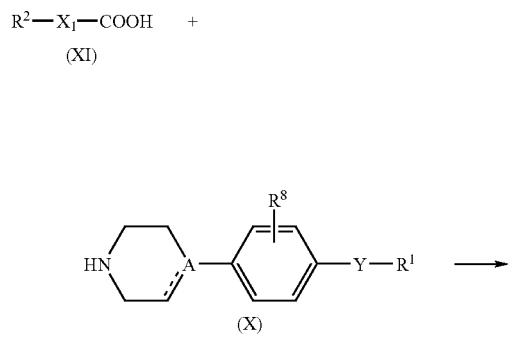

Compounds of formula (I) wherein X represents —S(=O)$_p$—, said compounds being represented by formula (I-e), can be prepared by reacting an intermediate of formula (XII) wherein $W_3$ represents a suitable leaving group, such as for example halo, e.g. chloro and the like, with an intermediate of formula (X) in the presence of a suitable base, such as for example N,N-diisopropyl-ethanamine or N,N-diethyl-ethanamine, and a suitable solvent, such as for example dichloromethane.

$R^2$—S(=O)$_p$—$W_3$ + 
(XII)

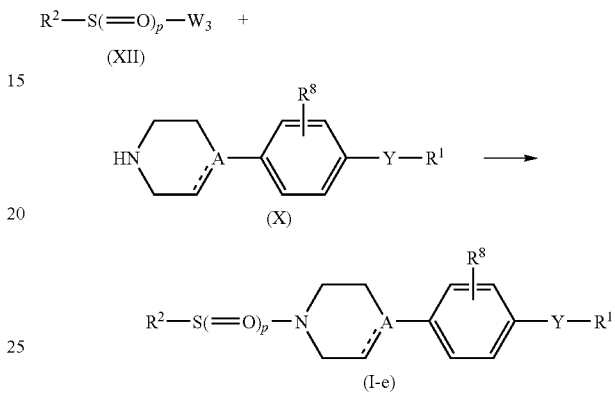

Compounds of formula (I) wherein X represents C(=O), said compounds being represented by formula (I-f), can be prepared by reacting an intermediate of formula (XIII) wherein $W_4$ represents a suitable leaving group, such as for example halo, e.g. chloro and the like, with an intermediate of formula (X) in the presence of a suitable base, such as for example N-methyl morpholine, and a suitable solvent, such as for example N,N-dimethylformamide.

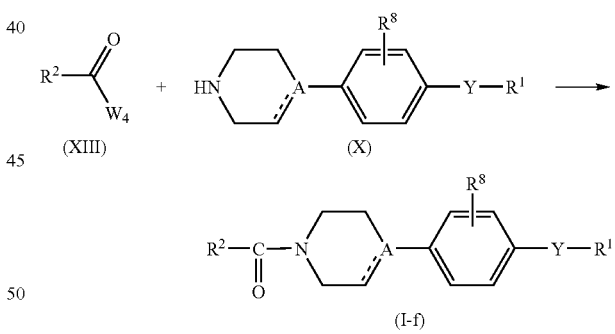

Compounds of formula (I) wherein X represents —C(=O)—$Z_1$—, said compounds being represented by formula (I-g), can be prepared by reacting an intermediate of formula (XIV) with an intermediate of formula (X) in the presence of a suitable solvent, such as for example an alcohol, e.g. ethanol.

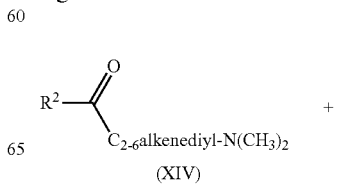

+

(XIV)

-continued

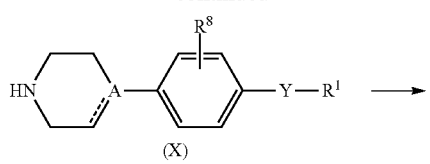
(X)

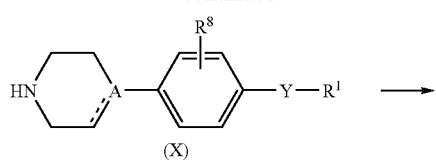
(X)

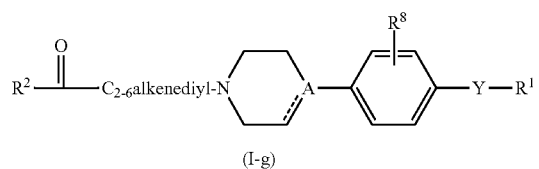
(I-g)

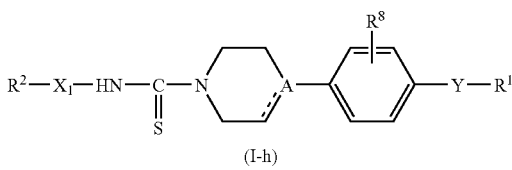
(I-h)

Compounds of formula (I) wherein X represents $X_1$—NH—C(=S)— with $X_1$ representing a direct bond or $Z^1$, said compounds being represented by formula (I-h), can be prepared by reacting an intermediate of formula (XV) with an intermediate of formula (X) in the presence of a suitable base, such as for example N,N-diethyl-ethanamine, and a suitable solvent, such as for example dichloromethane or tetrahydrofuran.

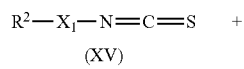
(XV)

Compounds of formula (I) wherein $R^2$ represents $R^3$, said $R^3$ being substituted with $R^5R^4N$—$C_{1-6}$alkyl, said $R^2$ being represented by $R^{3'}$—$C_{1-6}$alkyl-$NR^4R^5$ and said compounds being represented by formula (I-i), can be prepared by reacting an intermediate of formula (XVI) wherein $W_5$ represents a suitable leaving group, such as for example $CH_3$—S(=O)$_2$—O—, with $NHR^4R^5$ in the presence of a suitable solvent, such as for example acetonitrile. Intermediates of formula (XVI) can be prepared by reacting the corresponding OH derivatives with $CH_3$—S(=O)$_2$—Cl in the presence of a suitable base, such as for example pyridine, and a solvent, such as for example dichloromethane.

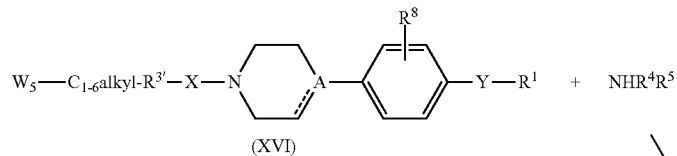
(XVI)    +    $NHR^4R^5$

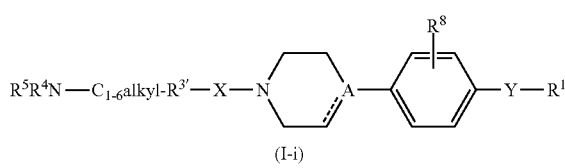
(I-i)

Compounds of formula (I) wherein Y represents —C(=O)—NR$^x$—Y$^2$, wherein Y$^2$ represents the remainder of the Y linker and said compounds being represented by formula (I-j), can be prepared by reacting an intermediate of formula (XXXIV) with an intermediate of formula (XXXV) in the presence of DECP, a suitable base, such as for example N,N-diethyl-ethanamine or N,N-diisopropyl-ethanamine, and a suitable solvent, such as for example dichloromethane or acetonitrile.

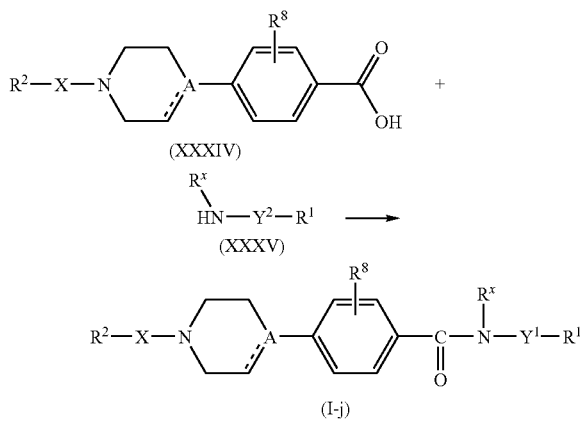

Compounds of formula (I) wherein R$^8$ represents C$_{1-4}$alkyl substituted with hydroxyl, said compounds being represented by formula (I-k), can be prepared by reacting an intermediate of formula (XXXVI) with an appropriate acid, such as for example HCl and the like, in the presence of a suitable solvent, such as for example an alcohol, e.g. 2-propanol.

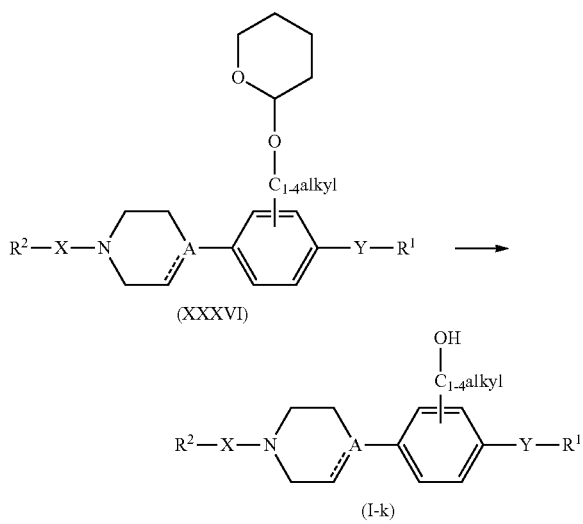

Compounds of formula (I) wherein X contains Z$^1$, said Z$^1$ being substituted with amino, said X being represented by Z$^1$(NH$_2$)—X$_2$, wherein X$_2$ represents the remainder of the linker X, and said compounds being represented by formula (I-l), can be prepared by deprotecting an intermediate of formula (XXXVII) wherein P represents a suitable leaving group, such as for example tert butoxycarbonyl, with a suitable acid, such as for example trifluoroacetic acid, in the presence of a suitable solvent, such as for example dichloromethane.

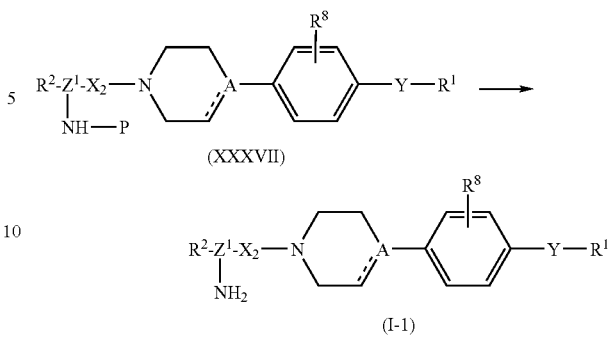

The compounds of formula (I) may further be prepared by converting compounds of formula (I) into each other according to art-known group transformation reactions.

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert-.butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Compounds of formula (I) wherein R$^1$ or R$^2$ is unsubstituted, can be converted into a compound wherein R$^1$ or R$^2$ contain a C$_{1-4}$alkyl-S(=O)$_p$— substituent, by reaction with C$_{1-4}$alkyl-S(=O)$_p$—W$_6$ wherein W$_6$ represents a suitable leaving group, such as for example halo, e.g. chloro and the like, in the presence of a suitable base, such as for example N,N-diethyl-ethanamine, and in the presence of a suitable solvent, such as for example acetonitrile.

Compounds of formula (I) wherein R$^1$ or R$^2$ contains a C$_{1-6}$alkyloxycarbonyl substituent, can be converted into a compound of formula (I) wherein R$^1$ or R$^2$ contain a carboxyl substituent, by reaction with a suitable base, such as for example sodium hydroxide, in the presence of a suitable solvent, such as for example dioxane.

Compounds of formula (I) wherein R$^1$ or R$^2$ contain a C$_{1-6}$alkyloxycarbonyl substituent, can also be converted into a compound of formula (I) wherein R$^1$ or R$^2$ contain a CH$_2$—OH substituent, by reaction with a suitable reducing agent, such as for example LiBH, in the presence of a suitable solvent, such as for example tetrahydrofuran or dioxane.

Compounds of formula (I) wherein R$^1$ or R$^2$ contain a C$_{1-6}$alkyloxycarbonyl substituent, can also be converted into a compound of formula (I) wherein R$^1$ or R$^2$ are unsubstituted by reaction with a suitable acid, such as for example hydrochloric acid and the like.

Compounds of formula (I) wherein R$^1$ or R$^2$ contain a C$_{1-5}$alkyl-carbonyl substituent, can be converted into a compound of formula (I) wherein R$^1$ or R$^2$ contain a C$_{1-5}$alkyl-CH(OH)— substituent, by reaction with a suitable reducing agent, such as for example NaBH$_4$, in the presence of a suitable solvent, such as for example an alcohol, e.g. methanol.

Compounds of formula (I) wherein $R^1$ or $R^2$ contain a $C_{1-6}$alkyloxy substituent, can be converted into a compound of formula (I) wherein $R^1$ or $R^2$ contain a OH substituent, by reaction with a suitable reducing agent, such as for example BBr$_3$, in the presence of a suitable solvent, such as for example dichloromethane or dichloroethane.

Compounds of formula (I) wherein $R^1$ or $R^2$ contain a carboxyl substituent, can be converted into a compound of formula (I) wherein $R^1$ or $R^2$ contain a Het-C(=O)— substituent wherein Het represents an optionally substituted monocyclic saturated heterocycle containing at least one N atom, said heterocycle being linked via the N atom to the C(=O) group, by reaction with said heterocycle in the presence a suitable dehydrating (coupling) agent, such as for example N'-(ethylcarbonimidoyl)-N,N-dimethyl-1,3-propanediamine monohydrochloride (EDCI), dicyclohexylcarbodiimide (DCC), carbonyl diimidazole (CDI), 1-[bis(di-methylamino)methylene]-1H-benzotriazoliumhexafluorophosphate(1-)3-oxide (HBTU), 1-[bis(dimethyl-amino)methylene]-5-chloro-1H-benzotriazolium-hexafluorophosphate(1-)3-oxide (HCTU), O-benzotriazolyl tetramethylisouronium tetrafluoroborate (TBTU) or diethyl cyanophosphonate (DECP), optionally combined with hydroxy benzotriazole or chloro hydroxybenzotriazole, in the presence of a suitable solvent, such as for example N,N-dimethylformamide, dichloromethane, acetonitrile or tetrahydrofuran, and optionally in the presence of a suitable base, such as for example N,N-diisopropyl-ethanamine or N,N-diethyl-ethanamine. This reaction can also be performed as a fast synthesis reaction thereby using appropriate reagents well-known for fast synthesis, such as for example dicyclohexylcarbodiimide (DCC) or carbonyl diimidazole (CDI), linked to an appropriate carrier, e.g. polystyrene. Also for the purification of the reaction mixture, appropriate fast-synthesis reagents can be used, such as for example 1-ethenyl-4-(isocyanatomethyl)-benzene polymer with ethenylbenzene.

Compounds of formula (I) wherein $R^y$ represents allyl, can be converted into a compound of formula (I) wherein $R^y$ represents hydrogen, by reaction with a suitable catalyst, such as for example Pd(PPh$_3$)$_4$, and a suitable nucleophilic agent, such as for example

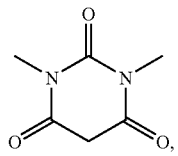

in the presence of a suitable solvent, such as for example dichloroethane.

Compounds of formula (I) wherein $R^y$ represents —S(=O)$_p$-aryl wherein aryl is nitro-substituted phenyl, can be converted into a compound of formula (I) wherein $R^y$ represents hydrogen, by reaction with LiOH and HS—CH$_2$—C(=O)—OH in the presence of a suitable solvent, such as for example N,N-dimethylformamide.

The compounds of formula (I) and some of the intermediates in the present invention may contain an asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, chiral liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

An alternative manner of separating the enantiomeric forms of the compounds of formula (I) and intermediates involves liquid chromatography or SCF (Super Critical Fluid) chromatography, in particular using a chiral stationary phase.

Some of the intermediates and starting materials are known compounds and may be commercially available or may be prepared according to art-known procedures.

Intermediates of formula (II) wherein X represents —X$_1$—NH—C(=O)— with X$_1$ representing a direct bond or $Z^1$, said intermediates being represented by formula (II-a), can be prepared by reacting an intermediate of formula (IX) with an intermediate of formula (XVII) wherein P represents a suitable protecting group, such as for example tertiair butyloxycarbonyl, in the presence of a suitable solvent, such as for example dichloromethane, followed by deprotecting the resulting intermediate of formula (XVIII) in the presence of a suitable acid, such as for example trifluoroacetic acid, and in the presence of a suitable solvent, such as for example dichloromethane. Before performing the deprotection reaction, the intermediate of formula (XVIII) can optionally be converted into an intermediate of formula (XVIII') by reaction with $C_{1-4}$alkyl halide, e.g. CH$_3$I, in the presence of a suitable base, such as for example NaH, and a suitable solvent, such as for example N,N-dimethylformamide.

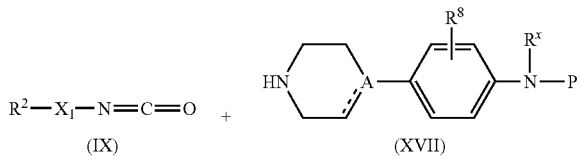

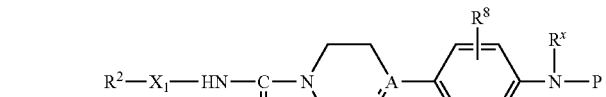

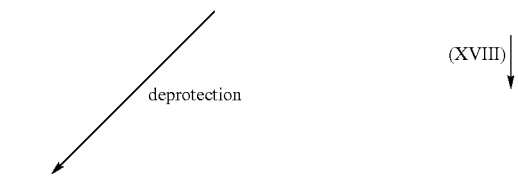

-continued

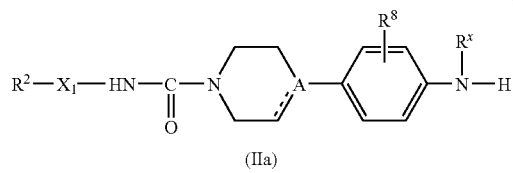
(IIa)

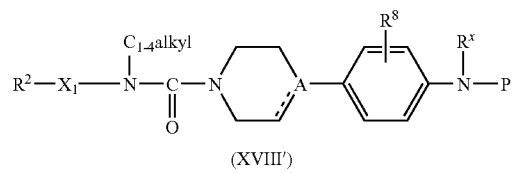
(XVIII′)

deprotection ↓

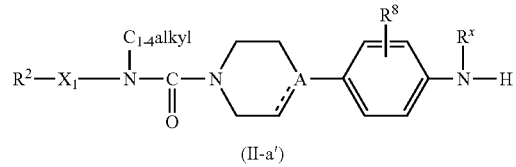
(II-a′)

Intermediates of formula (II-a) wherein $R^x$ represents hydrogen, said intermediates being represented by formula (II-a-1), can be prepared by reacting an intermediate of formula (IX) with an intermediate of formula (IXX) in the presence of a suitable solvent, such as for example dichloromethane, followed by hydrogenating ($H_2$ or $N_2H_4 \cdot H_2O$) the resulting intermediate of formula (XX) in the presence of a suitable catalyst, such as for example platinum on charcoal or raney nickel, optionally a suitable catalyst poison, such as for example a thiophene solution, and a suitable solvent, such as for example tetrahydrofuran or an alcohol, e.g. methanol. Before performing the hydrogenation reaction, the intermediate of formula (XX) can optionally be converted into an intermediate of formula (XX′) by reaction with $C_{1-4}$alkyl halide, e.g. $CH_3I$, in the presence of a suitable base, such as for example NaH, and a suitable solvent, such as for example N,N-dimethylformamide.

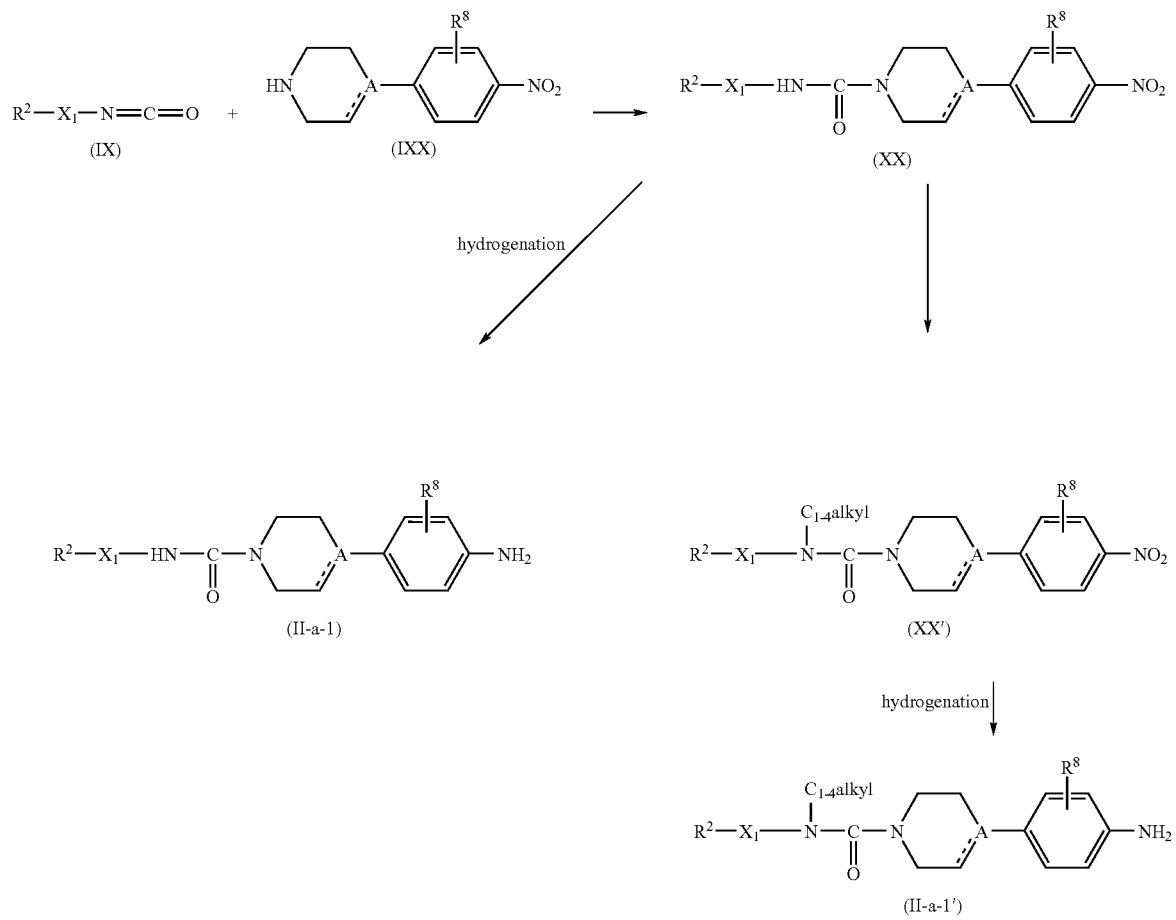

Intermediates of formula (II-a) wherein $R^x$ represents hydrogen and wherein $X_1$ represents a direct bond, said intermediates being represented by formula (II-a-2), can be prepared by reacting an intermediate of formula (XXI) with $Cl_3COC(=O)$—Cl followed by reaction with an intermediate of formula (IXX) in the presence of a suitable base, such as for example N,N-diethyl-ethanamine, and a suitable solvent, such as for example toluene, followed by hydrogenating ($H_2$ or $N_2H_4.H_2O$) the resulting intermediate of formula (XXII) in the presence of a suitable catalyst, such as for example platinum on charcoal or raney nickel, optionally a suitable catalyst poison, such as for example a thiophene solution, and a suitable solvent, such as for example tetrahydrofuran or an alcohol, e.g. methanol. Before performing the hydrogenation reaction, the intermediate of formula (XXII) can optionally be converted into an intermediate of formula (XXII') by reaction with $C_{1-4}$alkyl halide, e.g. $CH_3I$, in the presence of a suitable base, such as for example NaH, and a suitable solvent, such as for example N,N-dimethylformamide.

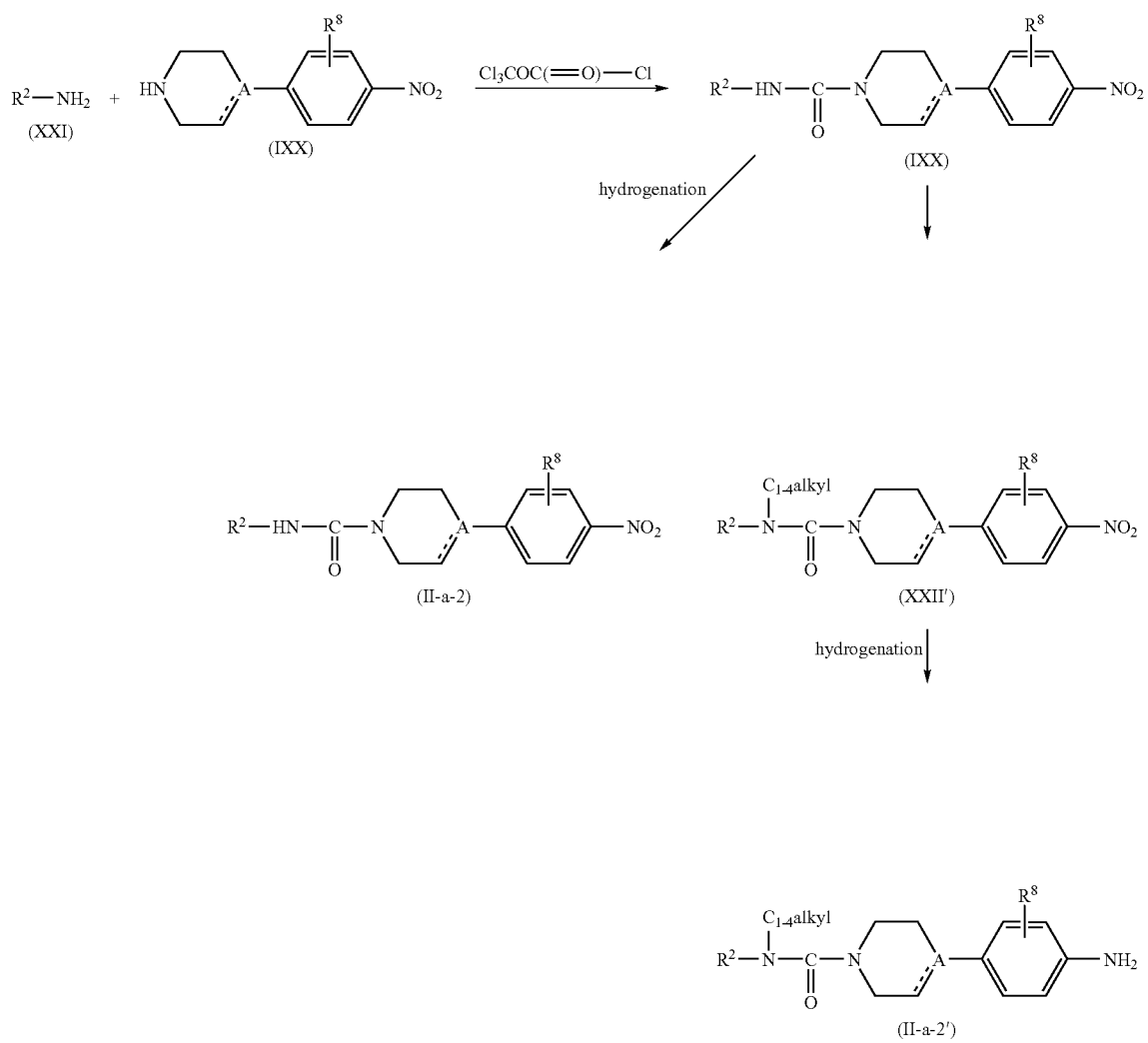

Intermediates of formula (II) wherein X represents —O—C(=O)—, said intermediates being represented by formula (II-b), can be prepared by reacting an intermediate of formula (LII) with an intermediate of formula (LIII) wherein $W_3$ represents a suitable leaving group, such as for example halo, e.g. chloro, in the presence of NaH, and a suitable solvent, such as for example tetrahydrofuran, followed by hydrogenating the resulting product of formula (LIV) in a next step in the presence of $H_2$, a suitable catalyst, such as for example platina on charcoal, a suitable catalyst poison, such as for example thiophene, and a suitable solvent, such as for example acetic acid.

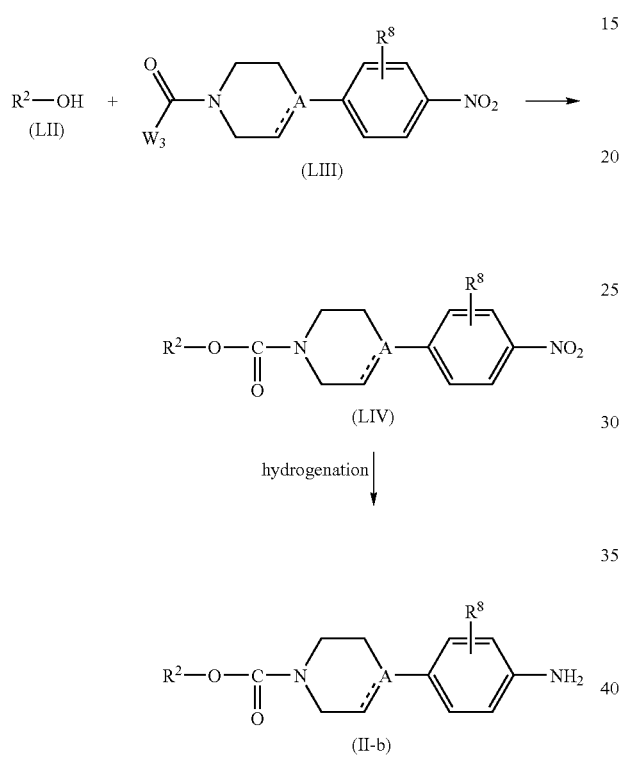

Intermediates of formula (V) can be prepared by reacting an intermediate of formula (II) with an intermediate of formula (XXIII) wherein $W_7$ represents a suitable leaving group, such as for example halo, e.g. chloro, bromo and the like, in the presence of a suitable base, such as for example N,N-diethyl-ethanamine, N,N-diisopropyl-ethanamine and a suitable solvent, such as for example dichloromethane or N,N-dimethylformamide.

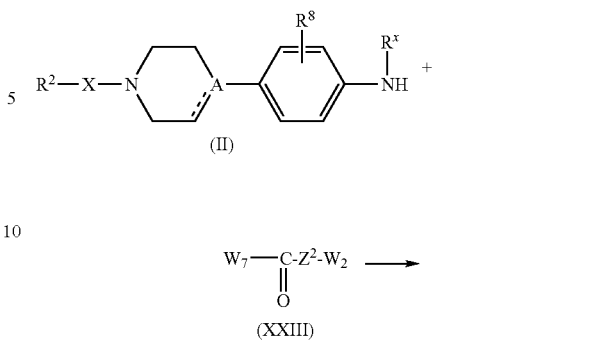

Intermediates of formula (X) wherein Y comprises NH—C(=O)—$Z^2$—, said intermediates being represented by formula (X-a), wherein $Y^1$ represents the remainder of the linker Y including a direct bond, can be prepared according to the following reaction scheme wherein an intermediate of formula (XXIV) wherein P represents a suitable protecting group, such as for example benzyloxycarbonyl or tertiair butyloxy or benzyl, and wherein $W_8$ represents a suitable leaving group, such as for example halo, e.g. chloro and the like, with an intermediate of formula (IXX) in the presence of a suitable base, such as for example $NaHCO_3$, and a suitable solvent, such as for example dichloromethane, resulting in an intermediate of formula (XXV), followed in a next step by hydrogenating ($H_2$) said intermediate of formula (XXV) in the presence of a suitable catalyst, such as for example platinum on charcoal, and a suitable solvent, such as for example tetrahydrofuran, and an alcohol, e.g. methanol, resulting in an intermediate of formula (XXVI). In a next step, said intermediate of formula (XXVI) is reacted with an intermediate of formula (IV) in the presence of a suitable base, such as for example $NaHCO_3$, and a suitable solvent, such as for example acetonitrile, resulting in an intermediate of formula (XXVII), which is deprotected in a next step in the presence of $H_2$, a suitable catalyst, such as for example palladium on charcoal, and a suitable solvent, such as for example an alcohol, e.g. methanol, and optionally in the presence of a suitable acid, such as for example methanesulfonic acid; or in the presence of a suitable acid, such as for example trifluoroacteic acid, and a suitable solvent, such as for example dichloromethane; or in the presence of ammonium formate, a suitable catalyst, such as for example palladium on charcoal, and a suitable solvent, such as for example an alcohol, e.g. methanol.

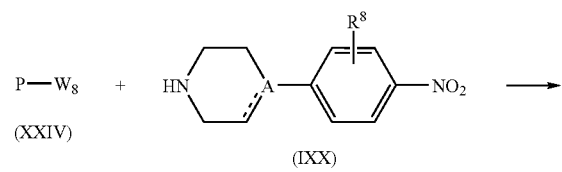

-continued

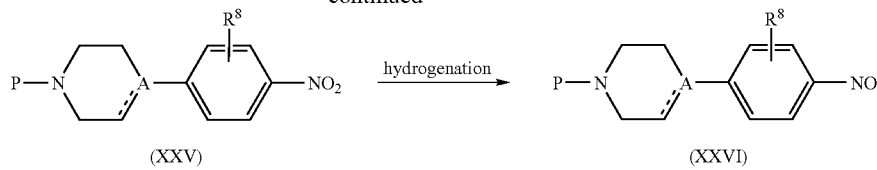

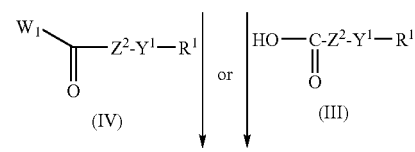

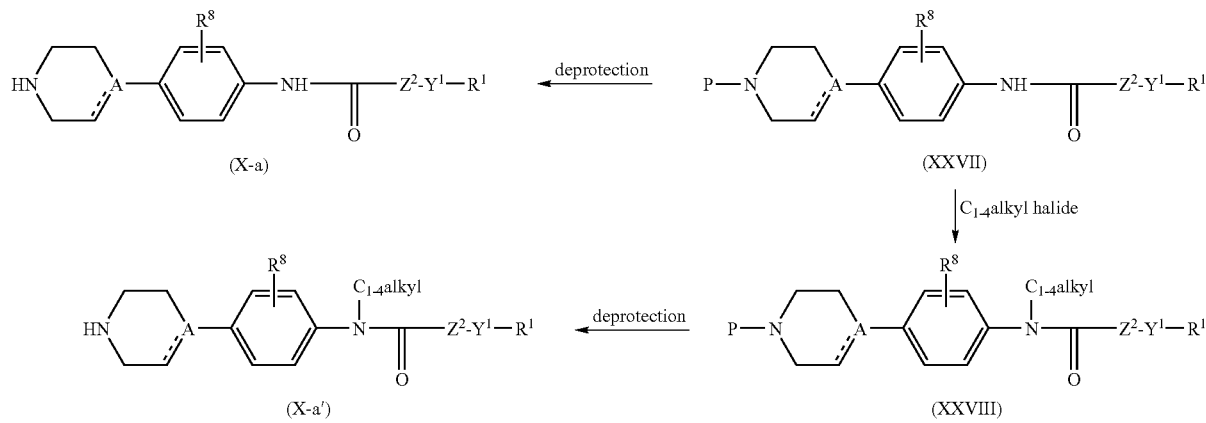

In the above reaction scheme, the intermediate of formula (XXVI) can also react with an intermediate of formula (III) in the presence of a suitable activating agent, such as for example $SOCl_2$ or $Cl—C(=O)—C(=O)—Cl$, a suitable base, such as for example N,N-diethyl-ethanamine or N,N-diisopropyl-ethanamine, and a suitable solvent, such as for example dichloromethane or N,N-dimethylformamide. Or an intermediate of formula (III) can react with an intermediate of formula (XXVI) in the presence of a suitable dehydrating (coupling) agent, such as for example N-(ethylcarbonimidoyl)-N,N-dimethyl-1,3-propanediamine monohydrochloride (EDCI), dicyclohexylcarbodiimide (DCC), carbonyl diimidazole (CDI), 1-[bis(di-methylamino)methylene]-1H-benzotriazoliumhexafluorophosphate(1-)3-oxide (HBTU), 1-[bis(dimethyl-amino)methylene]-5-chloro-1H-benzotriazolium-hexafluorophosphate(1-)3-oxide (HCTU), O-benzotriazolyl tetramethylisouronium tetrafluoroborate (TBTU) or diethyl cyanophosphonate (DECP), optionally combined with hydroxy benzotriazole or chloro hydroxybenzotriazole, in the presence of a suitable solvent, such as for example N,N-dimethylformamide, dichloromethane, acetonitrile or tetrahydrofuran, and optionally in the presence of a suitable base, such as for example N,N-diisopropyl-ethanamine or N,N-diethyl-ethanamine.

The intermediate of formula (XXVII) can also react with an $C_{1-4}$alkyl halide, e.g. $CH_3I$, in the presence of a suitable base, such as for example NaH, and a suitable solvent, such as for example N,N-dimethylformamide, to form an intermediate of formula (XXVIII) which can be deprotected according to the above described protocol to result in an intermediate of formula (X-a').

Intermediates of formula (X) wherein Y represents $—C(=O)—NR^x—Z^2—Y^1—$, with $Y^1$ as defined hereinabove, said intermediates being represented b formula (X-b) can be prepared by deprotecting an intermediate of formula (XLIV) wherein P represents a suitable leaving group, such as for example tertiair butyloxycarbonyl or benzyl, in the presence of a suitable acid, such as for example HCl or trifluoroacetic acid and the like, and a suitable solvent, such as for example an alcohol, e.g. isopropanol, or dichloromethane, or in the presence of $H_2$, and a suitable catalyst, such as for example palladium on charcoal, and a suitable solvent, such as for example an alcohol, e.g. methanol. Intermediates of formula (XLIV) can be prepared by reacting an intermediate of formula (XLV) with an intermediate of formula (XLVI) in the presence of a suitable dehydrating (coupling) agent, such as for example N'-(ethylcarbonimidoyl)-N,N-dimethyl-1,3-propanediamine monohydrochloride (EDCI), dicyclohexylcarbodiimide (DCC), carbonyl diimidazole (CDI), 1-[bis(di-methylamino)methylene]-1H-benzotriazoliumhexafluorophosphate(1-)3-oxide (HBTU), 1-[bis(dimethyl-amino)methylene]-5-chloro-1H-benzotriazolium-hexafluorophosphate(1-)3-oxide (HCTU), O-benzotriazolyl tetramethylisouronium tetrafluoroborate (TBTU) or diethyl cyanophosphonate (DECP), optionally combined with hydroxy benzotriazole or chloro hydroxybenzotriazole, in the presence of a suitable solvent, such as for example N,N-dimethylformamide, dichloromethane, acetonitrile or tetrahydrofuran, and optionally in the presence of a suitable base, such as for example N,N-diisopropyl-ethanamine or N,N-diethyl-ethanamine.

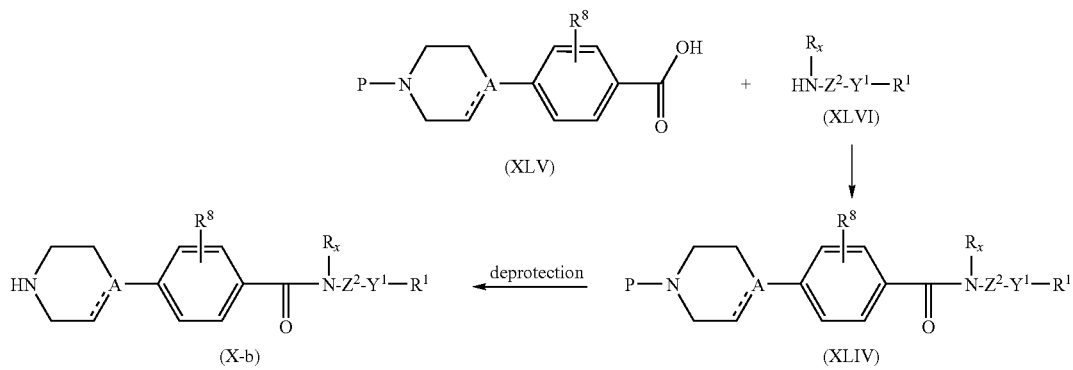

Intermediates of formula (III) can be prepared by hydrolizing an intermediate of formula (IXXX) with a suitable base, such as for example potassium hydroxide or sodium hydroxide, in the presence of a suitable solvent, such as for example water, tetrahydrofuran or an alcohol. e.g. methanol.

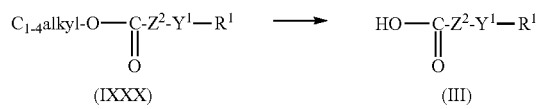

Intermediates of formula (IXXX) wherein $R^1$ represents $Het^1$ wherein said $Het^1$ is an optionally substituted heterocycle further substituted with either optionally substituted phenyl or an optionally substituted heterocycle, can be prepared by reacting the protected optionally substituted heterocycle with optionally substituted phenyl in the presence of a suitable catalyst, such as for example palladium acetate, in the presence of a suitable catalyst ligand, such as for example 1,1'-(1,5-pentanediyl)bis[1,1'-diphenylphosphine], a suitable base, such as for example potassium acetate, and a suitable solvent, such as for example N-methyl-pyrrolidin-2-one; or by reacting the protected optionally substituted heterocycle
  with optionally substituted phenyl carrying a suitable leaving group, such as for example halo, e.g. bromo, iodo and the like, in the presence of a suitable catalyst, such as for example palladium acetate, in the presence of a suitable catalyst ligand, such as for example 1,3-propanediylbis[diphenylphosphine], a suitable base, such as for example potassium acetate or cesium carbonate, and a suitable solvent, such as for example N-methyl-pyrrolidin-2-one; or
by reacting the protected optionally substituted heterocycle
  with an optionally substituted heterocycle carrying a suitable leaving group, such as for example halo, e.g. bromo, iodo and the like, in the presence of a suitable catalyst, such as for example palladium acetate, in the presence of a suitable catalyst ligand, such as for example 1,3-propanediylbis[diphenylphosphine], a suitable base, such as for example potassium acetate or cesium carbonate, and a suitable solvent, such as for example N-methyl-pyrrolidin-2-one.

Intermediates of formula (IXXX) wherein $R^1$ represents an optionally substituted phenyl further substituted with either optionally substituted phenyl or an optionally substituted heterocycle, can be prepared accordingly.

Intermediates of formula (IXXX) wherein $Y^1$ contains a $NR^y$ wherein $R^y$ represents $C_{2-4}$alkenyl, can be prepared from the corresponding intermediate wherein $R^y$ represents hydrogen, by reaction with $C_{2-4}$alkenyl-$W_9$ wherein $W_9$ represents a suitable leaving group, such as for example halo, e.g. iodo and the like, in the presence of a suitable base, such as for example $K_2CO_3$ or N,N-diisopropyl-ethanamine, and a suitable solvent, such as for example N,N-dimethylformamide or an alcohol, e.g. ethanol.

Intermediates of formula (IXXX) wherein $Y^1$ contains a $NR^y$ wherein $R^y$ represents —$S(=O)_p$-aryl, can be prepared from the corresponding intermediate wherein $R^y$ represents hydrogen, by reaction with $W_{10}$—$S(=O)_p$-aryl wherein $W_{10}$ represents a suitable leaving group, such as for example halo, e.g. chloro and the like, in the presence of a suitable base, such as for example N,N-diethyl-ethanamine, and a suitable solvent, such as for example acetonitrile.

Intermediates of formula (III) wherein $Y^1$ represents —$NR^y$—C(=O)—$NR^y$—, said intermediates being represented by formula (III-a), can be prepared by reacting an intermediate of formula (XXX) with an intermediate of formula (XXXI) in the presence of a suitable base, such as for example N,N-diethyl-ethanamine, and a suitable solvent, such as for example acetonitrile, followed by deprotecting the resulting intermediate of formula (XXXII) with a suitable base, such as for example KOH, in the presence of a suitable solvent, such as for example water and an alcohol, e.g. ethanol.

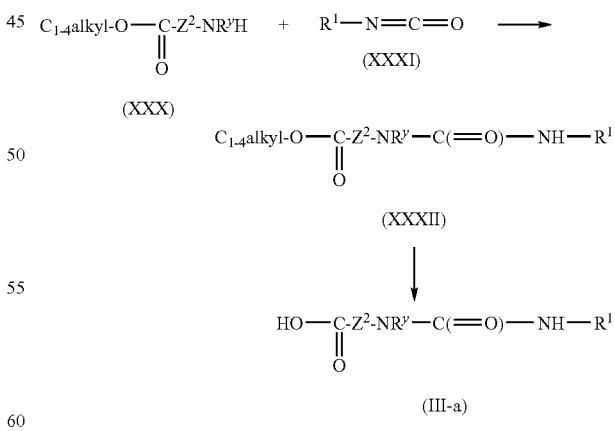

Intermediates of formula (IX) wherein $X_1$ represents a direct bond and $R^2$ contains a Het-$C_{1-4}$alkyl substituent, wherein Het represents a monocyclic, saturated N containing heterocycle represented by formula (XXXVIII), said intermediate of formula (IX) being represented by formula (IX-a), can be prepared by reacting an intermediate of formula (XXXVIII) with an intermediate of formula (XXXIX) in the represence of a suitable dehydrating (coupling) agent, such as for example N'-(ethylcarbonimidoyl)-N,N-dimethyl-1,3-propanediamine monohydrochloride (EDCI), dicyclohexyl-carbodiimide (DCC), carbonyl diimidazole (CDI), 1-[bis(di-methylamino)methylene]-1H-benzotriazoliumhexafluorophosphate(1-)3-oxide (HBTU), 1-[bis(dimethyl-amino)methylene]-5-chloro-1H-benzotria-zolium-hexafluorophosphate(1-)3-oxide (HCTU), O-benzo-triazolyl tetramethylisouronium tetrafluoroborate (TBTU) or diethyl cyanophosphonate (DECP), optionally combined with hydroxy benzotriazole or chloro hydroxybenzotriazole, in the presence of a suitable solvent, such as for example N,N-dimethylformamide, dichloromethane, acetonitrile or tetrahydrofuran, and optionally in the presence of a suitable base, such as for example N,N-diisopropyl-ethanamine or N,N-diethyl-ethanamine. The resulting intermediate of formula (XL) can then be reduced in a next step in the presence of a suitable reducing agent, such as for example borane, in the presence of a suitable solvent, such as for example tetrahydrofuran, to an intermediate of formula (XLI), which can then be converted into an intermediate of formula (IX-a) with phosgene in the presence of HCl in diethylether and a suitable solvent, such as for example toluene or acetonitrile.

Intermediates of formula (XL) can also be converted into an intermediate of formula (IX-b) with phosgene in the presence of HCl in diethylether and a suitable solvent, such as for example toluene or acetonitrile or dichloromethane.

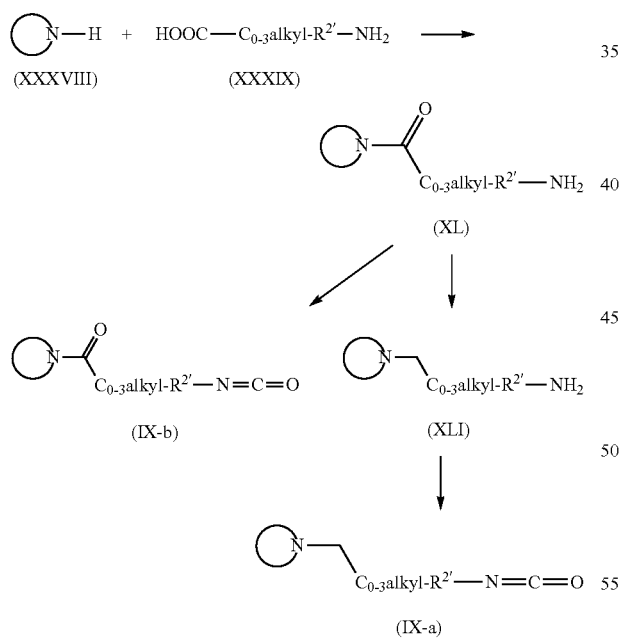

Intermediates of formula (IX-a) can also be prepared by reacting an intermediate of formula (XXXVIII) with an intermediate of formula (XLXI) wherein $W_4$ represents a suitable leaving group, such as for example halo, e.g. chloro and the like, in the presence of a suitable solvent, such as for example acetonitrile, resulting in an intermediate of formula (XLI') with can be converted into an intermediate of formula (IX-a) as described hereinabove for intermediate (XLI).

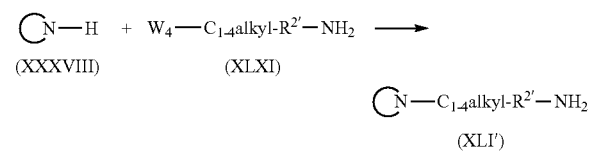

Intermediates of formula (XXXIV) wherein X represents $-X_1-HN-C(=O)-$, said intermediates being represented by formula (XXXIV-a), can be prepared by hydrolysis of an intermediate of formula (XLII) in the presence of a suitable base, such as for example sodium hydroxide, in the presence of a suitable solvent, such as for example dioxane and optionally an alcohol, e.g. methanol. Intermediates of formula (XLII) can be prepared by reacting an intermediate of formula (IX) with an intermediate of formula (XLIII) in the presence of a suitable base, such as for example N,N-diethyl-ethanamine, and a suitable solvent, such as for example dichloromethane.

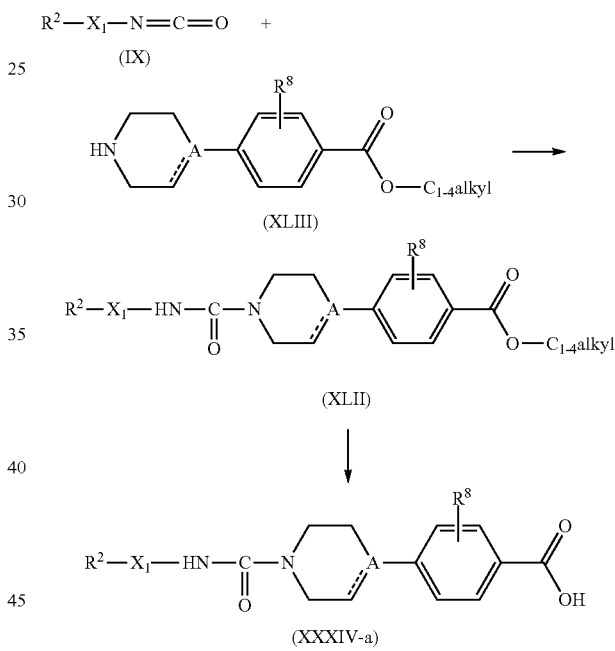

Intermediates of formula (XXXIV) wherein X represents $-X_1-C(=O)-$, said intermediates being represented by formula (XXXIV-b), can be prepared by hydrolysis of an intermediate of formula (XLII-a) in the presence of a suitable base, such as for example sodium hydroxide, in the presence of a suitable solvent, such as for example dioxane and optionally an alcohol, e.g. methanol. Intermediates of formula (XLII-a) can be prepared by reacting an intermediate of formula (XI) with an intermediate of formula (XLIII) in the presence of a suitable dehydrating (coupling) agent, such as for example N'-(ethylcarbonimidoyl)-N,N-dimethyl-1,3-propanediamine monohydrochloride (EDCI), dicyclohexyl-carbodiimide (DCC), carbonyl diimidazole (CDI), 1-[bis(di-methylamino)methylene]-1H-benzotriazoliumhexafluorophosphate(1-)3-oxide (HBTU), 1-[bis(dimethyl-amino)methylene]-5-chloro-1H-benzotria-zolium-hexafluorophosphate(1-)3-oxide (HCTU), O-benzo-triazolyl tetramethylisouronium tetrafluoroborate (TBTU) or diethyl cyanophosphonate (DECP), optionally combined with hydroxy benzotriazole or chloro hydroxybenzotriazole, in the presence of a suitable solvent, such as for example N,N-dimethylformamide, dichloromethane, acetonitrile or tetrahydrofuran, and optionally in the presence of a suitable base, such as for example N,N-diisopropyl-ethanamine or N,N-diethyl-ethanamine.

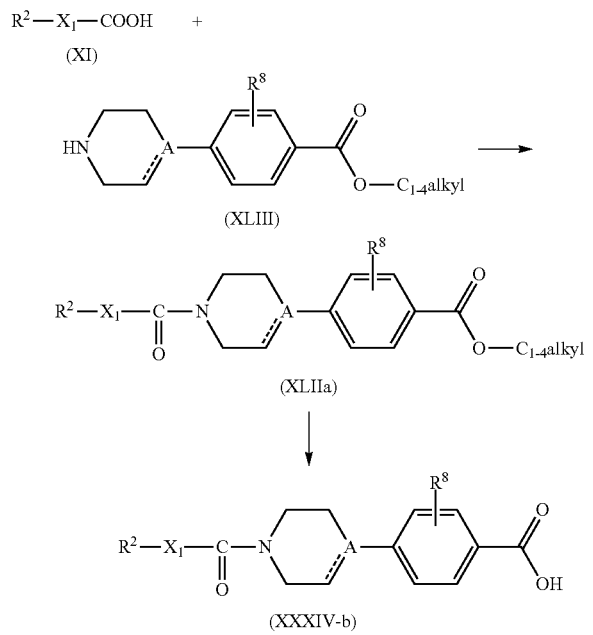

Intermediates of formula (XI) can be prepared by hydrolysis of an intermediate of formula (XLVII) in the presence of LiOH, an acid, such as for example HCl, and a suitable solvent, such as for example an alcohol, e.g. methanol. Intermediates of formula (XLVII) wherein $R^2$ contains Het-$C_{1-4}$alkyl as substituent, said intermediates being represented by formula (XLVII-a) can be prepared by reacting an intermediate of formula (XLVIII) wherein $W_5$ represents a suitable leaving group, such as for example halo, e.g. bromo and the like, with an intermediate of formula (XXXVIII).

Intermediates of formula (XLVIII-a) as depicted below, can be prepared by reacting an intermediate of formula (XLIX) with N-bromosuccinimide in the presence of 2,2'-(1,2-diazenediyl)bis[2-methylpropanenitrile] and a suitable solvent, such as for example $CCl_4$. Intermediates of formula (XLIX) wherein $X_1$ represents $CH_2$, said intermediates being represented by formula (XLIX-a), can be prepared by reacting an intermediate of formula (XLX) with sodium metal, in the presence of a suitable $C_{1-4}$alkyl-OH, followed by adding a suitable acid, such as for example sulfuric acid. Intermediates of formula (XLX) can be prepared by reacting an intermediate of formula (XXI-a) with 1,1-dimethylethyl-nitrous acid ester, $CuCl_2$, 1,1-dichloroethene in a suitable solvent, such as for example acetonitrile.

Intermediates of formula (XXXVI-a) can be prepared according to the following reaction scheme. In a first step, an intermediate of formula LV wherein $W_{11}$ represents a suitable leaving group, such as for example fluoro, is reacted with 3,4-dihydro-2H-pyran in the presence of 4-methyl-benzene-sulfonic acid and a suitable solvent, such as for example dichloromethane, resulting in an intermediate of formula (LVI). Said intermediate is in a next step reacted with an intermediate of formula (LVII) wherein P represents a suitable protecting group, such as for example benzyl, in the presence of $Na_2CO_3$ and a suitable solvent, such as for example N,N-dimethylformamide resulting in an intermediate of formula (LVIII). In a next step, said intermediate is hydrogenated with $H_2$ in the presence of a suitable catalyst, such as for example platinum on charcoal, a catalyst poison, such as for example thiophene, and a suitable solvent, such as for example tetrahydrofuran, resulting in an intermediate of formula (LIX). This intermediate is then reacted with an intermediate of formula (III) in the presence of a suitable dehydrating (coupling) agent, such as for example N'-(ethyl-carbonimidoyl)-N,N-dimethyl-1,3-propanediamine monohydrochloride (EDCI), dicyclohexylcarbodiimide (DCC), carbonyl diimidazole (CDI), 1-[bis(di-methylamino)methylene]-1H-benzotriazoliumhexafluorophosphate(1-)3-oxide (HBTU), 1-[bis(dimethyl-amino)methylene]-5-chloro-1H-benzotriazolium-hexafluorophosphate(1-)3-oxide (HCTU), O-benzotriazolyl tetramethylisouronium tetrafluoroborate (TBTU) or diethyl cyanophosphonate (DECP), optionally combined with hydroxy benzotriazole or chloro hydroxybenzotriazole, in the presence of a suitable solvent, such as for example N,N-dimethylformamide, dichloromethane, acetonitrile or tetrahydrofuran, and optionally in the presence of a suitable base, such as for example N,N-diisopropyl-ethanamine or N,N-diethyl-ethanamine. This reaction of an intermediate of formula (LIX) with an intermediate of formula (III) can also be performed in the presence of a suitable activating agent, such as for example Cl—C(=O)—C (=O)—Cl, a suitable base, such as for example N,N-diethyl-ethanamine, and a suitable solvent, such as for example N,N-dimethylformamide. This reaction can be performed as a fast synthesis reaction thereby using appropriate reagents well-known for fast synthesis, such as for example dicyclohexyl-carbodiimide (DCC) linked to an appropriate carrier, e.g. polystyrene. Also for the purification of the reaction mixture, appropriate fast-synthesis reagents can be used, such as for example 1-ethenyl-4-(isocyanatomethyl)-benzene polymer with ethenylbenzene. In a next step, the intermediate of formula (LX) is deprotected with $H_2$, in the presence of a suitable catalyst, such as for example palladium on charcoal, a suitable base, such as for example N,N-diethyl-ethanamine, and a suitable solvent, such as for example tetrahydrofuran resulting in an intermediate of formula (LXI) which can in a next step be reacted with an intermediate of formula (IX) in the presence of a suitable solvent, such as for example dichloromethane, to obtain an intermediate of formula (XXXVI-a).

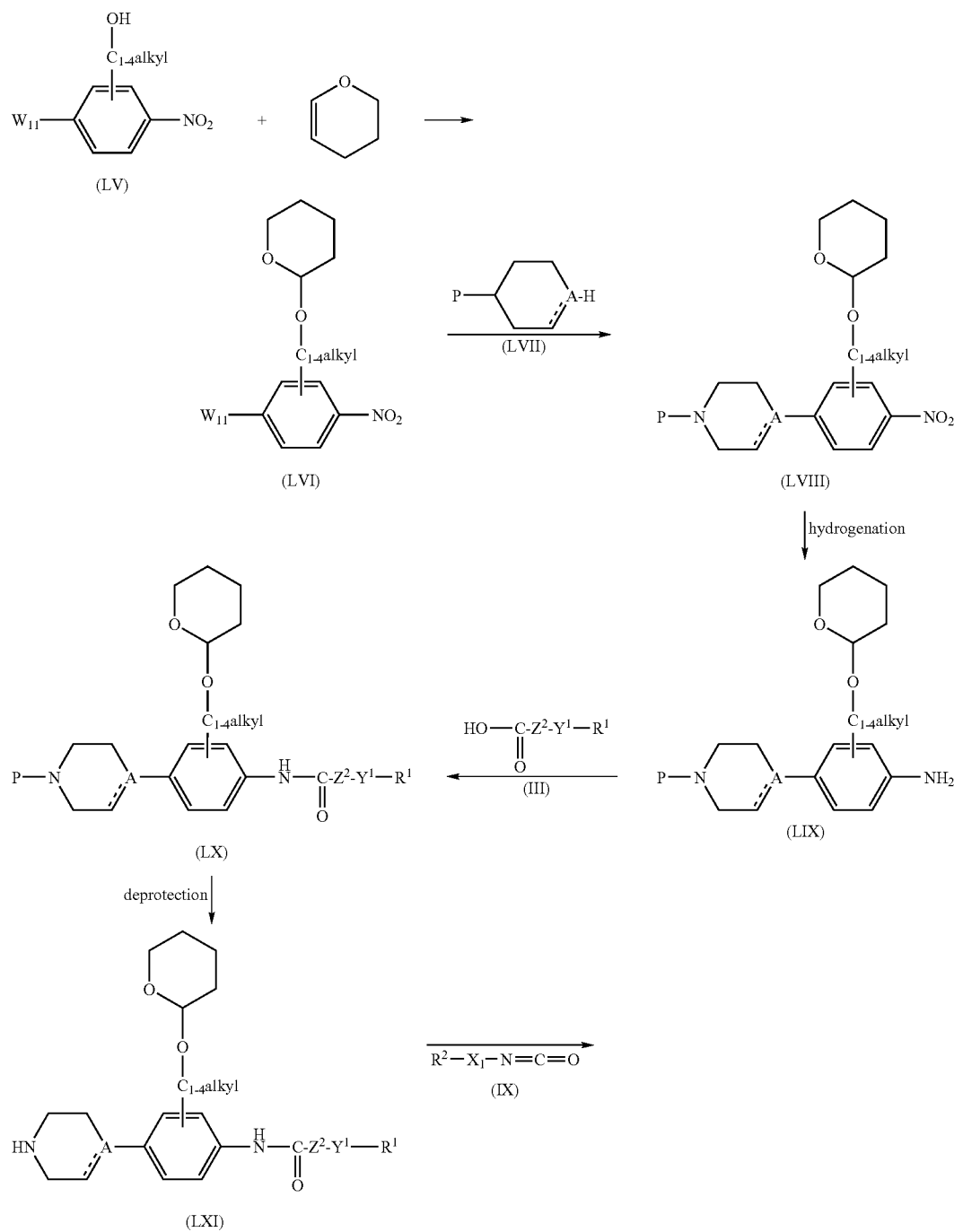

-continued

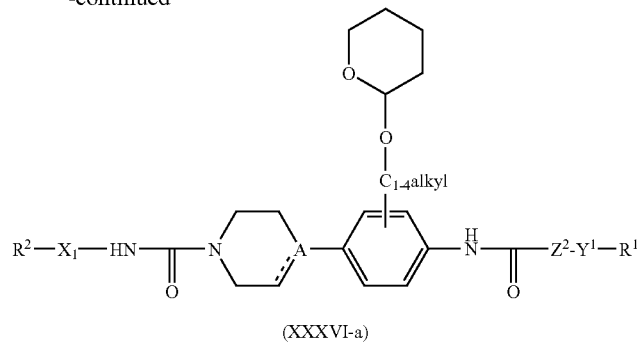

(XXXVI-a)

Intermediates of formula (XXXVII-a) can be prepared by reacting an intermediate of formula (XI) wherein $X_1$ is substituted with a protected (P, such as for example tertiair butyloxycarbonyl) amino group, said intermediate being represented by formula (XI-a), with an intermediate of formula (X) in the presence of a suitable dehydrating (coupling) agent, such as for example N'-(ethylcarbonimidoyl)-N,N-dimethyl-1,3-propanediamine monohydrochloride (EDCI), dicyclohexylcarbodiimide (DCC), carbonyl diimidazole (CDI), 1-[bis(di-methylamino)methylene]-1H-benzotriazolium-hexafluorophosphate(1-) 3-oxide (HBTU), 1-[bis(dimethylamino)methylene]-5-chloro-1H-benzotriazolium-hexafluorophosphate(1-)3-oxide (HCTU), O-benzotriazolyl tetramethylisouronium tetrafluoroborate (TBTU) or diethyl cyanophosphonate (DECP), optionally combined with hydroxy benzotriazole or chloro hydroxybenzotriazole, in the presence of a suitable solvent, such as for example N,N-dimethylformamide, dichloromethane, acetonitrile or tetrahydrofuran, and optionally in the presence of a suitable base, such as for example N,N-diisopropyl-ethanamine or N,N-diethyl-ethanamine.

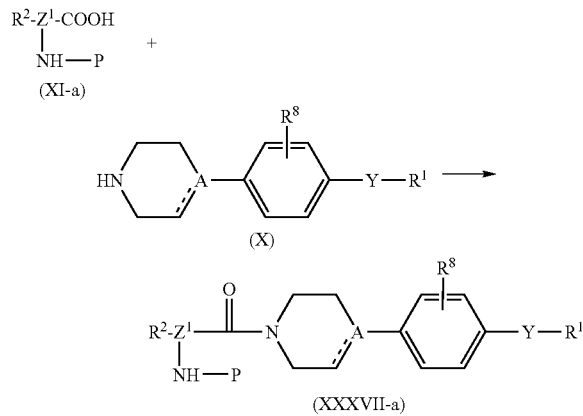

Intermediates of formula (XI) wherein $X_1$ represents CHOH, said intermediates being represented by formula (XI-b) can be prepared by reacting an intermediate of formula (LXII) in the presence of $ZnBr_2$, $Si(CH_3)_3$—CN and an acid, such as for example HCl, in the presence of a suitable solvent, such as for example dichloromethane. Intermediates of formula (LXII) can be prepared by reacting an intermediate of formula (LXIII) wherein $W_{12}$ represents a suitable leaving group, such as for example halo, e.g. bromo and the like, with N,N-dimethylformamide in the presence of BuLi and a suitable solvent, such as for example tetrahydrofuran.

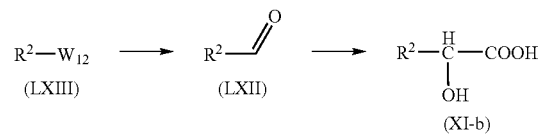

Pharmacological Part

As already indicated above, the present invention relates to the use of a DGAT inhibitor, in particular a DGAT1 inhibitor, to elevate levels of one or more satiety hormones, in particular GLP-1 levels. The present invention also relates to the use of a DGAT inhibitor, in particular a DGAT1 inhibitor, for the manufacture of a medicament for the prevention or the treatment, in particular for the treatment, of a disease which can benefit from an elevated level of one or more satiety hormones, in particular a disease which can benefit from an elevated GLP-1 level. In particular, GLP-1 levels are elevated in plasma or in portal blood, more in particular in plasma. By elevated GLP-1 levels, e.g. elevated GLP-1 plasma level or an elevated GLP-1 level in portal blood, it is meant that the GLP-1 level of a subject having taken a DGAT1 inhibitor is elevated or increased compared to the subject under the same conditions but not having taken the DGAT1 inhibitor. In particular GLP-1 levels are elevated in fasting conditions or postprandial, more in particular postprandial.

Therapeutic uses for a compound which elevates GLP-1 level include, but are not limited to, improving learning, enhancing neuro-protection, and/or alleviating a symptom of a disease or disorder of the central nervous system, e.g., through modulation of neurogenesis, and e.g., Parkinson's Disease, Alzheimer's Disease, Huntington's Disease, ALS, stroke, hemorrhage, cerebrovascular accident, ADD, and neuropsychiatric syndromes; converting liver stem/progenitor cells into functional pancreatic cells; preventing beta-cell deterioration and stimulation of beta-cell proliferation; treating pancreatitis; treating obesity; suppressing appetite and inducing satiety; treating irritable bowel syndrome or inflammatory bowel disease such as Crohn's disease and ulcerative colitis; reducing the morbidity and/or mortality associated with myocardial infarction and stroke; treating acute coronary syndrome characterized by an absence of Q-wave myocardial infarction; attenuating post-surgical catabolic changes; treating hibernating myocardium or diabetic cardiomyopathy; suppressing plasma blood levels of norepinepherine; increasing urinary sodium excretion, decreasing urinary potassium concentration; treating conditions or disorders associated with toxic hypervolemia, e.g., renal failure, congestive heart failure, nephrotic syndrome, cirrhosis, pulmonary edema, and hypertension; inducing an inotropic response and increasing cardiac contractility; treating polycystic ovary syndrome; treating respiratory distress; improving nutrition via a non-alimentary route, i.e., via intravenous, subcutaneous, intramuscular, peritoneal, or other injection or infusion; treating nephropathy; treating left ventricular systolic dysfunction, e.g., with abnormal left ventricular ejection fraction; inhibiting antro-duodenal motility, e.g., for the treatment or prevention of gastrointestinal disorders such as diarrhea, postoperative dumping syndrome and irritable bowel syndrome, and as premedication in endoscopic procedures; treating critical illness polyneuropathy (CIPN) and systemic inflammatory response syndrome (SIRS); modulating triglyceride levels and treating dyslipidemia; treating organ tissue injury (e.g. brain tissue injury) caused by reperfusion of blood flow following ischemia; improving the function of ischemic and reperfused brain tissue; treating coronary heart disease risk factor (CHDRF) syndrome. Further diseases which can benefit from an elevated GLP-1 level, include, but are not limited to, ischemic myocardial stunning; ishemic/reperfusion injury; acute myocardial infarction; left ventricular dysfunction; vascular disease; neuropathy, including periphere sensoric neuropathy associated with type II diabetes; bone-related disorders, including osteoporosis, obesity, diabetes. Because of the effect on GLP-1, the DGAT inhibitors can also be used to provide cardioprotection.

References supporting the above indications include Experimental Neurology, Vol. 203(2), pp 293-301 (2007); U.S. Pat. No. 7,186,683; J. Pharm. Exp. Ther. vol. 312, No. 1, pp 303-308 (2005); Diabetes, vol. 54, pp 146-151 (2005); US2007/0021339, which are incorporated herein by reference.

In view of the DGAT inhibitory activity, in particular the DGAT1 inhibitory activity, the present compounds of formula (I), their N-oxide forms, their pharmaceutically acceptable salts or their solvates, can be used as a medicine. In particular, the present invention relates to a compound of formula (I), a N-oxide form thereof, a pharmaceutically acceptable salt thereof or a solvate thereof for use as a medicine, in particular for use as a medicine for the prevention or the treatment of a disease which can benefit from an elevated GLP-1 level. In particular, the present invention also relates to the use of a compound of formula (I) for the manufacture of a medicament for the prevention or the treatment of a disease which can benefit from an elevated GLP-1 level, such as the diseases and disorders mentioned above.

In view of the above-described utility for a DGAT inhibitor, in particular a DGAT1 inhibitor, there is provided a method of treating a warm-blooded mammal, including a human, suffering from or a method of preventing a warm-blooded mammal, including a human, to suffer from a disease which can benefit from an elevated level of GLP-1, in particular a method of treating a warm-blooded mammal, including a human, suffering from a disease which can benefit from an elevated level of GLP-1. Said methods comprise the administration of an effective amount of a DGAT inhibitor, in particular a DGAT1 inhibitor, to a warm-blooded mammal, including a human.

In view of the DGAT inhibitory activity of the compounds of formula (I), there is provided a method of treating a warm-blooded mammal, including a human, suffering from or a method of preventing a warm-blooded mammal, including a human, to suffer from a disease which can benefit from an elevated level of GLP-1, in particular a method of treating a warm-blooded mammal, including a human, suffering from a disease which can benefit from an elevated level of GLP-1. Said methods comprise the administration of an effective amount of a compound of formula (I), a N-oxide form thereof, a pharmaceutically acceptable salt thereof or a solvate thereof, to a warm-blooded mammal, including a human.

In view of the DGAT inhibitory activity, in particular the DGAT1 inhibitory activity, the present invention also relates to a compound of formula (I), a N-oxide form thereof, a pharmaceutically acceptable salt thereof or a solvate thereof for use as a medicine, in particular for use as a medicine for the prevention or the treatment of a diseases which can benefit from inhibition of DGAT, in particular DGAT1. The invention also relates to the use of a compound of formula (I), a N-oxide form thereof, a pharmaceutically acceptable salt thereof or a solvate thereof, for the manufacture of a medicament for the prevention or the treatment of a disease or disorder which can benefit from inhibition of DGAT, in particular DGAT1. Diseases or disorders which can benefit from inhibition of DGAT, in particular DGAT1 include, but are not limited to metabolic disorders, such as obesity and obesity related disorders (including peripheral vascular disease, cardiac failure, myocardial ischaemia, cerebral ischaemia, cardiac myopathies), diabetes, in particular type II diabetes mellitus, and complications arising therefrom (such as retinopathy, neuropathy, nephropathy), syndrome X, insulin resistance, impaired glucose tolerance, conditions of impaired fasting glucose, hypoglycemia, hyperglycemia, hyperuricemia, hyperinsulinemia, pancreatitis, hypercholesterolemia, hyperlipidemia, dyslipidemia, mixed dyslipidemia, hypertriglyceridemia and nonalcoholic fatty liver disease, fatty liver, increased mesenteric fat, non-alcoholic steatohepatitis, liver fibrosis, metabolic acidosis, ketosis, dysmetabolic syndrome; dermatological conditions such as acne, psoriasis; cardiovascular diseases, such as atherosclerosis, arteriosclerosis, acute heart failure, congestive heart failure, coronary artery disease, cardiomyopathy, myocardial infarction, angina pectoris, hypertension, hypotension, stroke, ischemia, ischemic reperfusion injury, aneurysm, restenosis and vascular stenosis; neoplastic diseases, such as solid tumors, skin cancer, melanoma, lymphoma and endothelial cancers, e.g., breast cancer, lung cancer, colorectal cancer, stomach cancer, other cancers of the gastrointestinal tract (e.g., esophageal cancer and pancreatic cancer), prostate cancer, kidney cancer, liver cancer, bladder cancer, cervical cancer, uterine cancer, testicular cancer and ovarian cancer; and other diseases and conditions that are sensitive or responsive to modulation, in particular inhibition, of DGAT function, in particular DGAT1 function.

Particular diseases or disorders which can benefit from inhibition of DGAT, in particular DGAT1, are selected from obesity, hypercholesterolemia, hyperlipidemia, dyslipidemia, mixed dyslipidemia, hypertriglyceridemia, fatty liver, nonalcoholic fatty liver disease, liver fibrosis, non-alcoholic steatohepatitis and diabetes, in particular type II diabetes.

In view of the DGAT inhibitory activity of the compounds of formula (I), there is provided a method of treating a warm-blooded mammal, including a human, suffering from or a method of preventing a warm-blooded mammal, including a human, to suffer from a disease which can benefit from inhibition of DGAT, in particular a method of treating a warm-blooded mammal, including a human, suffering from a disease which can benefit from inhibition of DGAT. Said methods comprise the administration of an effective amount of a compound of formula (I), a N-oxide form thereof, a pharmaceutically acceptable salt thereof or a solvate thereof, to a warm-blooded mammal, including a human.

The present invention also provides compositions for preventing or treating a disease which can benefit from an elevated GLP-1 level or which can benefit from inhibition of DGAT, in particular DGAT1, in particular for treating a disease which can benefit from elevated GLP-1 levels or which can benefit from inhibition of DGAT, in particular DGAT1. Said compositions comprise a therapeutically effective amount of a compound of formula (I), a N-oxide form thereof, a pharmaceutically acceptable salt thereof or a solvate thereof, and a pharmaceutically acceptable carrier.

The compounds of the present invention may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations, which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

The compounds of the present invention may also be administered via inhalation or insufflation by means of methods and formulations employed in the art for administration via this way. Thus, in general the compounds of the present invention may be administered to the lungs in the form of a solution, a suspension or a dry powder. Any system developed for the delivery of solutions, suspensions or dry powders via oral or nasal inhalation or insufflation are suitable for the administration of the present compounds.

The compounds of the present invention may also be topically administered in the form of drops, in particular eye drops. Said eye drops may be in the form of a solution or a suspension. Any system developed for the delivery of solutions or suspensions as eye drops are suitable for the administration of the present compounds.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

Depending on the mode of administration, the pharmaceutical composition will preferably comprise from 0.05 to 99% by weight, more preferably from 0.1 to 70% by weight, even more preferably from 0.1 to 50% by weight of the compound of formula (I), and, from 1 to 99.95% by weight, more preferably from 30 to 99.9% by weight, even more preferably from 50 to 99.9% by weight of a pharmaceutically acceptable carrier, all percentages being based on the total weight of the composition.

In view of the above described effects of DGAT inhibitors and/or the effect on GLP-1 levels by DGAT inhibitors, the present invention also relates to a) a combination of a DGAT inhibitor, in particular a DGAT1 inhibitor, more in particular a compound of formula (I), a N-oxide form thereof, a pharmaceutically acceptable salt thereof or a solvate thereof, and a dipeptidyl peptidase-4 inhibitor (DPP-4 inhibitor).

DPP-4 is a membrane-spanning cell surface aminopeptidase widely expressed in many tissues, such as liver, lung, kidney, intestinal brush-border membranes, lymphocytes, endothelial cells. DPP-4 cleaves peptides with a proline or alanine residue in the second aminoterminal position. Many gastro-intestinal hormones are substrates for DPP-4, among them GLP-1. A DPP-4 inhibitor thus inhibits cleavage of GLP-1 and hence provides for an increase in the level of GLP-1. Therefore, a combination as indicated above can be used to combine the activity of the DGAT inhibitor and the DPP4 inhibitor in order to elevate GLP-1 levels. By administering a DGAT inhibitor, in particular a DGAT1 inhibitor, more in particular a compound of formula (I), a N-oxide thereof, a pharmaceutically acceptable salt thereof or a solvate thereof, with a DPP4 inhibitor, different mechanisms may be targeted in order to achieve elevated levels of GLP-1. In this way, the use of such a combination may reduce the dosage of the DGAT inhibitor and the DPP4 inhibitor required for a desired elevation in GLP-1 level as compared to when the DGAT inhibitor or the DPP4 inhibitor is administered as a monotherapy. Therefore, these combinations may reduce or eliminate side effects of monotherapy while not interfering with the GLP-1 level increasing activity. Also, the combination of a DGAT inhibitor, in particular a DGAT1 inhibitor, more in particular a compound of formula (I), a N-oxide form thereof, a pharmaceutically acceptable salt thereof or a solvate thereof, and a DPP4 inhibitor can be used as a medicine. The present invention also relates to a product comprising (a) a DGAT inhibitor, in particular a DGAT1 inhibitor, more in particular a compound of formula (I), a N-oxide form thereof, a pharmaceutically acceptable salt thereof or a solvate thereof, and (b) a DPP4 inhibitor, as a combined preparation for simultaneous, separate or sequential use in the treatment of a disease which can benefit from an elevated level of GLP-1. The different drugs of such a combination or product may be combined in a single preparation together with pharmaceutically acceptable carriers or they may each be present in a separate preparation together with pharmaceutically acceptable carriers. Said DPP4 inhibitor which may be combined with a DGAT inhibitor according to the present invention, in particular a DGAT1 inhibitor, may be a known DPP4 inhibitor such as for example sitagliptin, vildagliptin, and saxagliptin.

b) a combination of a DGAT inhibitor, in particular a DGAT1 inhibitor, more in particular a compound of formula (I), a N-oxide form thereof, a pharmaceutically acceptable salt thereof or a solvate thereof, and a GLP-1 analogue. Said GLP-1 analogue can be considered as an agonist at the GLP-1 receptor.

Also, the combination of a DGAT inhibitor, in particular a DGAT1 inhibitor, more in particular a compound of formula (I), a N-oxide form thereof, a pharmaceutically acceptable salt thereof or a solvate thereof, and a GLP-1 analogue can be used as a medicine. The present invention also relates to a product containing (a) a DGAT inhibitor, in particular a DGAT1 inhibitor, more in particular a compound of formula (I), a N-oxide form thereof, a pharmaceutically acceptable salt thereof or a solvate thereof, and (b) a GLP-1 analogue, as a combined preparation for simultaneous, separate or sequential use in the treatment of a disease which can benefit from an elevated level of GLP-1. The different drugs of such a combination or product may be combined in a single preparation together with pharmaceutically acceptable carriers or they may each be present in a separate preparation together with pharmaceutically acceptable carriers.

Said GLP-1 analogue which may be combined with a DGAT inhibitor according to the present invention may be a known GLP-1 analogue such as for example exenatide, exenatide LAR or liraglutide.

c) a combination of a DGAT inhibitor, in particular a DGAT1 inhibitor, more in particular a compound of formula (I), a N-oxide form thereof, a pharmaceutically acceptable salt thereof or a solvate thereof, and an anti-diabeticum.

Also, the combination of a DGAT inhibitor, in particular a DGAT1 inhibitor, more in particular a compound of formula (I), a N-oxide form thereof, a pharmaceutically acceptable salt thereof or a solvate thereof, and an anti-diabeticum can be used as a medicine. The present invention also relates to a product containing (a) a DGAT inhibitor, in particular a DGAT1 inhibitor, more in particular a compound of formula (I), a N-oxide form thereof, a pharmaceutically acceptable salt thereof or a solvate thereof, and (b) an anti-diabeticum, as a combined preparation for simultaneous, separate or sequential use in the treatment of a disease which can benefit from an elevated level of GLP-1 or DGAT inhibition, such as for example diabetes, in particular type II diabetes. The different drugs of such a combination or product may be combined in a single preparation together with pharmaceutically acceptable carriers or they may each be present in a separate preparation together with pharmaceutically acceptable carriers. Said anti-diabeticum which may be combined with a DGAT inhibitor according to the present invention may be a known anti-diabeticum such as for example metformin, glibenclamide, rosiglitazon, pioglitazon, repaglinide, glimepiride, acarbose, glicazide, glipizide, nateglinide, tolbutamide, a protein tyrosine phosphatase 1 inhibitor, or a 11-beta-hydroxysteroid dehydrogenase inhibitor.

d) a combination of a DGAT inhibitor, in particular a DGAT1 inhibitor, more in particular a compound of formula (I), a N-oxide form thereof, a pharmaceutically acceptable salt thereof or a solvate thereof, and a phosphodiesterase (PDE) inhibitor, in particular a PDE10A or PDE11A inhibitor. Phosphodiesterase (PDE) inhibitors, in particular PDE10A or PDE11A inhibitors, are known to be insulin secretagogues, and to enhance the signalling of GLP-1 by inhibition of the hydrolysis of cAMP. Also, the combination of a DGAT inhibitor, in particular a DGAT1 inhibitor, more in particular a compound of formula (I), a N-oxide form thereof, a pharmaceutically acceptable salt thereof or a solvate thereof, and a phosphodiesterase (PDE) inhibitor, in particular a PDE10A or PDE11A inhibitor, can be used as a medicine. The present invention also relates to a product containing (a) a DGAT inhibitor, in particular a DGAT1 inhibitor, more in particular a compound of formula (I), a N-oxide form thereof, a pharmaceutically acceptable salt thereof or a solvate thereof, and (b) a phosphodiesterase (PDE) inhibitor, in particular a PDE10A or PDE11A inhibitor, as a combined preparation for simultaneous, separate or sequential use in the treatment of a disease which can benefit from an elevated level of GLP-1 or DGAT inhibition, such as for example diabetes, in particular type II diabetes, or obesity. The different drugs of such a combination or product may be combined in a single preparation together with pharmaceutically acceptable carriers or they may each be present in a separate preparation together with pharmaceutically acceptable carriers. Said phosphodiesterase (PDE) inhibitor, in particular a PDE10A or PDE11A inhibitor, which may be combined with a DGAT inhibitor according to the present invention may be a known PDE inhibitor such as for example papaverine, PQ-10, dipyridamole, ibudilast or tadalafil.

e) a combination of a DGAT inhibitor, in particular a DGAT1 inhibitor, more in particular a compound of formula (I), a N-oxide form thereof, a pharmaceutically acceptable salt thereof or a solvate thereof, and an appetite suppressant.

Also, the combination of a DGAT inhibitor, in particular a DGAT1 inhibitor, more in particular a compound of formula (I), a N-oxide form thereof, a pharmaceutically acceptable salt thereof or a solvate thereof, and an appetite suppressant can be used as a medicine. The present invention also relates to a product containing (a) a DGAT inhibitor, in particular a DGAT1 inhibitor, more in particular a compound of formula (I), a N-oxide form thereof, a pharmaceutically acceptable salt thereof or a solvate thereof, and (b) an appetite suppressant, as a combined preparation for simultaneous, separate or sequential use in the treatment of a disease which can benefit from an elevated level of GLP-1 or DGAT inhibition, such as for example diabetes, in particular type II diabetes, or obesity. The different drugs of such a combination or product may be combined in a single preparation together with pharmaceutically acceptable carriers or they may each be present in a separate preparation together with pharmaceutically acceptable carriers. Said appetite suppressants, which may be combined with a DGAT inhibitor according to the present invention may be a known appetite suppressant such as for example sibutramine and phentermine.

f) a combination of a DGAT inhibitor, in particular a DGAT1 inhibitor, more in particular a compound of formula (I), a N-oxide form thereof, a pharmaceutically acceptable salt thereof or a solvate thereof, and an anti-obesity drug with a CNS (central nervous system) mode of action such as for example a CB1 antagonist or inverse agonists.

Also, the combination of a DGAT inhibitor, in particular a DGAT1 inhibitor, more in particular a compound of formula (I), a N-oxide form thereof, a pharmaceutically acceptable salt thereof or a solvate thereof, and an anti-obesity drug with a CNS (central nervous system) mode of action can be used as a medicine. The present invention also relates to a product containing (a) a DGAT inhibitor, in particular a DGAT1 inhibitor, more in particular a compound of formula (I), a N-oxide form thereof, a pharmaceutically acceptable salt thereof or a solvate thereof, and (b) an anti-obesity drug with a CNS (central nervous system) mode of action, as a combined preparation for simultaneous, separate or sequential use in the treatment of a disease which can benefit from an elevated level of GLP-1 or DGAT inhibition, such as for example diabetes, in particular type II diabetes, or obesity. The different drugs of such a combination or product may be combined in a single preparation together with pharmaceutically acceptable carriers or they may each be present in a separate preparation together with pharmaceutically acceptable carriers. Said anti-obesity drugs with a CNS (central nervous system) mode of action, which may be combined with a DGAT inhibitor according to the present invention may be a known a anti-obesity drug such as for example Rimonabant, orlistat, SLV-319, or MK-0364.

g) a combination of a DGAT inhibitor, in particular a DGAT1 inhibitor, more in particular a compound of formula (I), a N-oxide form thereof, a pharmaceutically acceptable salt thereof or a solvate thereof, and an hypolipidemic drug such as for example 3-hydroxy-3-methyl-glutaryl coenzyme A (HMG-CoA) reductase inhibitors, squalene synthase inhibitors, FXR (farnesoid X receptor) and LXR (liver X receptor) ligands, cholestyramine, fibrates, nicotinic acid and aspirin.

Also, the combination of a DGAT inhibitor, in particular a DGAT1 inhibitor, more in particular a compound of formula (I), a N-oxide form thereof, a pharmaceutically acceptable salt thereof or a solvate thereof, and an hypolipidemic drug can be used as a medicine. The present invention also relates to a product containing (a) a DGAT inhibitor, in particular a DGAT1 inhibitor, more in particular a compound of formula (I), a N-oxide form thereof, a pharmaceutically acceptable salt thereof or a solvate thereof, and (b) an hypolipidemic drug, as a combined preparation for simultaneous, separate or sequential use in the treatment of a disease which can benefit from an elevated level of GLP-1 or DGAT inhibition, such as for example diabetes, in particular type II diabetes, or obesity. The different drugs of such a combination or product may be combined in a single preparation together with pharmaceutically acceptable carriers or they may each be present in a separate preparation together with pharmaceutically acceptable carriers. Said hypolipidemic drug which may be combined with a DGAT inhibitor according to the present invention may be a known hypolipidemic drug such as for example lovastatin, pravastatin, simvastatin, pravastatin, cerivastatin, mevastatin, velostatin, fluvastatin, dalvastatin, atorvastatin, rosuvastatin and rivastatin.

h) a combination of a DGAT inhibitor, in particular a DGAT1 inhibitor, more in particular a compound of formula (I), a N-oxide form thereof, a pharmaceutically acceptable salt thereof or a solvate thereof, and an agonist of peroxisome proliferator-activator receptor such as for example fenofibrate.

Also, the combination of a DGAT inhibitor, in particular a DGAT1 inhibitor, more in particular a compound of formula (I), a N-oxide form thereof, a pharmaceutically acceptable salt thereof or a solvate thereof, and an agonist of peroxisome proliferator-activator receptor such as for example fenofibrate, can be used as a medicine. The present invention also relates to a product containing (a) a DGAT inhibitor, in particular a DGAT1 inhibitor, more in particular a compound of formula (I), a N-oxide form thereof, a pharmaceutically acceptable salt thereof or a solvate thereof, and (b) an agonist of peroxisome proliferator-activator receptor such as for example fenofibrate, as a combined preparation for simultaneous, separate or sequential use in the treatment of a disease which can benefit from an elevated level of GLP-1 or DGAT inhibition, such as for example diabetes, in particular type II diabetes, or obesity. The different drugs of such a combination or product may be combined in a single preparation together with pharmaceutically acceptable carriers or they may each be present in a separate preparation together with pharmaceutically acceptable carriers.

i) a combination of a DGAT inhibitor, in particular a DGAT1 inhibitor, more in particular a compound of formula (I), a N-oxide form thereof, a pharmaceutically acceptable salt thereof or a solvate thereof, and an antihypertensive agent.

Also, the combination of a DGAT inhibitor, in particular a DGAT1 inhibitor, more in particular a compound of formula (I), a N-oxide form thereof, a pharmaceutically acceptable salt thereof or a solvate thereof, and an antihypertensive agent, can be used as a medicine. The present invention also relates to a product containing (a) a DGAT inhibitor, in particular a DGAT1 inhibitor, more in particular a compound of formula (I), a N-oxide form thereof, a pharmaceutically acceptable salt thereof or a solvate thereof, and (b) an antihypertensive agent, as a combined preparation for simultaneous, separate or sequential use in the treatment of a disease which can benefit from an elevated level of GLP-1 or DGAT inhibition, such as for example diabetes, in particular type II diabetes, or obesity. The different drugs of such a combination or product may be combined in a single preparation together with pharmaceutically acceptable carriers or they may each be present in a separate preparation together with pharmaceutically acceptable carriers. Said anti-hypertensive agent which may be combined with a DGAT inhibitor according to the present invention may be a known anti-hypertensive agent, e g loop diuretics such as ethacrynic acid, furosemide and torsemide, angiotensin converting enzyme (ACE) inhibitors such as benazepril, captopril, enalapril, fosinopril, lisinopril, moexipril, perinodopril, quinapril, ramipril and trandolapril; inhibitors of the Na-K-ATPase membrane pump such as digoxin; neutralendopeptidase (NEP) inhibitors; ACE/NEP inhibitors such as omapatrilat, sampatrilat and fasidotril; angiotensin II antagonists such as candesartan, eprosartan, irbesartan, losartan, telmisartan and valsartan, in particular valsartan; renin inhibitors such as ditekiren, zankiren, terlakiren, aliskiren, RO 66-1132 and RO-66-1168; β-adrenergic receptor blockers such as acebutolol, atenolol, betaxolol, bisoprolol, metoprolol, nadolol, propranolol, sotalol and timolol; inotropic agents such as digoxin, dobutamine and milrinone; calcium channel blockers such as amlodipine, bepridil, diltiazem, felodipine, nicardipine, nimodipine, nifedipine, nisoldipine and verapamil; aldosterone receptor antagonists; and aldosterone synthase inhibitors.

The following examples are intended to illustrate the present invention.

Experimental Part

Hereinafter, the term 'm.p." means melting point, 'THF' means tetrahydrofuran, 'EtOAc' means ethyl acetate, 'MeOH' means methanol, 'HOBT' means 1-hydroxy-1H-benzotriazole, 'DIPE' means diisopropyl ether, 'DMF' means N,N-dimethylformamide, 'Et$_3$N' or 'TEA' means triethylamine, 'DPPENT' means 1,1'-(1,5-pentanediyl)bis[1,1'-diphenylphosphine], "resin-linked-N=C=O" means a polystyrene based resin functionalized with icocyanato-groups such as for example 1-ethenyl-4-(isocyanatomethyl)-benzene polymer with ethenylbenzene, "PS-Carbodiimide" means polystyrene resin-bound N-cyclohexylcarbodiimide, "DCM" means dichloromethane, "TBTU" means 1-[bis (dimethylamino)methylene]-1H-benzotriazolium tetrafluoroborate(1-)3-oxide, "MP-carbonate" is macroporous triethylammonium methylpolystyrene carbonate (a macroporous polystyrene anion-exchange resin that is a resin-bound equivalent of tetraalkylammonium carbonate), "DECP" means diethyl cyanophosphonate, "DIPEA" means diisopropylethylamine, "TFA" means trifluoro acetic acid, "NBS" means N-bromosuccinimide, "AIBN" means 2,2'-azobis[isobutyronitrile] and "HBTU" means 1-[bis(dimethylamino)methylene]-1H-benzotriazoliumhexafluorophosphate(1-)3-oxide.

MiniBlock™ (Mettler Toledo) is a flexible, easy to use tool designed for parallel synthesis.

ArgoScoop™ resin (Biotage) dispenser is a variable volumn resin scoop designed for convenient dispensing of polymer scavengers and reagents.

For some compounds that were purified by reversed phase high-performance liquid chromatography (HPLC) the used method is described below (indicated in the compound procedure with HPLC method A). When necessary, this method can be slightly adjusted by a person skilled in the art to obtain a more optimal result for the separation.

HPLC Method A

The product was purified by reversed-phase high-performance liquid chromatography (Shandon Hyperprep® C18 BDS (Base Deactivated Silica) 8 µm, 250 g, I.D. 5 cm). Two mobile phases were used (phase A: 90% of a 0.5% $NH_4OAc$ solution in water+10% $CH_3CN$; phase B: $CH_3CN$). First, 85% A and 15% B with a flow rate of 40 ml/min was hold for 0.5 minutes. Then a gradient was applied to 10% A and 90% B in 41 minutes with a flow rate of 80 ml/min. Then a gradient was applied to 100% B in 20 minutes with a flow rate of 80 ml/min and hold for 4 minutes.

A. Preparation of the Intermediates

Example A1 a. Preparation of Intermediate 1

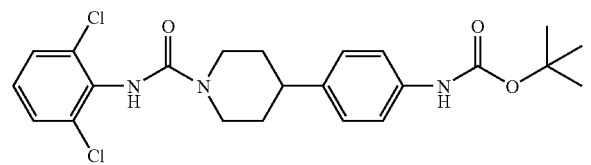 [SMILES: CC(C)(C)OC(=O)Nc1ccc(C2CCN(C(=O)Nc3c(Cl)cccc3Cl)CC2)cc1]

A mixture of [4-(4-piperidinyl)phenyl]carbamic acid 1,1-dimethylethylester (0.025 mol) in $CH_2Cl_2$ (100 ml) was stirred while cooling on an ice-bath. A solution of 1,3-dichloro-2-isocyanatobenzene (0.027 mol) in $CH_2Cl_2$ (25 ml) was added dropwise. The reaction mixture was allowed to warm to room temperature. The reaction mixture was stirred for one hour at room temperature. The resulting precipitate was filtered off, washed with DIPE and dried. Yield: 6.2 g of intermediate 1. The corresponding filtrate's solvent was evaporated. The residue was triturated under DIPE, filtered off and dried. Yield: 4.2 g of intermediate 1.

b. Preparation of Intermediate 2

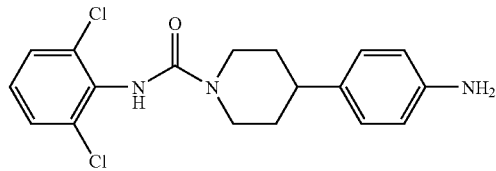

A mixture of intermediate 1 (prepared according to A1.a) (0.022 mol) and trifluoroacetic acid (25 ml) in $CH_2Cl_2$ (250 ml) was stirred for 2 hours at room temperature. The solvent was evaporated. The residue was triturated under DIPE, filtered off and dried. This fraction (11.2 g) was converted into the free base by adding aqueous ammonia. This mixture was extracted with DCM. The separated organic layer was dried, filtered and the solvent evaporated. Yield: 7.6 g of intermediate 2.

c. Preparation of Intermediate 3

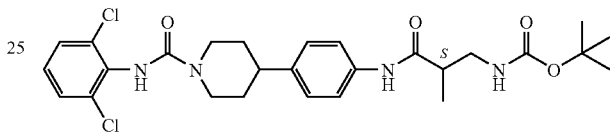

3-[[(1,1-dimethylethoxy)carbonyl]amino]-2-methylpropanoic acid (0.001 mol) was dissolved in DMF (5 ml) to get stock solution (I). Part of stock solution (I) (1.2 ml, containing 0.00024 mol of 3-[[(1,1-dimethylethoxy)carbonyl]amino]-2-methylpropanoic acid was put into the MiniBlock. PS-Carbodiimide, 1.9 mmol/g (0.0004 mol) was added with ArgoScoop. A solution of 1-hydroxy-M-benzotriazole (0.00030 mol) in DMF (1 ml) was added and the mixture was shaken for 30 minutes. A solution of intermediate 2 (prepared according to A1.b) (0.0002 mol) in DMF (3.5 ml) was added and the reaction mixture was shaken overnight. MP-carbonate, 2.8 mmol/g (0.00090 mol) and resin-linked-N=C=O, 1.8 mmol/g (0.0002 mol) were added with ArgoScoop. The reaction mixture was shaken overnight, then filtered. DCM (4 ml) was added and the mixture was shaken for 2 hours. The mixture was filtered and the filtrate's solvent was evaporated (Genevac). The residue was purified by HPLC. The product fractions were collected and worked-up. Yield: 0.066 g of intermediate 3 (S-enantiomer).

d. Preparation of Intermediate 25

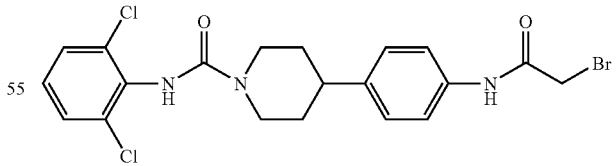

A mixture of intermediate 2 (prepared according to A1.b) (0.00027 mol) and $Et_3N$ (0.0004 mol) in $CH_2Cl_2$ (5 ml) was stirred and cooled on an ice-bath. Bromoacetylchloride (0.00027 mol) was added dropwise. The reaction mixture was stirred for one hour while cooling on the ice-bath. The solvent was evaporated. The residue was triturated under $CH_3CN$/DIPE. The precipitate was filtered off and dried, yielding intermediate 25 (used as such in the next reaction step).

Example A2 a. Preparation of Intermediate 4

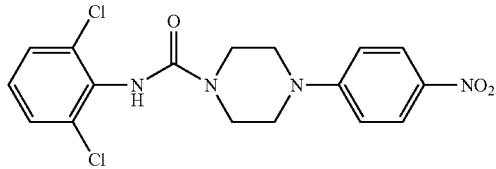 [SMILES: O=C(Nc1c(Cl)cccc1Cl)N1CCN(c2ccc([N+](=O)[O-])cc2)CC1]

A mixture of 1-(4-nitrophenyl)-piperazine (0.02413 mol) in CH$_2$Cl$_2$ p.a. (100 ml) was stirred on an ice bath. Then 1,3-dichloro-2-isocyanatobenzene (0.02660 mol) in DCM p.a. (20 ml) was added dropwise while the reaction mixture was stirred on the ice bath. For 2 hours, the reaction mixture was let to warm up to room temperature and was stirred at room temperature. The reaction mixture was filtered off and washed with DIPE (q.s.). The precipitate was dried in vacuo. Yield: 8.923 g of intermediate 4 (94%; yellow powder)

b. Preparation of Intermediate 5

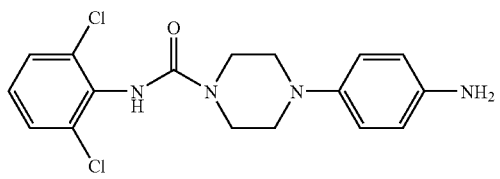 [SMILES: Nc1ccc(N2CCN(C(=O)Nc3c(Cl)cccc3Cl)CC2)cc1]

A mixture of intermediate 4 (prepared according to A2.a) (0.047 mol) in CH$_3$OH (200 ml), THF (200 ml) and NH$_3$ in CH$_3$OH (100 ml) was stirred for 15 minutes at room temperature and then hydrogenated at room temperature (atmospheric pressure) with Pt/C 5% (4 g) as a catalyst in the presence of thiophene solution (3 ml; 4% in DIPE). After uptake of H$_2$ (3 equiv), the catalyst was filtered off (the product was also a precipitate and was therefore dissolved by washing the filter residue with DCM). The combined filtrate's solvent was evaporated. Yield: 14.616 g of intermediate 5.

c. Preparation of Intermediate 26

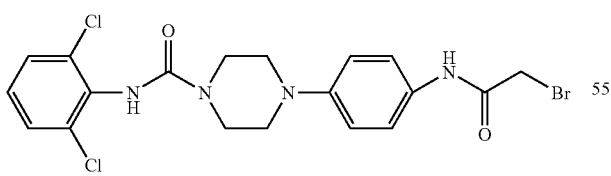

Et$_3$N (1100 ml) was added to a solution of intermediate 5 (0.006023 mol) in DMF (20 ml). 2-bromoacetylbromide (0.007228 mol) was added dropwise at stirring. The reaction mixture was stirred for 3 hours at room temperature, after that 50 ml of water was added. The formed precipitate was filtered off and washed with water. Yield: 2.454 g of intermediate 26 (84%) (light-green crystalline).

Example A3 a. Preparation of Intermediate 6

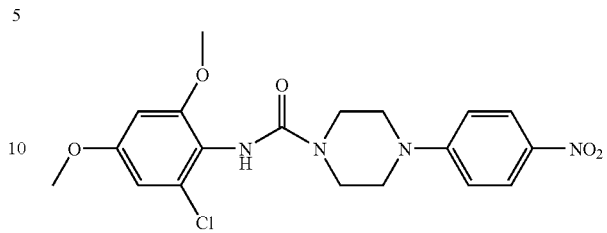

Trichloromethyl carbonochloridic acid ester (0.008 mol) was added dropwise to a solution of 2-chloro-4,6-dimethoxy-benzenamine hydrochloride (0.008 mol) and Et$_3$N (4.1 ml) in dry toluene (100 ml) at stirring. The reaction mixture was stirred at 60° C. for 2 hours till the starting aniline reacted completely (control by TLC). The solution of 1-(4-nitrophenyl)piperazine (1.63 g; 0.008 mol) in DCM (25 ml) was added to the reaction mixture at 60° C. at stirring. The stirring was continued at 60-70° C. for 1 hour. Then, the reaction mixture was concentrated in vacuum. The formed yellow sediment was treated with water and filtered off. Then, it was washed with water, ether and dried on air for 24 hours. Yield: 3.19 g of intermediate 6 (98%; yellow powder).

b. Preparation of Intermediate 7

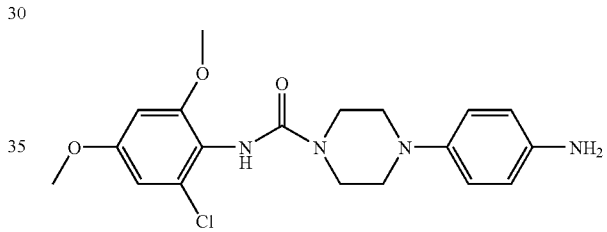

Small portions of Raney nickel were added to a solution of intermediate 6 (0.00757 mol) and hydrazine.H$_2$O (3.5 ml) in methanol (170 ml) at 45° C. and stirring in such a way as to prevent the violent reaction. When the reaction was completed (control by TLC) the catalyst was filtered off and washed with hot methanol (50 ml) and chloroform (70 ml). Washings and filtrate were concentrated in vacuum. The residue was diluted in benzene and concentrated. This procedure was repeated twice. The final compound was triturated with hexane and filtered off. Yield: 2.705 g of intermediate 7 (91%; dark crystalline powder).

Example A4 a. Preparation of Intermediate 8

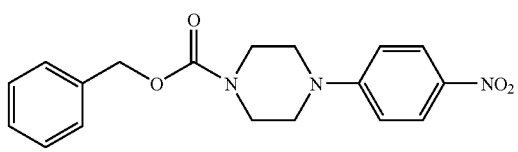 [SMILES: O=C(OCc1ccccc1)N1CCN(c2ccc([N+](=O)[O-])cc2)CC1]

A mixture of 1-(4-nitrophenyl)piperazine (0.244 mol) and NaHCO$_3$ (0.269 mol) in CH$_2$Cl$_2$ (300 ml) was stirred on a cold-water bath. A solution of phenylmethyl carbonochloridic acid ester (0.257 mol) in DCM (60 ml) was added dropwise over one hour. The reaction mixture was stirred further for 20 hours. CH$_3$CN (50 ml) was added. Water (250 ml) was added. The mixture was stirred over the weekend. The layers were separated The separated organic layer was dried (MgSO$_4$), filtered and the solvent evaporated, then co-evaporated with toluene. The residue was stirred in DIPE (250 ml), filtered off, washed, then dried (vacuum, 50° C.). Yield: 77.5 g of intermediate 8 (93%).

b. Preparation of Intermediate 9

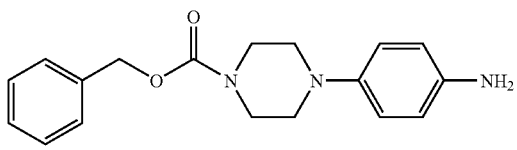 [SMILES: Nc1ccc(N2CCN(C(=O)OCc3ccccc3)CC2)cc1]

A mixture of intermediate 8 (0.23 mol) in CH$_3$OH (150 ml) and THF (150 ml) was hydrogenated at 50° C. with Pt/C, 5% (5 g) as a catalyst. After uptake of H$_2$ (17 l), the catalyst was filtered off and the filtrate was evaporated, then co-evaporated with toluene. The residue was triturated under DIPE (250 ml) and EtOAc (20 ml), then filtered off, washed with DIPE and dried in vacuo at 50° C. Yield: 54.9 g of intermediate 9 (77%).

c. Preparation of Intermediate 10

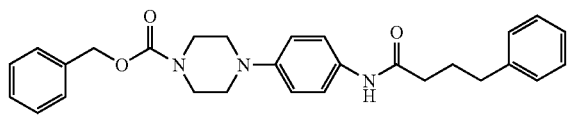 [SMILES: O=C(CCCc1ccccc1)Nc1ccc(N2CCN(C(=O)OCc3ccccc3)CC2)cc1]

A mixture of intermediate 9 (0.115 mol) and NaHCO$_3$ (0.13 mol) in CH$_3$CN (400 ml) was stirred on a water-bath. A solution of benzenebutanoyl chloride (0.12 mol) in CH$_3$CN (50 ml) was added dropwise. The reaction mixture was stirred further at room temperature for 3 days. The mixture was poured out into water (2 l), then stirred for one hour. The precipitate was filtered off, washed with water, then recrystallized from ethanol. The precipitate was filtered off, washed with ethanol, and dried (vacuum, 50° C.). Yield: 45.9 g of intermediate 10 (87%).

c-1. Preparation of Intermediate 37

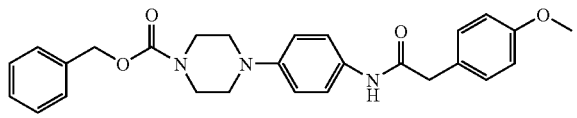 [SMILES: COc1ccc(CC(=O)Nc2ccc(N3CCN(C(=O)OCc4ccccc4)CC3)cc2)cc1]

A blood-red solution of 4-methoxybenzene acetic acid (1.000 g, 0.00602 mol) and SOCl$_2$ (4.4 ml, 0.0602 mol) was stirred for 45 minutes at 60° C. The solution was evaporated and co-evaporated with toluene. The residue was dissolved in DCM (10 ml) and the solution was cooled on an ice-bath. Then intermediate 9 (prepared according to A4.b) (1.875 g, 0.00602 mol) and N,N-diisopropyl-ethanamine (1.50 ml, 0.00903 mol) were added and the reaction mixture was stirred overnight at room temperature. The solution was treated with 5% citric acid (20 ml) and extracted twice with DCM. The combined organic layers were subsequently treated with 10% Na$_2$CO$_3$ (20 ml), resulting in a suspension in the organic layer which was separated, evaporated and co-evaporated. Yield: 2.862 g of intermediate 37 (off white solid; pure; m.p.: 173° C. (DSC method)).

d. Preparation of Intermediate 11

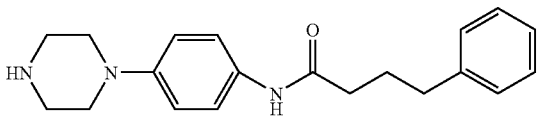 [SMILES: O=C(CCCc1ccccc1)Nc1ccc(N2CCNCC2)cc1]

A solution of intermediate 10 (0.095 mol) in CH$_3$OH, p.a. (500 ml) was hydrogenated in a Parr apparatus (8 pounds pressure) with Pd/C, 10% (5 g) as a catalyst. After uptake of H$_2$ (1 equiv), the catalyst was filtered off and the filtrate was evaporated. Toluene was added and azeotroped on the rotary evaporator. The oily residue solidified upon standing. Except for 1 g, the residue was dried at room temperature in a desiccator under pump vacuum. Yield: 30.4 g intermediate 11 (98.9%).

d-1. Preparation of Intermediate 38

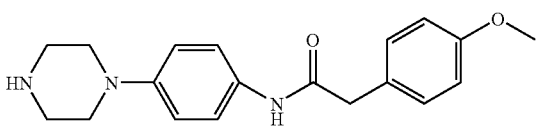

•methanesulfonate

A mixture of intermediate 37 (prepared according to A4.c-1) (2.35 g, 0.00511 mol), Pd/C 10% (0.5 g), methanesulfonic acid (0.5 g, 0.00520 mol), H$_2$ (q.s) and CH$_3$OH (50 ml) was hydrogenated overnight at room temperature. The product was worked-up. Yield: 1.982 g of intermediate 38 (methanesulfonic acid salt) (m.p.: 202° C. (DSC method).

Example A5 a. Preparation of Intermediate 12

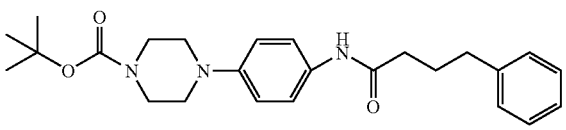 [SMILES: CC(C)(C)OC(=O)N1CCN(c2ccc(NC(=O)CCCc3ccccc3)cc2)CC1]

A mixture of benzenebutanoic acid (0.0113 mol) and SOCl$_2$ (1.17 ml) in CH$_2$Cl$_2$ (20 ml) was refluxed for 2 hours. The solvent was evaporated and co-evaporated 2 times with toluene. The residue was dissolved in CH$_2$Cl$_2$ (20 ml). This mixture was added drop wise at room temperature in 20 minutes to a solution of 4-(4-aminophenyl)-1-piperazinecarboxylic acid 1,1-dimethylethyl ester (0.0094 mol) and Et$_3$N (1.8 ml) in CH$_2$Cl$_2$ (30 ml) and stirred for 91 hours at room temperature. The reaction mixture was extracted with H$_2$O and then washed with Na$_2$CO$_3$ aqueous solution (10%). The separated organic layer was dried (MgSO$_4$), filtered and the solvent was evaporated. The residue was purified by reversed-phase high-performance liquid chromatography. (Shandon Hyperprep® C18 BDS (Base Deactivated Silica) 8 μm, 250 g, I.D. 5 cm). A gradient with the mentioned mobile phases was applied (phase A: a 0.25% NH$_4$HCO$_3$ solution in water; phase B: CH$_3$OH (optional); phase C: CH$_3$CN). The desired product fractions were collected, the solvent was evaporated and co-evaporated with CH$_3$OH. The residue was dissolved in H$_2$O. This mixture was extracted with DCM. The organic layer was dried (MgSO$_4$), filtered and the solvent was evaporated. Yield: 2.012 g of intermediate 12.

b. Preparation of Intermediate 13

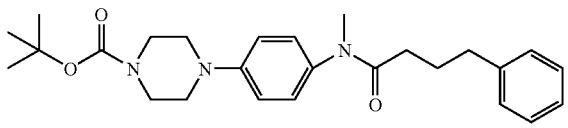 [SMILES: CN(C(=O)CCCc1ccccc1)c1ccc(N2CCN(C(=O)OC(C)(C)C)CC2)cc1]

NaH 60% in paraffine (0.0016 mol) was added to a solution of intermediate 12 (0.0014 mol) in DMF, dry (20 ml) and then stirred for 1 hour at room temperature. CH$_3$I (0.0027 mol) was added to the reaction mixture and stirred for 21 hours. The solvent was evaporated. The residue was partitioned between H$_2$O and CH$_2$Cl$_2$. The separated organic layer was dried (MgSO$_4$), filtered and the solvent was evaporated. The residue was purified by reversed-phase high-performance liquid chromatography. (Shandon Hyperprep® C18 BDS (Base Deactivated Silica) 8 µm, 250 g, I.D. 5 cm). A gradient with the mentioned mobile phases was applied (phase A: a 0.25% NH$_4$HCO$_3$ solution in water; phase B: CH$_3$OH (optional); phase C: CH$_3$CN). The product fractions were collected, the solvent was evaporated and co-evaporated with CH$_3$OH/CH$_3$CN. Yield: 0.444 g of intermediate 13 c. Preparation of Intermediate 14

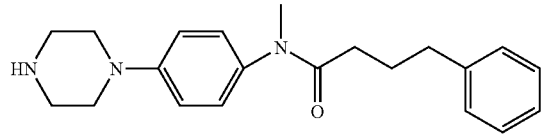 [SMILES: CN(C(=O)CCCc1ccccc1)c1ccc(N2CCNCC2)cc1]

CF$_3$COOH (0.550 ml) was added to a solution of intermediate 13 (0.0007 mol) in CH$_2$Cl$_2$ (10 ml) and the mixture was stirred for 40 hours at room temperature. The reaction mixture was extracted with Na$_2$CO$_3$ aqueous solution (10%). The separated organic layer was dried (MgSO$_4$), filtered and the solvent was evaporated. The residue was purified by reversed-phase high-performance liquid chromatography. (Shandon Hyperprep® C18 BDS (Base Deactivated Silica) 8 µm, 250 g, I.D. 5 cm). A gradient with the mentioned mobile phases was applied (phase A: a 0.25% NH$_4$HCO$_3$ solution in water; phase B: CH$_3$OH (optional); phase C: CH$_3$CN). The product fractions were collected and the solvent was evaporated. Yield: 0.200 g of intermediate 14.

Example A6 a. Preparation of Intermediate 15

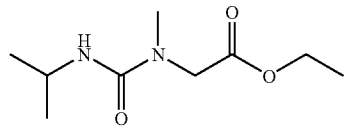

A mixture of compounds N-methylglycine ethyl ester hydrochloride (7.00 mmol) and Et$_3$N (1.033 ml) in acetonitrile (5 ml) was stirred for 20 minutes at room temperature. Compound 2-isocyanatopropane (6.65 mmol) was added dropwise to the reaction mixture and stirring was continued for 5 hours at room temperature. Then the reaction mixture was diluted with DCM (20 ml) and washed with H$_2$O (10 ml). The organic layer was separated, dried over Na$_2$SO$_4$ and concentrated in vacuum. The residue was purified by Flash-chromatography (eluent: ethyl acetate). Yield: 0.908 g of intermediate 15 (64%; yellowish oil).

b. Preparation of Intermediate 16

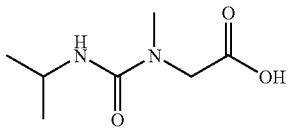

A solution of KOH (6 mmol)) in H$_2$O (3 ml) was added to a solution of intermediate 15 (0.003 mol) in ethanol (3 ml). The reaction mixture was stirred for 18 hours at room temperature. Then the reaction mixture was diluted with H$_2$O (20 ml) and extracted with DCM (5 ml). The aqueous layer was separated, acidified with concentrated HCl to pH=3-4 and extracted with a mixture dichloromethane/ethanol—10/1 (3×5 ml). Combined organic extract was dried over Na$_2$SO$_4$ and concentrated in vacuum. Yield: 0.275 g of intermediate 16 (58%; yellowish oil). It was used in the next step of the synthesis without additional purification.

c. Preparation of Intermediate 17

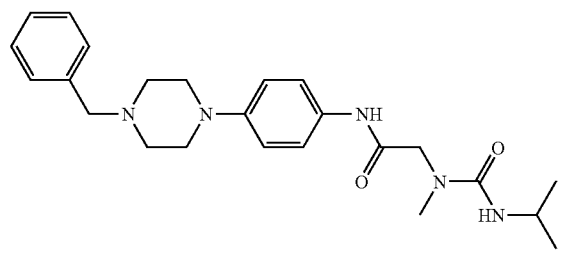 [SMILES: CC(C)NC(=O)N(C)CC(=O)Nc1ccc(N2CCN(Cc3ccccc3)CC2)cc1]

A mixture of intermediate 16 (0.002342 mol), EDCI (0.002253 mol), Et$_3$N (0.582 ml) in THF (20 ml) was stirred for 20 minutes at room temperature. Then compounds 4-[4-(phenylmethyl)-1-piperazinyl]benzenamine (0.001802 mol) and HOBT (0.002253 mol) were added and stirring was continued for 24 hours at room temperature. After that the solvent was evaporated in vacuum, the residue was diluted with water (20 ml), and the formed precipitate was filtered off and washed with water. The washed precipitate was dissolved in a mixture of DCM/ethanol—10/1 (50 ml). This solution was passed through silica gel on Shott's filter. The filtrate was evaporated in vacuum. The residue was triturated with ethyl acetate. The precipitate was filtered off and washed with ethyl acetate. Yield: 0.239 g of intermediate 17 (31%).

d. Preparation of Intermediate 18

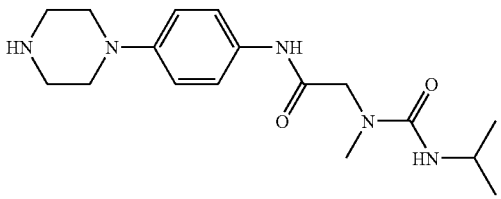 [SMILES: CC(C)NC(=O)N(C)CC(=O)Nc1ccc(N2CCNCC2)cc1]

CH$_3$OH (10 ml) was added to a mixture of intermediate 17 (0.496 mmol), ammonium formate (1.983 mmol) and Pd/C 10% (0.106 g) under argon. The reaction mixture was stirred for 2 hours at 50° C. The catalyst was filtered off and washed with methanol. Combined filtrate was concentrated in vacuum. The residue was dissolved in DCM (30 ml) and washed with water (10 ml). The organic layer was separated, dried over Na₂SO₄ and concentrated in vacuum. The residue was triturated with water; the obtained precipitate was filtered off, washed with water and dried on air. Yield: 0.091 g of intermediate 18 (55%).

Example A7 a. Preparation of Intermediate 19

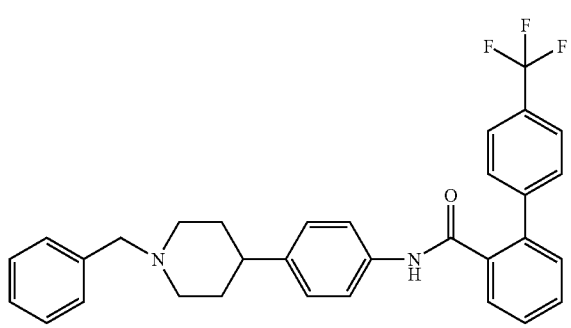 [SMILES: O=C(Nc1ccc(C2CCN(Cc3ccccc3)CC2)cc1)c1ccccc1-c1ccc(C(F)(F)F)cc1]

[4'-(trifluoromethyl)-[1,1'-biphenyl]-2-carboxylic acid (0.09 mol) in CH₂Cl₂ (500 ml) and DMF (5 ml) was stirred. Ethanedioyl dichloride (0.09 mol) was added dropwise. The mixture was stirred for 1 hour to give mixture 1. 4-[1-(phenylmethyl)-4-piperidinyl]-benzenamine.hydrochloride (0.046 mol) in CH₂Cl₂ (500 ml) and Et₃N (20 ml) was stirred on an ice-bath to give mixture 2. Mixture 1 was added dropwise to mixture 2. The resulting mixture was stirred and refluxed overnight, then cooled and washed with water. The organic layer was separated, dried, filtered and the solvent was evaporated. The residue was purified by column chromatography over silica gel (eluent: DCM/CH₃OH 98/2). The desired product fractions were collected and the solvent was evaporated. The residue was triturated in DIPE. The precipitate was filtered off and dried. Yield: 5.6 g of intermediate 19.

b. Preparation of Intermediate 20

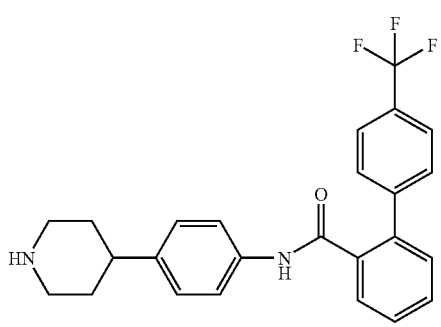 [SMILES: O=C(Nc1ccc(C2CCNCC2)cc1)c1ccccc1-c1ccc(C(F)(F)F)cc1]

A mixture of intermediate 19 (prepared according to A7.a) (0.025 mol) in CH₃OH (250 ml) was hydrogenated at 50° C. overnight with Pd/C 10% (2 g) as a catalyst. After uptake of H₂ (1 equiv), the catalyst was filtered off and the filtrate was evaporated. The residue was triturated in DIPE. The precipitate was filtered off and dried. Yield: 7.7 g of intermediate 20 (73%).

Example A8 a. Preparation of Intermediate 21

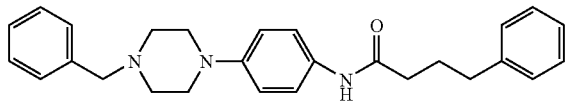 [SMILES: O=C(CCCc1ccccc1)Nc1ccc(N2CCN(Cc3ccccc3)CC2)cc1]

A mixture of benzenebutanoic acid (0.0131 mol) and SOCl₂ (12 ml) was refluxed for 1 hour while stirring. The excess of SOCl₂ was removed in vacuo. The residue was diluted with dry benzene (15 ml) and then concentrated (repeated twice). Then, a solution of acyl chloride in benzene (10 ml) was added dropwise to a mixture of 4-[4-(phenylmethyl)-1-piperazinyl]benzenamine (0.0094 mol), Et₃N (2.8 ml) and dry benzene (45 ml) while stirring. The reaction mixture was refluxed for 3 hours at stirring. Sedimentation was observed. The reaction mixture with formed precipitate was concentrated. Then, residue was partitioned between DCM (60 ml) and 10% aqueous K₂CO₃ (40 ml). The organic layer was separated, washed with water, dried over MgSO₄, and concentrated in vacuum. The residue was triturated with an ether-hexane mixture. The formed precipitate was filtered off and dried on air. Yield: 3.71 g of intermediate 21 (96%).

a-1. Preparation of Intermediate 22

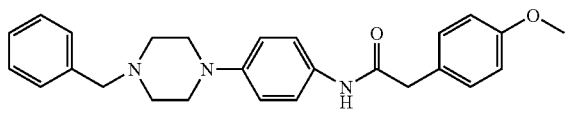 [SMILES: COc1ccc(CC(=O)Nc2ccc(N3CCN(Cc4ccccc4)CC3)cc2)cc1]

Intermediate 22 was prepared according to A8.a except for benzenebutanoic acid which should be replaced by 4-methoxybenzene acetic acid. Yield: 3.9 g (100%) of intermediate 22.

b. Preparation of Intermediate 23

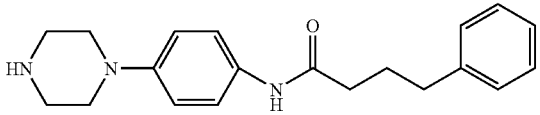

Intermediate 21 (prepared according to A8.a) (0.0897 mol) was dissolved in methanol (350 ml) and stirred for 1 hour under reflux (bad solubility). Then Pd/C 10% (0.6 g) and NH₄HCO₃ (4 g) were added to the reaction mixture. The resulting mixture was refluxed for 4 hours. An additional amount of Pd/C 10% (0.2 g) and NH₄HCO₃ (2 g) were added. The resulting mixture was refluxed for 4 hours more. Then, the catalyst was filtered off on a paper filter. The filtrate was concentrated in vacuum. The residue was diluted with CH₂Cl₂ (100 ml) and washed with K₂CO₃ (50 ml 10% solution). The organic layer was separated, washed with water, dried over MgSO₄, and concentrated in vacuum. Yield: 2.437 g (80%) of intermediate 23 (greenish solid compound). (According to LC/MS the N-formyl derivative was found in the target product, approximately 7%).

c. Preparation of Intermediate 24

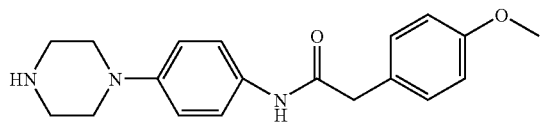 [SMILES: COc1ccc(CC(=O)Nc2ccc(N3CCNCC3)cc2)cc1]

Intermediate 22 (0.0939 mol) (prepared according to A8.a-1) was dissolved in methanol (350 ml) and stirred for 1 hour under reflux. Then Pd/C 10% (0.8 g) and $NH_4HCO_3$ (0.088 mol) were added to the reaction mixture. The resulting mixture was refluxed for 4 hours. The catalyst was filtered off by a paper filter. The filtrate was concentrated in vacuum. The residue was diluted in DCM (100 ml) and washed with $K_2CO_3$ (50 ml 10% solution). The organic layer was separated, washed with water, dried over $MgSO_4$, and concentrated in vacuum. Yield: 2.503 g (81%) of crude intermediate 24 was obtained as a solid. According to LC/MS, the admixture of N-formyl derivative was found in the target product (approximately 12%). The crude product was purified by column chromatography on silica gel and eluted with acetone and then with methanol. The appropriate eluent for the target product is the mixture of $MeOH/Et_3N$ (3/1). The desired fractions were collected and worked-up. Yield: 2.08 g (67%) of intermediate 24.

Example A9 a. Preparation of Intermediate 27

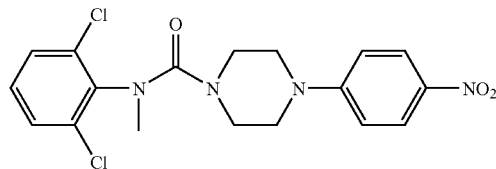 [SMILES: CN(C(=O)N1CCN(c2ccc([N+](=O)[O-])cc2)CC1)c1c(Cl)cccc1Cl]

A mixture of intermediate 4 (prepared according to A2.a) (0.0025 mol) and NaH 60% (0.00030 mol) in DMF (50 ml; dried over 3 Å molecular sieve) was stirred for 25 minutes at room temperature. Then $CH_3I$ (0.173 ml) was added to the reaction mixture. The reaction mixture was stirred for 45 minutes and then again $CH_3I$ (0.032 ml) was added. The reaction mixture was stirred for 270 minutes. The solvent was evaporated. The residue was purified by reversed-phase high-performance liquid chromatography. (Shandon Hyperprep® C18 BDS (Base Deactivated Silica) 8 µm, 250 g, I.D. 5 cm). A gradient with the mentioned mobile phases was applied (phase A: a 0.25% $NH_4HCO_3$ solution in water; phase B: $CH_3OH$ (optional); phase C: $CH_3CN$). The product fractions were collected and the solvent was co-evaporated with toluene and $CH_3CN$. Yield: 0.410 g of intermediate 27 (yellow powder)

b. Preparation of Intermediate 28

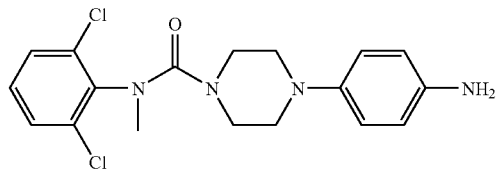 [SMILES: CN(C(=O)N1CCN(c2ccc(N)cc2)CC1)c1c(Cl)cccc1Cl]

A mixture of intermediate 27 (prepared according to A9.a) (0.001 mol) in $CH_3OH$ (25 ml) and THF (25 ml) was hydrogenated at room temperature with Pt/C 5% (0.2 g) as a catalyst in the presence of thiophene solution (0.2 ml; 4% in DIPE). After uptake of $H_2$ (3 equiv.), the catalyst was filtered off and the filtrate's solvent was evaporated. The residue was suspended in DCM and then filtered again over Celite (Column was prewashed with $CH_3OH$ in order to remove small amounts of catalyst, still present in the residue). The filtrate was evaporated. Yield: 0.376 g of intermediate 28.

Example A10

Preparation of Intermediate 29

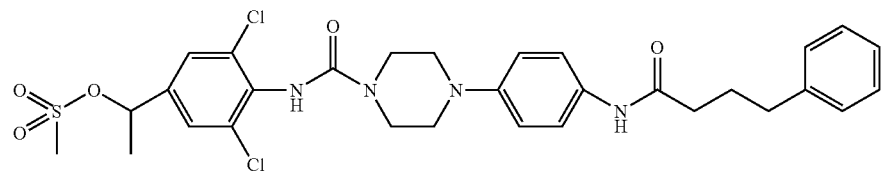 [SMILES: CC(OS(C)(=O)=O)c1cc(Cl)c(NC(=O)N2CCN(c3ccc(NC(=O)CCCc4ccccc4)cc3)CC2)c(Cl)c1]

A solution of compound 29 (prepared according to B17) (0.0004 mol) in pyridine, p.a., dried on molecular sieves (3 ml) was stirred on an ice-bath. A solution of methanesulfonyl chloride (0.0007 mol) in CH$_2$Cl$_2$, p.a. (0.5 ml) was added dropwise by means of a syringe. After addition, the reaction mixture was stirred further at 0° C. for 1 hour, and at room temperature for 2 hours. The solvents were evaporated. Yield: intermediate 29. The residue was used as such.

Example A11

Preparation of Intermediate 30

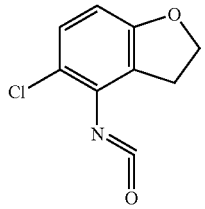 [SMILES: O=C=Nc1c(Cl)ccc2c1CCO2]

A mixture of 5-chloro-2,3-dihydro-4-benzofuranamine (0.0019 mol) and 20% phosgene in toluene (3 ml) was reacted in a pressure vessel at 140° C. for 18 hours. During the heat-up phase the mixture started to become a solution. The reaction mixture was allowed to reach room temperature, and the volatiles were evaporated, and co-evaporated with toluene. The crude intermediate 30 was used as such in the next reaction step.

Example A12 a. Preparation of Intermediate 31

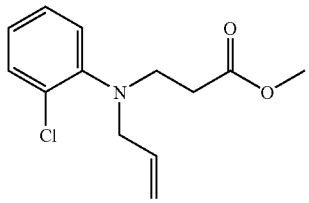 [SMILES: C=CCN(CCC(=O)OC)c1ccccc1Cl]

A mixture of N-(2-chlorophenyl)-β-alanine methyl ester (0.0137 mol), 3-iodo-1-propene (0.042 mol), and N-ethyl-N-(1-methylethyl)-2-propanamine (6.90 ml) in DMF (15 ml) was stirred for 6 hours at 60° C. Then the volatile matters were evaporated under reduced pressure at 95° C./30 mm Hg. The residue was treated with a mixture of DCM (20 ml) and K$_2$CO$_3$ (7% aqueous solution, 20 ml). The organic layer was separated, dried over MgSO$_4$, and the solvent was removed under reduced pressure. The residue was purified by chromatography (eluent: hexane/ethyl acetate—10/1). Yield: (84%) of intermediate 31 (yellow oil).

b. Preparation of Intermediate 32

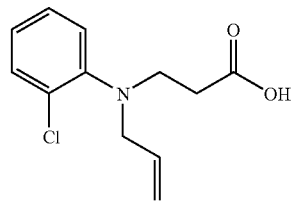 [SMILES: C=CCN(CCC(=O)O)c1ccccc1Cl]

A solution of KOH (0.016 mol) in water (9 ml) was added to a solution of intermediate 31 (0.0114 mol) in MeOH (60 ml). The reaction mixture was stirred at room temperature for 5 hours. Then the solvent was evaporated in vacuum to dryness. The residue was dissolved in MeOH (40 ml) and neutralized with concentrated HCl (d=1.19; V=1.30 ml). Precipitated KCl was removed by filtration and washed with MeOH (10 ml). The solvent from filtrate was removed under reduced pressure. The residue was purified by chromatography (eluent: CHCl$_3$/acetone—25/1). Yield: 1.954 g of intermediate 32 (72%).

Example A13 a. Preparation of Intermediate 33

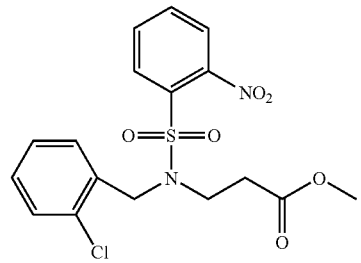 [SMILES: COC(=O)CCN(Cc1ccccc1Cl)S(=O)(=O)c1ccccc1[N+](=O)[O-]]

2-Nitrobenzenesulfonylchloride (0.0127 mol) was added to a solution of N-(o-chlorobenzyl)-β-alanine methyl ester (0.0127 mol) in dioxane (10 ml). The reaction mixture was stirred under reflux for 8 hours. When the reaction was over, the reaction mixture was diluted with water (100 ml) and extracted with CH$_2$Cl$_2$ (3×50 ml). The combined organic layers were dried over Na$_2$SO$_4$. The solvent was removed under reduced pressure. The target product crystallized after addition of hexane. Yield: 3.627 g of intermediate 33 (94%; white crystalline powder).

b. Preparation of Intermediate 34

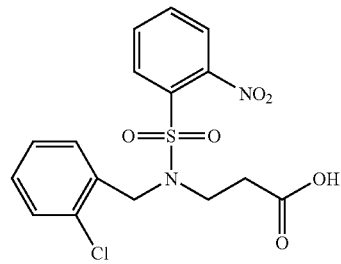 [SMILES: O=C(O)CCN(Cc1ccccc1Cl)S(=O)(=O)c1ccccc1[N+](=O)[O-]]

Concentrated HCl (7.00 ml) was added to a solution of intermediate 33 (0.0117 mol) in dioxane (10 ml). The reaction mixture was stirred under reflux for 8 hours. When the reaction was over, the reaction mixture was diluted with water (100 ml) and extracted with DCM (3×50 ml). Combined organic extract was dried over Na₂SO₄. The solvent was removed under reduced pressure. The target product crystallized after addition of hexane. Yield: 3.627 g of intermediate 34 (94%; white crystalline powder).

Example A14 a. Preparation of Intermediate 35

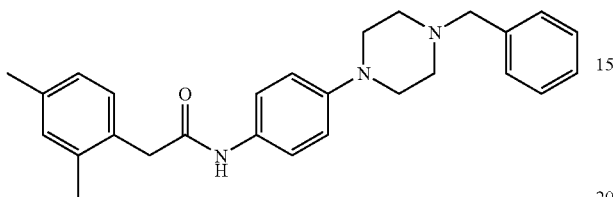

A mixture of 2,4-dimethylbenzeneacetic acid (0.5 g, 0.003 mol), DCM (20 ml) and DMF (1 ml) was stirred at room temperature. SOCl₂ (1 ml) was added. The reaction mixture was stirred and refluxed for 2 hours. The solvent was evaporated (2×DCM). The residue was dissolved in DCM and this solution was added dropwise to a mixture of 4-[4-(phenylmethyl)-1-piperazinyl]benzenamine (0.813 g, 0.003 mol), DCM (30 ml) and DIPEA (1.5 ml) at 10° C. The reaction mixture was stirred overnight at room temperature. Then H₂O was added and the mixture was stirred for 15 minutes. The organic layer was separated, dried and the solvent was evaporated. The residue was worked-up in DIPE. The solid was filtered off and dried. Yield: 0.780 g of intermediate 35.

b. Preparation of Intermediate 36

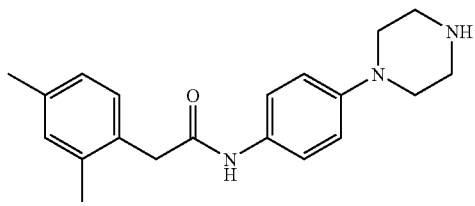 [SMILES: Cc1ccc(CC(=O)Nc2ccc(N3CCNCC3)cc2)c(C)c1]

A mixture of intermediate 35 (0.0018 mol) in CH₃OH (50 ml) was hydrogenated with Pd/C 10% (0.050 g) as a catalyst. After uptake of H₂ (47 ml), the mixture was filtered over Dicalite. The solvent was evaporated and the residue was crystallized from DIPE. The solid was filtered off and dried. Yield: 0.483 g of intermediate 36.

Example A15 a. Preparation of Intermediate 39

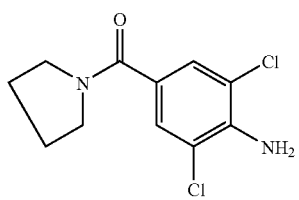 [SMILES: Nc1c(Cl)cc(C(=O)N2CCCC2)cc1Cl]

A solution of 4-amino-3,5-dichlorobenzoylchloride (0.0680 mol) in CH₂Cl₂, p.a. (100 ml) was added dropwise to a stirring solution of pyrrolidine (14.8 ml; 0.18 mol) in CH₂Cl₂, p.a. (100 ml), while cooling on an ice-bath. After addition, the reaction mixture was stirred further at 0° C. for 1 hour. The reaction mixture was washed with H₂O (150 ml). The separated organic layer was dried with MgSO₄, filtered off, evaporated, and co-evaporated with toluene. The residue (19 g) was filtered over silica using CH₂Cl₂—CH₃OH 99/1 as eluent. The desired fractions were combined and evaporated, and co-evaporated with toluene. Yield: 16.5 g of intermediate 39 (94%)

b. Preparation of Intermediate 40

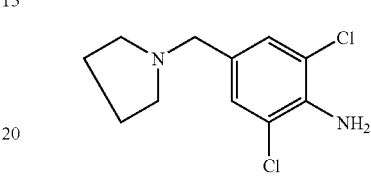

A solution of intermediate 39 (prepared according to A15.a) (16.5 g; 0.0636 mol) and borane-THF 1M in THF (175 ml) was stirred and refluxed for 4 hours. The reaction mixture was allowed to reach room temperature, and more borane-THF 1M in THF (200 ml) was added, and the reaction mixture was stirred and refluxed further for 3 hours. The reaction mixture was allowed to reach room temperature, and poured slowly into 1 L stirring ice-water. Stirring was continued for 18 hours. NaHCO₃ (35 g) was added, and the resulting suspension was extracted with CH₂Cl₂. The separated organic layer was washed with H₂O, dried with MgSO₄, filtered off, evaporated, and co-evaporated with toluene. The residue was triturated in iPrOH (75 ml), and the solid was filtered off, washed with 2× iPrOH, and to the filtrate was added HCl-iPrOH 6N (25 ml), and the solvents were evaporated. The residue (10.5 g) was stirred with EtOAc (75 ml), and decanted. The residue was triturated with EtOAc (75 ml), filtered off, and washed with 2× EtOAc. The resulting solid on the filter was dissolved in CH₂Cl₂+NaHCO₃ aqueous saturated solution, and the resulting biphasic solution was stirred for 30 minutes. The organic layer was separated, dried with MgSO₄, filtered off, evaporated, and co-evaporated with toluene. Yield: 3.5 g of intermediate 40 (22%).

c. Preparation of Intermediate 41

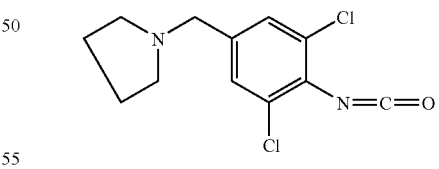

HCl 1M in diethylether (4.9 ml; 0.0049 mol) was added to a stirring solution of intermediate 40 (prepared according to A15.b) (0.57 g; 0.0023 mol) in CH₃CN p.a. dried on molecular sieves (20 ml) under N₂ flow. The reaction mixture was put on an ice-bath, and phosgene 20% in toluene (1.75 ml) was added. The reaction mixture was stirred further at room temperature (ice-bath was removed immediately after addition) for 18 hours. More phosgene 20% in toluene (0.6 ml) was added, and the reaction mixture was stirred further at room temperature for 65 hours. The crude intermediate 41 was used as such in the next reaction step.

d. Preparation of Intermediate 42

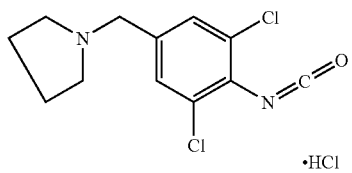 [SMILES: O=C=Nc1c(Cl)cc(CN2CCCC2)cc1Cl ; Cl]
•HCl

HCl 1M in Et$_2$O (10.32 ml; 0.0206 mol) was added to a stirring solution of intermediate 40 (4.6 g; 0.0188 mol) in CH$_3$CN p.a. dried on molecular sieves (75 ml) and CH$_2$Cl$_2$ p.a (10 ml). Stirring was continued for 1 hour. A precipitate was formed. The reaction mixture was cooled on an ice-bath, and phosgene 20% in toluene (14 ml) was added. The reaction mixture was stirred further for 3 hours. Extra phosgene 20% in toluene (7 ml) was added, and the reaction mixture was stirred further at room temperature for 18 hours. The product was filtered off, washed with CH$_3$CN (3×), and dried at 50° C. in vacuo for 1 hour. Yield: 5.45 g of intermediate 42 (94%).

e. Preparation of Intermediate 43

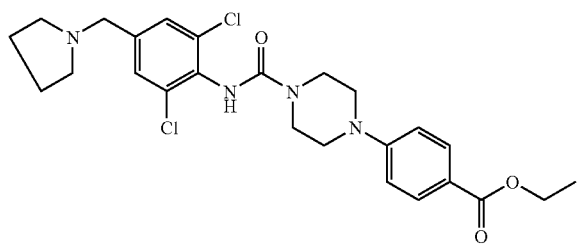 [SMILES: CCOC(=O)c1ccc(N2CCN(C(=O)Nc3c(Cl)cc(CN4CCCC4)cc3Cl)CC2)cc1]

Ethyl 4-(1-piperazinyl)benzoic acid ester (3.732 g; 0.0159 mol) was added to a stirring mixture of intermediate 42 (4.9 g; 0.0159 mol) and CH$_2$Cl$_2$ (100 ml). TEA (4.478 ml; 0.0319 mol) was added, and the resulting solution was stirred further at room temperature for 18 hours. The reaction mixture was washed with NaHCO$_3$ aqueous saturated solution, dried with MgSO$_4$, filtered off, and evaporated. The residue was stirred in Et$_2$O, filtered off, washed with 3× Et$_2$O, and dried at 50° C. in vacuo. Yield: 6.55 g of intermediate 43 (81.35%; m.p. 161-167° C.).

f. Preparation of Intermediate 44

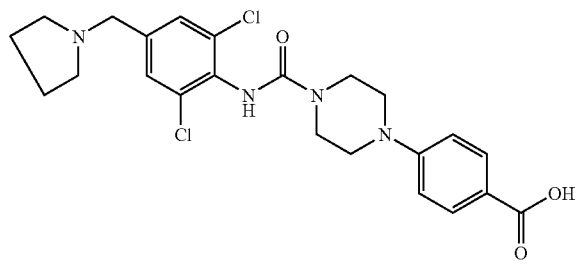 [SMILES: O=C(O)c1ccc(N2CCN(C(=O)Nc3c(Cl)cc(CN4CCCC4)cc3Cl)CC2)cc1]

Intermediate 43 (5.88 g; 0.0116 mol) was added to 1,4-dioxane (75 ml) and stirred. NaOH (35 ml; 0.035 mol) was added gently and the reaction mixture was stirred for 18 hours at room temperature. A turbid mixture was formed. The reaction mixture was stirred for another 72 hours at room temperature. MeOH (25 ml) was added. The reaction mixture was stirred for another 72 hours. HCl 1 N (35 ml) was added and the reaction mixture was stirred for 18 hours. Filtered off and washed with H$_2$O. Dried at 50° C. in vacuo for 24 hours. Yield: 4.88 g intermediate 44 (88%).

Example A16 a. Preparation of Intermediate 46

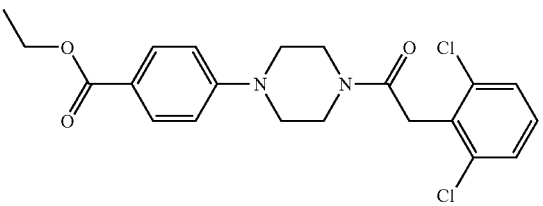 [SMILES: CCOC(=O)c1ccc(N2CCN(C(=O)Cc3c(Cl)cccc3Cl)CC2)cc1]

DECP (3.168 g; 0.01942 mol) was added to a solution of 2,6-dichlorobenzeneacetic acid (3.063 g; 0.01494 mol), ethyl 4-(1-piperazinyl)benzoic acid ester (3.5 g; 0.01494 mol) and DIPEA (0.6 ml) in THF (30 ml) at room temperature. The reaction mixture was stirred overnight at room temperature. Solid products were precipitated, filtered, washed with CH$_3$OH and dried in vacuo. Yield: 6 g of intermediate 46 (95%).

b. Preparation of Intermediate 47

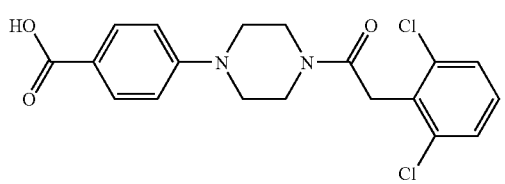 [SMILES: O=C(O)c1ccc(N2CCN(C(=O)Cc3c(Cl)cccc3Cl)CC2)cc1]

NaOH (3.418 g; 0.0854 mmol) was added to a suspension of intermediate 46 (6 g; 0.0142 mol) in H$_2$O (30 ml), CH$_3$OH (30 ml) and dioxane (90 ml) at room temperature. Then the reaction mixture was stirred at room temperature for 4 days. Then HCl 1N was added to the reaction mixture (pH≤3). The solid product was precipitated, filtered off, washed with H$_2$O and dried in vacuum. Yield: 5.2 g of intermediate 47 (93%).

Example A11 a. Preparation of Intermediate 48

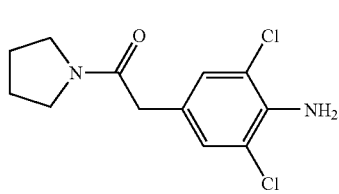 [SMILES: Nc1c(Cl)cc(CC(=O)N2CCCC2)cc1Cl]

DCM (75 ml) was added to 4-amino-3,5-dichlorobenzene-acetic acid (2.86 g; 0.013 mol) and stirred, a turbid mixture was formed. After adding Et$_3$N (5.5 ml; 0.0391), pyrrolidine (1.3 ml; 0.0158 mol) was added. DECP (2.5 ml; 0.015 mol) was added. A N$_2$-flow was added for a few minutes and vessel was closed. After 18 hours reaction mixture was extracted by washing the DCM layer with a saturated aqueous NaHCO$_3$ solution and extracting the CH$_2$Cl$_2$-layer. This layer was dried with MgSO$_4$, filtered off, evaporated and co-evaporated with toluene, yielding 4.317 g. The residue was purified by column chromatography over silica (eluent: 97/3 CH$_2$Cl$_2$/MeOH). The pure fractions were collected and the solvent was evaporated and co-evaporated with toluene. Yield: 3.104 g of intermediate 48 (87%).

b. Preparation of Intermediate 49

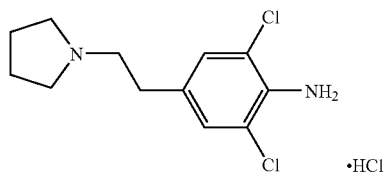 [SMILES: Nc1c(Cl)cc(CCN2CCCC2)cc1Cl ; Cl]

Borane THF 1M (30 ml; 0.03 mol) was added to a mixture of intermediate 48 (2.88 g; 0.0105 mol) in THF (dry) (60 ml) and was refluxed for 18 hours. The reaction mixture was cooled to room temperature. The reaction mixture was added to a stirring solution of H$_2$O (300 ml) and HCl (concentrated) (300 ml) on an ice bath and refluxed for 30 minutes. The reaction mixture was cooled again and put on an ice bath. K$_2$CO$_3$-powder was added slowly. The reaction mixture was extracted with CH$_2$Cl$_2$ and some water was added. The CH$_2$Cl$_2$-layer was separated, dried with MgSO$_4$, filtered off, evaporated and co-evaporated with toluene.

The residue was stirred in Et$_2$O and extracted with HCl 1N, layers separated, extracted a second time with HCl 1N. HCl-layer was separated and joint with the first fraction. It was neutralised with NaHCO$_3$ until pH 8 and extracted with CH$_2$Cl$_2$. Some water was added to solve the salts that were precipitated. Layers were separated, CH$_2$Cl$_2$-layer was dried with MgSO$_4$, filtered off, evaporated and co-evaporated with toluene. Dried in vacuo for 18 h at 50° C. The residue was stirred in Et$_2$O with 1M HCl/Et$_2$O (15 ml), filtered off and washed with Et$_2$O. Yield: 3.05 g of intermediate 49 (.HCl) (98%).

c. Preparation of Intermediate 50

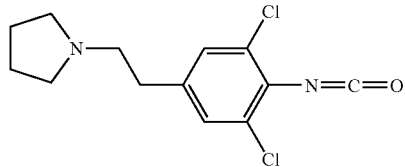 [SMILES: O=C=Nc1c(Cl)cc(CCN2CCCC2)cc1Cl]

Intermediate 49 (3 g; 0.0101 mol) was dissolved in HCl 1M in Et$_2$O (10 ml; 0.01 mol) and CH$_3$CN dry (150 ml) at room temperature and stirred for 30 minutes. 20% Phosgene in toluene (706 ml; 0.0152 mol) was added in portions to the stirring mixture. The reaction mixture was stirred softly for 20 hours at room temperature. Then, the reaction mixture was evaporated and co-evaporated with toluene (dry). Yield: 2.89 g of intermediate 50 (99%).

Example A18 a. Preparation of Intermediate 51

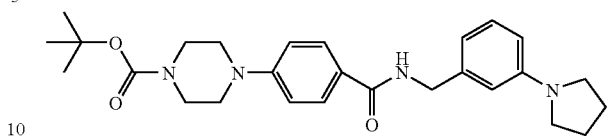

(3-Pyrrolidin-1-ylphenyl)methylamine (8 g; 0.0408 mol) was dissolved in DCM (50 ml). Et$_3$N (25 ml; 0.178 mol) was added to a stirring solution. 1-(1,1-dimethylethyl)-4-(4-carboxyphenyl)-1-piperazinecarboxylic acid ester (10.429 g; 0.034 mol) was added and the mixture was stirred. CH$_2$Cl$_2$ (100 ml) was added and then DECP (11.9 ml; 0.0796 mol) was added. The reaction mixture was stirred for 18 hours. Then the mixture was stirred in a saturated NaHCO$_3$-solution. The organic layer was separated, dried with MgSO$_4$, filtered off, evaporated and co-evaporated with toluene. Yield: 15.815 g of intermediate 51 (99%).

b. Preparation of Intermediate 52

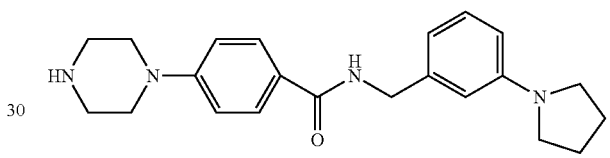

Intermediate 51 (1 g; 0.00215 mol) was dissolved in iPrOH (125 ml) and HCl iPrOH (2.152 ml; 0.0129 mol) was added. The reaction mixture was heated to 60° C. and stirred for 18 hours. HCl iPrOH (0.36 ml; 1 eq) was added. The reaction mixture was stirred for 48 hours at 60° C. The reaction mixture was evaporated and co-evaporated with toluene. The reaction mixture was stirred in Et$_2$O and filtered off. The residue was stirred for 1 hour in a NaHCO$_3$ solution and extracted with CH$_2$Cl$_2$. Layers were separated, CH$_2$Cl$_2$-layer was dried with MgSO$_4$, filtered off, evaporated and co-evaporated with toluene. The residue was stirred in DIPE and filtered off. Dried in vacuum at 50° C. for 18 hours. Yield: 0.514 g of intermediate 52 (66%).

Example A19 a. Preparation of Intermediate 53

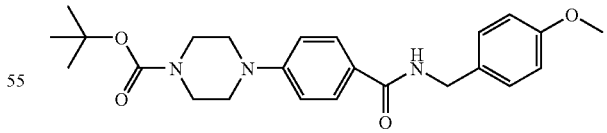

DECP (5.9 ml; 0.0395 mol) was added to a stirring solution of 1-(1,1-dimethylethyl)-4-(4-carboxyphenyl)-1-piperazinecarboxylic acid ester (10 g; 0.0326 mol) and 4-methoxybenzylamine (4.7 ml; 0.036 mol) in Et$_3$N (9.2 ml; 0.0655 mol) and CH$_2$Cl$_2$ (250 ml). The reaction mixture was stirred at room temperature for 18 hours. Saturated NaHCO$_3$ solution (150 ml) was added and the mixture was stirred for 30 minutes. Then H$_2$O (100 ml) was added and the mixture was stirred for 30 minutes. The layers were separated and CH$_2$Cl$_2$-layer was dried with MgSO$_4$, evaporated, co-evaporated with toluene and dried at 50° C. in vacuum for 3 hours. Yield: 15.21 g of intermediate 53 (107%).

b. Preparation of Intermediate 54

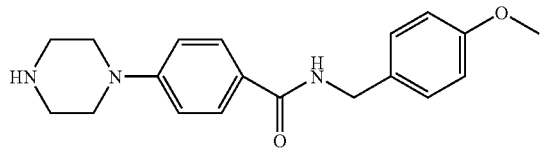

Intermediate 53 (0.998 g; 0.00235 mol) was added to CH$_2$Cl$_2$ (20 ml) and stirred, then TFA (1.75 ml; 0.0236 mol) was slowly added and the mixture was stirred for 18 hours. CH$_2$Cl$_2$ and some excess of TFA were evaporated and resolved in CH$_2$Cl$_2$ (100 ml). H$_2$O (200 ml) was added, the mixture was stirred vigorous and some NaHCO$_3$ was added until there was no more CO$_2$ produced and the water layer became basic. The layers were separated and the CH$_2$Cl$_2$-layer was dried with MgSO$_4$, filtered off and evaporated (yield=0.682 g). The residue was stirred in DIPE and filtered off, dried at 50° C. in vacuo for 72 hours. Yield: 0.563 g of intermediate 54 (74%).

Example A20 a. Preparation of Intermediate 55

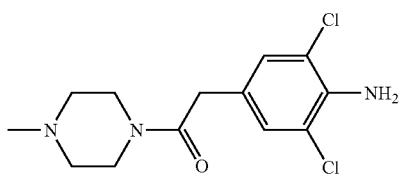 [SMILES: CN1CCN(C(=O)Cc2cc(Cl)c(N)c(Cl)c2)CC1]

DCM (25 ml) was added to 4-amino-3,5-dichlorobenzene-acetic acid (0.754 g; 0.00343 mol) and stirred. Et$_3$N (1.45 ml; 0.0103 mol) was added, then methylpiperazine (0.46 ml; 0.00415 mol) was added. After adding DECP (0.65 ml; 0.00391 mol), some N$_2$ was flushed in and the vessel was closed. After 72 hours of stirring at room temperature the reaction mixture was stirred in a saturated solution of NaHCO$_3$ in water and the layers were separated. The organic layer was dried with MgSO$_4$, filtered off, evaporated and co-evaporated with toluene. Yield: 1.172 g. The dry compound was stirred in DCM with a saturated K$_2$CO$_3$-solution. The layers were separated, some water was added. CH$_2$Cl$_2$-layer was dried with MgSO$_4$, filtered off, evaporated and co-evaporated with xylene. To purify the product from DECP, the HCl-salt was reacted by stirring the residue in HCl/2-propanol 6N (3 ml). The residue was dissolved in DIPE. After 15 hours of stirring, the residue (solid) was filtered off and washed with DIPE. It was dried in vacuum for 1 hour at 50° C. Yield: 1.3 g of intermediate 55 (99%).

b. Preparation of Intermediate 56

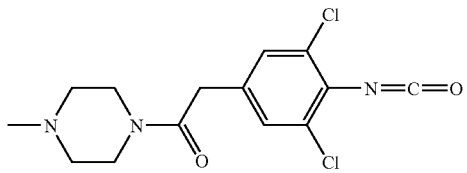 [SMILES: CN1CCN(C(=O)Cc2cc(Cl)c(N=C=O)c(Cl)c2)CC1]

Intermediate 55 (1.3 g; 0.00384 mol) was dissolved in HCl 1M in Et$_2$O (4.2 ml; 0.0042 mol) and CH$_3$CN, dry (20 ml) at 0° C., 20% phosgene in toluene was added carefully to the stirring solution. The reaction mixture was stirred for 2 hours, then was removed from ice and was stirred further at room temperature for 50 hours. 20% Phosgene in toluene (1.92 ml; 1 eq.) was added and the reaction mixture was stirred further for 36 hours. Then 20% Phosgene in toluene (1.0 ml; 0.5 eq.) was added. The reaction mixture was stirred for another 18 hours. The reaction mixture was evaporated and co-evaporated with dry toluene. Yield: 1 g of intermediate 56 (79%).

Residue was directly used in next reaction step.

Example A21 a. Preparation of Intermediate 57

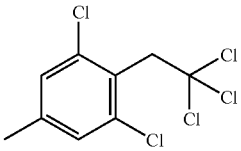

1,1-Dichloroethene (26.0 ml; 0.327 mol) was added drop-wise to a mixture of 1,1-dimethylethyl nitrous acid ester (20.0 ml; 0.167 mol) and anhydrous CuCl$_2$ (17.6 g; 0.131 mol) in 100 ml of anhydrous acetonitrile well-cooled on ice bath. The reaction temperature was kept below 10° C. Then, 2,6-dichloro-4-methylbenzeneamine (19.2 g; 0.109 mol) dissolved in anhydrous acetonitrile (100 ml) was added drop-wise at a temperature below 15° C. The resulting mixture was stirred at room temperature until the evolution of gas has ceased, and the mixture was left overnight at room temperature. The reaction mixture was poured carefully into 20% HCl (200 ml) and extracted with CH$_2$Cl$_2$ (3×100 ml). The combined organic phases were washed with 20% HCl, dried over Na$_2$SO$_4$ and concentrated in vacuum. The resulting oil was diluted with hexane (100 ml) and filtered off, yielding the crystalline product of 2-(2,6-dichloro-4-methyl-phenyl)-acetamide. The filtrate was concentrated in vacuum at temperature below 50° C. Yield: 29.36 g of intermediate 57 (crude product was used in the next step without additional purification).

b. Preparation of Intermediate 58

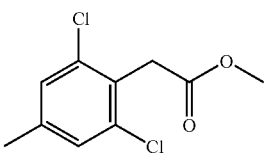

Sodium metal (11.5 g; 0.502 mol) dissolved in MeOH (100 ml) was added drop-wise to a solution of intermediate 57 (29.361 g; 0.10 mol) in MeOH (100 ml). The mixture was refluxed for 5 hours. Sulfuric acid (95%, 20 ml) was added to the cooled reaction mixture. The mixture was refluxed for 1 hour, cooled to room temperature and poured into H₂O (500 ml). The mixture was extracted with CH₂Cl₂ (3×100 ml). The organic layers were combined, dried over sodium sulphate and evaporated in vacuum. The obtained product (28.088 g) was distilled in vacuum.

Yield: fraction 1: 2.999 g, fraction 2: 1.951 g and fraction 3: 13.127 g.

Fraction 2 and Fraction 3 were combined and distilled one more time:

Yield: fraction 4: 2.649 g and 11.610 g of intermediate 58 (fraction 5).

c. Preparation of Intermediate 59

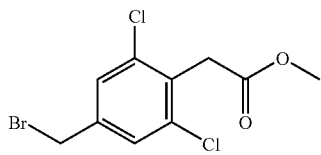

Methyl 2,6-dichloro-4-methylbenzene acetic acid ester (10.27 g; 0.044 mol) was dissolved in CCl₄ (100 ml). Then NBS (9.41 g; 0.053 mol) and AIBN (0.363 g; 0.0022 mol) were added to the solution. The resulting mixture was refluxed at stirring for 10 hours. The solution was cooled and passed through a silica gel layer. Silica gel was washed with CCl₄ (100 ml) and hexane (200 ml). The combined filtrates were concentrated in vacuum. The obtained residue became crystalline after cooling. Yield: 12.85 g. The residue was recrystallized from hexane. Yield: 10.30 g of intermediate 59 (mixture, used as such in the next step).

d. Preparation of Intermediate 60

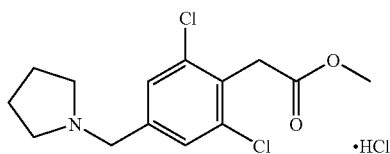 [SMILES: COC(=O)Cc1c(Cl)cc(CN2CCCC2)cc1Cl ; Cl]

Intermediate 59 (8.682 g) and pyrrolidine (6.86 ml; 0.0835 mol) were mixed and heated to 90-100° C. for 5 minutes. Water (50 ml) was added, and the resulting mixture was extracted with CH₂Cl₂ (3×50 ml). The combined organic layer was separated, dried over Na₂SO₄ and evaporated in vacuo. The obtained residue (8.178 g as brown oil) was treated with ether solution of HCl (2 M, 25 ml). A semi-crystalline precipitate was obtained. An excess of HCl ether solution was decanted, ether (30 ml) was added to the precipitate and acetone was added drop-wise at stirring till a crystalline product was formed. The formed precipitate was filtered off, washed with acetone and dried on the air. Yield: 5.347 g of intermediate 60 (43%).

e. Preparation of Intermediate 61

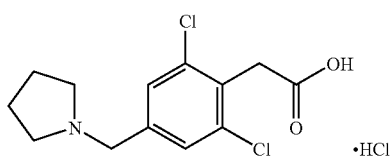 [SMILES: O=C(O)Cc1c(Cl)cc(CN2CCCC2)cc1Cl ; Cl]

Intermediate 60 (5.00 g; 14.76 mmol) and LiOH.H₂O (1.24 ml; 29.53 mmol) were dissolved in a mixture of water (20 ml) and CH₃OH (40 ml) and refluxed for 20 minutes. HCl concentrated (3 ml) was added and the mixture was evaporated in vacuo. HCl concentrated (5 ml) was added and the resulting suspension was diluted with acetone (20 ml). The suspension was refluxed for 5 minutes and cooled till room temperature. The formed yellowish crystalline product was filtered off, washed with acetone and dried on the air. Yield: 3.791 g of intermediate 61 (79%).

f. Preparation of Intermediate 62

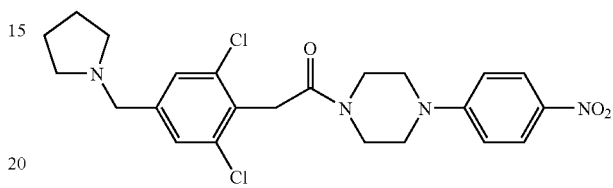

TEA (1.20 ml; 8.62 mmol) was added to a suspension of intermediate 61 (0.700 g; 2.156 mmol) in CH₂Cl₂ (15 ml). A clear solution formed immediately. DECP (0.400 ml; 2.587 mmol) was added to the reaction mixture. The resulting mixture was stirred for 10 minutes at room temperature. A solution of 1-(4-nitrophenyl)piperazine (0.536 g; 2.587 mmol) in CH₂Cl₂ (10 ml) was added to the reaction mixture. The mixture was stirred for 5 hours at room temperature. The reaction mixture was washed with 2% potassium carbonate aqueous solution, dried over Na₂SO₄ and passed through silica gel pad. The obtained solution was concentrated in vacuum. The obtained residue was treated with hexane. A formed crystalline product was filtered off and dried on the air. Yield: 0.525 g of intermediate 62 (51%).

g. Preparation of Intermediate 63

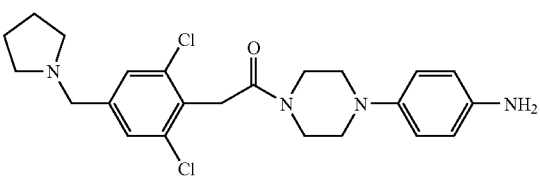 [SMILES: O=C(Cc1c(Cl)cc(CN2CCCC2)cc1Cl)N1CCN(c2ccc([N+](=O)[O-])cc2)CC1]

Intermediate 62 (0.500 g; 1.047 mmol), hydrazine monohydrate (0.265 g; 5.237 mmol) and Raney Nickel®, 50% slurry in H₂O (0.50 g) dissolved in CH₃OH (50 ml) were stirred for 10 minutes at reflux. The catalyst was filtered from the hot solution and washed with hot methanol. The filtrate was concentrated in vacuum. The residue was treated with a mixture of water and i-PrOH (1/1). A formed crystalline product was filtered, washed with small amount of i-PrOH, hexane and dried on the air.

The yield was 0.272 g of intermediate 63 (58%):

All filtrates after isolation of target compound were collected, diluted with water (20 ml) and extracted with CH₂Cl₂.

CH$_2$Cl$_2$ solution was dried over Na$_2$SO$_4$ and concentrated in vacuum. The residue yielded 0.150 g of intermediate 63 which was used on the next step without purification.

Intermediate 85

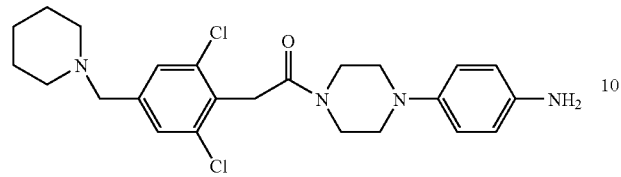

was prepared in a similar way.

Example A22 a. Preparation of Intermediate 64

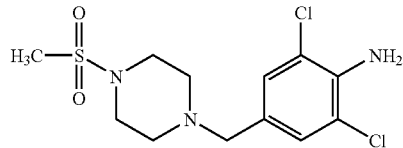 [SMILES: CS(=O)(=O)N1CCN(Cc2cc(Cl)c(N)c(Cl)c2)CC1]

2,6-Dichloro-4-chloromethylphenylamine (3.68 g; 0.0149 mol) was added portionwise to a stirring solution (in a water bath) of 1-methylsulfonylpiperazine (2.971 g; 0.0181 mol) and diisopropylamine (8.2 ml; 0.058 mol) in CH$_3$CN (100 ml). The reaction mixture was stirred further at room temperature for 18 hours. Two fractions P1 and P2 were purified by reversed phase high-performance liquid chromatography (Shandon Hyperprep® C18 BDS (Base Deactivated Silica) 8 μm, 250 g, I.D. 5 cm). A gradient with 3 mobile phases was applied. Phase A: 90% of a 0.5% NH$_4$OAc solution in water+10% CH$_3$CN; phase B: CH$_3$OH; phase C: CH$_3$CN). The desired fraction was collected and worked-up. The solvent was evaporated and coevaporated with toluene. Yield: 2.24 g of intermediate 64 (44%).

b. Preparation of Intermediate 65

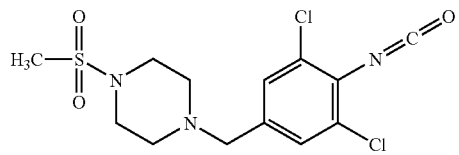 [SMILES: CS(=O)(=O)N1CCN(Cc2cc(Cl)c(N=C=O)c(Cl)c2)CC1]

HCl 1 M in Et2O (1.22 ml; 0.00244 mol) was added to a stirring solution of intermediate 62 (750 mg; 0.00222 mol) in CH$_3$CN p.a. dried on molecular sieves (10 ml). Stirring was continued for 15 minutes. A precipitate was formed. The reaction mixture was cooled on an ice-bath, and phosgene 20% in toluene (1.66 ml; 0.00332 mol) was added. The reaction mixture was stirred further for 18 hours. The mixture was filtered, washed 3× with dry CH$_3$CN and dried for 18 hours in vacuo at 50° C. Yield: 0.365 g of intermediate 65 (45%).

Example A23 a. Preparation of Intermediate 66

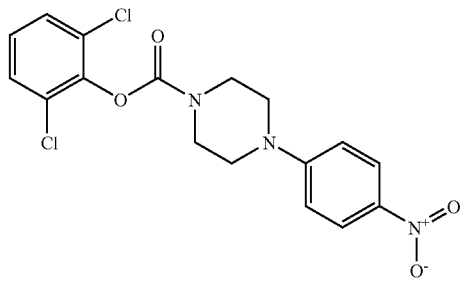 [SMILES: O=C(Oc1c(Cl)cccc1Cl)N1CCN(c2ccc([N+](=O)[O-])cc2)CC1]

NaH 60% (0.396 g; 0.0099 mol) was added portionwise to a stirring solution of 2,6-dichlorophenol (1.614 g; 0.0099 mol) in THF p.a. dried on molecular sieves (50 ml) under N$_2$ atm. After addition, stirring was continued for 15 minutes. 4-(4-nitrophenyl)-1-piperazinecarbonyl chloride (0.89 g; 0.0033 mol) was added, and the reaction mixture was stirred further at room temperature for 1 hour. The reaction mixture was stirred further at reflux for 17 hours 30 minutes. The reaction mixture was allowed to reach room temperature, and was poured into 200 ml ice-water. Stirring was continued for 15 minutes. The product was filtered off, washed with 3× H$_2$O, and dried at 50° C. in vacuo. Yield: 1.3 g of intermediate 66 (99%).

b. Preparation of Intermediate 67

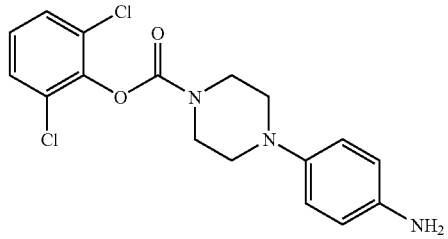 [SMILES: Nc1ccc(N2CCN(C(=O)Oc3c(Cl)cccc3Cl)CC2)cc1]

A solution of intermediate 66 (1.3 g; 0.00328 mol) in acetic acid (50 ml) and thiophene (6.901 ml; 0.00328 mol) was hydrogenated over Pt/C 5% (0.3 g). After the calculated amount of H$_2$ (0.00984 mol) was taken up, the catalyst was filtered off. The filtrate was evaporated, and 2× co-evaporated with toluene. The residue was dissolved in CH$_2$Cl$_2$, and washed with NaHCO$_3$ aqueous saturated solution. The separated organic layer was dried with MgSO$_4$, filtered off, and evaporated, and co-evaporated with toluene. The residue was stirred in Et$_2$O, filtered off, washed with 3× Et$_2$O, and dried at 50° C. in vacuo. Yield: 0.94 g of intermediate 67 (78%).

Example A24 a. Preparation of Intermediate 83

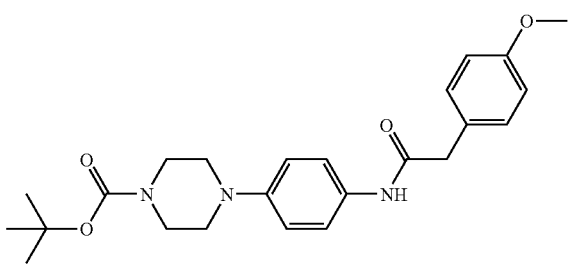 [SMILES: COc1ccc(CC(=O)Nc2ccc(N3CCN(C(=O)OC(C)(C)C)CC3)cc2)cc1]

A solution of 4-methoxybenzeneacetic acid (5.0 g; 0.03009 mol) in CH₂Cl₂ (100 ml) was stirred at room temperature. 4-(4-Aminophenyl)-1-piperazinecarboxylic acid 1,1-dimethylethyl ester (8.35 g; 0.03009 mol) and Et₃N (6.3 ml; 0.04514 mol) were added. Then, EDCI (5.77 g; 0.03009 mol) and HOBT (4.07 g; 0.03009 mol) were added to the mixture. The resultant reaction mixture was stirred overnight at room temperature. The solvent was evaporated in vacuo. The residue was washed with methanol, then dried. Yield: 11.9 g of intermediate 83 (93%).

b. Preparation of Intermediate 84

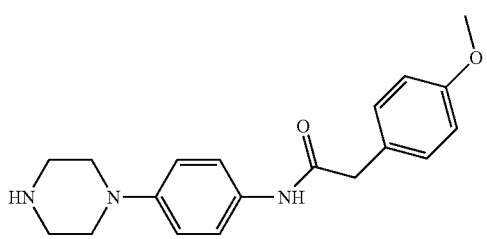 [SMILES: COc1ccc(CC(=O)Nc2ccc(N3CCNCC3)cc2)cc1]

A mixture of intermediate 83 (11.9 g; 0.028 mol) in 1,4-dioxane (20 ml) was stirred at room temperature. HCl, 4 M in 1,4-dioxane (50 ml; 0.200 mol) was added to the mixture. Then the reaction mixture was stirred for 2 hours at room temperature. The solvent was evaporated in vacuo. Yield 10.0 g of intermediate 84 (99%).

Example A25 a. Preparation of Intermediate 68

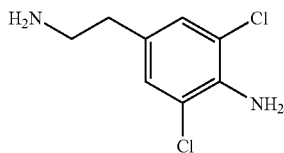 [SMILES: NCCc1cc(Cl)c(N)c(Cl)c1]

4-Amino-3,5-dichlorobenzeneacetonitrile (3.41 g; 0.017 mol) was dissolved in THF (25 ml) and borane in THF 1 M (25 ml; 0.025 mol) was added. After 72 hours the reaction mixture became turbid, yellow and a gel. The reaction mixture was added to a stirring solution of 200 ml HCl 1 M (in water) in ice, neutralised with NaHCO₃ (powder) and extracted with CH₂Cl₂. The layers were separated, CH₂Cl₂-layer was dried with MgSO₄, filtered off, evaporated and co-evaporated with toluene. Yield=2.90 g. Water-layer was extracted again with CH₂Cl₂, separated, dried with MgSO₄, filtered off and evaporated. The water-layer was extracted again like before. Different batches were combined yielding 3.93 g. The product was purified by reversed-phase high-performance liquid chromatography (Shandon Hyperprep® C18 BDS (Base Deactivated Silica) 8 µm, 250 g, I.D. 5 cm). A gradient with 3 mobile phases was applied. Phase A: a 0.25% NH₄HCO₃ solution in water; phase B: CH₃OH; phase C: CH₃CN). The desired fractions were collected and worked-up. The desired fractions were evaporated, 3× co-evaporated with methanol and co-evaporated with toluene. Dried for 18 hours in vacuo at 50° C. Yield=1.065 g of intermediate 68 (31%).

b. Preparation of Intermediate 69

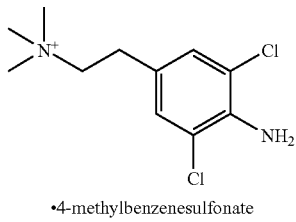

·4-methylbenzenesulfonate

Methyl p-tosylate (2.128 g; 0.0114 mol) solved in CH₂Cl₂ (70 ml) was added dropwise to a stirring solution of intermediate 68 (1.065 g; 0.00519 mol) in DIPEA (2.146 ml; 0.013 mol) and CH₂Cl₂ (70 ml) at 0° C. The reaction mixture was kept at 0° C. for 8 hours then the mixture was allowed to warm up to room temperature. After 152 hours the reaction mixture was filtered off and washed 1× with CH₂Cl₂. Dried in vacuo for 18 hours at 50° C. Yield=1.230 g of intermediate 69 (56%).

c. Preparation of Intermediate 70

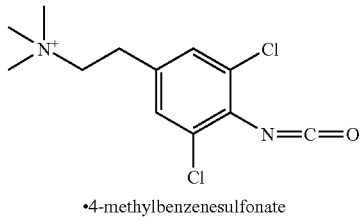 [SMILES: C[N+](C)(C)CCc1cc(Cl)c(N=C=O)c(Cl)c1]

·4-methylbenzenesulfonate

Phosgene 20% in toluene (895 µl; 1.5 eq.) was added to a stirring solution of intermediate 69 (0.5 g; 0.00119 mol) in CH₃CN p.a. dried on molecular sieves (10 ml) on an ice-bath. Phosgene 20% in toluene (600 ml; 1 eq.) was added and the reaction mixture was stirred further at room temperature. The reaction mixture was evaporated until no phosgene, the reaction mixture was concentrated. The crude reaction mixture was used in the next reaction step.

Example A26 a. Preparation of Intermediate 71

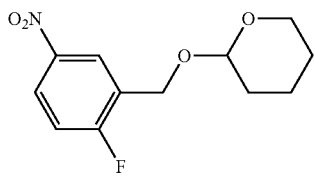

3,4-Dihydro-2H-pyran (4.27 ml; 0.0468 mol) and 4-methyl-benzenesulfonic acid (0.02 g; 0.000116 mol) were added to a solution of 2-fluoro-5-nitrobenzenemethanol (8.0 g; 0.0468 mol) in CH₂Cl₂ (200 ml) and stirred for 1 hour. The reaction mixture was washed with a saturated aqueous NaHCO₃ solution (20 ml), H₂O (50 ml) and brine (20 ml). The two layers were separated. The organic layer was dried (Na₂SO₄), filtered and the solvent was evaporated. Yield: intermediate 71 (crude used as such in next reaction step).

b. Preparation of Intermediate 72

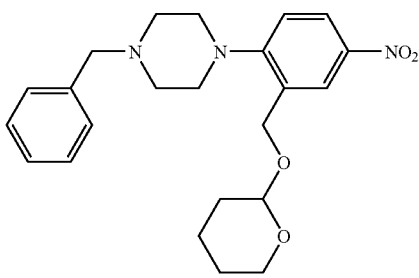 [SMILES: O=[N+]([O-])c1ccc(N2CCN(Cc3ccccc3)CC2)c(COC2CCCCO2)c1]

A mixture of intermediate 71 (0.0468 mol), 1-(phenylmethyl)piperazine (8.2 g; 0.0468 mol) and $Na_2CO_3$ (11.8 g; 0.0936 mol) in DMF (100 ml) was warmed to 60° C. and stirred overnight. The solvent was evaporated and the residue was partitioned between EtOAc (20 ml) and $H_2O$ (400 ml). The two layers were separated. The organic layer was dried with $Na_2SO_4$, filtered and the solvent was evaporated. The residue was purified over silica gel on a glass filter (eluent: n-hexane/EtOAc from 100/0 to 5/2). The pure fractions were collected and the solvent was evaporated. Yield: 13.2 g of intermediate 72 (68%).

c. Preparation of Intermediate 73

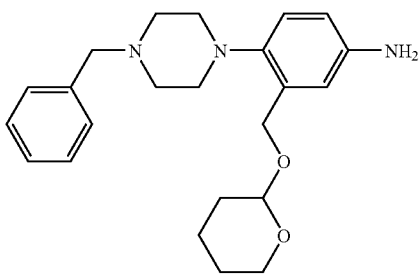

A mixture of intermediate 72 (13.0 g; 0.032 mol) in THF (150 ml) was hydrogenated with Pt/C 5% (2 g) as a catalyst in the presence of thiophene solution (1 ml). After uptake of $H_2$ (3 equiv), the catalyst was filtered off and the filtrate was evaporated. The reaction mixture was concentrated to dryness. Yield: 12 g of intermediate 73 (98%).

d. Preparation of Intermediate 74

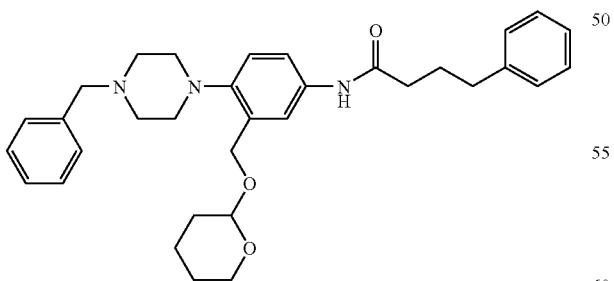

Benzenebutanoic acid (0.24 g; 0.0014 mol) in DMF (12 ml) was stirred at room temperature. PS-Carbodiimide resin (1.4 g; 0.0026 mol) and then HOBT (0.270 g; 0.002 mol) were added and the reaction mixture was stirred for 30 minutes at room temperature. Intermediate 73 (0.5 g; 0.0013 mol) in DMF (18 ml) was added and the reaction mixture was shaken overnight. MP-carbonate resin (1.4 g; 0.004 mol) and then resin-linked-N═C═O (0.7 g; 0.0013 mol) were added to the reaction mixture. The reaction mixture was shaken overnight. The reaction mixture was filtered and the filtrate's solvent was evaporated. Yield: 0.7 g of intermediate 74.

e. Preparation of Intermediate 75

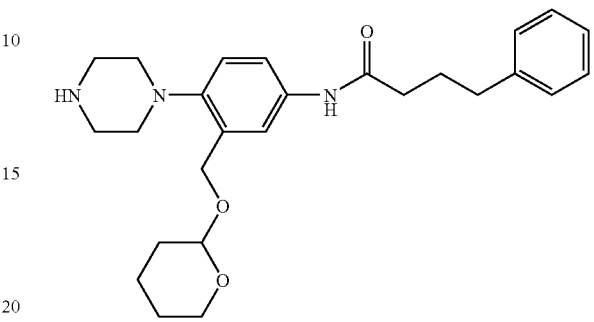

A mixture of intermediate 74 (0.7 g; 0.0013 mol) in THF (50 ml) was hydrogenated at 50° C. with Pd/C 10% (0.2 g; 0.2 g) as a catalyst in the presence of $Et_3N$ (1 ml). After uptake of $H_2$ (1 equiv), the catalyst was filtered off and the filtrate was evaporated. Yield: intermediate 75 (used as such in next reaction step)

f. Preparation of Intermediate 76

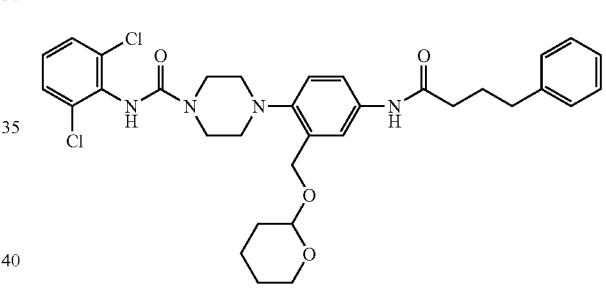

A mixture of intermediate 75 (0.7 g; 0.0016 mol) and 1,3-dichloro-2-isocyanatobenzene (0.34 g; 0.0018 mol) in $CH_2Cl_2$ (10 ml) was stirred at room temperature for 2 hours. The solvent was evaporated. Yield: intermediate 76 (used as such in next reaction step)

Example A27 a. Preparation of Intermediate 77

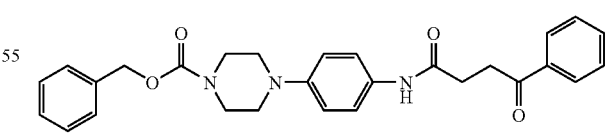

EDCI (0.713 g; 3.72 mmol) was added to a solution of γ-oxo-benzenebutanoic acid (0.602 g; 3.38 mmol), intermediate 9 (prepared according to A4.b), HOBT (0.041 g; 0.3 mmol), DIPEA (0.67 ml; 4.06 mmol) in THF/DMF 1:1 dried on molecular sieves (20 ml) and stirred at room temperature over the weekend. The reaction was evaporated to dryness yielding 4.897 g. This residue was extracted with 1% citric acid and $CH_2Cl_2$, and the combined extract was washed with NaHCO₃ solution. The organic phase yielded 1.798 g. It contains 86% product and 14% starting material. While dissolving this residue in CH₃CN/MeOH (1/1 v/v) and acidifying it with a few drops of 12 N HCl followed by addition of water to ratio 1/4 water/organic solvents, for RP HPLC purification, some crystalline material was obtained, which was isolated and dried to yield 830 mg. In the filtrate a second crop crystalline material was recovered the same way yielding 233 mg, which is also pure compound. These two fractions were combined and purified by reversed phase high-performance liquid chromatography (Shandon Hyperprep® C18 BDS (Base Deactivated Silica) 8 μm, 250 g, I.D. 5 cm). A gradient with 3 mobile phases was applied. Phase A: 90% of a 0.5% NH₄OAc solution in water+10% CH₃CN; phase B: CH₃OH; phase C: CH₃CN). The desired fractions were collected and worked-up.

After partial evaporation of the solvent (to which a little Na₂CO₃ solution was added to obtain an alkaline pH before the start of the evaporation), the solution was extracted with CH₂CL2, dried (MgSO₄) and worked up yielding 167 mg of intermediate 77.

b. Preparation of Intermediate 78

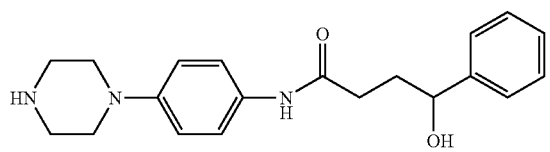

A mixture of intermediate 77 (1.052 g; 2.23 mmol) in CH₃OH (50 ml) was hydrogenated at room temperature overnight with 10% Pd/C (0.3 g) as a catalyst. After work up the yield was 685 mg of intermediate 78 (91%).

Example A28

Preparation of Intermediate 79

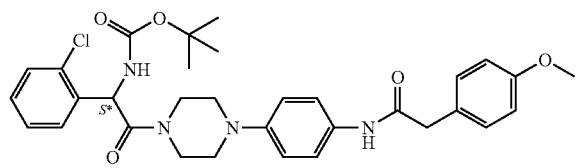 [SMILES: COc1ccc(CC(=O)Nc2ccc(N3CCN(C(=O)C(NC(=O)OC(C)(C)C)c4ccccc4Cl)CC3)cc2)cc1]

HBTU (6.37 g, 16.80 mmol) is added to a solution of intermediate 38 (prepared according to A4.d-1), 2-chloro-α-[[(1,1-dimethylethoxy)carbonyl]amino]-benzeneacetic acid (4.00 g; 14. mmol), DIPEA (9.3 ml; 56 mmol) in DMF dried on molecular sieves (100 ml). The reaction mixture was stirred at room temperature overnight. The reaction was evaporated to yield 22.53 g. The product was purified by reversed-phase high-performance liquid chromatography (Shandon Hyperprep® C18 BDS (Base Deactivated Silica) 8 μm, 250 g, I.D. 5 cm). A gradient with 2 phases was applied. Phase A: a 0.25% NH₄HCO₃ solution in water; phase B: CH₃CN). The desired fractions were collected and worked-up. After partial evaporation at 30-35° C., extraction with CH₂Cl₂ (2×400 ml) followed by EtOAc extraction (300 ml), drying (MgSO₄) and work up the organic phases, 4512 mg residue was obtained from CH₂Cl₂ and 45 mg from EtOAc. Yield: 4512 mg (54.3%) (mixture of R and S-enantiomers).

This fraction was separated on SFC (column OJ-H, 30% CH₃OH containing 0.2% isopropylamine) into its enantiomers. Fraction A yielded 1780 mg (R* enantiomer) and fraction B yielded 1770 mg of intermediate 79 (S* enantiomer).

Example A29 a. Preparation of Intermediate 80

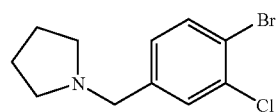 [SMILES: Clc1cc(CN2CCCC2)ccc1Br]

Pyrrolidine (45.2 g; 0.650 mol) was added dropwise to a solution of 1-bromo-4-(bromomethyl)-2-chlorobenzene (168 g; 0.590 mol) and Et₃N (98 ml; 0.708 mol) in THF (q.s.) (500 ml). The reaction mixture was stirred overnight. The mixture was washed with water, separated, dried over Na₂SO₄, filtered and evaporated. The residue was purified by column chromatography over silica gel (eluent: CH₂Cl₂). The desired fractions were collected and the solvent was removed. Yield: 50 g of intermediate 80 (31%).

b. Preparation of Intermediate 81

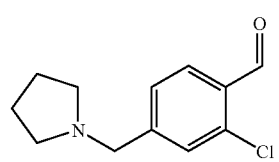 [SMILES: O=Cc1ccc(CN2CCCC2)cc1Cl]

Reaction under N₂ atmosphere. A solution of intermediate 80 (14.0 g; 0.05099 mol) in THF (200 ml) was stirred at −78° C. for 15 minutes. n-BuLi, 2.5 M in THF (20 ml; 0.05099 mol) was added to the mixture over a period of 15 minutes. 30 minutes later, a solution of DMF (3.95 ml; 0.05099 mol) in THF (20 ml) was added dropwise to the mixture. The reaction temperature was allowed to rise to room temperature slowly, and the mixture was stirred overnight. The reaction was quenched by adding water at 0° C. The mixture was extracted with ethyl acetate (3×100 ml). The organic layers were combined, washed with brine, dried (MgSO₄), filtered and the solvent was evaporated in vacuo. Yield: 10.4 g of intermediate 81. The crude product was used in the next step directly without further purification.

c. Preparation of Intermediate 82

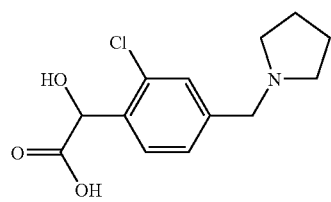 [SMILES: O=C(O)C(O)c1ccc(CN2CCCC2)cc1Cl]

To a solution of intermediate 81 (6 g; 0.0268 mol) in CH₂Cl₂ (50 ml) was added trimethylsilanecarbonitrile (6 ml) and ZnBr₂ (0.3 g). The reaction mixture was stirred for 5 hours at room temperature. Then the mixture was heated to 50° C. and stirred overnight. The reaction mixture was cooled to 0° C. and HCl concentrated (q.s.) was added. The mixture was stirred overnight at room temperature, then stirred and refluxed for 1 hour. After cooling, the reaction mixture was poured into water and extracted with ethyl acetate. The solvent was evaporated to give 3.0 g crude product. 0.8 g crude product was purified by preparative HPLC. (Ymc: 250×20 mm Mobile Phase: 0-25% CH$_3$CN % in H$_2$O (0.1% Trifluoro-acetic acid) Flow Rate: 15 ml/min Finished Time: 17.2 min). The product fractions were collected and the solvent was evaporated. Yield: 0.1 g of intermediate 82.

B. Preparation of the Final Compounds

Example B1

Preparation of Compound 1

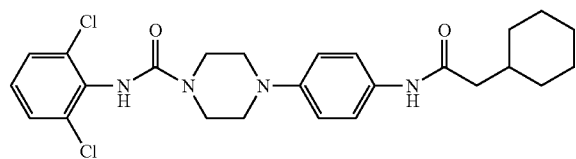 [SMILES: O=C(CC1CCCCC1)Nc1ccc(N2CCN(C(=O)Nc3c(Cl)cccc3Cl)CC2)cc1]

Cyclohexane acetic acid (0.00012 mol) was dissolved in DMF (1.2 ml). PS-Carbodiimide, 2.1 mmol/g and HOBT (0.00015 mol) were added. The reaction mixture was shaken for 30 minutes. A solution of intermediate 5 (prepared according to A2.b) (0.0001 mol) in DMF (2 ml) was added. The reaction mixture was shaken overnight. MP-carbonate, 6.2 mmol/g (0.00045 mol) and resin-linked-NCO, 1.8 mmol/g (0.0001 mol) were added. The mixture was shaken overnight at room temperature. The mixture was filtered. CH$_2$Cl$_2$ (2 ml) was added. The mixture was shaken for one hour, then filtered again. The filtrate's solvent was evaporated (GeneVac). The residue was purified by HPLC. The product fractions were collected and worked-up. Yield: 0.0128 g of compound 1.

Example B2 a. Preparation of Compound 2

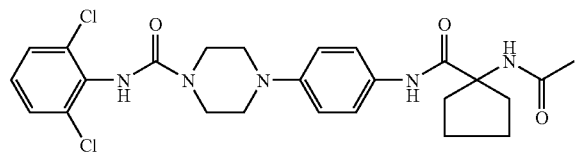 [SMILES: CC(=O)NC1(C(=O)Nc2ccc(N3CCN(C(=O)Nc4c(Cl)cccc4Cl)CC3)cc2)CCCC1]

EDCI (0.000302 mol) was added to a mixture of intermediate 5 (prepared according to A2.b) (0.000275 mol), 1-(acetylamino)-cyclopentanecarboxylic acid (0.000275 mol), HOBT (0.000028 mol) and N-ethyl-N-(1-methylethyl)-2-propanamine (0.000329 mol) in THF, dried over 3 Å molecular sieves (5 ml) and then stirred for 64 hours at room temperature. The solvent was evaporated. The residue was dissolved in CH$_3$OH (5 ml). The solution's solvent was evaporated (under N$_2$). The dried residue was purified by reversed-phase high-performance liquid chromatography. (Shandon Hyperprep® C18 BDS (Base Deactivated Silica) 8 μm, 250 g, I.D. 5 cm). A gradient with the mentioned mobile phases was applied (phase A: a 0.25% NH$_4$HCO$_3$ solution in water; phase B: CH$_3$OH (optional); phase C: CH$_3$CN). The desired product fraction was collected and the solvent was evaporated and then co-evaporated with CH$_3$OH. Yield: 0.038 g of compound 2.

b. Preparation of Compound 3

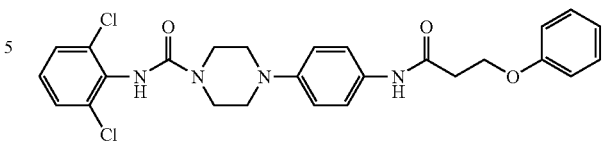

EDCI (0.0015 mol) was added to a solution of intermediate 5 (prepared according to A2.b) (0.0014 mol), 3-phenoxypropanoic acid (0.0014 mol), HOBT (0.0001 mol) and THF/DMF 1/1 dry (10 ml) in N-ethyl-N-(1-methylethyl)-2-propanamine (0.272 ml) and then stirred for 116 hours at room temperature. The solvent was evaporated. The residue was purified by reversed-phase high-performance liquid chromatography (Shandon Hyperprep® C18 BDS (Base Deactivated Silica) 8 μm, 250 g, I.D. 5 cm). A gradient with the mentioned mobile phases was applied (phase A: (0.5% NH$_4$OAc in H$_2$O)/CH$_3$CN 90/10); phase B: CH$_3$OH (optional); phase C: CH$_3$CN). The product fractions were collected and the solvent was worked-up. Yield: 0.293 g of compound 3.

c. Preparation of Compound 4

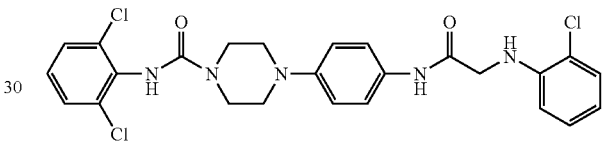

A mixture of N-(2-chlorophenyl)glycine (0.377 mmol), EDCI (0.377 mmol) and Et$_3$N in CH$_2$Cl$_2$ (6 ml) was stirred for 20 minutes at room temperature. Then intermediate 5 (prepared according to A2.b) (0.342 mmol) and HOBT (0.377 mmol) were added and the stirring was continued for 24 hours at room temperature (control by LC/MS). The solvent was removed under reduced pressure. The residue was treated with water; the formed precipitate was filtered off and washed with water. The target product was purified by flash-chromatography (eluent: CH$_2$Cl$_2$/MeOH—50/1) and then by HPLC (CH$_3$CN/H$_2$O—9/1). The desired fractions were collected and worked-up. Yield: 0.021 g (11.5%) of compound 4 (beige crystalline powder).

d. Preparation of Compound 5

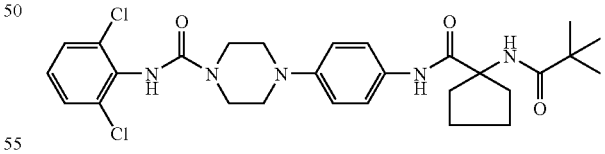

A mixture of intermediate 5 (prepared according to A2.b) (2.73 mmol), 1-[[(1,1-dimethylethoxy)carbonyl]amino]cyclopentanecarboxylic acid (2.75 mmol) and HOBT (2.8 mmol) in Et$_3$N (0.4 ml) and DMF, p.a., dried on molecular sieves (50 ml) was stirred at room temperature. EDCI (2.8 mmol) was added. The reaction mixture was stirred under N$_2$ atmosphere for 18 hours at room temperature. The solvent was evaporated. The residue was stirred in water (50 ml), filtered off, washed with water, then dried at 50° C. (vacuum, stream of air). The product was stirred in boiling ethanol (60 ml), filtered hot through dicalite and the filtrate was stood for 3 days. The product was filtered off, washed with ethanol (3x), and dried at 50° C. under vacuum. Yield: 0.44 g of compound 5 (28%).

e. Preparation of Compound 6

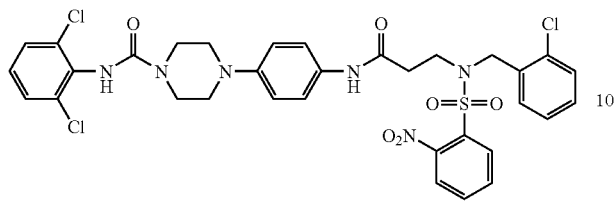

DMF (0.2 ml) was added to a mixture of intermediate 34 (prepared according to A13.b) (1.50 mmol) and ethanedioyl dichloride (2.00 mmol) in DCM (7 ml). Then the reaction mixture was stirred at room temperature for 2 hours. The solvent was removed under reduced pressure. The residue was resuspended in $CHCl_3$ (10 ml), then the solvent was evaporated again. The residue dissolved in DCM (2 ml) was added to a mixture of intermediate 5 (prepared according to A2.b) and $Et_3N$ (0.280 ml) in $C_6H_6$ (8 ml). The reaction mixture was refluxed for 4 hours and held overnight at room temperature. Then the solvent was removed under reduced pressure and the residue was washed with water. Precipitate was filtered off, washed with water and with the mixture of ether-ethanol. Yield: 0.380 g of compound 6 (51%).

f. Preparation of Compound 7

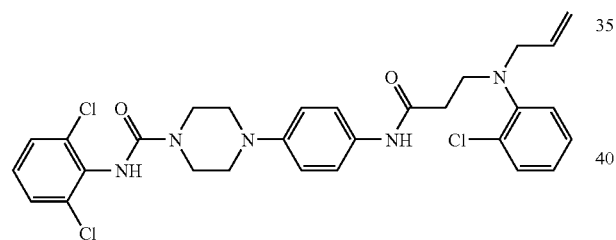

A mixture of intermediate 32 (prepared according to A12.b) (1.200 mmol), TBTU (1.400 mmol) and $Et_3N$ (0.031 ml) in $CH_3CN$ (10 ml) was stirred at room temperature for 1 hour. Then intermediate 5 (prepared according to A2.b) was added and stirring was continued at room temperature for 18 hours. The formed precipitate was filtered off, washed with ether and dried on air. Yield: 0.479 g of compound 7 (82%).

Example B3

Preparation of Compound 8

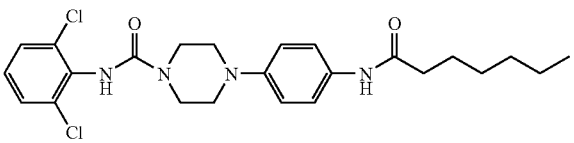 [SMILES: CCCCCCC(=O)Nc1ccc(N2CCN(C(=O)Nc3c(Cl)cccc3Cl)CC2)cc1]

Heptanoyl chloride (0.0014 mol) was added to a solution of intermediate 5 (prepared according to A2.b) (0.0014 mol) and N-ethyl-N-(1-methylethyl)-2-propanamine (0.210 ml) in $CH_2Cl_2$ (20 ml) and DMF, dry (0.1 ml) and was then stirred at room temperature for 17 hours. The solvent was evaporated. The residue was stirred in $H_2O$ (10 ml) and $CH_3OH$ (1 ml). $Na_2CO_3$ (0.2 g) was added to the mixture and stirred for 1 hour. The precipitate was filtered off, washed with EtOAc and washed with $Et_2O$. The residue and the filtrate were combined again. The organic solvents were evaporated to leave an aqueous concentrate. This mixture was stirred and the resulting precipitate was filtered and washed with $Et_2O$. The residue is dried (vacuo). Yield: 0.395 g of compound 8.

Example B4 a. Preparation of Compound 9

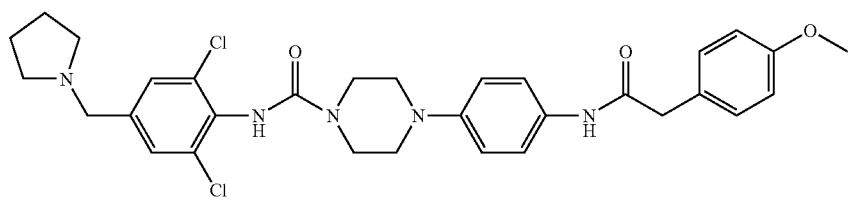 [SMILES: COc1ccc(CC(=O)Nc2ccc(N3CCN(C(=O)Nc4c(Cl)cc(CN5CCCC5)cc4Cl)CC3)cc2)cc1]

Intermediate 5 (prepared according to A2.b) (0.410 mmol), 2-pyridinepropanoyl chloride hydrochloride (prepared according to art-known procedures) (0.435 mmol) and $Et_3N$ (0.133 ml) were dissolved in $CH_3CN$ (5 ml) and stirred for 5 hours at 80° C. Then, 5 ml water was added, and the reaction mixture was extracted with DCM. The extract was dried over $Na_2SO_4$ and concentrated in vacuum. The resulting residue was purified by column chromatography on silica gel (eluent: DCM/methanol—10/1). Yield: 0.014 g of compound 9 (7%).

b. Preparation of Compound 351

4-Methoxybenzeneacetyl chloride (0.135 g; 0.730 mmol) was added to a solution of intermediate 63 (prepared according to A21.g) (0.272 g; 0.608 mmol) and TEA (0.130 ml; 0.912 mmol) dissolved in DCM (5 ml). The reaction mixture was stirred for 0.5 hours at room temperature. The reaction mixture was concentrated in vacuum. The residue was treated with i-PrOH/hexane (3/1). A formed crystalline product was filtered, washed with small amount of i-PrOH, hexane and dried on air. Yield: 0.098 g of compound 351 (45%).

Example B5

Preparation of Compound 10

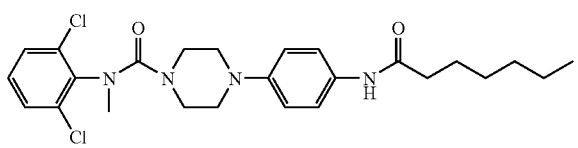 [SMILES: CCCCCCC(=O)Nc1ccc(N2CCN(C(=O)N(C)c3c(Cl)cccc3Cl)CC2)cc1]

NaH 60% (0.000183 mol) was added to a mixture of intermediate 28 (prepared according to A9.b) (0.000166 mol) in DMF (2 ml; dried over 3 Å molecular sieves) and stirred for 155 minutes. This mixture was added to heptanoylchloride (0.000332 mol) in THF (1 ml; dried over 3 Å molecular sieves) and then stirred for 24 hours at room temperature. The solvent was evaporated. The residue was purified by reversed-phase high-performance liquid chromatography. (Shandon Hyperprep® C18 BDS (Base Deactivated Silica) 8 μm, 250 g, I.D. 5 cm). A gradient with the mentioned mobile phases was applied (phase A: a 0.25% NH$_4$HCO$_3$ solution in water; phase B: CH$_3$OH (optional); phase C: CH$_3$CN). The product fractions were collected and worked-up. Yield: 0.043 g of compound 10 (lightly brown oily gum)

Example B6 a. Preparation of Compound 11

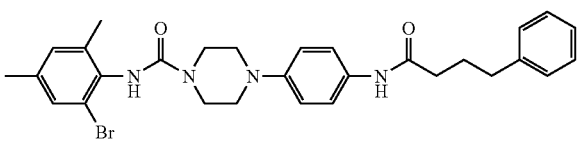 [SMILES: Cc1cc(C)c(NC(=O)N2CCN(c3ccc(NC(=O)CCCc4ccccc4)cc3)CC2)c(Br)c1]

A mixture of intermediate 11 (prepared according to A4.d) (0.0002 mol) and 1-bromo-2-isocyanato-3,5-dimethylbenzene (0.0002 mol) in DCM (3 ml) was stirred for 2 hours at room temperature. The solvent was evaporated. Yield: 0.060 g of compound 11.

b. Preparation of Compound 12

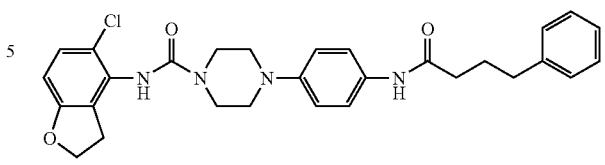

A mixture of intermediate 11 (prepared according to A4.d) (0.0005 mol), intermediate 30 (prepared according to A11) (0.0005 mol), and DCM (3 ml), was stirred at room temperature for 48 hours. The solid part was filtered off, washed with 3×DCM, and dried at 50° C. (vacuum). Yield: 0.24 g. This fraction was stirred in 5 ml DCM/MeOH 90/10 for 5 hours, and filtered off, and washed with 2×DCM/MeOH 90/10. The filtrate was evaporated, stirred in 5 ml boiling EtOH, filtered off hot, washed with 3× hot EtOH, and dried at 50° C. (vacuum). Yield: 0.03 g of compound 12 (13%).

c. Preparation of Compound 13

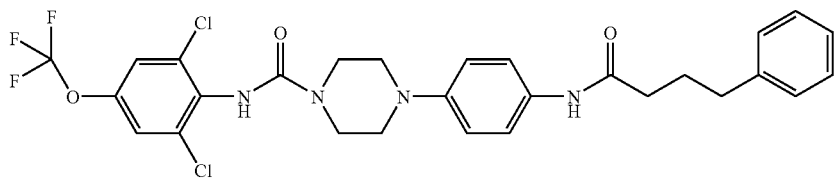 [SMILES: O=C(CCCc1ccccc1)Nc1ccc(N2CCN(C(=O)Nc3c(Cl)cc(OC(F)(F)F)cc3Cl)CC2)cc1]

Intermediate 11 (prepared according to A4.d) (0.0005 mol) was added to a stirring solution of 1,3-dichloro-2-isocyanato-5-(trifluoromethoxy)benzene (0.00125 mol) and DCM (3 ml). The reaction mixture was stirred further at room temperature for 18 hours. More 1,3-dichloro-2-isocyanato-5-(trifluoromethoxy)benzene (0.00125 mol) was added, and the reaction mixture was stirred further at room temperature for 24 hours. The solvent was evaporated. The residue was filtered over silica using DCM/MeOH 98/2 as eluent. The desired fractions were combined and evaporated, and co-evaporated with MeOH. Yield: 0.051 g of compound 13 (17%).

d. Preparation of Compound 14

1,3-Dichloro-2-isocyanatobenzene (0.256 mmol) was added to a solution of intermediate 18 (prepared according to A6.d) (0.270 mmol) in acetonitrile (5 ml). The reaction mixture was stirred at room temperature for 24 hours. The formed precipitate was filtered off, washed with DCM and dried on air. According to LC/MS, about 10% of intermediate 18 remained in the reaction mixture. Therefore the precipitate was diluted with DCM (5 ml) and 1,3-dichloro-2-isocyanatobenzene (0.008 g) was added to this suspension. The mixture was stirred for 24 hours at room temperature. Formed precipitate was filtered off, washed with DCM and dried on air. Yield: 0.095 g of compound 14 (67%).

e. Preparation of Compound 223

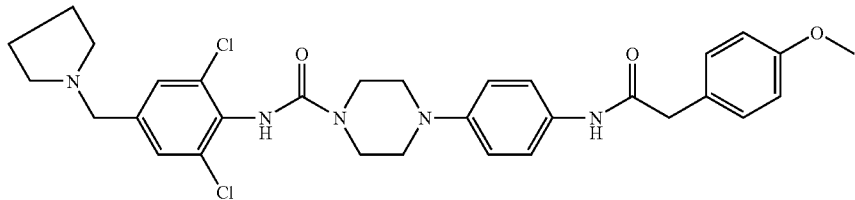 [SMILES: COc1ccc(CC(=O)Nc2ccc(N3CCN(C(=O)Nc4c(Cl)cc(CN5CCCC5)cc4Cl)CC3)cc2)cc1]

A mixture of intermediate 38 (prepared according to A4.d-1) (0.97 g; 0.0023 mol), Et₃N (2.8 ml; 0.0200 mol), CH₃CN, dried on molecular sieves (20 ml), and DMF, dried on molecular sieves (5 ml), was added to a stirring mixture of intermediate 41 (prepared according to A15.c) (crude; 0.0023 mol) and CH₃CN, dried on molecular sieves (20 ml). The reaction mixture was stirred further at room temperature for 2 hours. The reaction mixture was poured into 200 ml H₂O, and the product was extracted with 150 ml CH₂Cl₂. The separated organic layer was washed with NaHCO₃ aqueous saturated solution, dried with MgSO₄, filtered off, and evaporated. The residue was stirred in CH₃CN, filtered off, washed with 3× CH₃CN, and dried at 50° C. (vacuum). Yield: 0.75 g of compound 223 (54.7%).

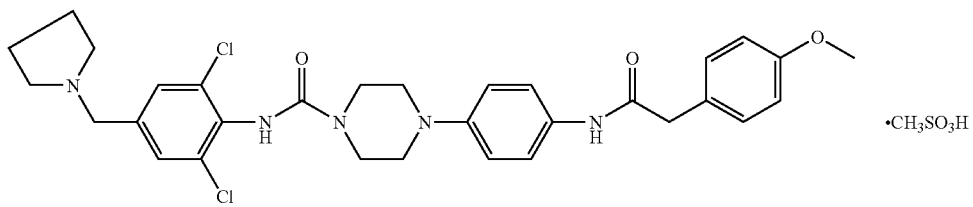

Compound 223a (methanesulfonic acid salt)

Compound 223 was converted into its methanesulfonic acid salt (mesylate salt) by adding methanol (70 ml; 1.73 mol) to compound 223 (4 g; 6.71 mmol) and then methanesulfonic acid (1 equiv.; 6.71 mmol) was added. After 30 minutes of stirring at room temperature, the solution was evaporated to dryness. The solidified material was then triturated with acetone (60 ml), filtered off, washed with acetone and DIPE, dried in vacuum oven at 45° C. for 3 hours, yielding 0.87 g of compound 223a (methanesulfonic acid salt).

3.3 g of compound 223a prepared in this way (combination of different batches) was further suspended in PGMEE (polyethyleneglycol monomethylether or 1-methoxy-2-propanol) at 90° C. After cooling down to room temperature, the product crystallized after 2 days under stirring. The crystallized material was filtered off, washed with PGMEE (5 ml) and dried in a vacuum oven at 45° C., yielding 0.87 g of compound 223a.

f. Preparation of Compound 227

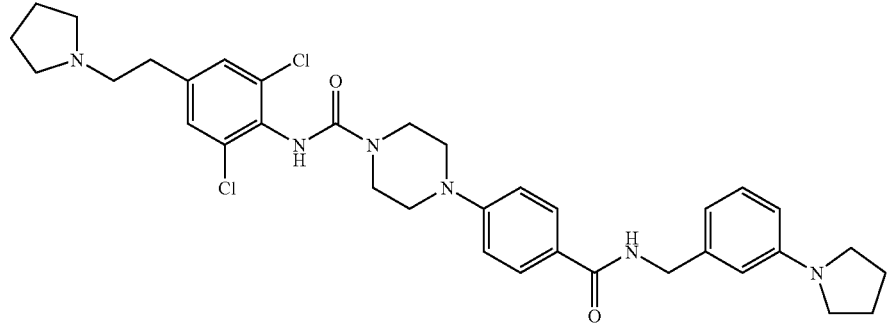 [SMILES: O=C(NCc1cccc(N2CCCC2)c1)c1ccc(N2CCN(C(=O)Nc3c(Cl)cc(CCN4CCCC4)cc3Cl)CC2)cc1]

Intermediate 52 (prepared according to A18.b) (0.514 g; 1.41 mmol) was dissolved in TEA (1 ml; 7.115 mmol) and DCM (50 ml) and intermediate 50 (prepared according to A17.c)(0.402 g; 1.41 mmol) were added and dissolved in 100 ml DCM (50 ml; 2500 mmol). The reaction mixture was stirred for 48 hours. The reaction mixture was stirred in saturated solution of $NaHCO_3$ in $H_2O$. To the layers was added $CH_2Cl_2$/MeOH 90/10 and water. The layers were separated, the $CH_2Cl_2$-layer was dried with $MgSO_4$, filtered off, evaporated and co-evaporated. The residue was stirred in DIPE and filtered off, washed with EtOH and washed one time with DIPE. The filtrate precipitated and was filtered off, washed with DIPE and dried in vacuum at 50° C. for 18 hours. Yield: 0.369 g of compound 227 (40%).

g. Preparation of Compound 228

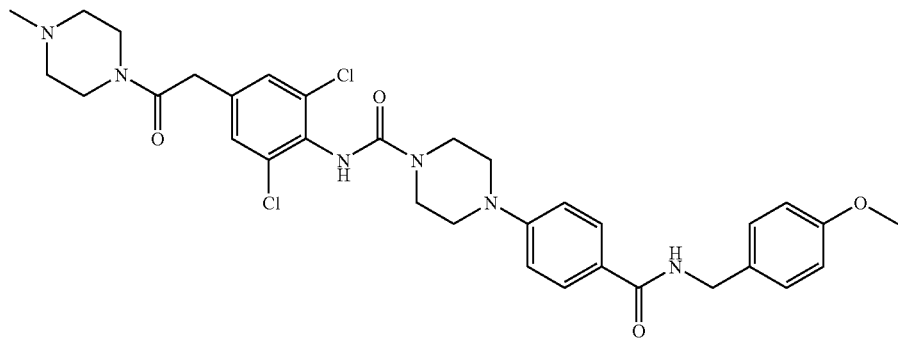

Intermediate 56 (prepared according to A20.b) (0.5 g; 0.00152 mol) was dissolved in DCM (10 ml) and was stirred. The solution was added to a stirring solution of intermediate 54 (prepared according to A19.b) (0.5 g; 0.00152 mol) in TEA (1 ml) and DCM (20 ml). The reaction mixture was stirred in $NaHCO_3$ saturated aqueous solution. The layers were separated, the organic layer was dried with $MgSO_4$, filtered off, evaporated and co-evaporated with toluene, yielding 1.33 g.

The product was purified by reversed-phase high-performance liquid chromatography (Shandon Hyperprep® C18 BDS (Base Deactivated Silica) 8 µm, 250 g, I.D. 5 cm). A gradient with 3 mobile phases was applied. Phase A: a 0.25% $NH_4HCO_3$ solution in water; phase B: $CH_3OH$; phase C: $CH_3CN$). The desired fractions were collected and evaporated until dry, co-evaporated with MeOH and afterwards with toluene. The residue was stirred in $Et_2O$, filtered off, dried in vacuo for 18 hours at 50° C. Yield: 0.330 g of compound 228 (33%).

h. Preparation of Compound 268

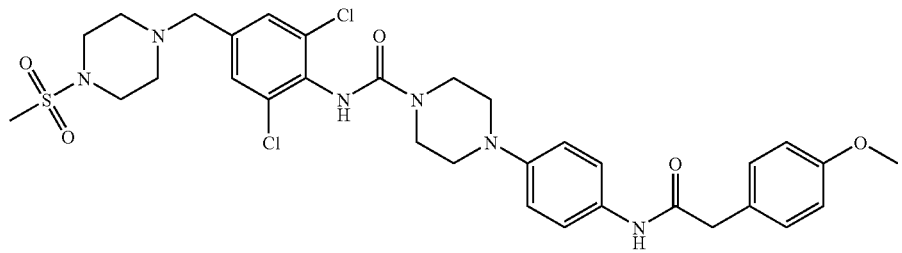

Intermediate 65 (prepared according to A22.b) (0.365 g; 0.001 mol) was added to a stirring solution of intermediate 38 (prepared according to A4.d-1) (0.326 g; 0.001 mol) in triethylamine (0.704 ml; 0.00501 mol) and $CH_2Cl_2$ (10 ml). After 3 hours of continuous stirring, formation of precipitation was observed. The stirring was slowed down. After 36 hours of slow stirring the reaction mixture was filtered off, washed 3× with $CH_2Cl_2$ and dried in vacuo at 50° C. for 20 hours. Yield: 0.335 g of compound 268 (48%).

i. Preparation of Compound 317

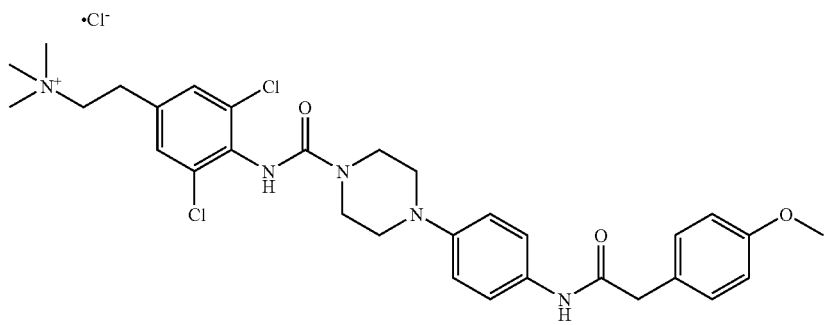

Intermediate 38 (prepared according to A4.d-1) (1.183 g; 0.00281 mol) was dissolved in DMF (5 ml) and extracted with $CH_2Cl_2$/$NaHCO_3$ saturated solution. The layers were separated and the $CH_2Cl_2$-layer was dried with $MgSO_4$ and filtered off. Intermediate 70 (prepared according to A25.c) (crude reaction mixture in $CH_3CN$) was added to the filtrate in $CH_2Cl_2$ (25 ml) with DIPEA (0.557 ml; 0.00337 mol). After 18 hours, a precipitate was formed, it was filtered off, washed 1× with $CH_2Cl_2$/DMF and 2× with $CH_2Cl_2$ and dried in vacuo for 20 hours at 50° C. Yield=0.573 g of compound 317 (80%).

Example B7 a. Preparation of Compound 15

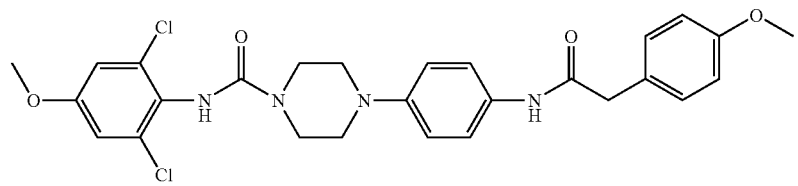

Trichloromethyl carbonochloridic acid ester (0.0065 mol) was added to the solution of 2,6-dichloro-4-methoxybenzenamine (0.001 mol) and Et₃N (0.4 ml) in dry toluene (16 ml). The reaction mixture was stirred for 2 hours at 60° C. till the starting aniline reacted completely (control by TLC). Then, a solution of intermediate 24 (prepared according to A8.c) in DCM (4 ml) was added to the reaction mixture at 60° C. at stirring. Formation of precipitate was observed. The stirring was continued at 60-70° C. for 1 hour. Then, the reaction mixture was concentrated in vacuum. The formed sediment was treated with water and filtered off. Then, it was washed with water, ethyl acetate, ether, and dried on the air. Yield: 0.360 g of compound 15 (66%).

b. Preparation of Compound 16

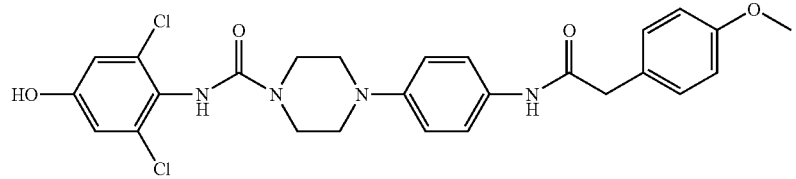 [SMILES: COc1ccc(CC(=O)Nc2ccc(N3CCN(C(=O)Nc4c(Cl)cc(O)cc4Cl)CC3)cc2)cc1]

Trichloromethyl carbonochloridic acid ester (0.001 mol) was added to a solution of 4-amino-3,5-dichlorophenol (0.002 mol) in dry ethyl acetate (30 ml) while cooling, and then the reaction mixture was refluxed for 2 hours followed by addition of intermediate 24 (prepared according to A8.c) (0.00154 mol) in chloroform. The reaction mixture was refluxed for 19 hours. The formed solid was filtered off and dried on the air. The product was purified by washing the sediment with hot methanol. The formed sediment was refluxed with methanol (10 ml) and then filtered off Yield: 0.260 g of compound 16 (32%, white solid compound).

Example B8

Preparation of Compound 17

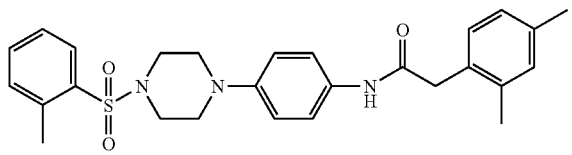 [SMILES: Cc1ccc(CC(=O)Nc2ccc(N3CCN(S(=O)(=O)c4ccccc4C)CC3)cc2)c(C)c1]

A mixture of intermediate 36 (prepared according to A14.b) (0.2 mmol) and N-ethyl-N-(1-methylethyl)-2-propanamine (q.s.) in DCM (2 ml) was stirred at 10° C. A mixture of 2-methylbenzenesulfonylchloride (0.2 mmol) in CH₂Cl₂ (1 ml) was added dropwise and the reaction mixture was stirred at room temperature for 1 hour. The solvent was evaporated. The residue was purified by reversed phase high performance liquid chromatography. The product fractions were collected and worked-up. The residue was dissolved in DCM and dried over an Isolute filter. The filtrate was evaporated. Yield: 0.057 g of compound 17.

Example B9

Preparation of Compound 18

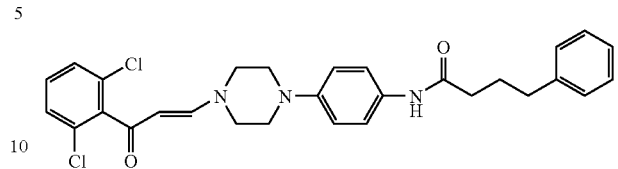

A mixture of intermediate 11 (prepared according to A4.d) (0.433 mmol) and 1-(2,6-dichlorophenyl)-3-(dimethylamino)-2-propen-1-one (0.476 mmol) in EtOH, p.a. (4 ml) was stirred in a sealed tube at 110° C. for 85 hours. The reaction mixture was allowed to reach room temperature and the solvent was evaporated. The residue was filtered purified silica gel using DCM/MeOH (98:2) as eluent. The desired fractions were collected and the solvent was evaporated and co-evaporated with EtOH. The residue solidified upon standing. The product was stirred in EtOH (2.5 ml), filtered off, washed with EtOH, filtered off again and dried at 50° C. (vacuum). Yield: 0.127 g of compound 18 (56%).

Example B10 a) Preparation of Compound 19

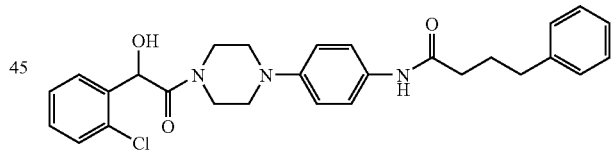

EDCI (0.0012 mol) was added to a mixture of 2-chloro-α-hydroxybenzene acetic acid (0.0011 mol), intermediate 11 (prepared according to A4.d) (0.0011 mol), HOBT (0.0001 mol) and N-ethyl-N-(1-methylethyl)-2-propanamine (0.213 ml) in DMF/THF (1/1 dried on molecular sieves) (10 ml) at room temperature. A second reaction mixture with 0.050 g of 2-chloro-α-hydroxybenzene acetic acid was set up (same conditions) and both mixtures were combined and evaporated to dryness. The residue was purified by HPLC method A. The recovered fraction was partially evaporated at 22° C. to remove the volatiles, followed by extraction with CH₂Cl₂. After drying (MgSO₄), filtration and evaporation 380 mg yellow oily residue was obtained. This was suspended in boiling DIPE with few drops MeOH and stirred overnight at room temperature. After filtration and drying in vacuo at 50° C. a white powdery material was recuperated. Yield: 328 mg of compound 19 (RS).

b) Preparation of Intermediate 352

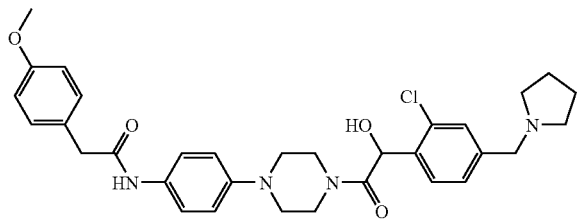 [SMILES: COc1ccc(CC(=O)Nc2ccc(N3CCN(C(=O)C(O)c4ccc(CN5CCCC5)cc4Cl)CC3)cc2)cc1]

Intermediate 29 (prepared according to A29.c) (0.2 g; 0.00074 mol) in CH$_2$Cl$_2$ (10 ml) was stirred at room temperature. Et$_3$N (0.3 ml; 0.00222 mol) was added, then EDCI (0.14 g; 0.00074 mol) and HOBT (0.1 g; 0.00074 mol) were added. Intermediate 84 (prepared according to A24.b) (0.2 g; 0.00074 mol) was added to the mixture. The resultant reaction mixture was stirred overnight at room temperature. Water was added, and the mixture was extracted with CH$_2$Cl$_2$ (3×10 ml). The organic layers were combined, dried (MgSO$_4$), filtered and the solvent was evaporated in vacuo. The residue was purified by high performance liquid chromatography (Column: Venusil 250×21.5 mm, Mobile Phase: 21-51% CH$_3$CN % (0.1% TFA), Flow Rate: 15 ml/min, Finished Time: 20 min). The desired fraction was collected and evaporated to remove CH$_3$CN in vacuo. The residue was neutralized to pH=8 with saturated NaHCO$_3$, then extracted with CH$_2$Cl$_2$ (3×10 ml). The organic layers were combined, washed with brine, dried over MgSO$_4$, filtered and the filtrate's solvent was evaporated in vacuo. Yield: 0.050 g of compound 352 (12%).

Example B11 a. Preparation of Compound 20

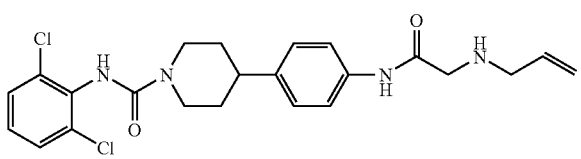 [SMILES: C=CCNCC(=O)Nc1ccc(C2CCN(C(=O)Nc3c(Cl)cccc3Cl)CC2)cc1]

A mixture of intermediate 25 (prepared according to A1.d) (0.0001 mol), 2-propen-1-amine (0.0001 mol) and Na$_2$CO$_3$ (0.0001 mol) in DMF (3 ml) was stirred for 18 hours at room temperature. The solvent was evaporated under a stream of N$_2$ at 50° C. The residue was stirred in water (2 ml). This mixture was extracted with DCM (10 ml). The separated organic layer was filtered through an Isolute filter (for drying). The filtrate's solvent was evaporated under a stream of N$_2$ at 50° C. Yield: 0.015 g of compound 20.

b. Preparation of Compound 21

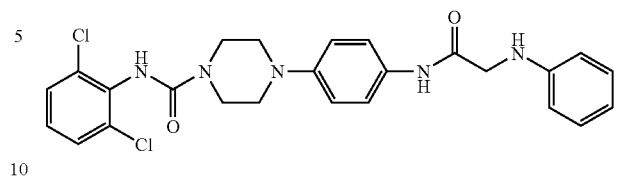

A mixture of intermediate 26 (prepared according to A2.c) (0.000247 mmol), benzenamine (0.000247 mol) and K$_2$CO$_3$ (0.000371 mol) was stirred in DMF (2 ml) at room temperature for 24 hours. Then the reaction mixture was heated up to 50° C. and the stirring was continued for 8 hours at 50° C. (control by LC/MS). After that water (10 ml) was added to the reaction mixture, the formed precipitate was filtered off and washed with water. The residue was purified by column chromatography (eluent:ethyl acetate/acetone—1/1). Yield: 0.050 g of compound 21 (41%) (white crystals).

c. Preparation of Compound 22

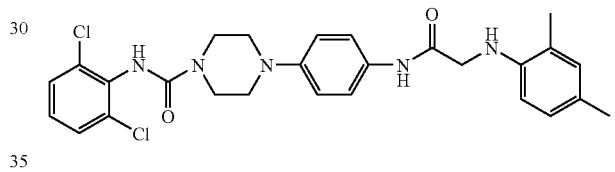

A mixture of intermediate 26 (prepared according to A2.c) (0.000411 mol), 2,4-dimethylbenzenamine (0.000432 mol) and Et$_3$N (0.070 ml) was stirred in DMF (10 ml) at room temperature for 20 hours (control by LC/MS). When the reaction was completed the solvent was evaporated under reduced pressure. The residue was separated by column chromatography (eluent: DCM/MeOH—20/1). Yield: 0.042 g of compound 22 (21%) (white crystals).

Example B12

Preparation of Compound 23

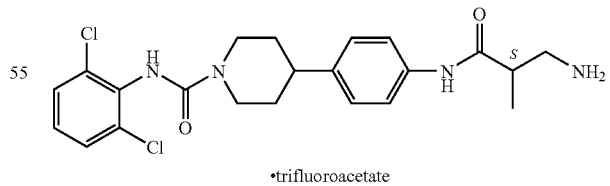

•trifluoroacetate

A mixture of intermediate 3 (prepared according to A1.c) (max. 0.0002 mol) and trifluoro acetic acid (0.2 ml) in CH$_2$Cl$_2$ (2 ml) was shaken for 4 hours at room temperature. The solvent was evaporated. Toluene was added and azeotroped on the rotary evaporator. Yield: 0.068 g of compound 23 (S-enantiomer).

Example B13

Preparation of Compound 24

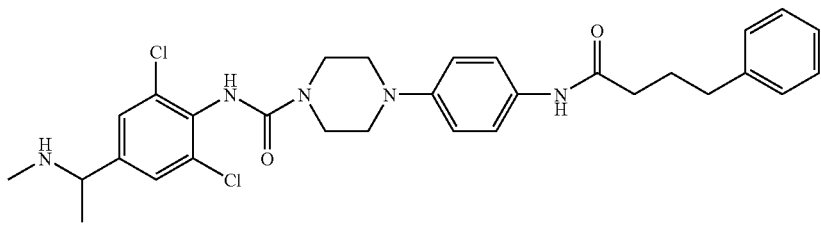 [SMILES: CNC(C)c1cc(Cl)c(NC(=O)N2CCN(c3ccc(NC(=O)CCCc4ccccc4)cc3)CC2)c(Cl)c1]

CH$_3$NH$_2$, 40% in H$_2$O (1 ml) was added to a stirring mixture of intermediate 29 (prepared according to A10) (0.0003 mol) and CH$_3$CN (2.5 ml) on an ice-bath. The resulting solution was stirred further at 0° C. for 5 minutes, and at room temperature for 18 hours. The solvents were evaporated. The residue was purified by reversed-phase high-performance liquid chromatography. (Shandon Hyperprep® C18 BDS (Base Deactivated Silica) 8 μm, 250 g, I.D. 5 cm). A gradient with the mentioned mobile phases was applied (phase A: a 0.25% NH$_4$HCO$_3$ solution in water; phase B: CH$_3$OH (optional); phase C: CH$_3$CN). The desired fractions were combined and the organic volatiles were evaporated. The product was filtered off, washed with 3× H$_2$O, and dried at 50° C. (vacuum). Yield: 0.05 g of compound 24 (33%).

Example B14 a. Preparation of Compound 25

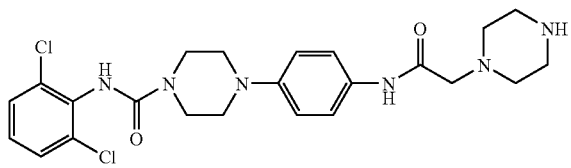 [SMILES: O=C(CN1CCNCC1)Nc1ccc(N2CCN(C(=O)Nc3c(Cl)cccc3Cl)CC2)cc1]

Compound 222 (prepared according to B11.c) (0.000161 mol) was dissolved in HCl (5 ml of 15% aqueous solution) and stirred for 4 hours at room temperature. The reaction mixture was held overnight. Insoluble sediment was filtered off through the folded filter. A saturated Na$_2$CO$_3$ solution was added to the filtrate up to pH=10. The formed precipitate was filtered off, washed with water and 3% aqueous solution of Na$_2$CO$_3$. Then it was purified by column chromatography (eluent: ethyl acetate/acetone—1/1). Yield: 0.024 g of compound 25 (30%)(white crystalline powder).

b. Preparation of Compound 26

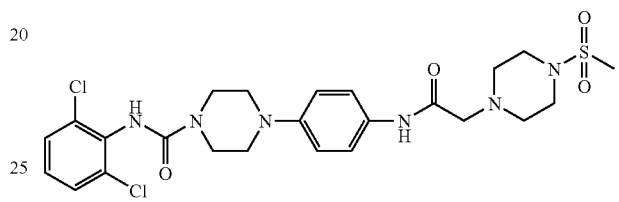

Et$_3$N (0.093 ml) was added to a suspension of compound 25 (prepared according to B14.a) in CH$_3$CN (7 ml) and this mixture was stirred for 10 minutes at 40° C. Then methanesulfonyl chloride (0.023 ml) was added dropwise at stirring. The reaction mixture was refluxed for 2 hours at stirring (control by LC/MS). The solvent was removed under reduced pressure. The target product was purified by flash-chromatography (eluent: CH$_2$Cl$_2$/MeOH—10/1). Yield: 0.055 g of compound 26 (36%) (white crystalline powder).

Example B15

Preparation of Compound 27

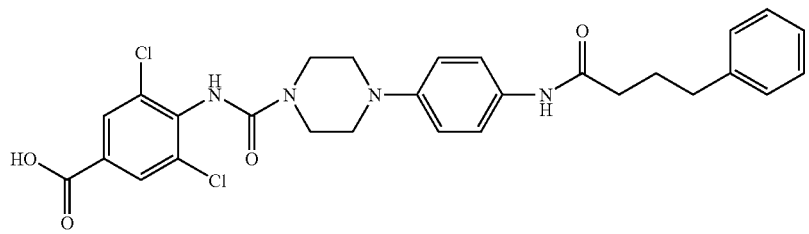 [SMILES: O=C(CCCc1ccccc1)Nc1ccc(N2CCN(C(=O)Nc3c(Cl)cc(C(=O)O)cc3Cl)CC2)cc1]

1N NaOH aqueous solution (0.4 ml) was added to a stirring mixture of compound 47 (prepared according to B6.a) (0.0001 mol) and 1,4-dioxane (2 ml). The resulting solution was stirred further at room temperature for 2 hours. The reaction mixture was cooled on an ice-bath, and 0.4 ml HCl 1N was added. The volume was concentrated to about 0.5 ml, and 4 ml H$_2$O was added. The mixture was stirred for 1 hour, filtered off, washed with 3× H$_2$O, and dried at 50° C. (vacuum). Yield: 0.067 g of compound 27 (91%).

Example B16

Preparation of Compound 28

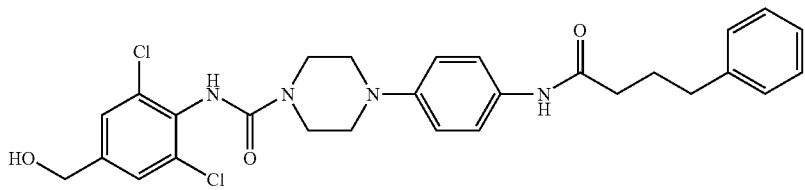 [SMILES: O=C(CCCc1ccccc1)Nc1ccc(N2CCN(C(=O)Nc3c(Cl)cc(CO)cc3Cl)CC2)cc1]

2M LiBH$_4$ in THF (2 ml) was added to a stirring mixture of compound 47 (prepared according to B6.a) (0.0005 mol) and THF p.a. (6 ml) (dried on molecular sieves). The resulting solution was stirred further at room temperature for 18 hours. More 2M LiBH$_4$ in THF (0.8 ml) was added, and the reaction mixture was stirred further at room temperature for 24 hours. More 2M LiBH$_4$ in THF (0.4 ml) was added, and the reaction mixture was stirred further at room temperature for 65 hours. To the reaction mixture was added slowly 20 ml H$_2$O, then 20 ml DCM. Stirring was continued for 5 hours. The solid part was filtered off, washed with 2× H$_2$O, and 2×DCM, and dried at 50° C. (vacuum). Yield: 0.12 g of compound 28 (42%).

Example B17

Preparation of Compound 29

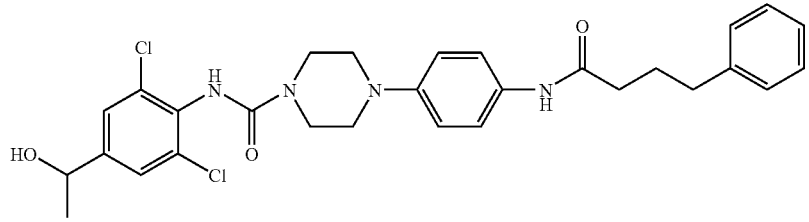 [SMILES: CC(O)c1cc(Cl)c(NC(=O)N2CCN(c3ccc(NC(=O)CCCc4ccccc4)cc3)CC2)c(Cl)c1]

NaBH$_4$ (0.0072 mol) was added portionwise to a stirring mixture of compound 53 (prepared according to B6.a) (0.0060 mol) and CH$_3$OH (100 ml). The reaction mixture was stirred further at room temperature for 18 hours. The reaction mixture was cooled on a cold water batch, and 40 ml H$_2$O was added dropwise. After addition, stirring was continued for 1 hour, then the mixture was left standing for 2 hours. The solid part was filtered off, washed with 3×15 ml MeOH/H$_2$O 1/2, and dried at 50° C. (vacuum, airstream). Yield: 2.85 g of compound 29 (86%).

Example B18

Preparation of Compound 30

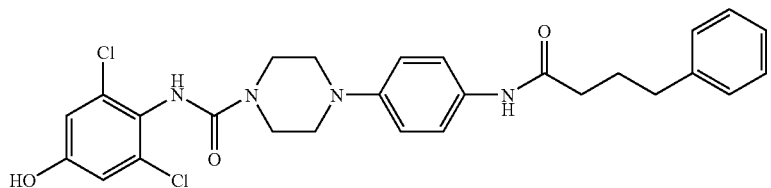 [SMILES: O=C(CCCc1ccccc1)Nc1ccc(N2CCN(C(=O)Nc3c(Cl)cc(O)cc3Cl)CC2)cc1]

The mixture of the compound 190 (prepared according to B7.a) (0.00117 mol) and BBR₃ (0.0047 mol) in dry dichloroethane (15 ml) was stirred for 10 hours at 20° C. and hold for a night at room temperature. Then, the reaction mixture was poured out on a cooled aqueous ammonia solution (50 ml 7%-solution, 5° C.) while stirring. The mixture was filtered and the sediment was washed with water, with a mixture of ether/ethanol (4/1); ether, and dried on the air. Yield: 0.480 g of compound 30 (78%).

Example B19

Preparation of Compound 31

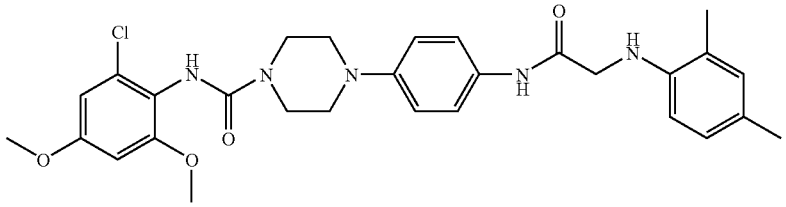

A mixture of compound 221 (prepared according to B2.f) (0.00216 mol), 1,3-dimethyl-2,4,6(1H,3H,5H)-pyrimidinetrione (0.011 mol) and Pd(PPh₃)₄ (0.00026 mol) in dry dichloroethane (40 ml) was stirred at 50° C. for 6 hours under argon atmosphere. The solvent was removed in vacuum. The residue was dissolved in CH₂Cl₂ (50 ml). The resulting solution was filtered to remove insoluble components and washed with aqueous K₂CO₃ (40 ml 10% solution). The organic layer was separated, washed with water, dried over MgSO₄ and concentrated in vacuum. The dark-red residue was purified by column chromatography on silica gel (eluent: CHCl₃/Me₂CO—7/1). The fractions containing a target product were concentrated. Yield: 0.78 g of compound 31 (white-pink powder).

Example B20

Preparation of Compound 32

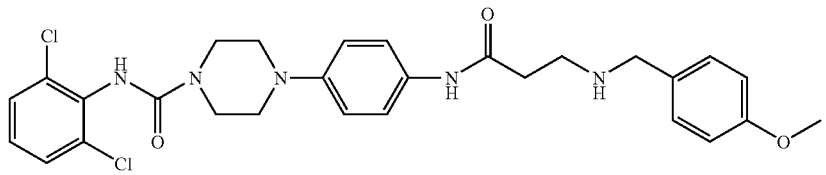 [SMILES: COc1ccc(CNCCC(=O)Nc2ccc(N3CCN(C(=O)Nc4c(Cl)cccc4Cl)CC3)cc2)cc1]

A mixture of compound 173 (prepared according to B2.c) (0.000458 mol), 2-mercapto acetic acid (0.064 ml) and LiOH.H₂O (0.000456 mol) in DMF (6 ml) was stirred at room temperature for 24 hours. The reaction mixture was diluted with water and the formed precipitate was filtered off, washed with water and dried on air. The residue was purified by flash-chromatography (eluent: DCM/MeOH 20/1). Yield: 0.040 g of compound 32 (16%) (crystalline powder).

a) Preparation of Compound 224

Example B21

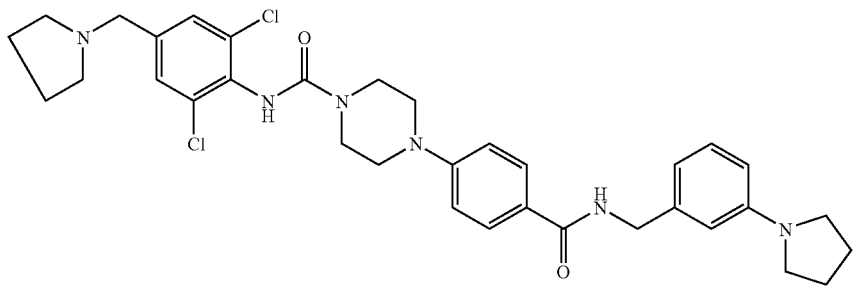

DECP (0.412 ml; 0.00276 mol) was added to a stirring mixture of intermediate 44 (prepared according to A15.f) (0.94 g; 0.00197 mol), 3-(1-pyrrolidinyl)-benzenemethanamine (0.482 g; 0.00246 mol), CH$_2$Cl$_2$ p.a. (20 ml) and TEA (0.553 ml, 0.00394 mol). The reaction mixture was stirred at room temperature for 24 hours. The solid part was filtered off, washed with CH$_2$Cl$_2$ (3×), and dried at 50° C. in vacuo. Yield: 0.94 g of compound 224 (75%; m.p. 224-230° C.)

b) Preparation of Compound 225

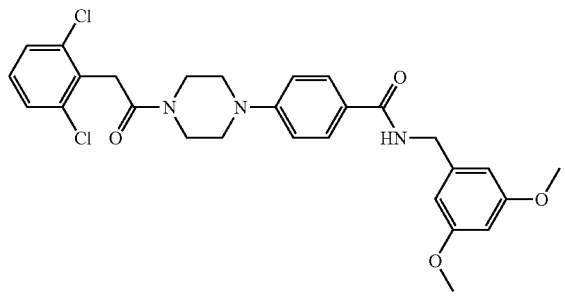 [SMILES: COc1cc(CNC(=O)c2ccc(N3CCN(C(=O)Cc4c(Cl)cccc4Cl)CC3)cc2)cc(OC)c1]

DECP (0.108 g; 0.00066 mol) was added to a solution of intermediate 47 (prepared according to A16.b) (0.2 g; 0.000509 mol), 3,5-dimethoxybenzenemethanamine (0.102 g; 0.00061 mol) and DIPEA (0.1 ml) in CH$_3$CN (5 ml) at room temperature. Then the reaction mixture was stirred at room temperature for 1 hour. Then the reaction mixture was concentrated to be dry, the residues were washed with EtOAc. Yield: 159 mg of compound 225 (58%).

Example B22

Preparation of Compound 267

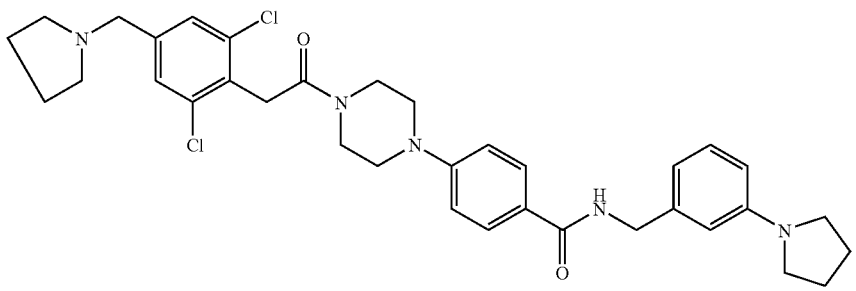 [SMILES: O=C(NCc1cccc(N2CCCC2)c1)c1ccc(N2CCN(C(=O)Cc3c(Cl)cc(CN4CCCC4)cc3Cl)CC2)cc1]

TEA (0.84 ml; 6.04 mmol) was added to a suspension of intermediate 61 (prepared according to A21.e) in CH$_2$Cl$_2$ (15 ml). DECP (0.275 ml; 1.811 mmol) was added to the reaction mixture. The mixture was stirred for 10 minutes at room temperature. Intermediate 52 (prepared according to A18.b) (0.660 g; 1.811 mmol) was added to the reaction mixture. The mixture was stirred for 3 hours at room temperature. The crystalline product was filtered off, washed with CH$_2$Cl$_2$ and dried on the air. Yield: 0.313 g of compound 267 (27%).

Example B23

Preparation of Compounds 270 and 271 compound 270

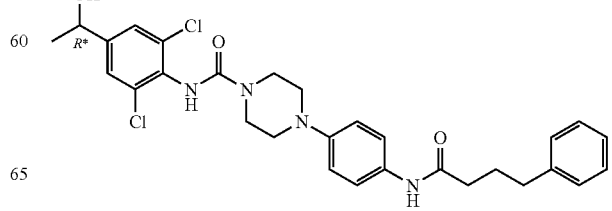

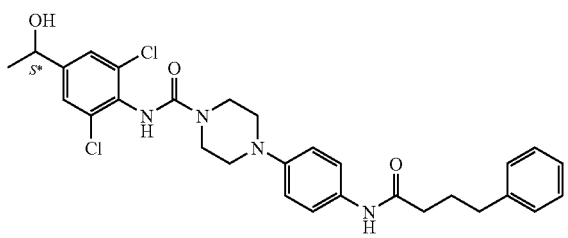

compound 271

Compound 29 (prepared according to B17) (0.08 g, 0.0001 mol) was separated into its enantiomers by supercritical fluid chromatography over an AS—H column (diameter: 20 mm×length: 250 mm); method: gradient elution with (20-60% 2-propanol with 0.2% 2-propylamine)/CO$_2$ (at 1.6 rate and hold 0.1 min); flow: 40 ml/min; column heater: 40° C.; and Nozzle pressure: 100 bar; Injection: 4 mg/ml; collection method: fixed time).

Two product fraction groups were collected.

The solvent of the first eluted fraction group (the (A)-group, stereo centre marked with *R; relative stereochemistry) was evaporated, then co-evaporated with MeOH. Yield: 0.019 g of compound 270.

The solvent of the second eluted fraction group (the (B)-group, stereo centre marked with *S; relative stereochemistry) was evaporated, then co-evaporated with CH$_3$OH. Yield: 0.017 g of compound 271.

Example B24

Preparation of Compound 275

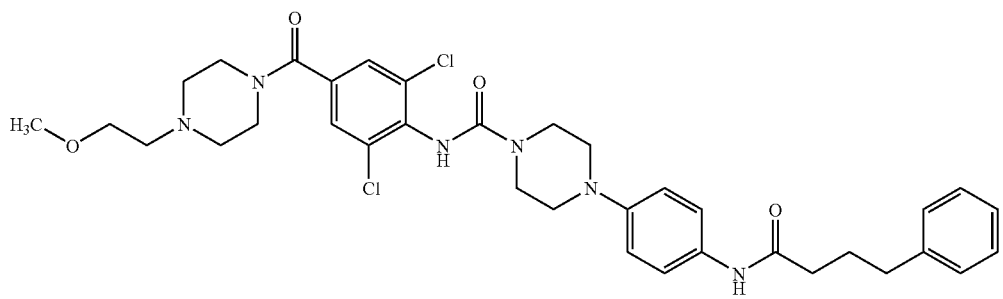 [SMILES: COCCN1CCN(C(=O)c2cc(Cl)c(NC(=O)N3CCN(c4ccc(NC(=O)CCCc5ccccc5)cc4)CC3)c(Cl)c2)CC1]

Compound 27 (prepared according to B15) (0.133 g; 0.0002 mol) was dissolved in DMF (2 ml). PS-CDI, 1.9 mmol/g (0.320 g; 0.0006 mol) was added and HOBT (0.041 g; 0.003 mol) in DMF (2 ml) was added. The reaction mixture was shaken for 1 hour at room temperature. 1-(2-Methoxyethyl)piperazine (0.0002 mol) in DMF (2 ml) was added. The reaction mixture was shaken overnight. MP-carbonate, 1 mmol/g (0.5 g) and polymer-bound isocyanate (0.111 g; 0.0002 mol) were added. The reaction mixture was shaken overnight. The reaction mixture was filtered, CH$_2$Cl$_2$ (3 ml) was added, and the mixture was shaken for 2 hours and filtered again. The filtrate was evaporated with the Genevac. The product was purified by reversed-phase high-performance liquid chromatography (Shandon Hyperprep® C18 BDS (Base Deactivated Silica) 8 µm, 250 g, I.D. 5 cm). A gradient with 3 mobile phases was applied. Phase A: a 0.25% NH$_4$HCO$_3$ solution in water; phase B: CH$_3$OH; phase C: CH$_3$CN). The desired fractions were collected and the solvent was evaporated. Yield: 22 mg of compound 275.

Example B25

Preparation of Compounds 299 and 300 compound 299

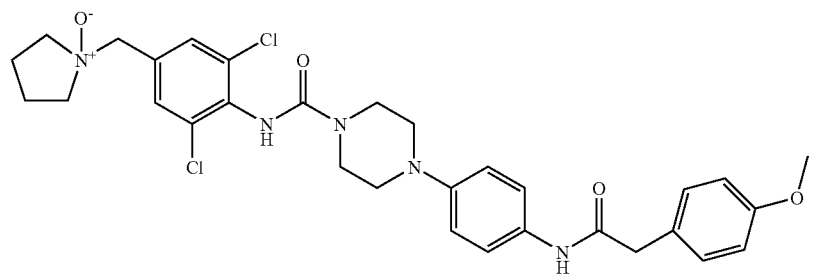

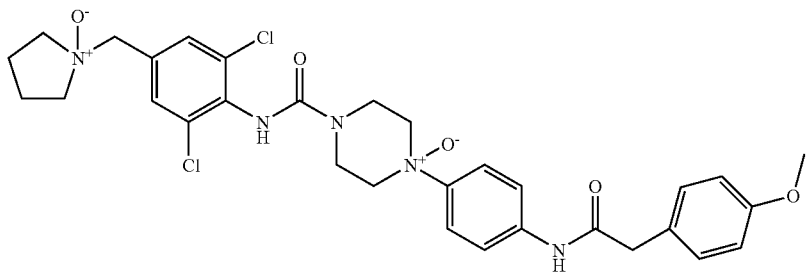

compound 300

3-Chloro-benzenecarboperoxoic acid (3333.18 mg; 1.931 mmol) was added to a solution of compound 223 (prepared according to B6.e) (886 mg; 1.485 mmol) in DCM (20 ml) and $CH_3OH$ (20 ml) and stirred at room temperature. The reaction was evaporated to dryness at 30° C. The product was purified by reversed-phase high-performance liquid chromatography (Shandon Hyperprep® $C_{18}$ BDS (Base Deactivated Silica) 8 μm, 250 g, I.D. 5 cm). A gradient with 3 mobile phases was applied. Phase A: a 0.25% $NH_4HCO_3$ solution in water; phase B: $CH_3OH$; phase C: $CH_3CN$). The two desired fractions were collected and worked up.

After partial evaporation at 35° C. the two fractions were extracted first with EtOAc, followed by DCM, dried ($MgSO_4$) and worked up yielding for fraction A 9 mg from EtOAc extraction and 7 mg residue from DCM extraction. The EtOAc extract of fraction B yielded 15 mg residue and no residue in the DCM extract. The two remaining aqueous layers were evaporated to dryness and coevaporated with $MeOH/CH_3CN$ at 30° C. yielding 106 mg from fraction A, 200 mg from fraction B. Fraction A and fraction B were coevaporated with $MeOH/CH_3CN$ at 50° C. Yield: 195 mg of compound 299 and 100 mg of compound 300.

Example B26

Preparation of Compound 308

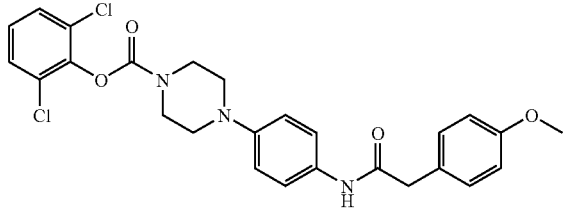 [SMILES: COc1ccc(CC(=O)Nc2ccc(N3CCN(C(=O)Oc4c(Cl)cccc4Cl)CC3)cc2)cc1]

4-Methoxybenzeneacetylchloride (0.162 ml; 0.00106 mol) was added to a stirring mixture of intermediate 67 (prepared according to A23.b) (0.37 g; 0.00101 mol), $NaHCO_3$ (0.0934 g; 0.00111 mol) and $CH_3CN$. The reaction mixture was stirred further under $N_2$ atm for 18 hours. $H_2O$ (35 ml) was added, and stirring was continued for 10 minutes. The product was filtered off, washed with 3× $H_2O$, and dried at 50° C. in vacuo. Yield: 0.46 g of compound 308 (89%).

Example B27

Preparation of Intermediate 326

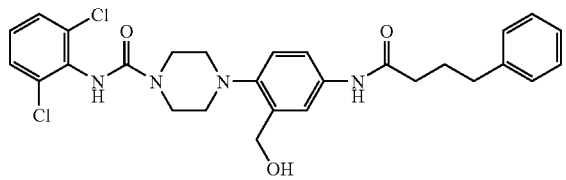 [SMILES: O=C(CCCc1ccccc1)Nc1ccc(N2CCN(C(=O)Nc3c(Cl)cccc3Cl)CC2)c(CO)c1]

A mixture of intermediate 76 (prepared according to A26.f) (0.0016 mol) in HCl in 2-propanol (2 ml) and 2-propanol (2 ml) was stirred at room temperature for 2 hours. The solvent was evaporated. The residue was stirred in $H_2O$ and $NH_4OH$ (q.s.). This mixture was extracted with $CH_2Cl_2$. The separated organic layer was dried ($MgSO_4$), filtered and the solvent was evaporated. The residue was purified by high-performance liquid chromatography (standard gradient elution with $NH_4HCO_3$ buffer). The product fractions were collected and the solvent was evaporated. Yield: 0.160 g of compound 326.

Example B28

Preparation of Intermediate 333

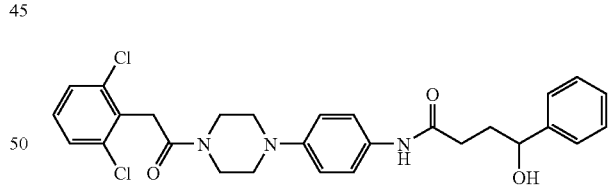

HBTU (722.654 mg; 1.906 mmol) was added to a solution of 2,6-dichlorophenyl acetic acid (325.587 mg; 1.588 mmol), intermediate 78 (prepared according to A27.b) (539 mg; 1.588 mmol), DIPEA (789.353 mg; 4.764 mmol) in DMF dried on molecular sieves (20 ml) and stirred at room temperature. The reaction was evaporated to yield 2204 mg. The product was purified by reversed-phase high-performance liquid chromatography (Shandon Hyperprep® C18 BDS (Base Deactivated Silica) 8 μm, 250 g, I.D. 5 cm). A gradient with 3 mobile phases was applied. Phase A: a 0.25% $NH_4HCO_3$ solution in water; phase B: $CH_3OH$; phase C: $CH_3CN$). The desired fractions were collected and partial evaporated at 30° C., extracted with $CH_2Cl_2$, dried ($MgSO_4$) and worked up. Yield: 434 mg of compound 333 (52%).

Example B29

Preparation of Intermediate 337

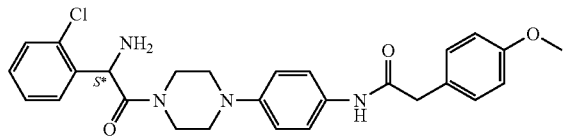 [SMILES: COc1ccc(CC(=O)Nc2ccc(N3CCN(C(=O)C(N)c4ccccc4Cl)CC3)cc2)cc1]

Intermediate 79 (prepared according to A28) (1203 mg; 2.028 mmol) was treated with a mixture of TFA (2.5 ml; 33.655 mmol) and CH$_2$Cl$_2$ (22.5 ml) and stirred at room temperature overnight. The solvent was evaporated yielding 2.656 g. The residue was extracted with 1 M NaOH/CH$_2$Cl$_2$. After drying (MgSO$_4$) and work up the obtained product was triturated overnight by stirring in diethyl ether. Yield: 944 mg compound 337.

Example B30

Preparation of Intermediate 351

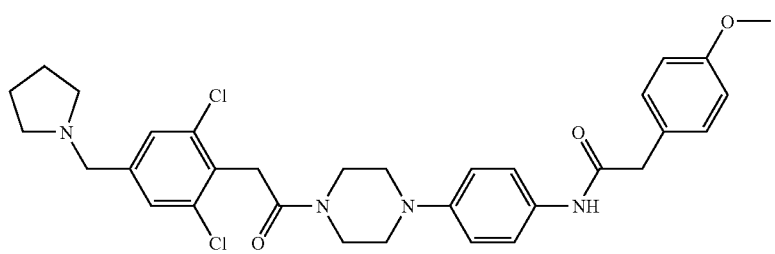 [SMILES: COc1ccc(CC(=O)Nc2ccc(N3CCN(C(=O)Cc4c(Cl)cc(CN5CCCC5)cc4Cl)CC3)cc2)cc1]

4-Methoxybenzeneacetyl chloride (0.135 g; 0.730 mmol) was added to a mixture of intermediate 63 (prepared according to A21.g) (0.272 g; 0.608 mmol) and TEA (0.130 ml; 0.912 mmol) dissolved in CH$_3$CN (5 ml). The reaction mixture was stirred for 2 hours at room temperature. The formed crystalline product was filtered off, washed with water, i-PrOH, and hexane and dried on the air. Yield: 0.242 g of compound 351 (67%).

Example B31

Preparation of Intermediate 292

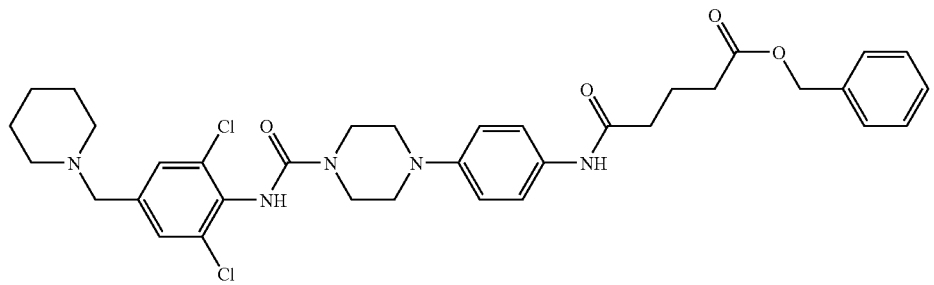 [SMILES: O=C(CCCC(=O)OCc1ccccc1)Nc1ccc(N2CCN(C(=O)Nc3c(Cl)cc(CN4CCCCC4)cc3Cl)CC2)cc1]

The mixture of compounds mono(phenylmethyl)pentanedioic acid ester (1.478 g; 6.75 mmol), TBTU (2.56 g; 7.84 mmol) and Et$_3$N (1.71 ml; 12.2 mmol) in acetonitrile (50 ml) was stirred for 1 hour at 20° C. Then intermediate 85 (prepared according to A21.g) was added, and the resulting mixture was stirred for 24 hours more at 20° C. The solution was evaporated, the residue was treated with 10%-aqueous solution of K$_2$CO$_3$ (20 ml) and with CH$_2$Cl$_2$ (30 ml). The organic layer was separated and dried over MgSO$_4$. The solvent was removed in vacuum. The obtained crude product (2,843 g) was purified by column chromatography (eluent: EtOAc/Et$_3$N-1300:1). Yield: 1.262 g of compound 292 (34%).

Table 1 lists the compounds that were prepared according to one of the above Examples.

TABLE 1

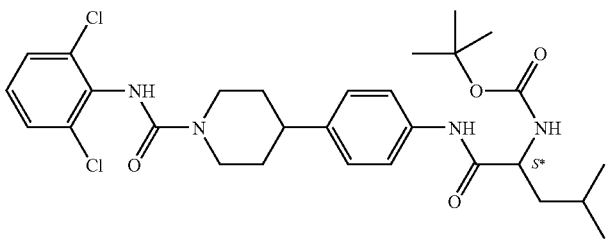

Co. No. 33; Ex. [B1]

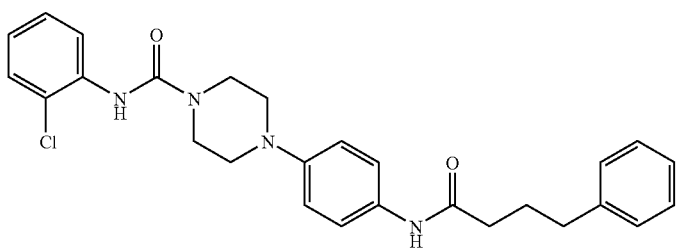

Co. No. 34; Ex. [B6.a]

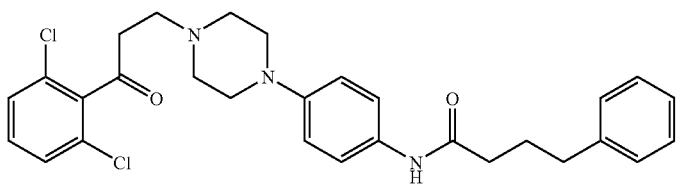

Co. No. 18; Ex. [B9]

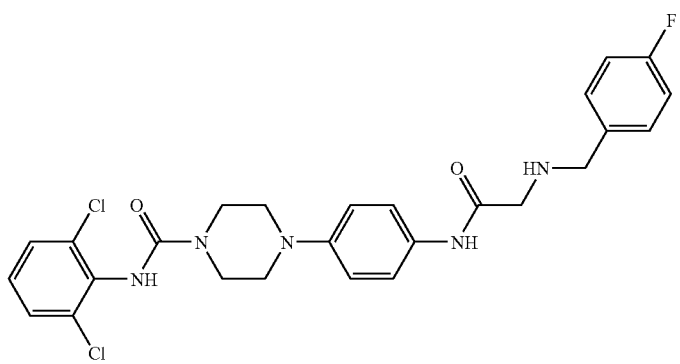

Co. No. 35; Ex. [B11.a]

TABLE 1-continued
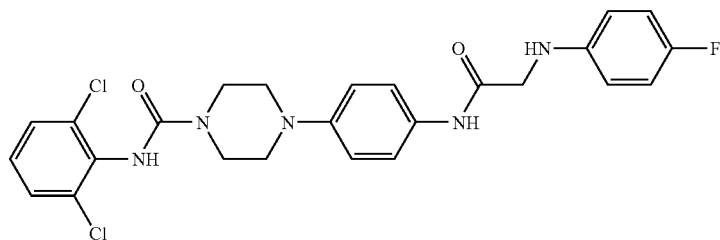
Co. No. 36; Ex. [B11.a]
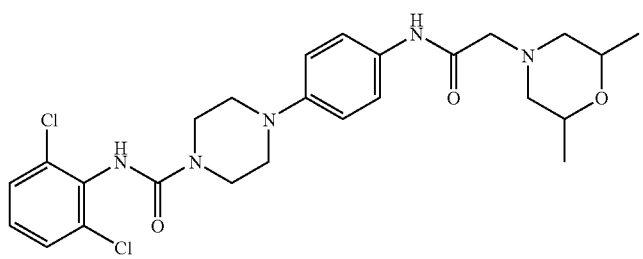
Co. No. 37; Ex. [B11.a]
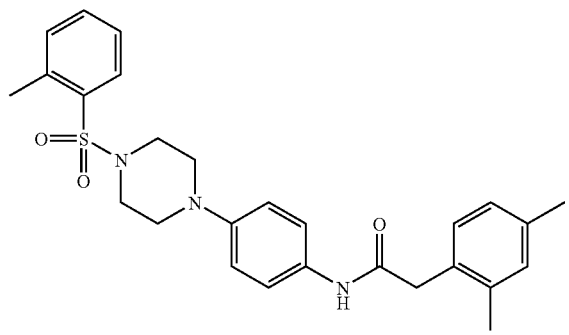
Co. No. 17; Ex. [B8]
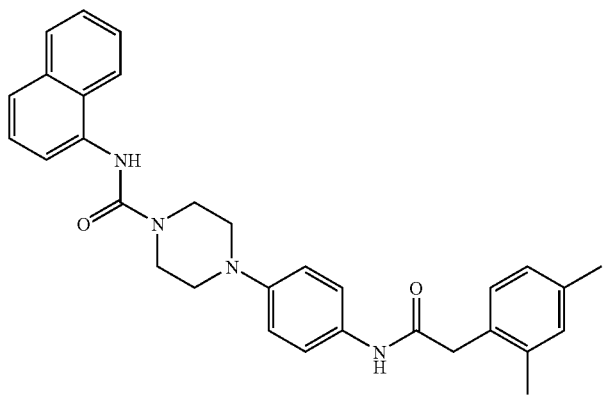
Co. No. 38; Ex. [B6.a]

TABLE 1-continued
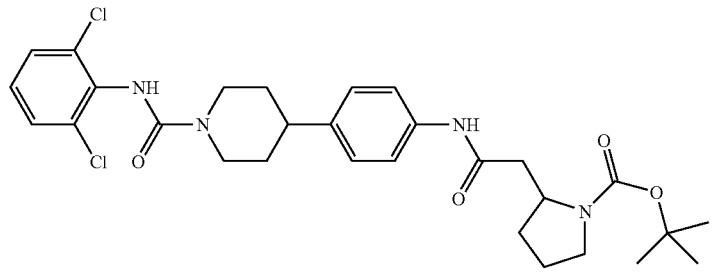
Co. No. 39; Ex. [B1]
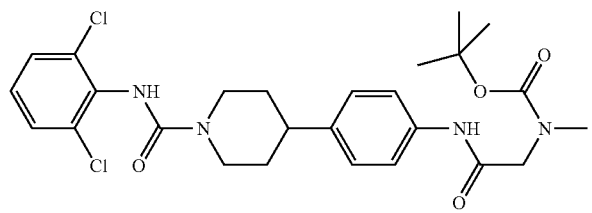
Co. No. 40; Ex. [B1]
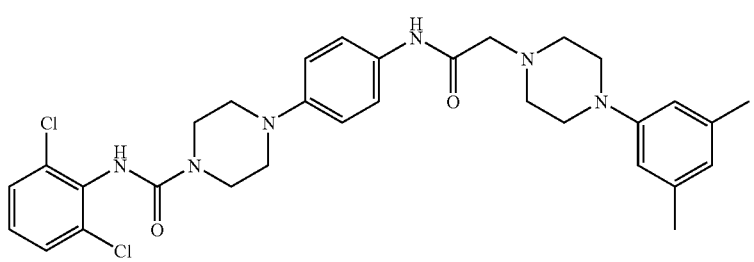
Co. No. 41; Ex. [B11.a]
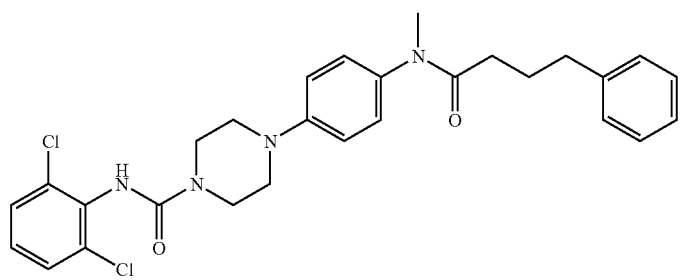
Co. No. 42; Ex. [B6.c]
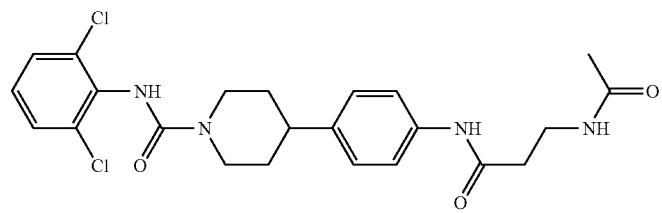
Co. No. 43; Ex. [B2.a]

TABLE 1-continued
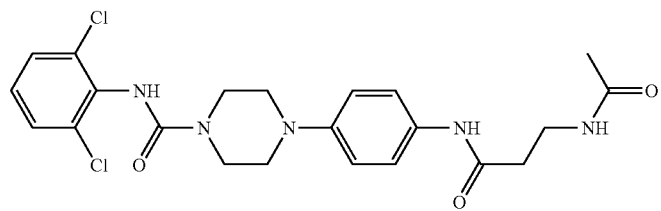
Co. No. 44; Ex. [B2.a]
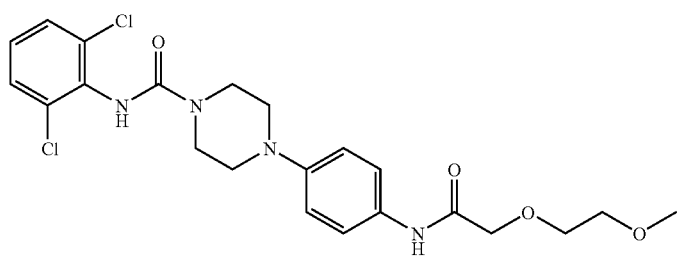
Co. No. 45; Ex. [B2.b]
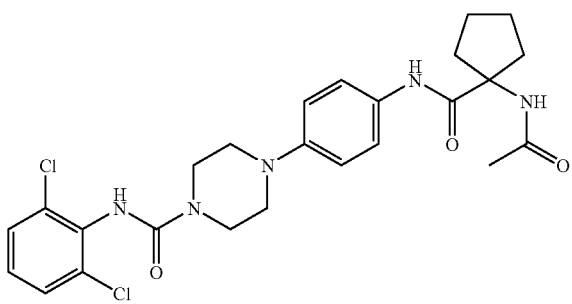
Co. No. 2; Ex. [B2.a]
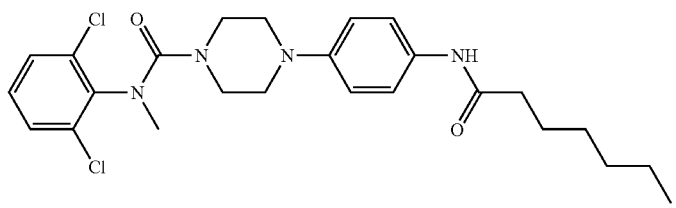
Co. No. 10; Ex. [B5]
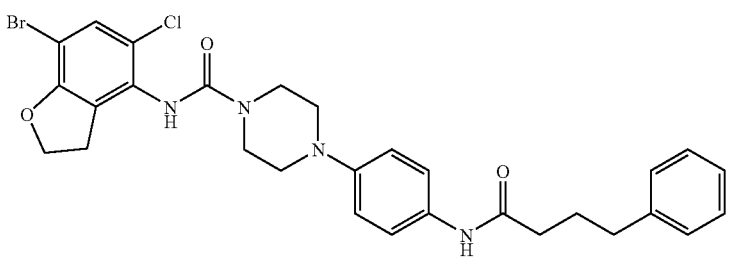
Co. No. 46; Ex. [B6.a]

TABLE 1-continued
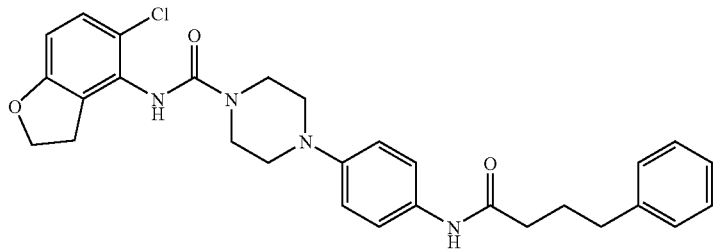
Co. No. 12; Ex. [B6.b]
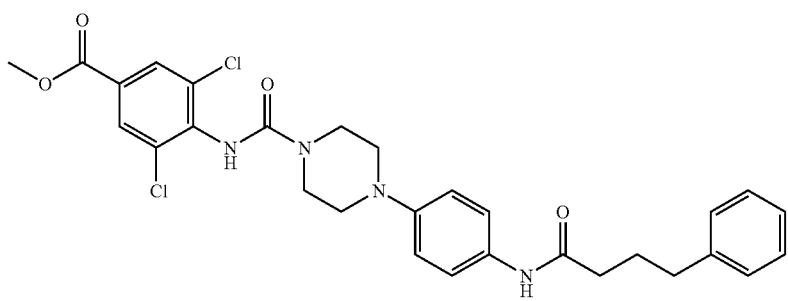
Co. No. 47; Ex. [B6.a]
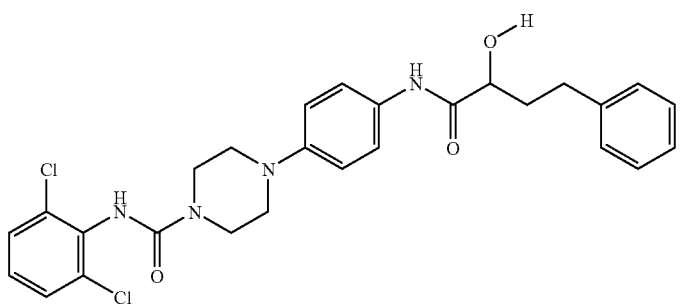
Co. No. 48; Ex. [B2.b]
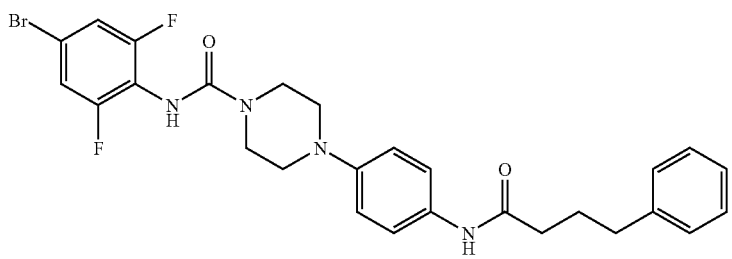
Co. No. 49; Ex. [B6.a]
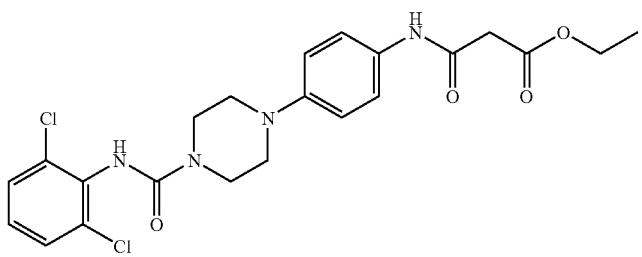
Co. No. 50; Ex. [B6.a]

TABLE 1-continued
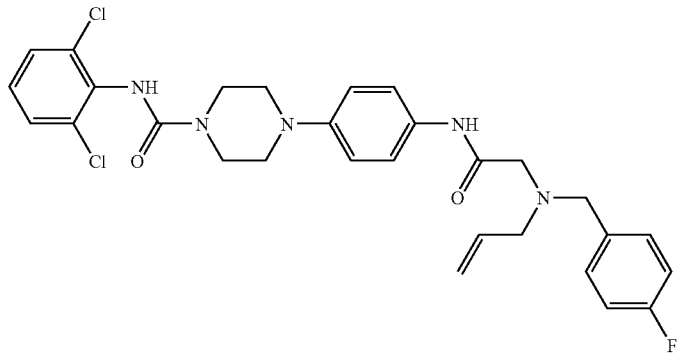
Co. No. 51; Ex. [B6.a]
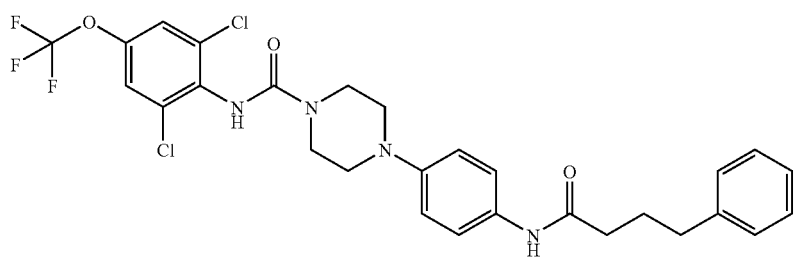
Co. No. 13; Ex. [B6.c]
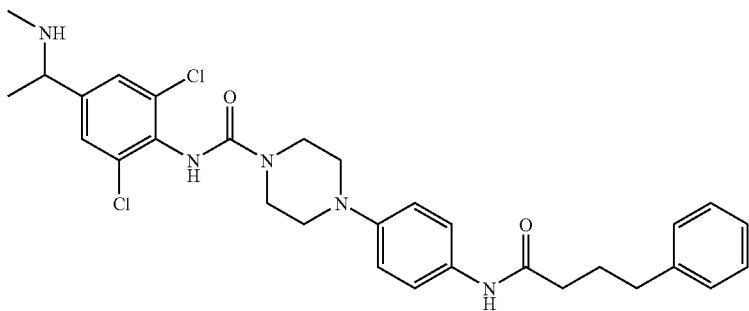
Co. No. 24; Ex. [B13]
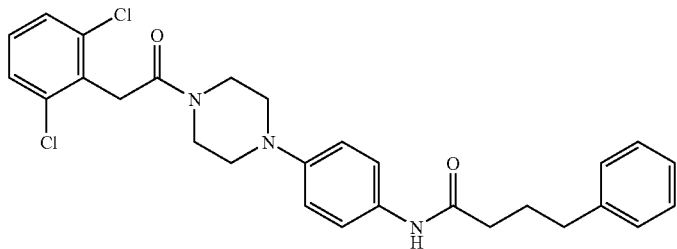
Co. No. 52; Ex. [B2.b]
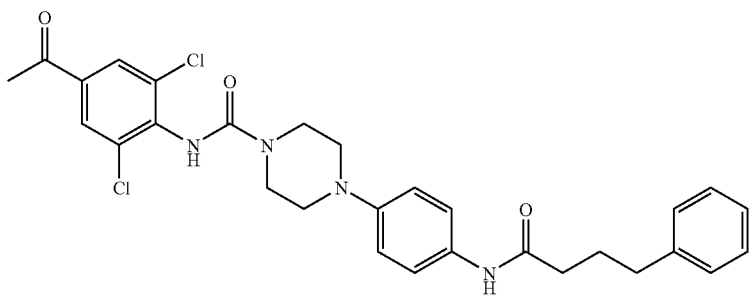
Co. No. 53; Ex. [B6.a]

TABLE 1-continued
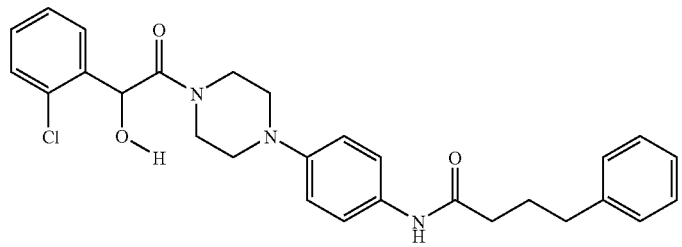
Co. No. 19; Ex. [B10]; RS mixture
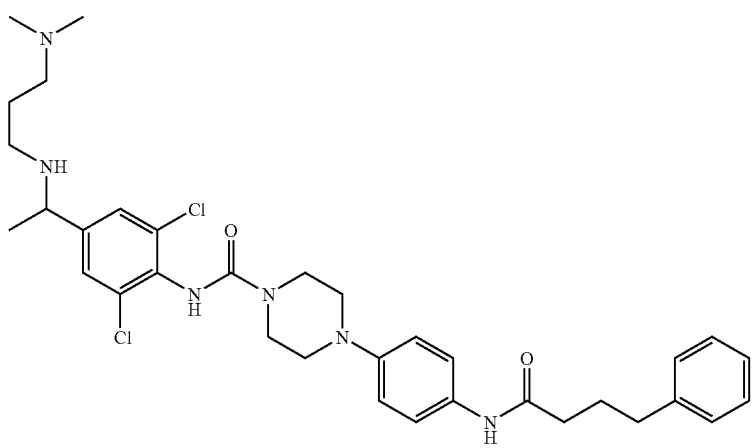
Co. No. 54; Ex. [B13]
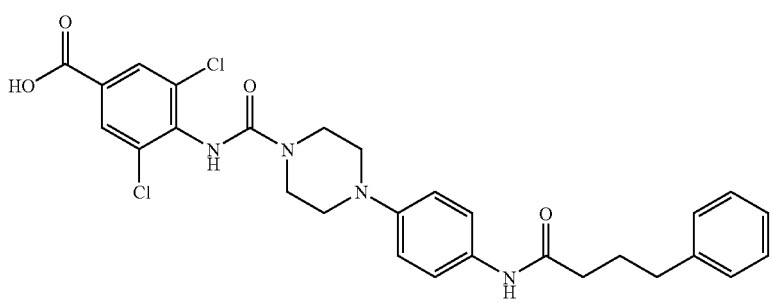
Co. No. 27; Ex. [B15]
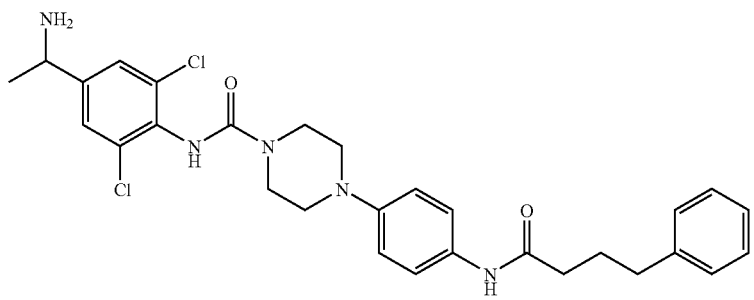
Co. No. 55; Ex. [B13]

TABLE 1-continued
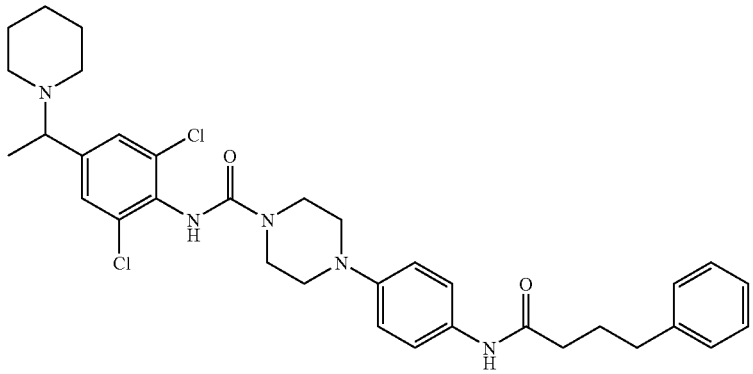
Co. No. 56; Ex. [B13]
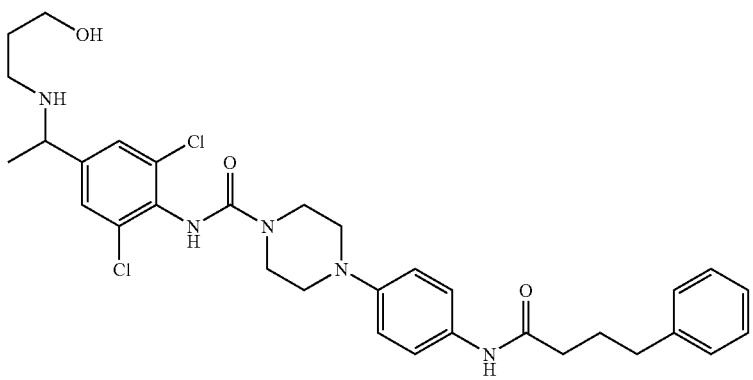
Co. No. 57; Ex. [B13]
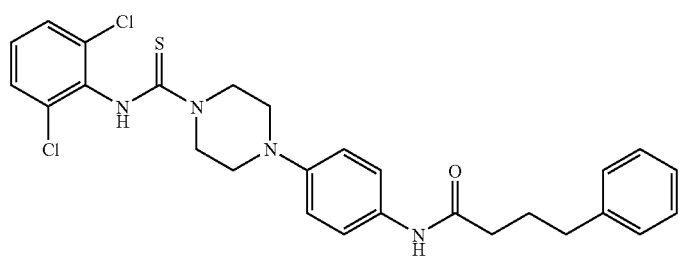
Co. No. 189; Ex. [B6.a]
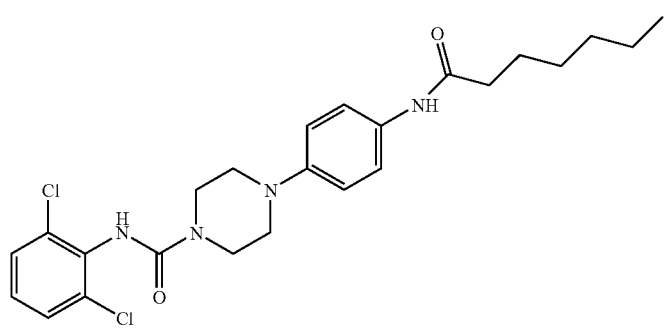
Co. No. 8; Ex. [B3]

TABLE 1-continued
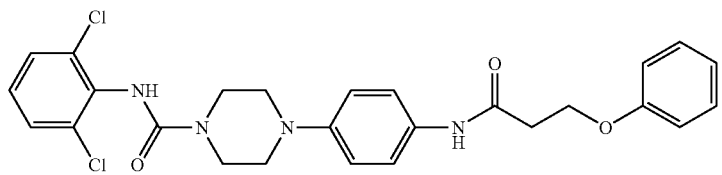
Co. No. 3; Ex. [B2.b]
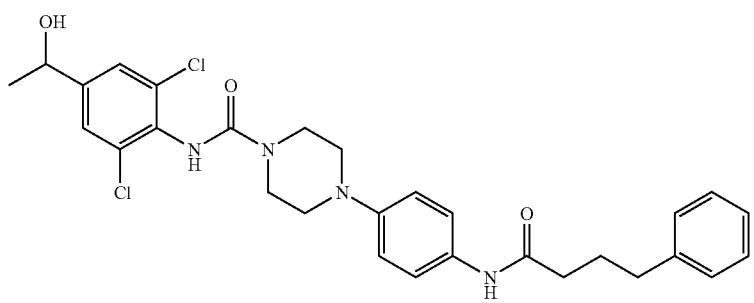
Co. No. 29; Ex. [B17]
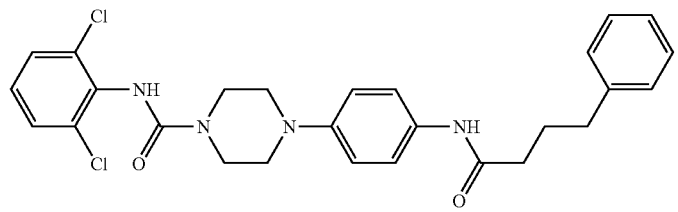
Co. No. 58; Ex. [B1]
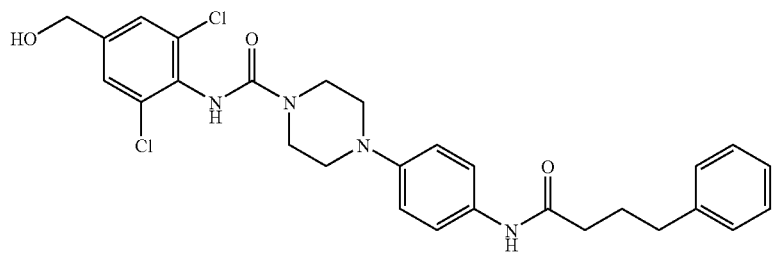
Co. No. 28; Ex. [B16]
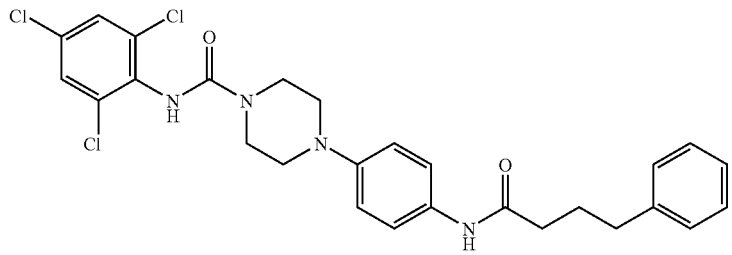
Co. No. 59; Ex. [B6.a]

TABLE 1-continued
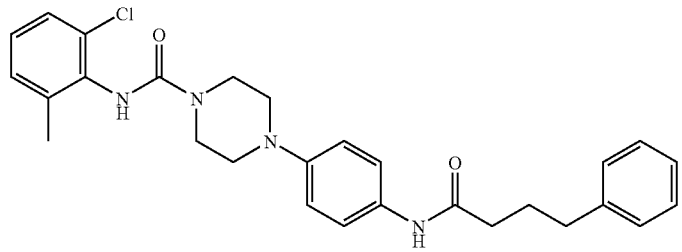
Co. No. 60; Ex. [B6.a]
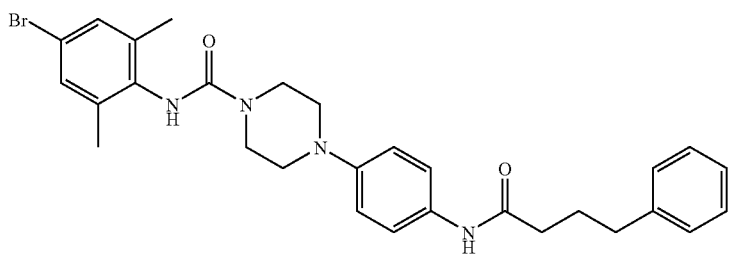
Co. No. 61; Ex. [B6.a]
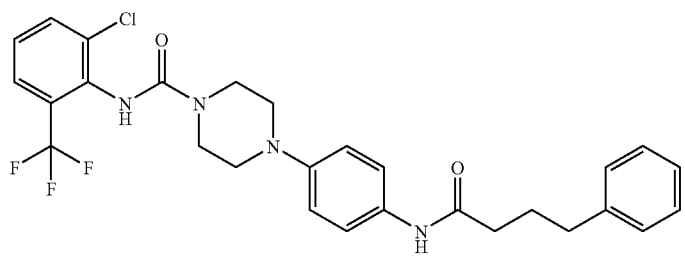
Co. No. 62; Ex. [B6.a]
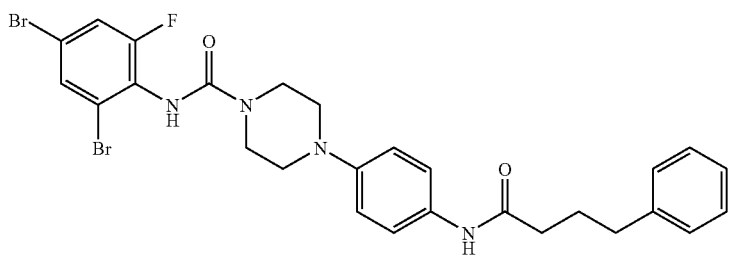
Co. No. 63; Ex. [B6.a]
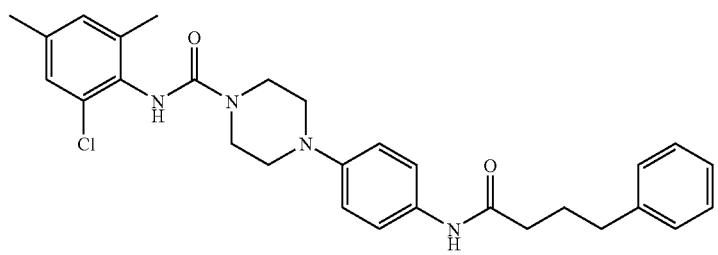
Co. No. 64; Ex. [B6.a]

TABLE 1-continued
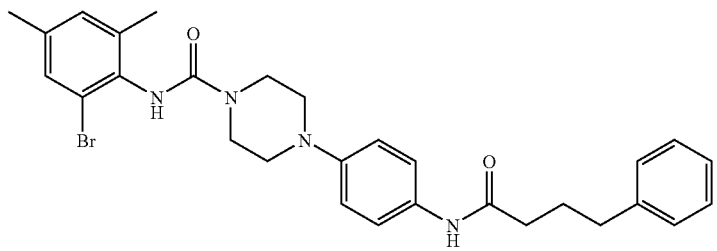
Co. No. 11; Ex. [B6.a]
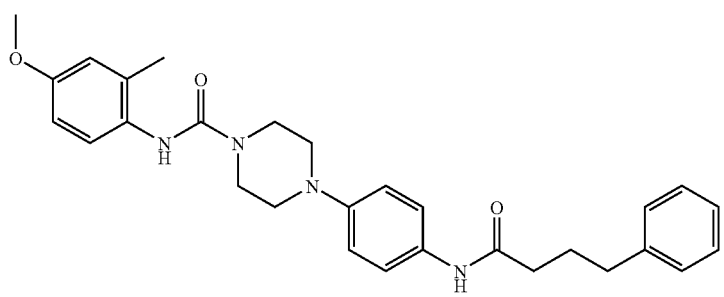
Co. No. 65; Ex. [B6.a]
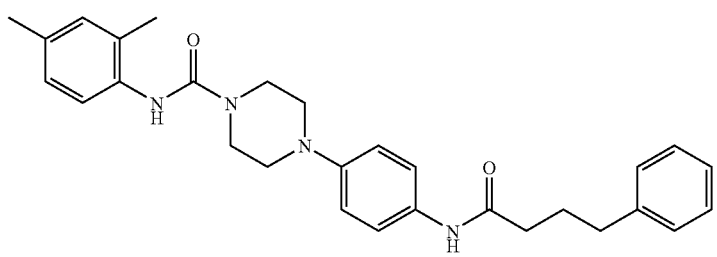
Co. No. 66; Ex. [B6.a]
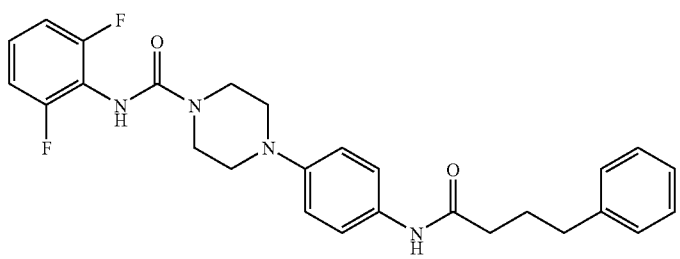
Co. No. 67; Ex. [B6.a]
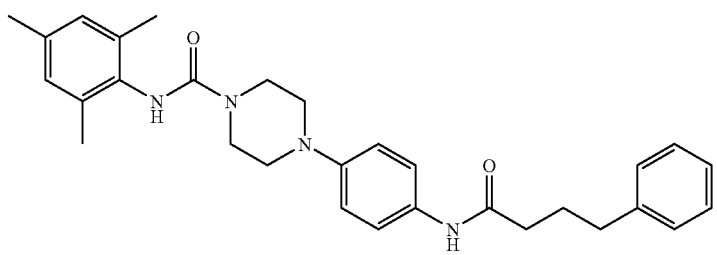
Co. No. 68; Ex. [B6.a]

TABLE 1-continued
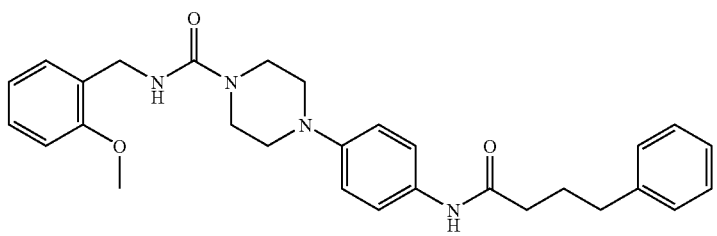
Co. No. 71; Ex. [B6.a]
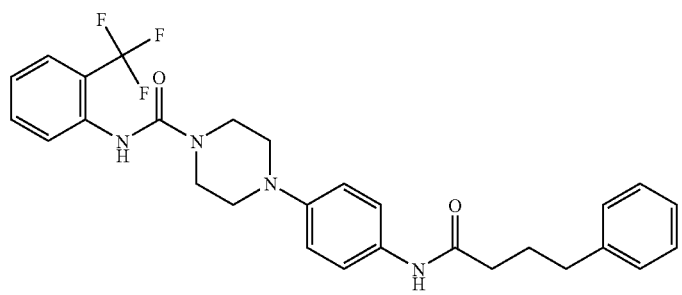
Co. No. 70; Ex. [B6.a]
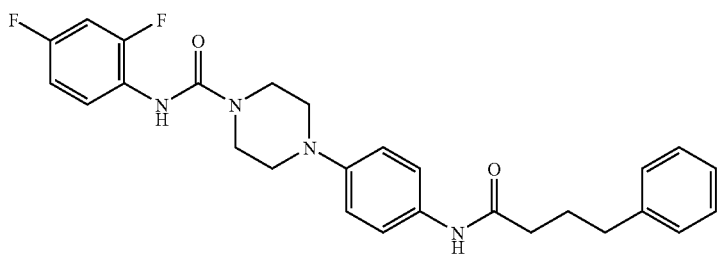
Co. No. 73; Ex. [B6.a]
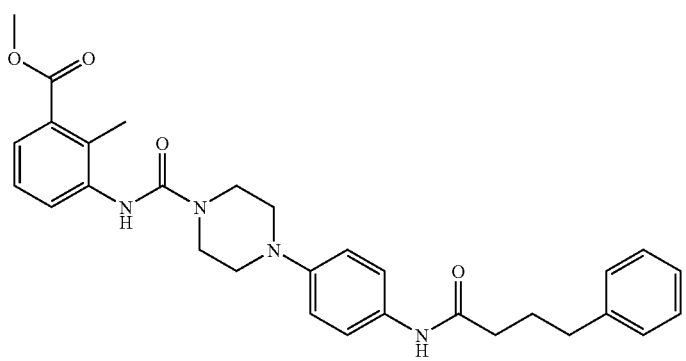
Co. No. 72; Ex. [B6.a]
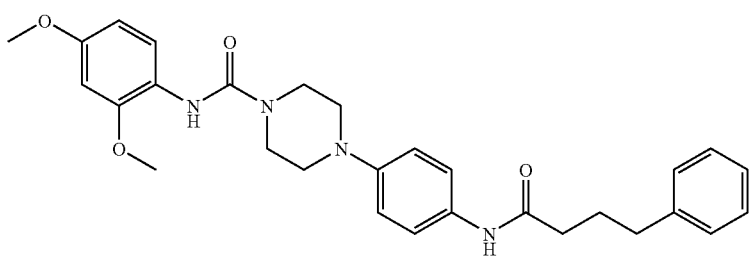
Co. No. 75; Ex. [B6.a]

TABLE 1-continued
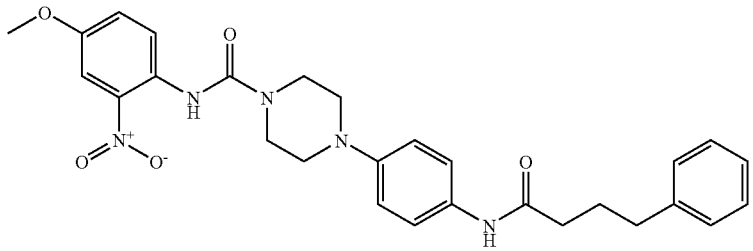
Co. No. 74; Ex. [B6.a]
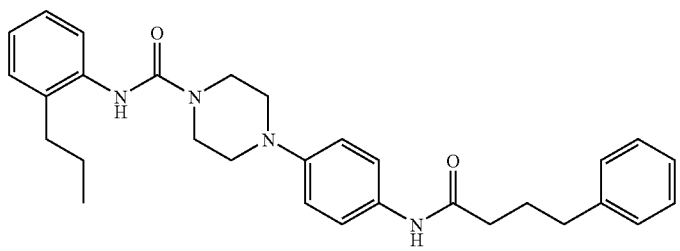
Co. No. 77; Ex. [B6.a]
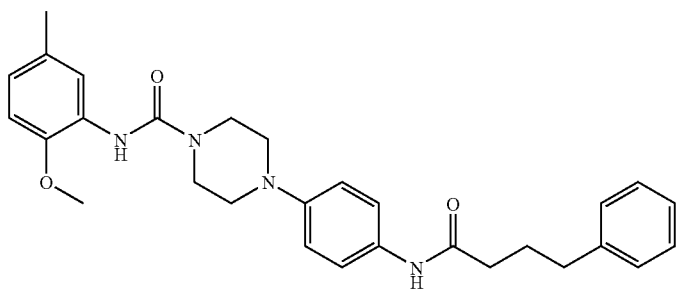
Co. No. 76; Ex. [B6.a]
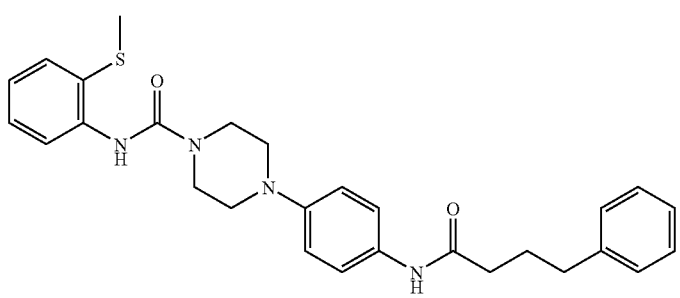
Co. No. 79; Ex. [B6.a]
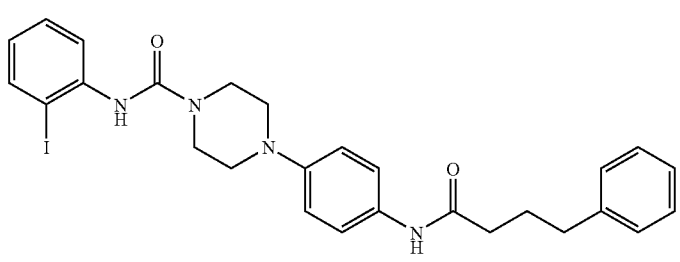
Co. No. 78; Ex. [B6.a]

TABLE 1-continued
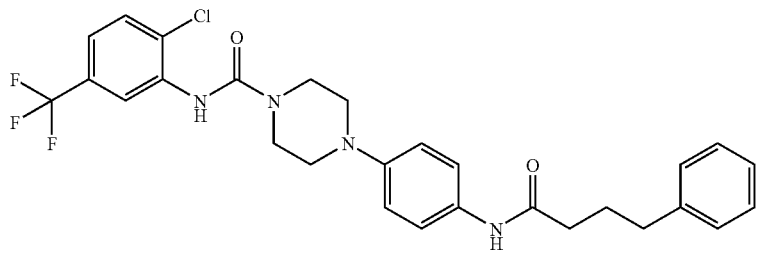
Co. No. 81; Ex. [B6.a]
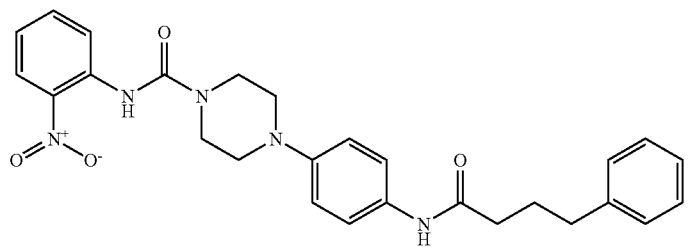
Co. No. 80; Ex. [B6.a]
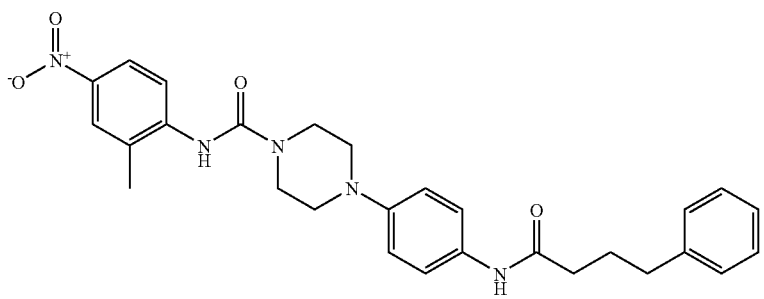
Co. No. 83; Ex. [B6.a]
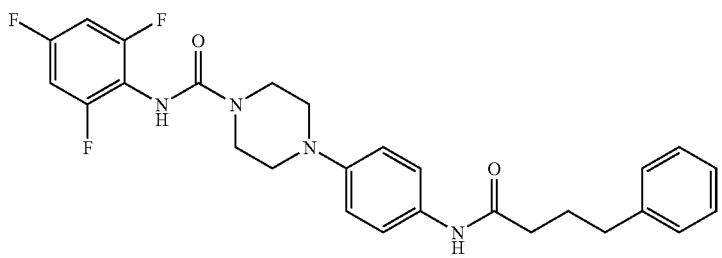
Co. No. 82; Ex. [B6.a]
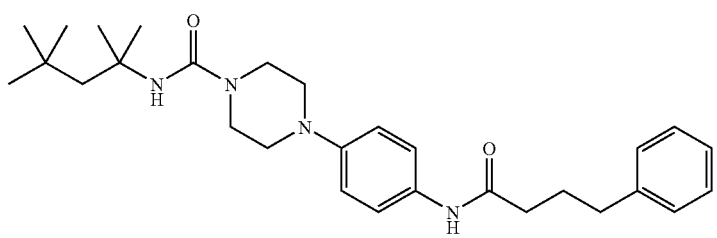
Co. No. 85; Ex. [B6.a]

TABLE 1-continued
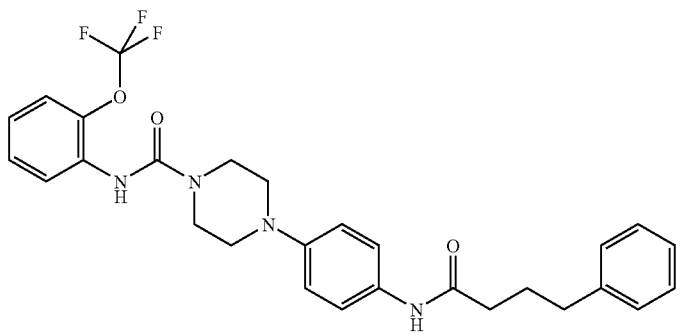
Co. No. 84; Ex. [B6.a]
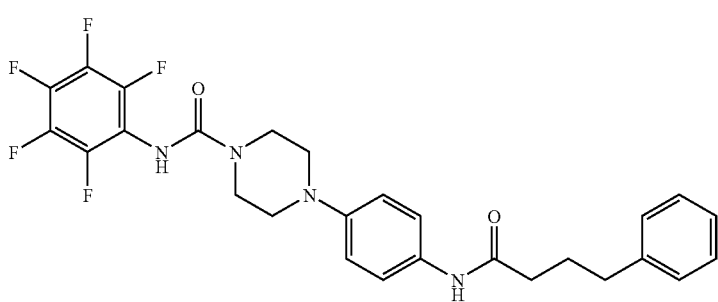
Co. No. 87; Ex. [B6.a]
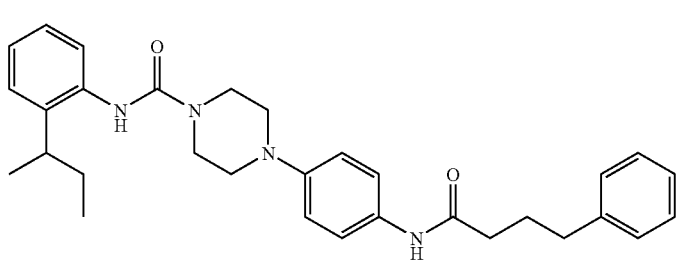
Co. No. 86; Ex. [B6.a]
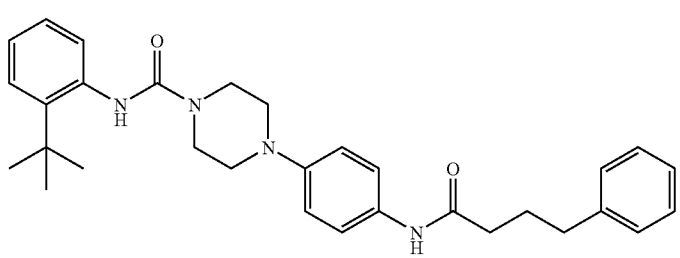
Co. No. 89; Ex. [B6.a]
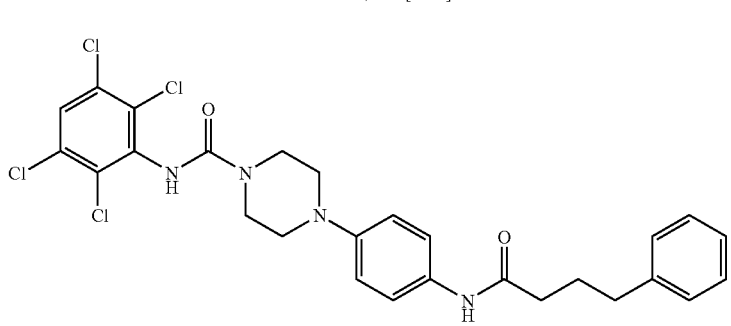
Co. No. 88; Ex. [B6.a]

TABLE 1-continued
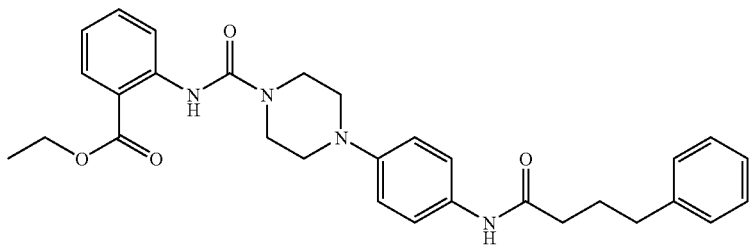
Co. No. 91; Ex. [B6.a]
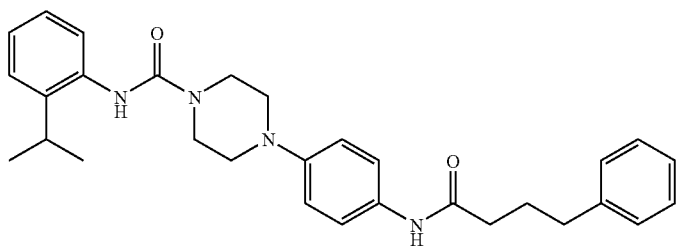
Co. No. 90; Ex. [B6.a]
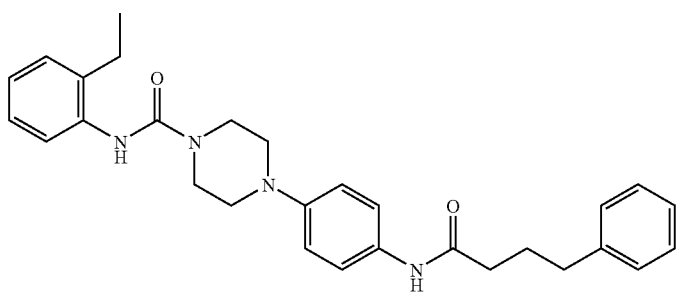
Co. No. 93; Ex. [B6.a]
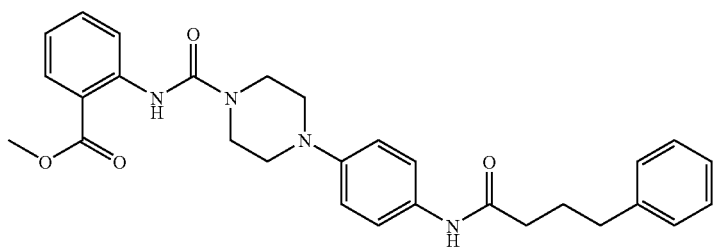
Co. No. 92; Ex. [B6.a]
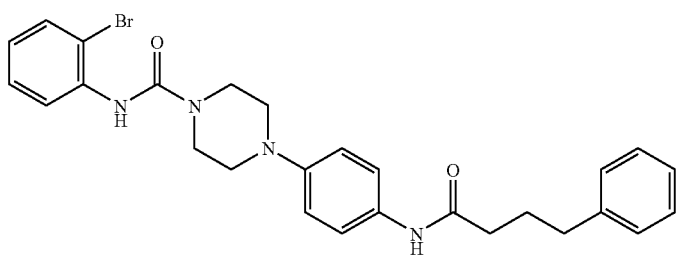
Co. No. 95; Ex. [B6.a]

TABLE 1-continued
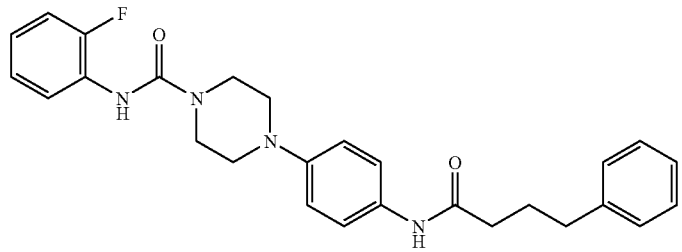
Co. No. 94; Ex. [B6.a]
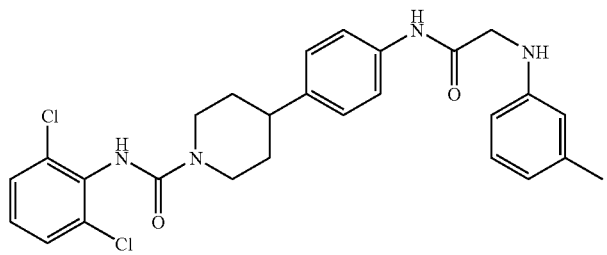
Co. No. 97; Ex. [B11.a]
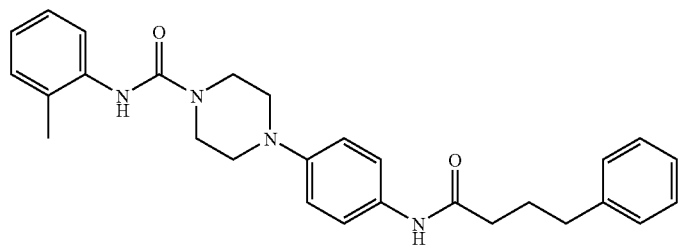
Co. No. 96; Ex. [B6.a]
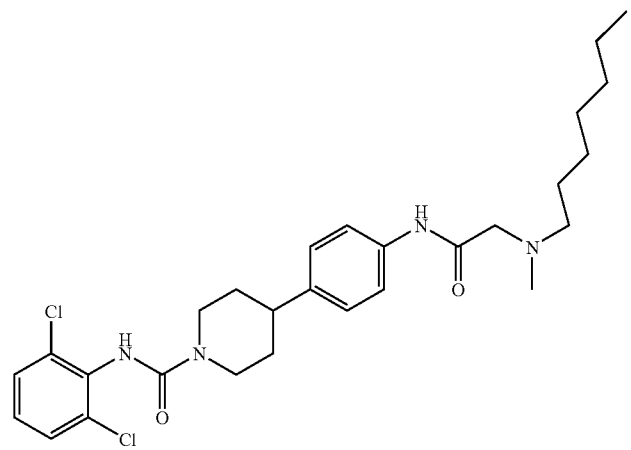
Co. No. 99; Ex. [B11.a]
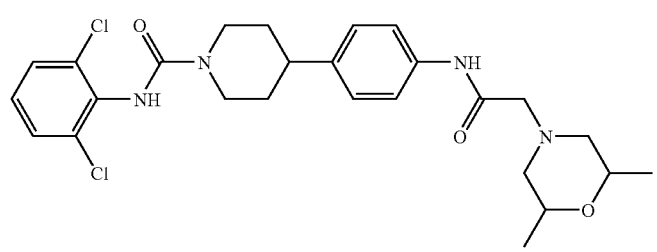
Co. No. 98; Ex. [B11.a]

TABLE 1-continued
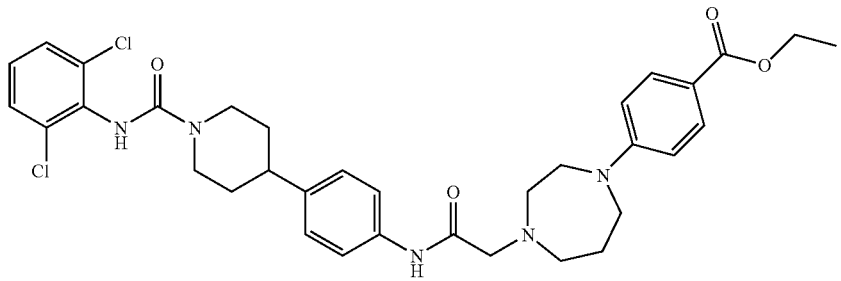
Co. No. 101; Ex. [B11.a]
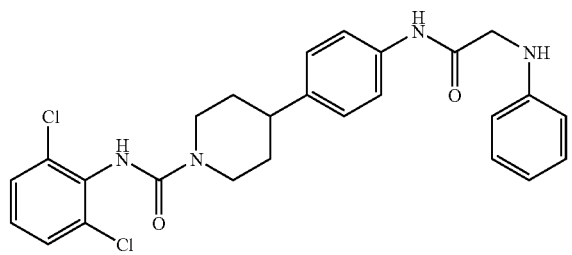
Co. No. 100; Ex. [B11.a]
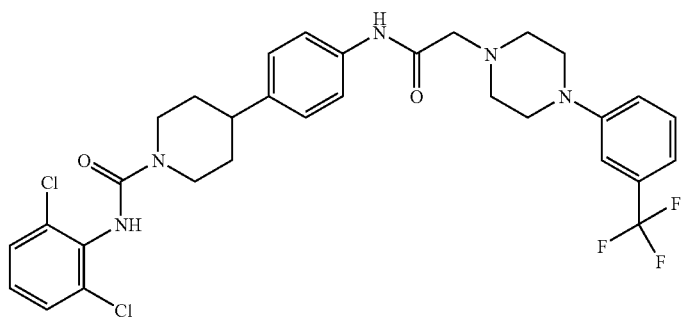
Co. No. 103; Ex. [B11.a]
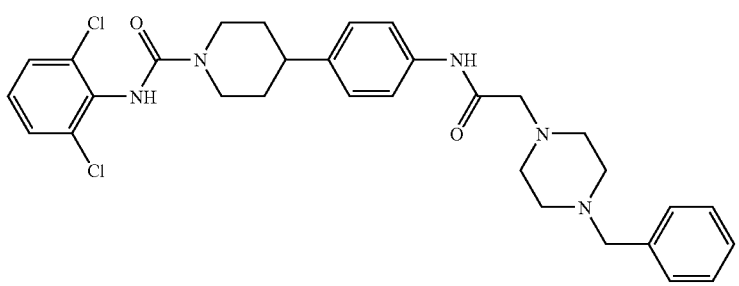
Co. No. 102; Ex. [B11.a]
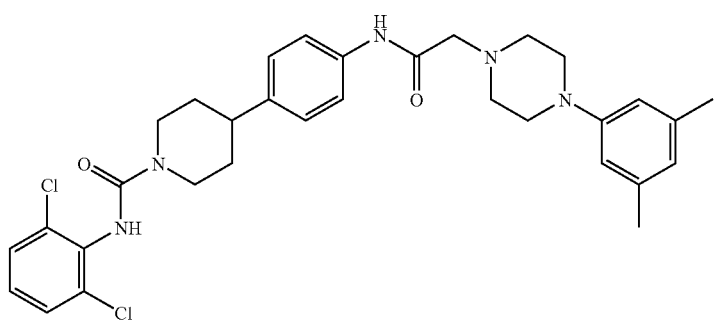
Co. No. 105; Ex. [B11.a]

TABLE 1-continued
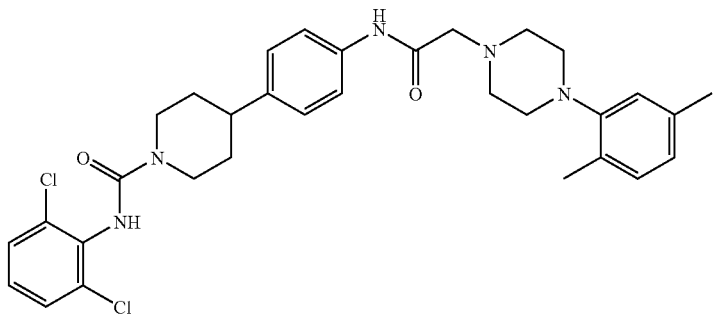
Co. No. 104; Ex. [B11.a]
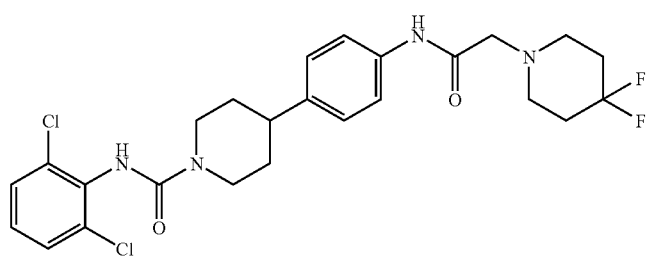
Co. No. 107; Ex. [B11.a]
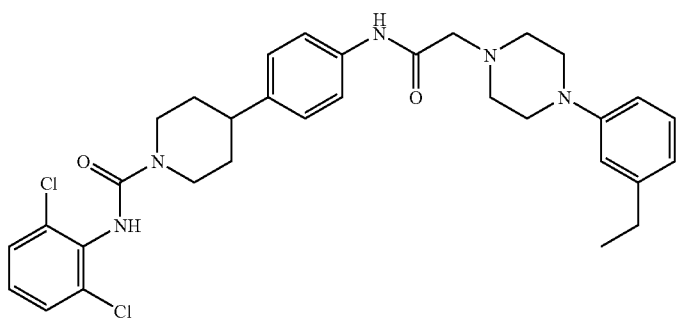
Co. No. 106; Ex. [B11.a]
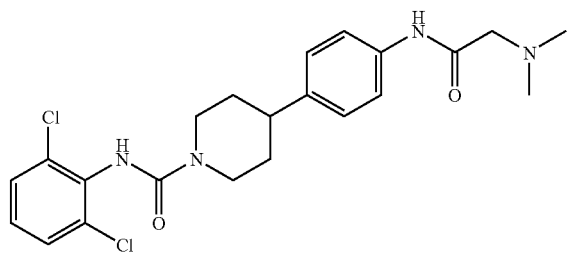
Co. No. 109; Ex. [B11.a]
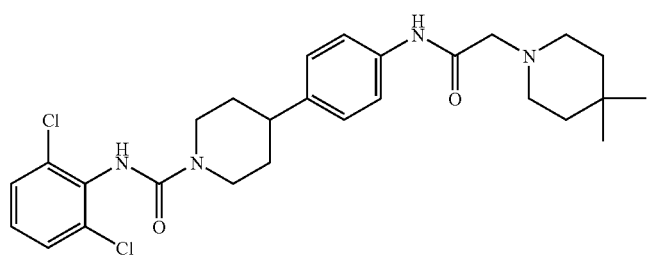
Co. No. 108; Ex. [B11.a]

TABLE 1-continued
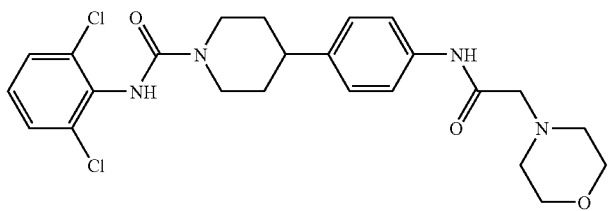
Co. No. 111; Ex. [B11.a]
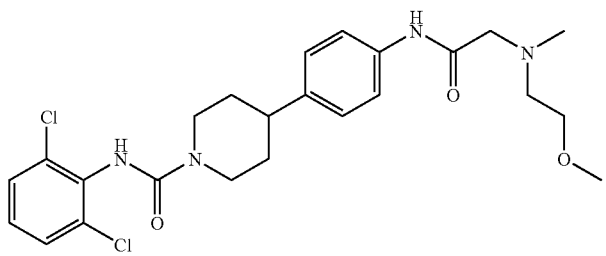
Co. No. 110; Ex. [B11.a]
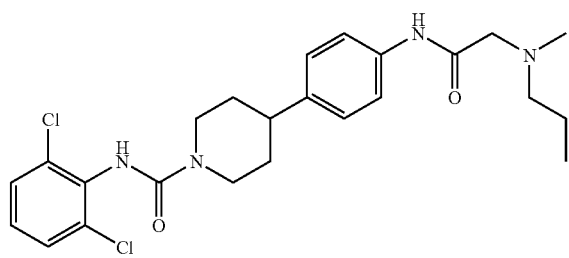
Co. No. 113; Ex. [B11.a]
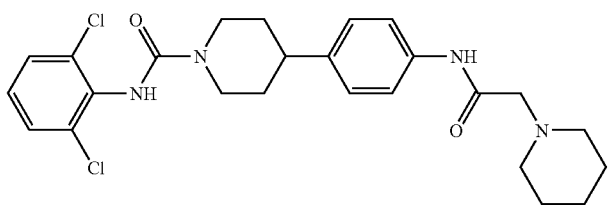
Co. No. 112; Ex. [B11.a]
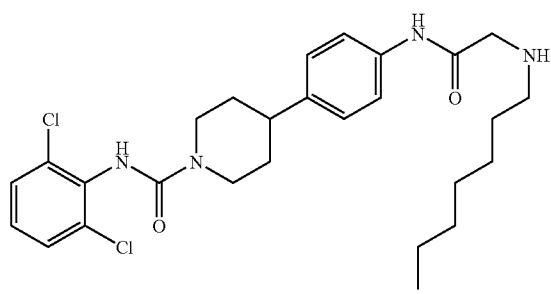
Co. No. 115; Ex. [B11.a]

TABLE 1-continued
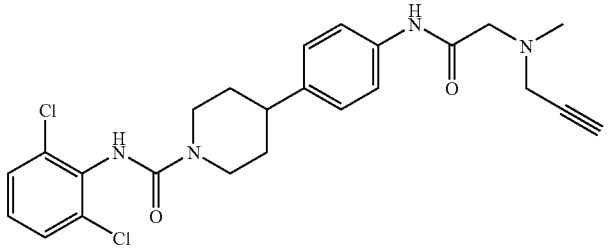
Co. No. 114; Ex. [B11.a]
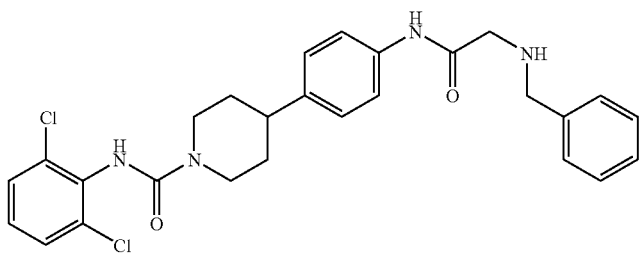
Co. No. 117; Ex. [B11.a]
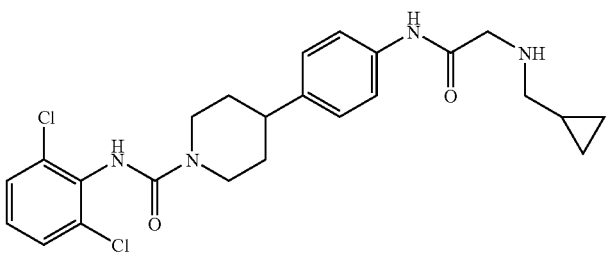
Co. No. 116; Ex. [B11.a]
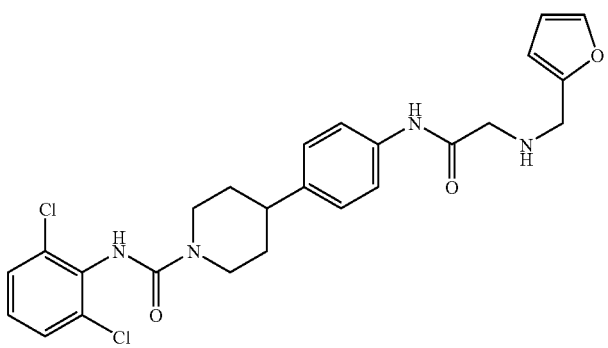
Co. No. 119; Ex. [B11.a]
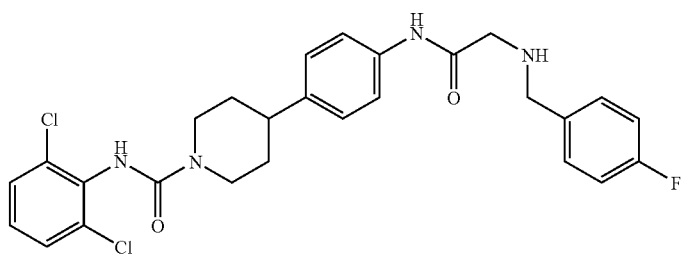
Co. No. 118; Ex. [B11.a]

TABLE 1-continued
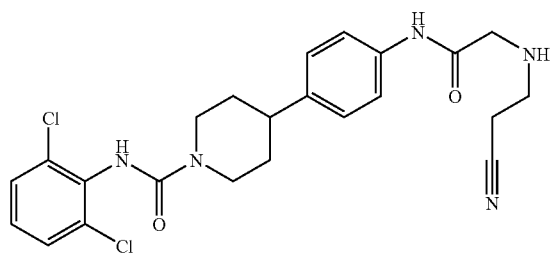
Co. No. 121; Ex. [B11.a]
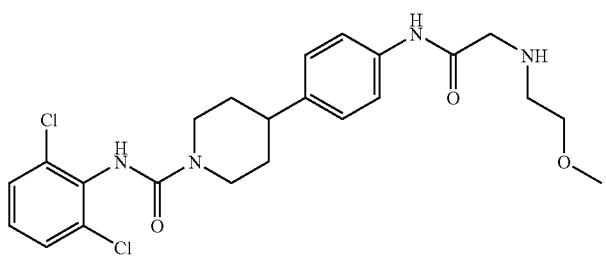
Co. No. 120; Ex. [B11.a]
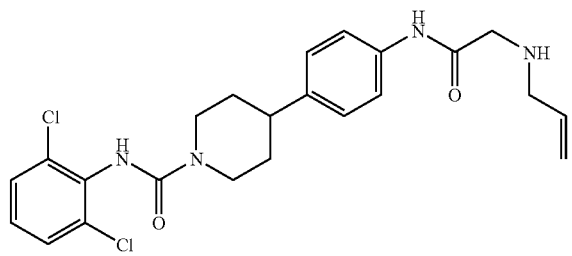
Co. No. 20; Ex. [B11.a]
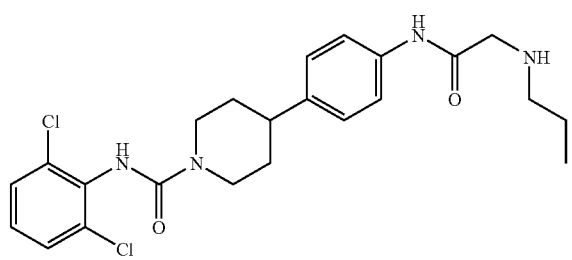
Co. No. 122; Ex. [B11.a]
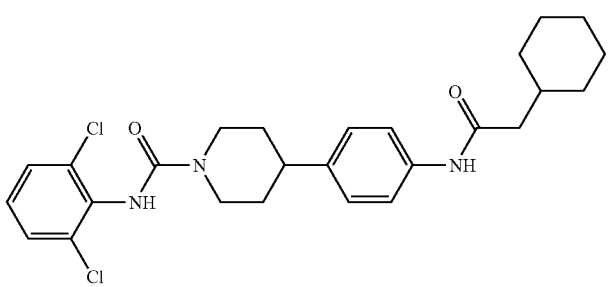
Co. No. 124; Ex. [B1]

TABLE 1-continued
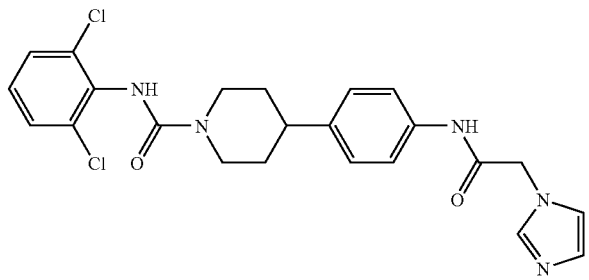
Co. No. 123; Ex. [B1]
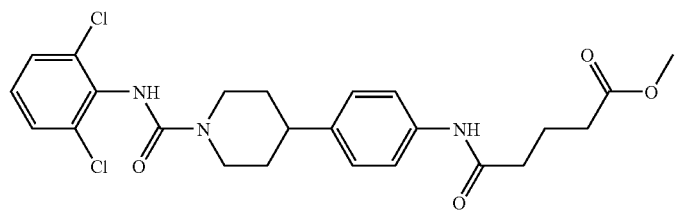
Co. No. 126; Ex. [B1]
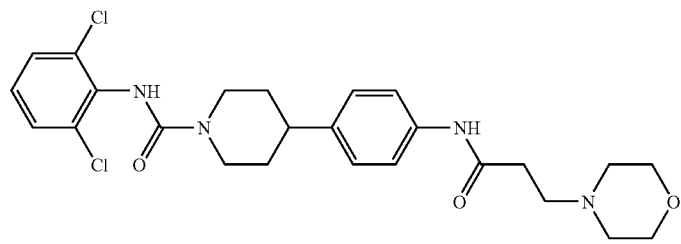
Co. No. 125; Ex. [B1]
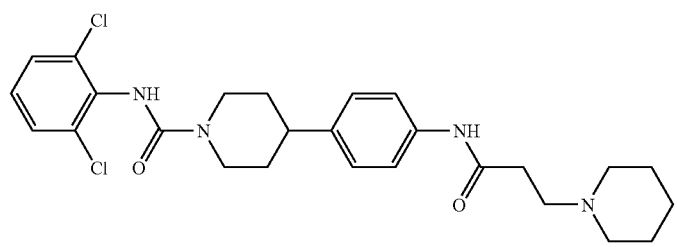
Co. No. 128; Ex. [B1]
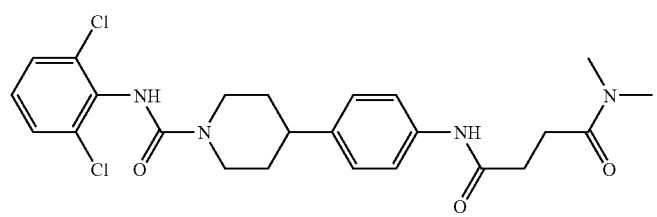
Co. No. 127; Ex. [B1]
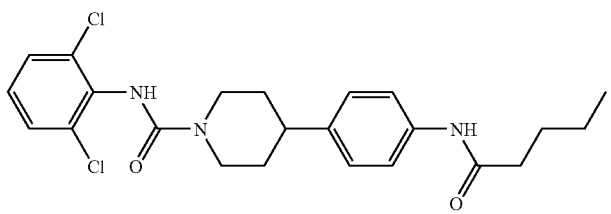
Co. No. 130; Ex. [B1]

TABLE 1-continued
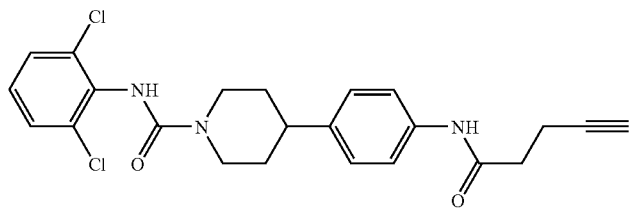
Co. No. 129; Ex. [B1]
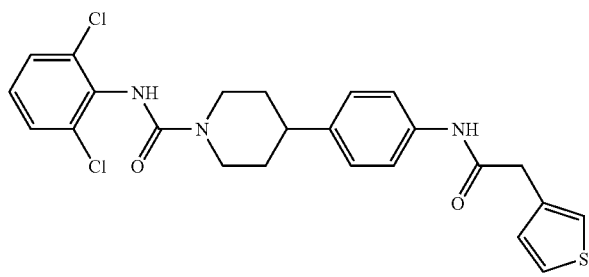
Co. No. 132; Ex. [B1]
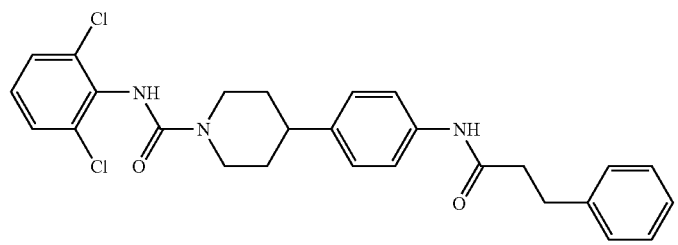
Co. No. 131; Ex. [B1]
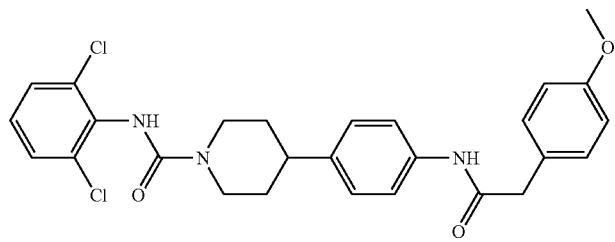
Co. No. 134; Ex. [B1]
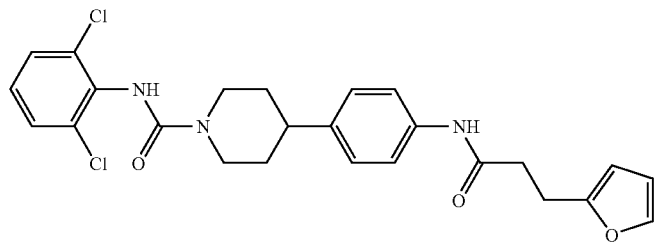
Co. No. 133; Ex. [B1]

TABLE 1-continued
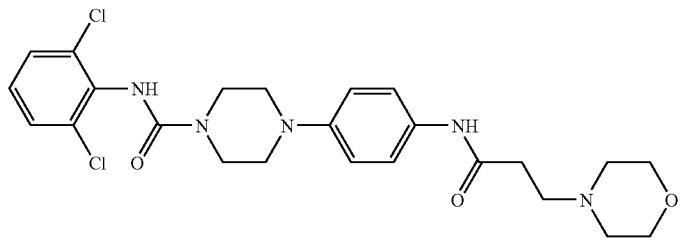
Co. No. 136; Ex. [B1]
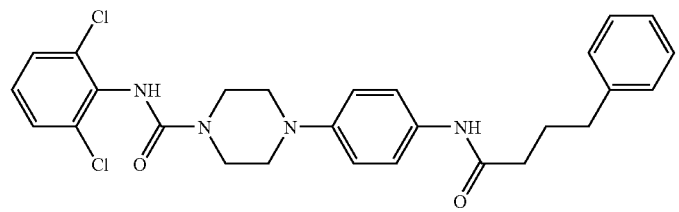
Co. No. 135; Ex. [B1]
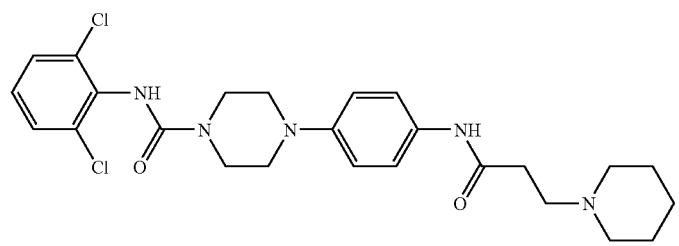
Co. No. 138; Ex. [B1]
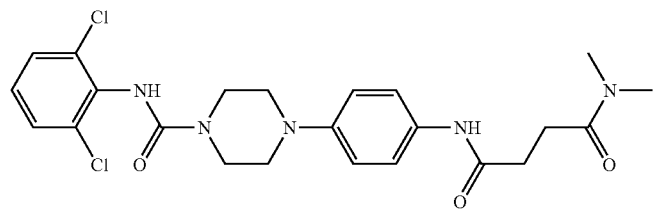
Co. No. 137; Ex. [B1]
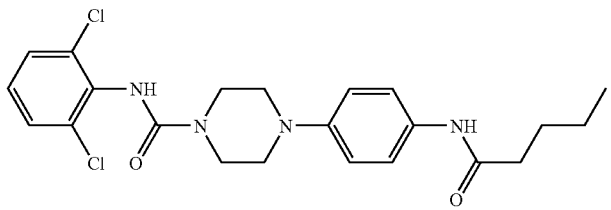
Co. No. 140; Ex. [B1]
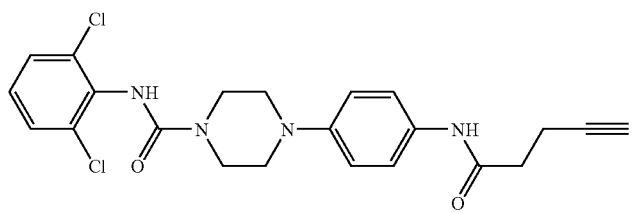
Co. No. 139; Ex. [B1]

TABLE 1-continued
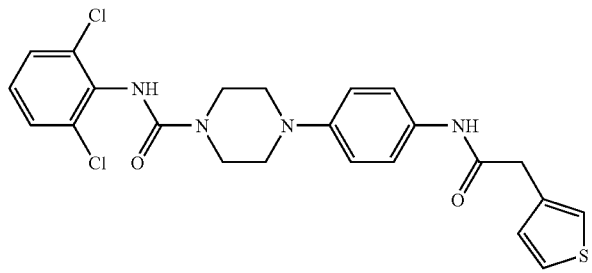
Co. No. 142; Ex. [B1]
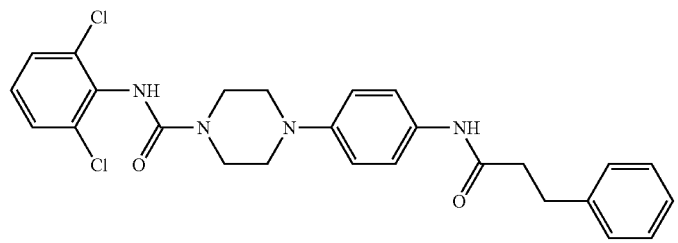
Co. No. 141; Ex. [B1]
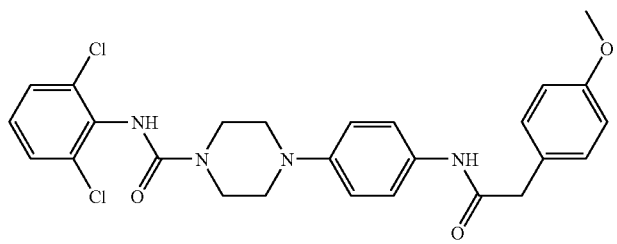
Co. No. 144; Ex. [B1]
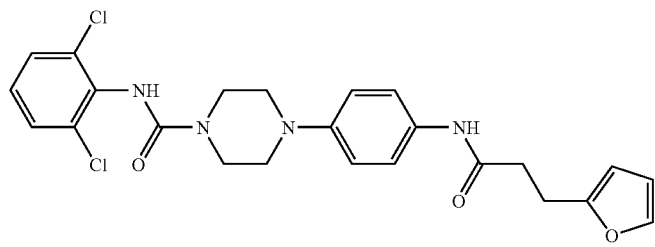
Co. No. 143; Ex. [B1]
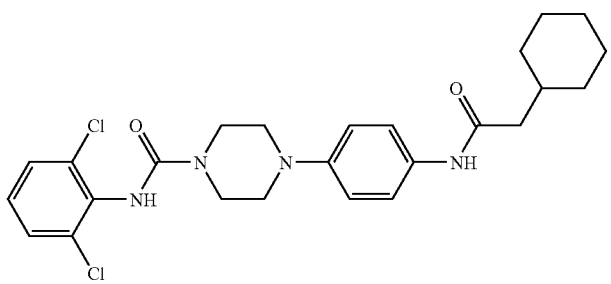
Co. No. 1; Ex. [B1]

TABLE 1-continued
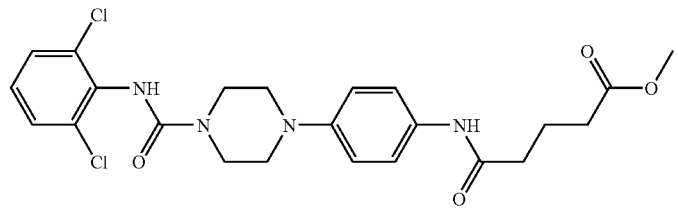
Co. No. 145; Ex. [B1]
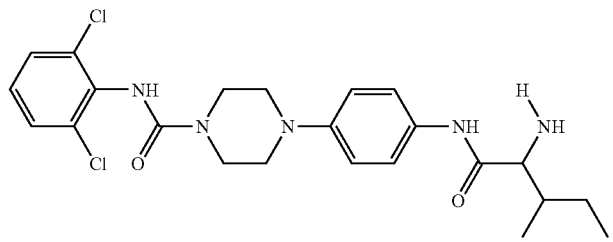
•trifluoroacetate
Co. No. 147; Ex. [B12]
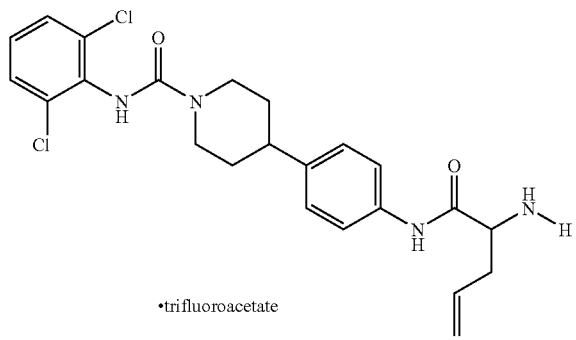
•trifluoroacetate
Co. No. 146; Ex. [B12]
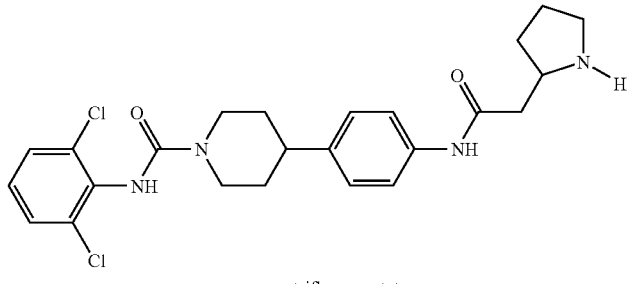
•trifluoroacetate
Co. No. 149; Ex. [B12]
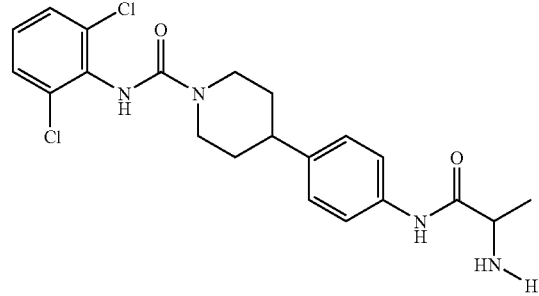
•trifluoroacetate
Co. No. 148; Ex. [B12]

TABLE 1-continued
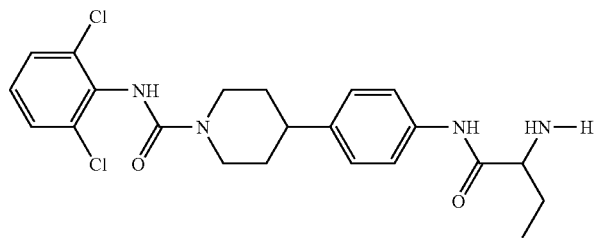
•trifluoroacetate
Co. No. 151; Ex. [B12]
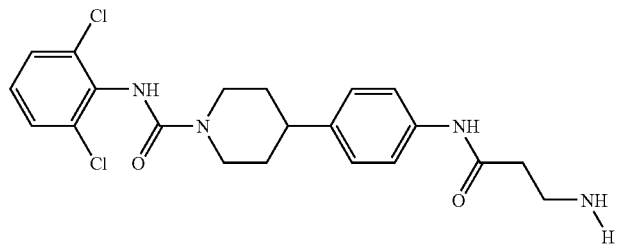
•trifluoroacetate
Co. No. 150; Ex. [B12]
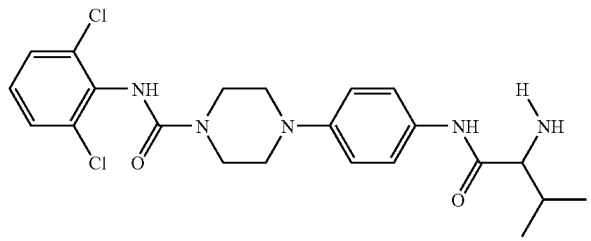
•trifluoroacetate
Co. No. 153; Ex. [B12]
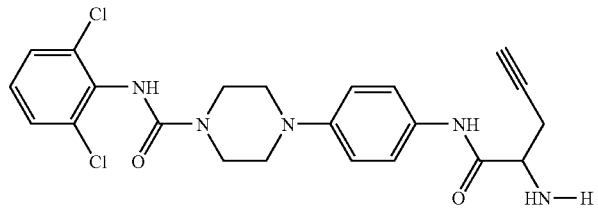
•trifluoroacetate
Co. No. 152; Ex. [B12]
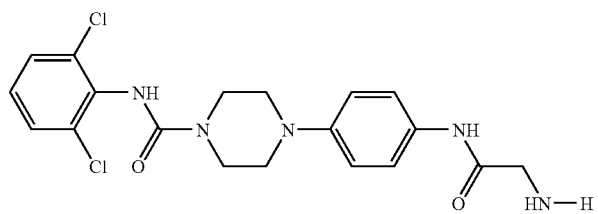
•trifluoroacetate
Co. No. 155; Ex. [B12]

TABLE 1-continued
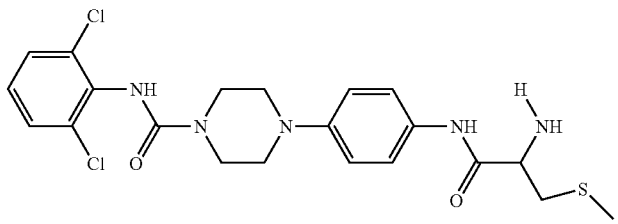
•trifluoroacetate
Co. No. 154; Ex. [B12]
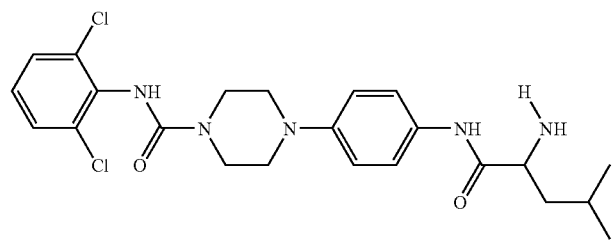
•trifluoroacetate
Co. No. 157; Ex. [B12]
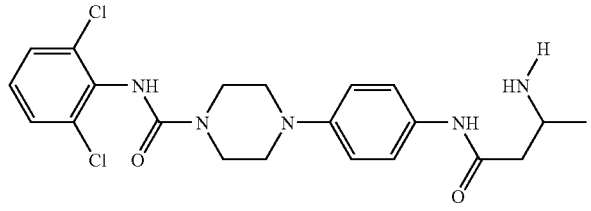
•trifluoroacetate
Co. No. 156; Ex. [B12]
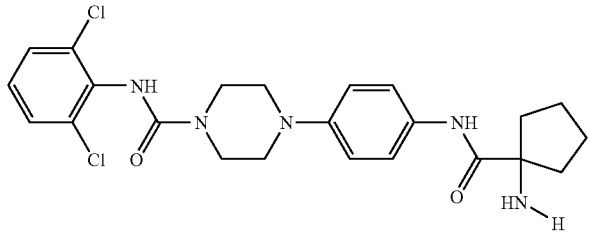
•trifluoroacetate
Co. No. 159; Ex. [B12]
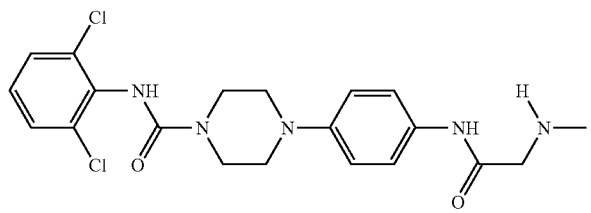
•trifluoroacetate
Co. No. 158; Ex. [B12]

TABLE 1-continued
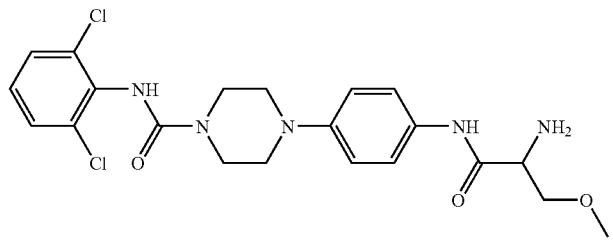
•trifluoroacetate
Co. No. 161; Ex. [B12]
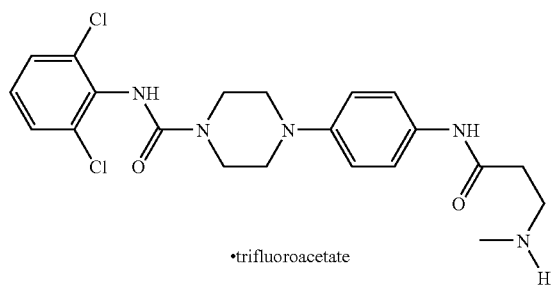
•trifluoroacetate
Co. No. 160; Ex. [B12]
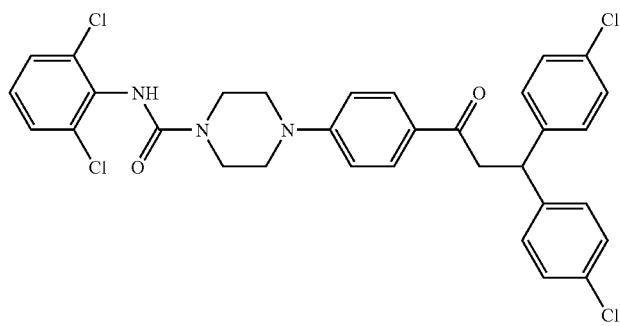
Co. No. 162; Ex. [B6.a]
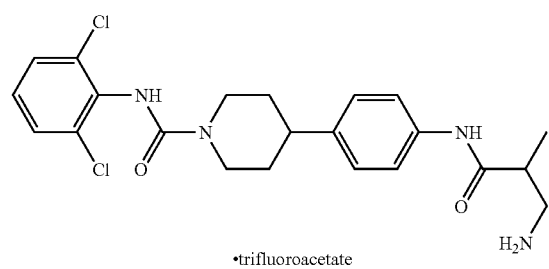
•trifluoroacetate
Co. No. 23; Ex. [B12]
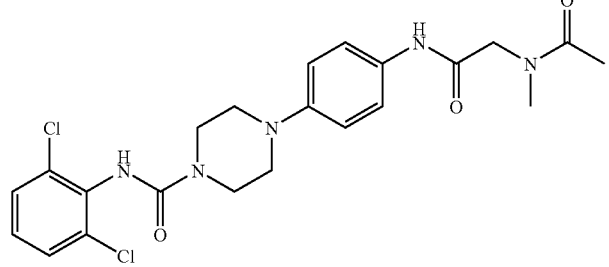
Co. No. 164; Ex. [B2.c]

TABLE 1-continued
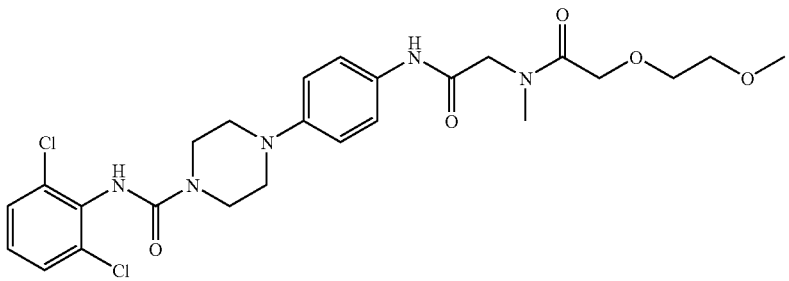
Co. No. 163; Ex. [B2.d]
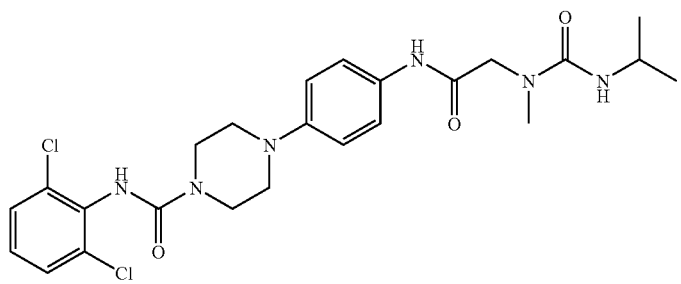
Co. No. 14; Ex. [B6.d]
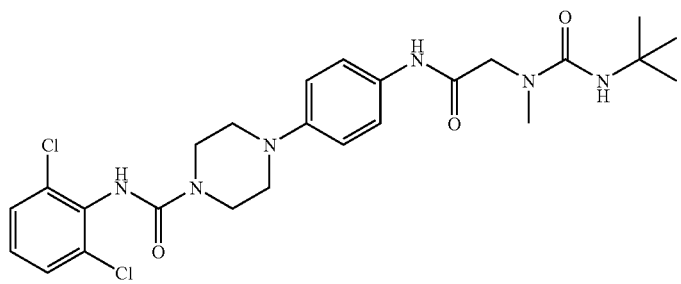
Co. No. 165; Ex. [B2.d]
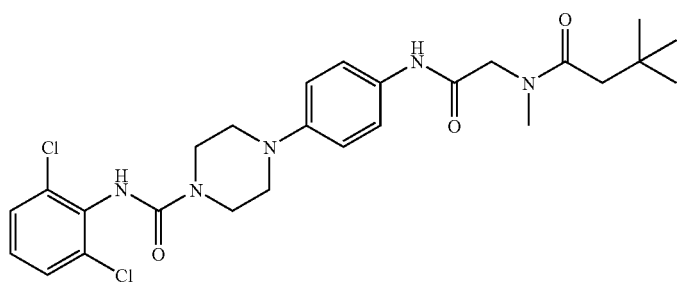
Co. No. 167; Ex. [B2.c]
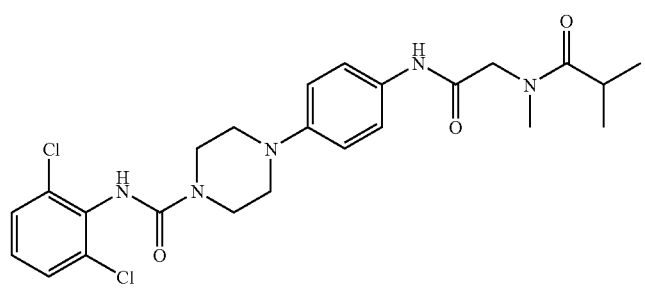
Co. No. 166; Ex. [B2.d]

TABLE 1-continued
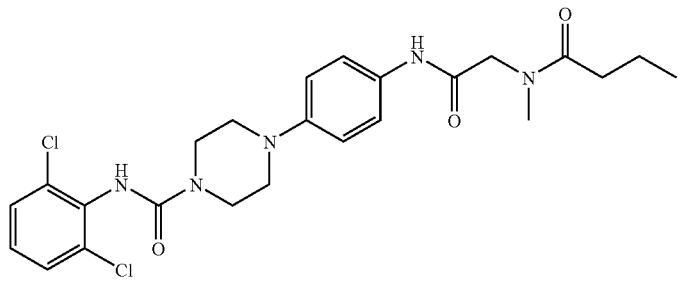
Co. No. 169; Ex. [B2.c]
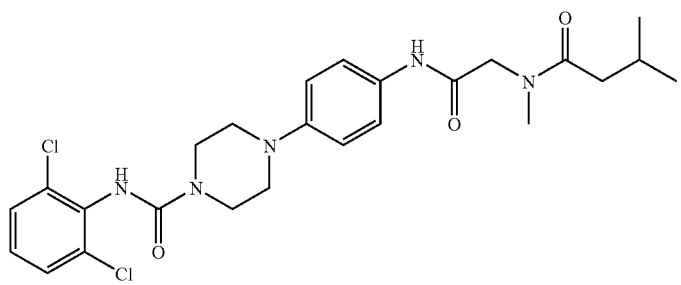
Co. No. 168; Ex. [B2.c]
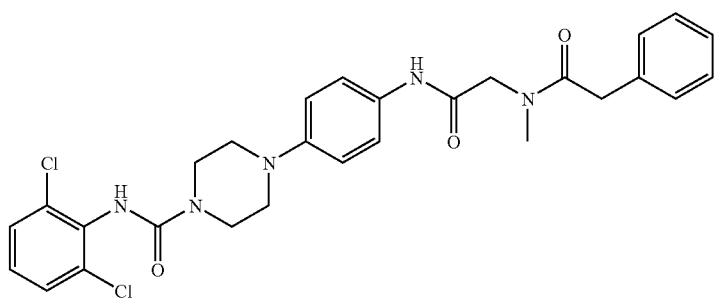
Co. No. 171; Ex. [B2.c]
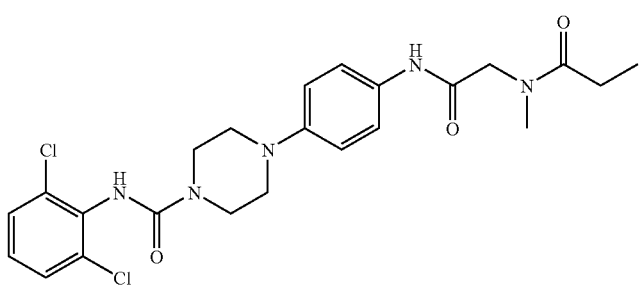
Co. No. 170; Ex. [B2.c]
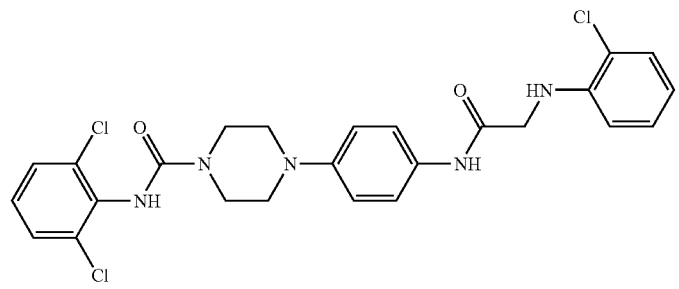
Co. No. 4; Ex. [B2.c]

TABLE 1-continued
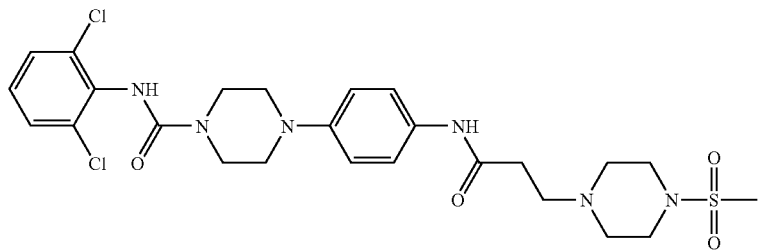
Co. No. 172; Ex. [B2.c]
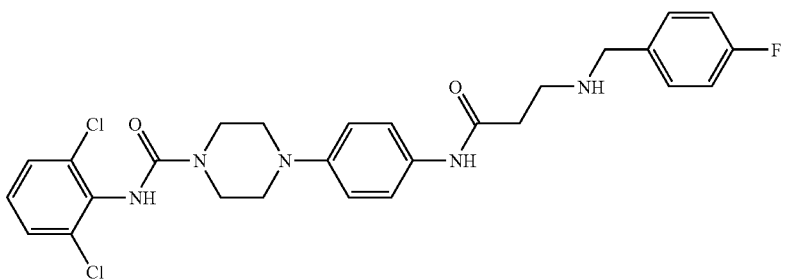
Co. No. 174; Ex. [B20]
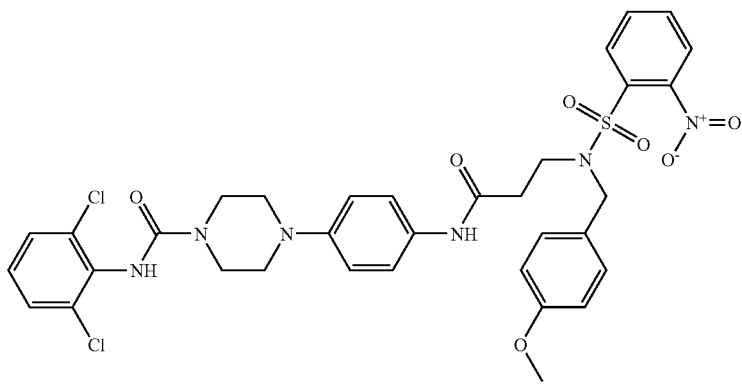
Co. No. 173; Ex. [B2.c]
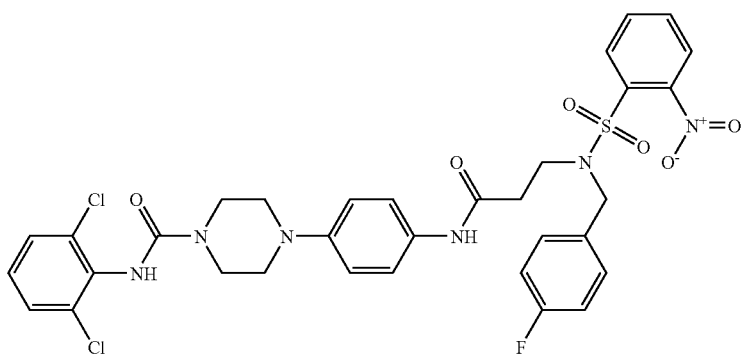
Co. No. 175; Ex. [B2.c]

TABLE 1-continued
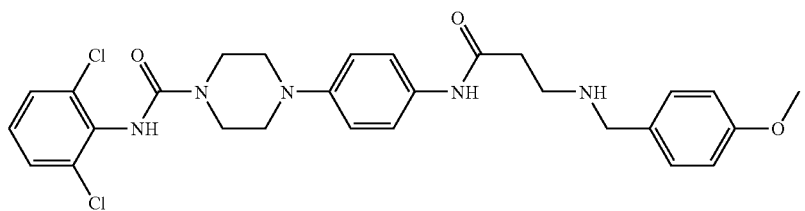
Co. No. 32; Ex. [B20]
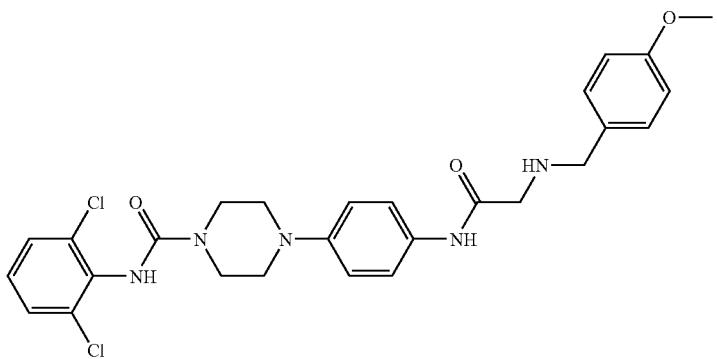
Co. No. 177; Ex. [B11.c]
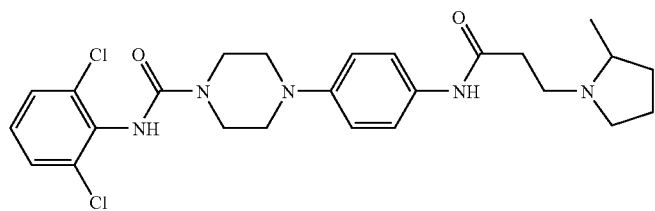
Co. No. 176; Ex. [B2.c]
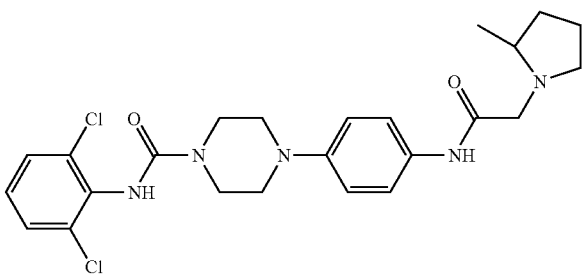
Co. No. 179; Ex. [B11.c]
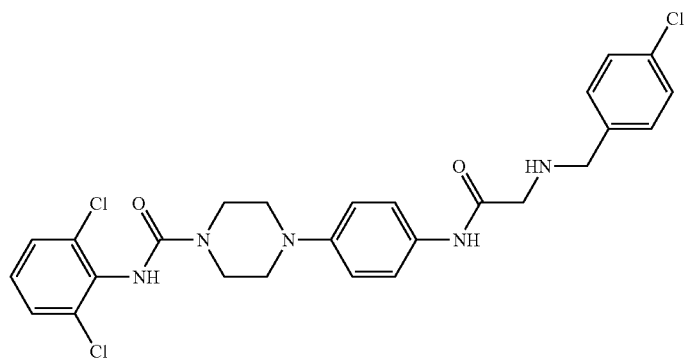
Co. No. 178; Ex. [B11.c]

TABLE 1-continued
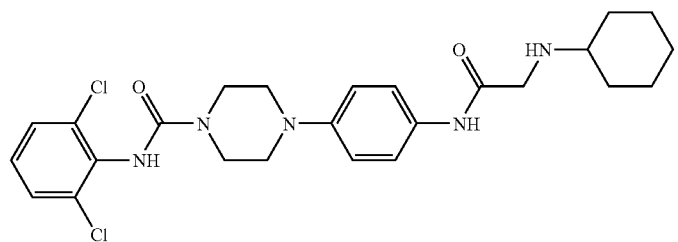
Co. No. 180; Ex. [B11.c]
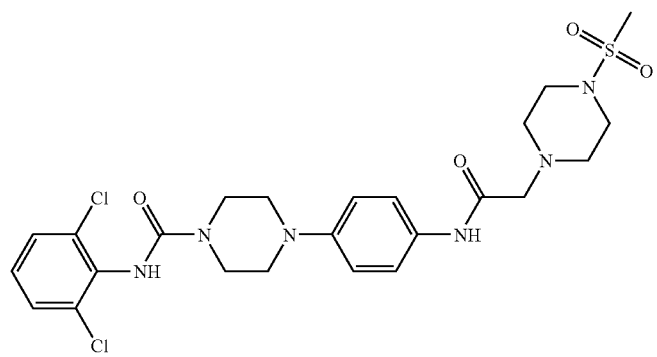
Co. No. 26; Ex. [B14.b]
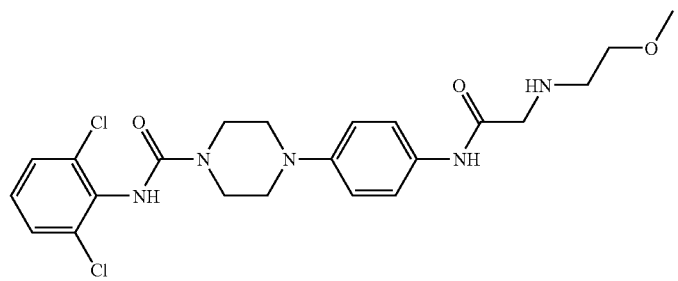
Co. No. 182; Ex. [B11.c]
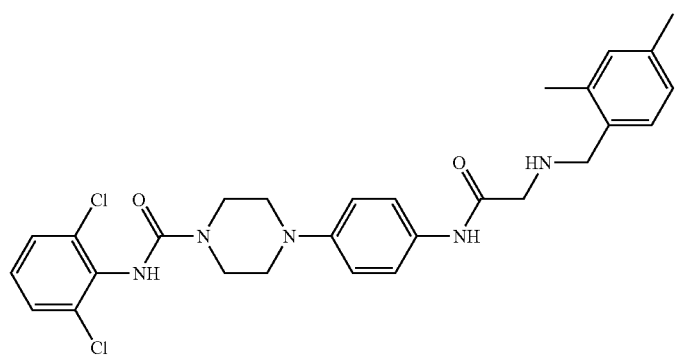
Co. No. 181; Ex. [B11.c]

TABLE 1-continued
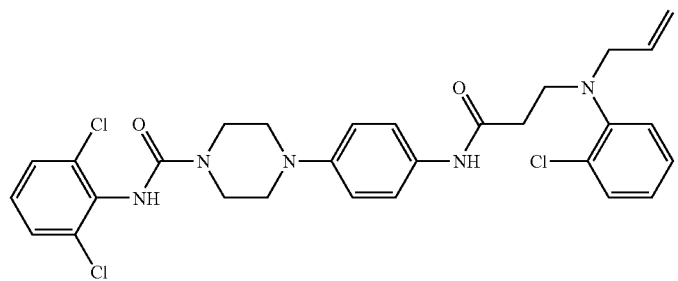
Co. No. 7; Ex. [B2.f]
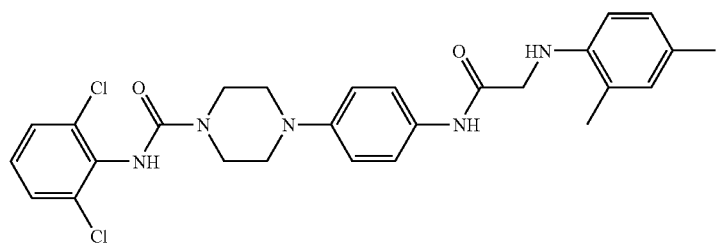
Co. No. 22; Ex. [B11.c]
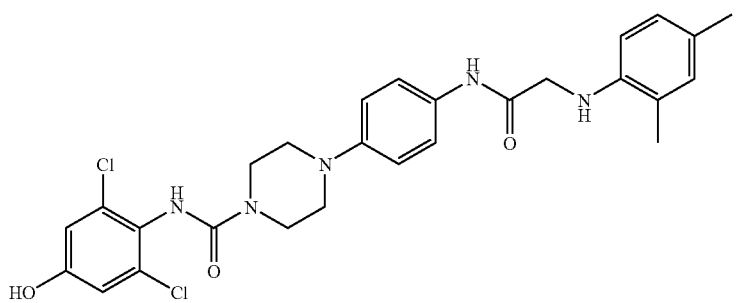
Co. No. 185; Ex. [B18]
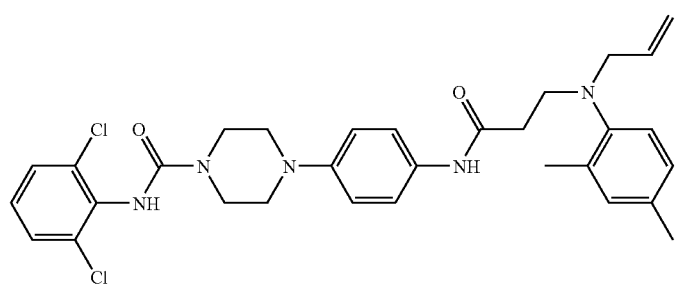
Co. No. 183; Ex. [B2.f]
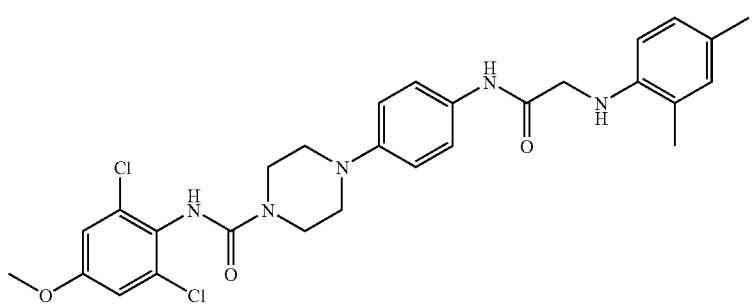
Co. No. 31; Ex. [B19]

TABLE 1-continued
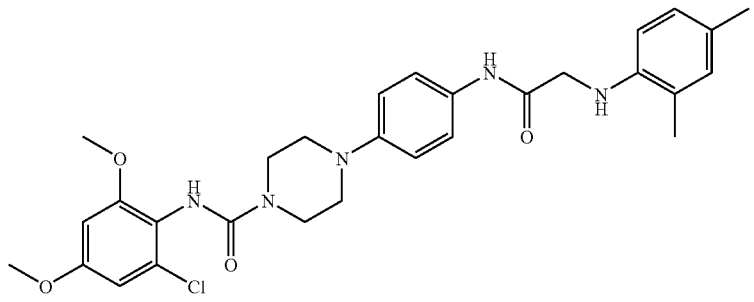
Co. No. 184; Ex. [B18]
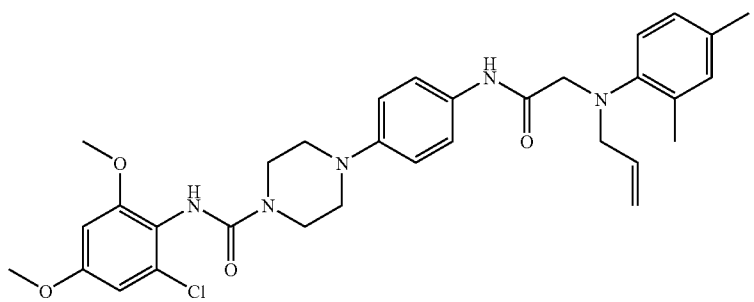
Co. No. 186; Ex. [B2.f]
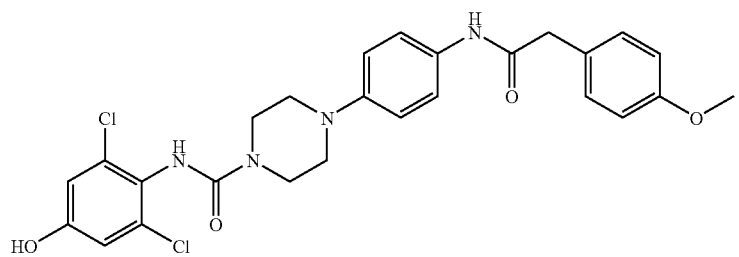
Co. No. 16; Ex. [B7.b]
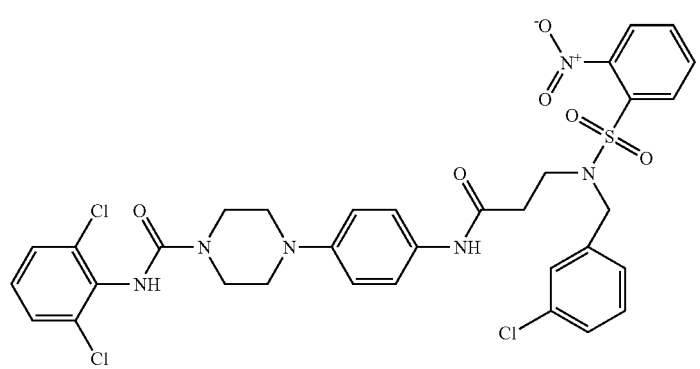
Co. No. 187; Ex. [B2.e]
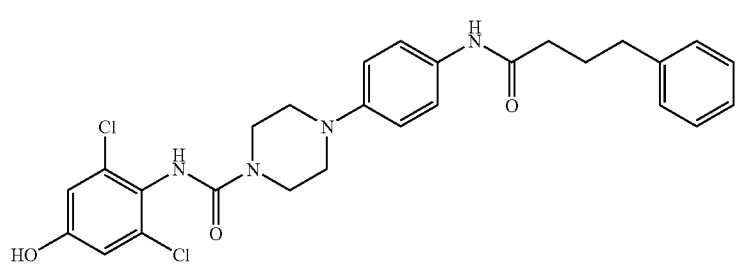
Co. No. 30; Ex. [B18]

TABLE 1-continued
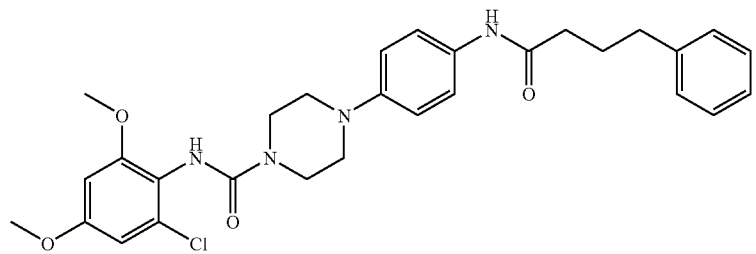
Co. No. 188; Ex. [B7.a]
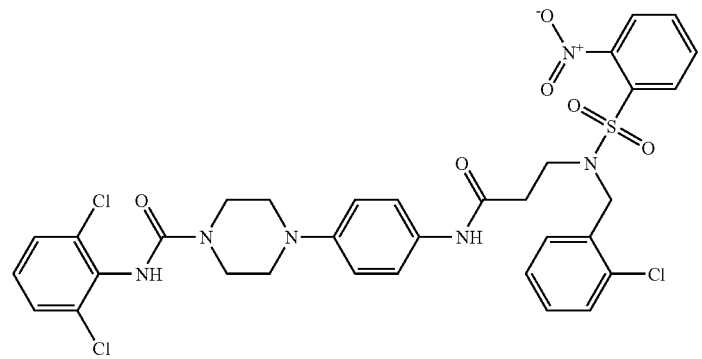
Co. No. 6; Ex. [B2.e]
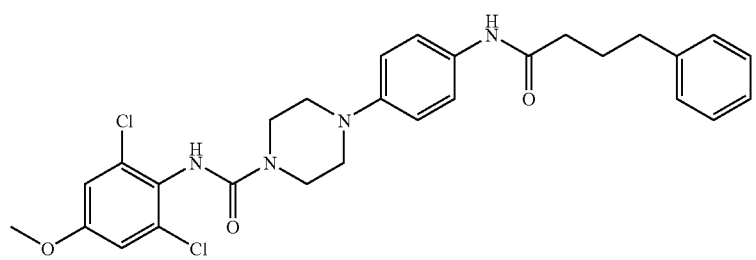
Co. No. 190; Ex. [B7.a]
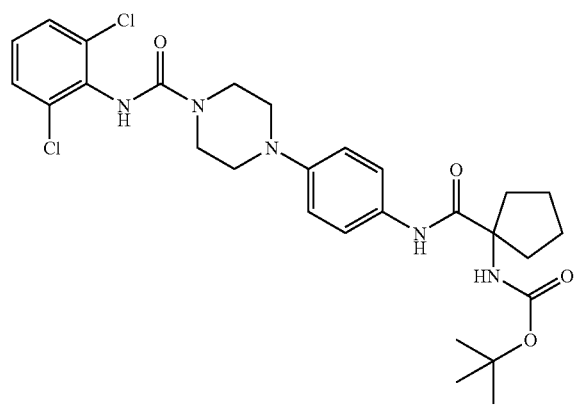
Co. No. 5; Ex. [B2.d]

TABLE 1-continued
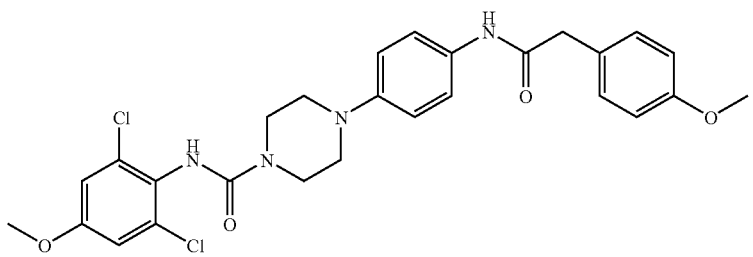
Co. No. 15; Ex. [B7.a]
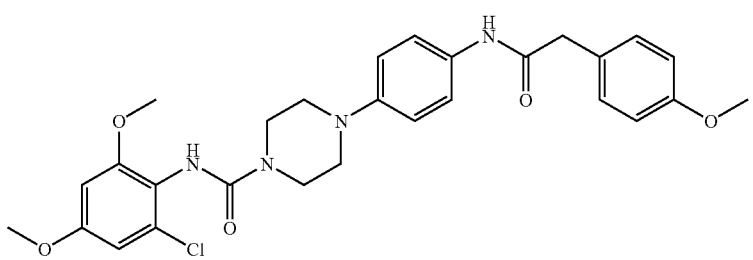
Co. No. 191; Ex. [B7.a]
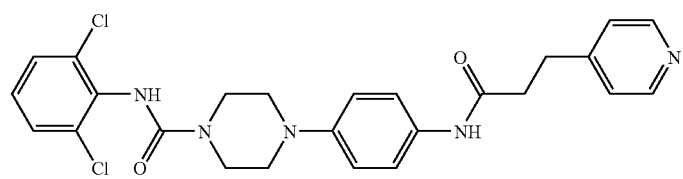
Co. No. 193; Ex. [B2.e]
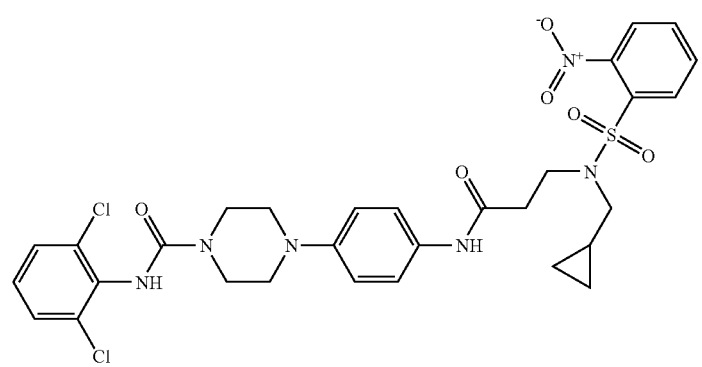
Co. No. 192; Ex. [B2.c]
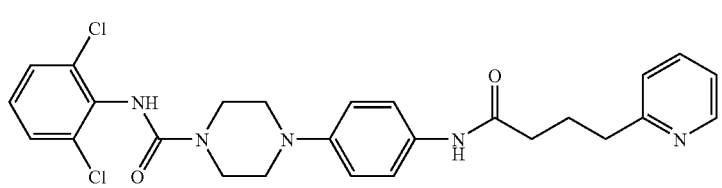
Co. No. 195; Ex. [B2.c]

TABLE 1-continued
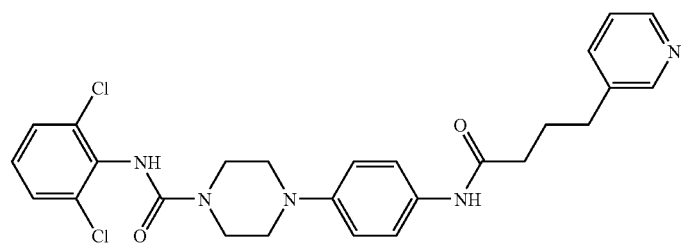
Co. No. 194; Ex. [B2.c]
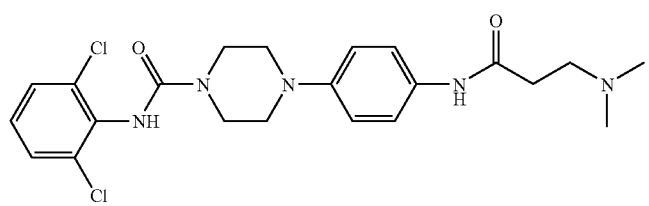
Co. No. 196; Ex. [B2.c]
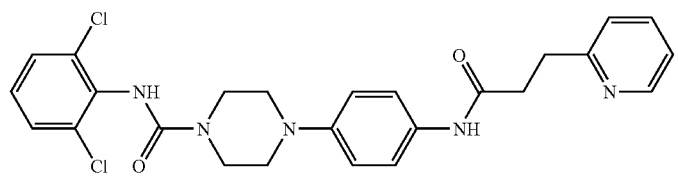
Co. No. 9; Ex. [B4.a]
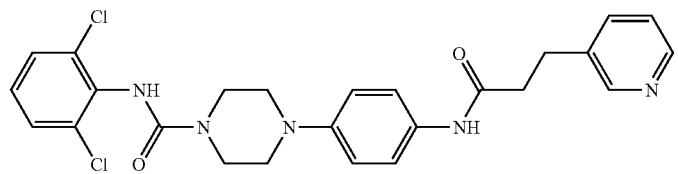
Co. No. 198; Ex. [B2.c]
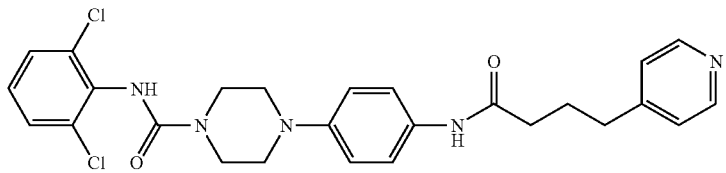
Co. No. 197; Ex. [B2.d]
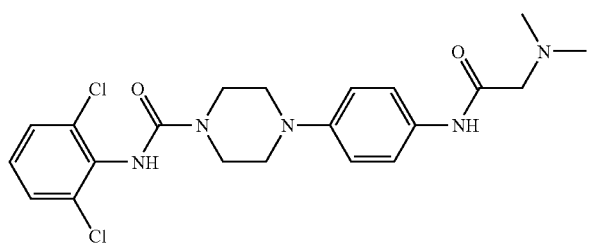
Co. No. 200; Ex. [B2.c]

TABLE 1-continued
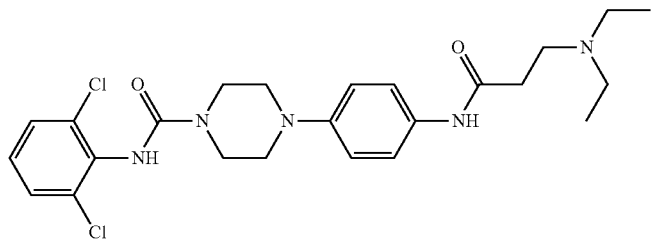
Co. No. 199; Ex. [B2.c]
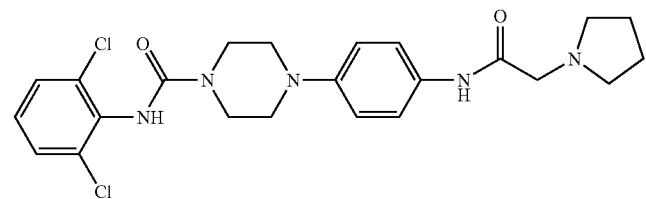
Co. No. 201; Ex. [B11.c]
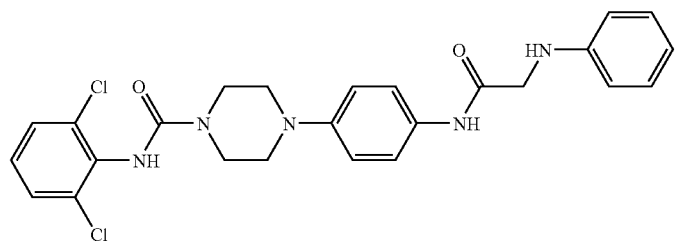
Co. No. 21; Ex. [B10.b]
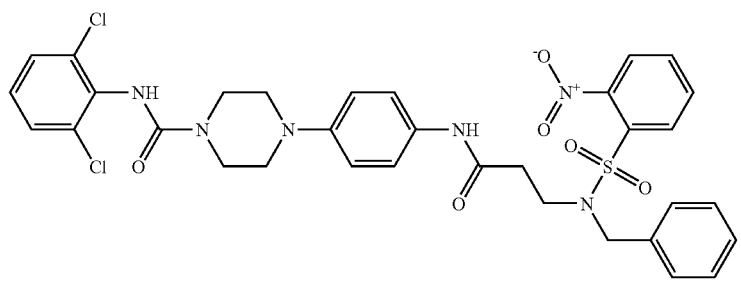
Co. No. 203; Ex. [B2.c]
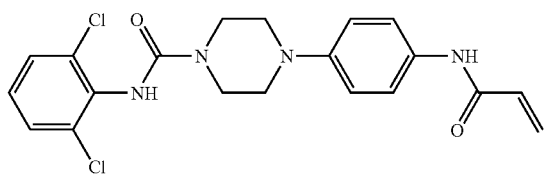
Co. No. 202; Ex. [B4.a]
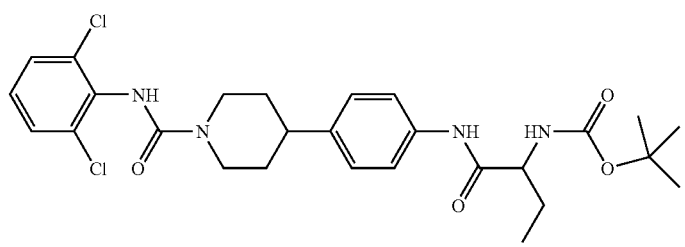
Co. No. 205; Ex. [B1]

TABLE 1-continued
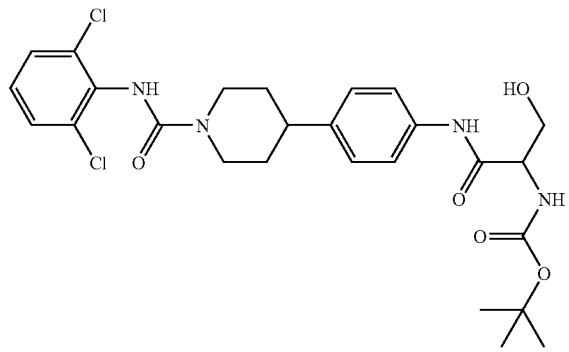
Co. No. 204; Ex. [B1]
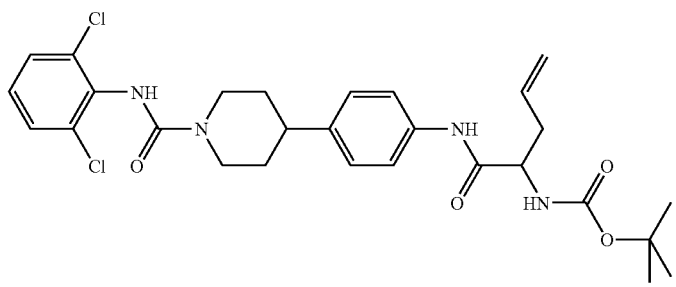
Co. No. 207; Ex. [B1]
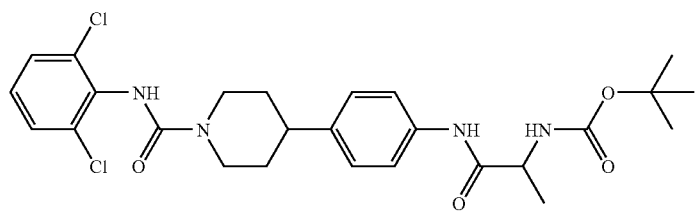
Co. No. 206; Ex. [B1]
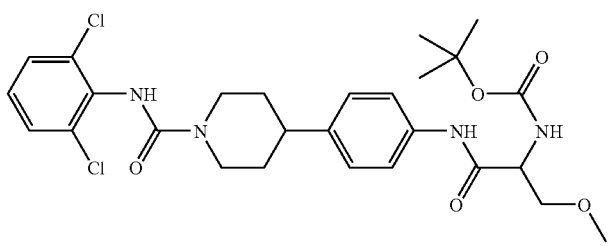
Co. No. 209; Ex. [B1]
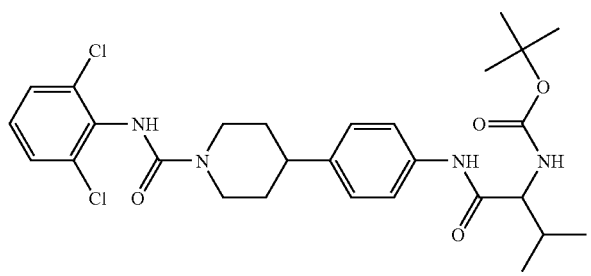
Co. No. 208; Ex. [B1]

TABLE 1-continued
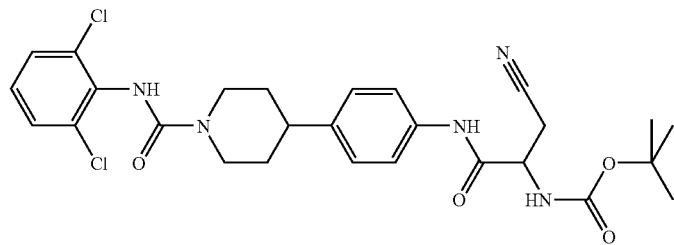
Co. No. 211; Ex. [B1]
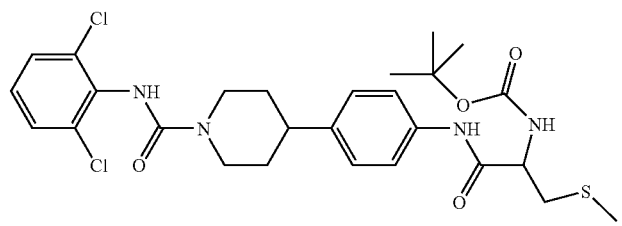
Co. No. 210; Ex. [B1]
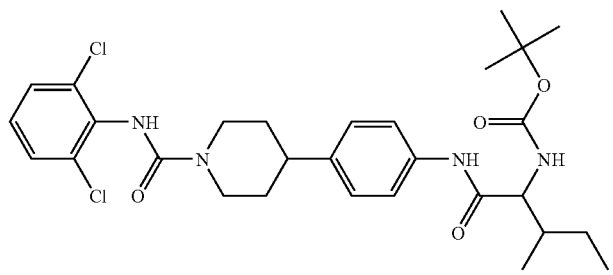
Co. No. 213; Ex. [B1]
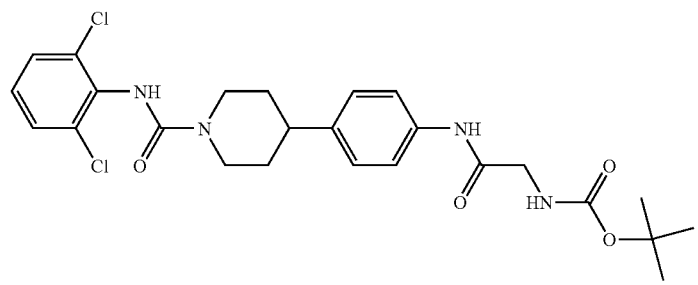
Co. No. 212; Ex. [B1]
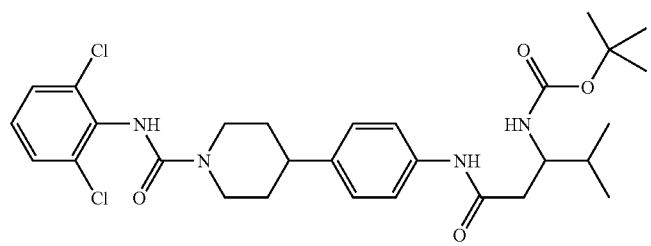
Co. No. 215; Ex. [B1]

TABLE 1-continued
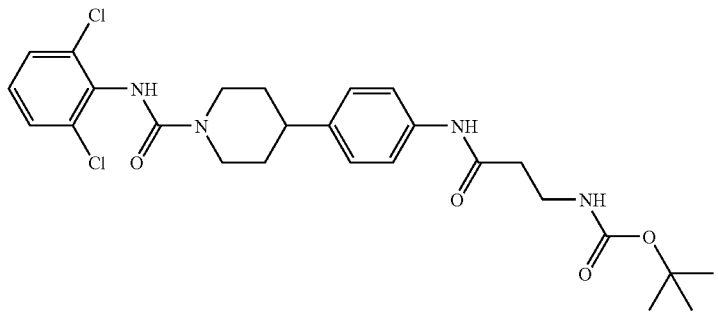
Co. No. 214; Ex. [B1]
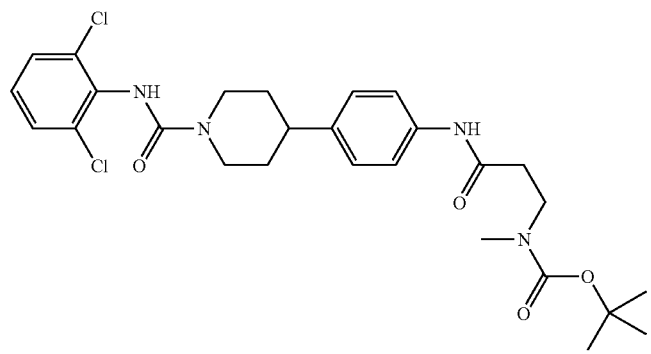
Co. No. 217; Ex. [B1]
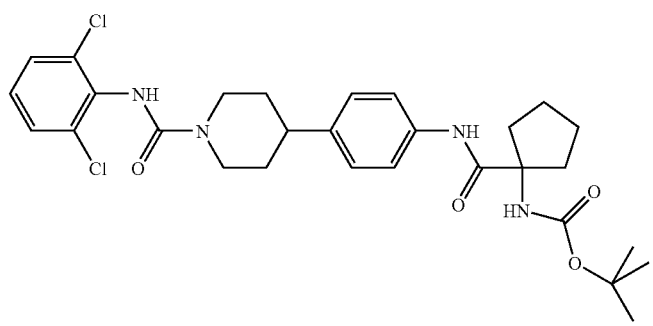
Co. No. 216; Ex. [B1]
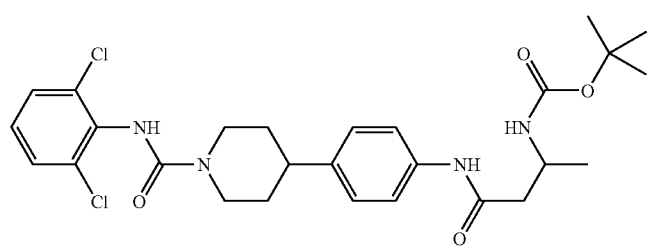
Co. No. 219; Ex. [B1]
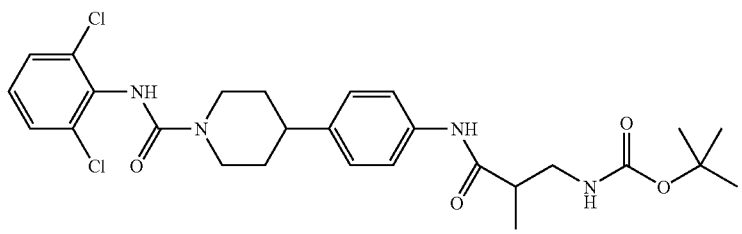
Co. No. 218; Ex. [B1]

TABLE 1-continued
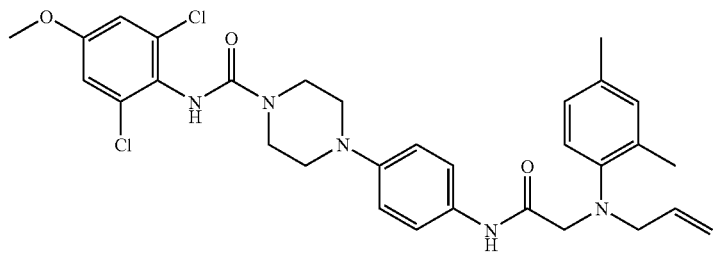
Co. No. 221; Ex. [B1]
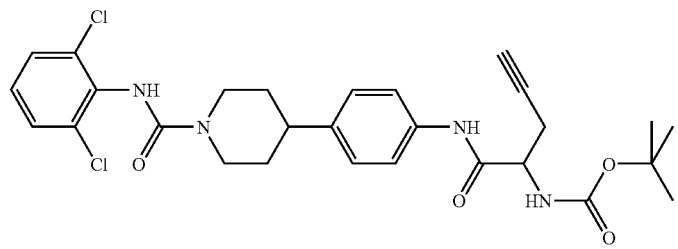
Co. No. 220; Ex. [B1]
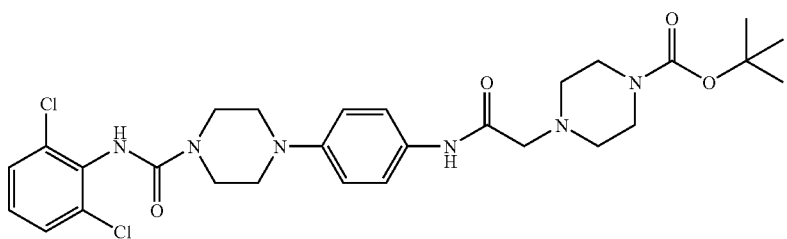
Co. No. 222; Ex. [B11.c]
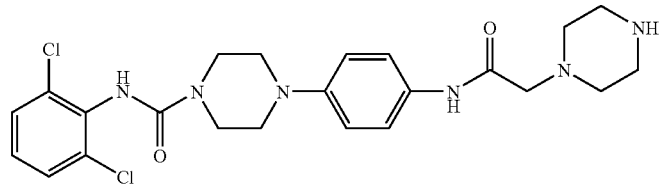
Co. No. 25; Ex. [B14.a]
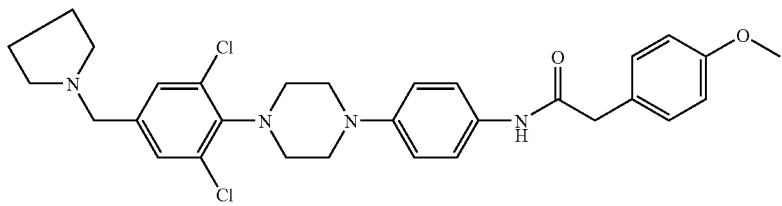
Co. No. 223; Ex. [B6.e]

TABLE 1-continued
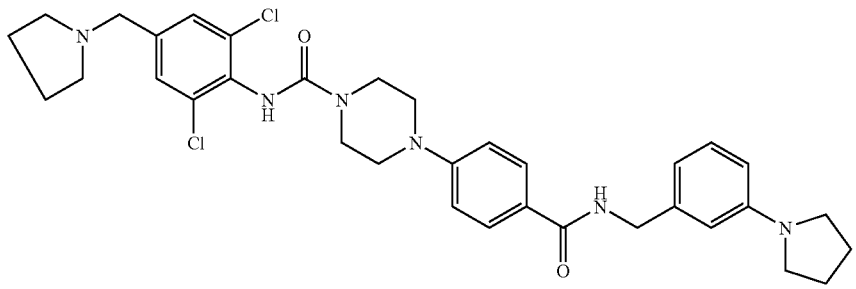
Co. No. 224; Ex. [B21.a]
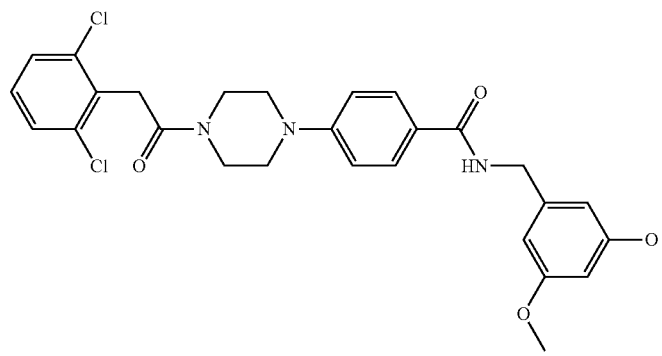
Co. No. 225; Ex. [B21.b]
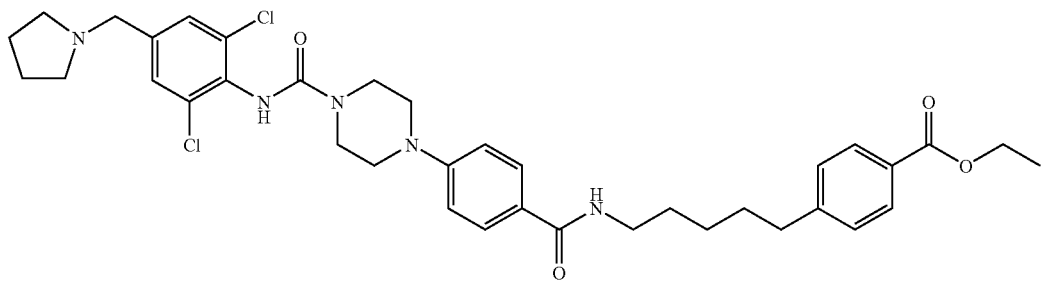
Co. No. 226; Ex. [B21.a]
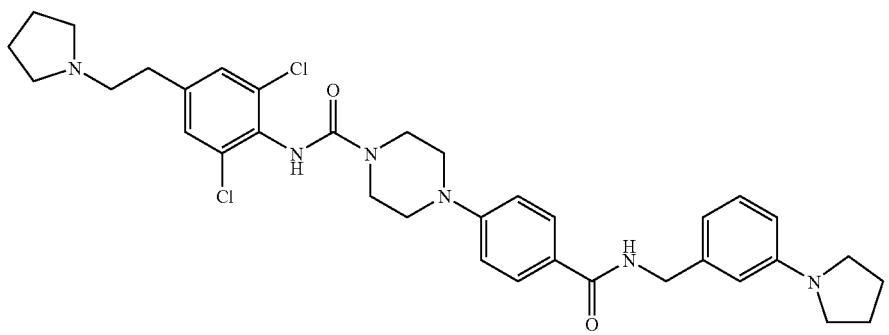
Co. No. 227; Ex. [B6.f]

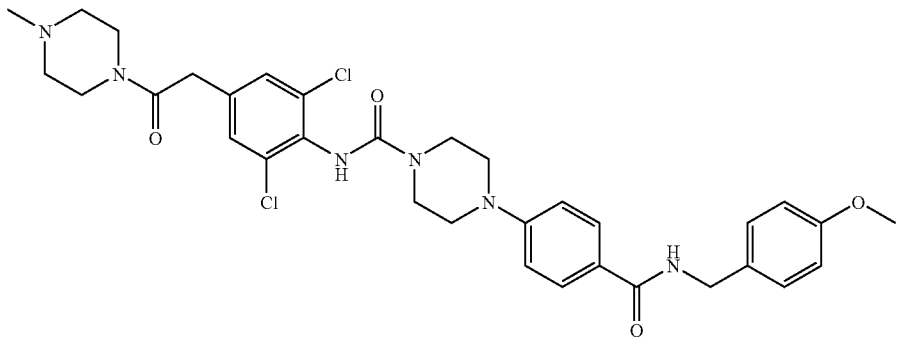
Co. No. 228; Ex. [B6.g]
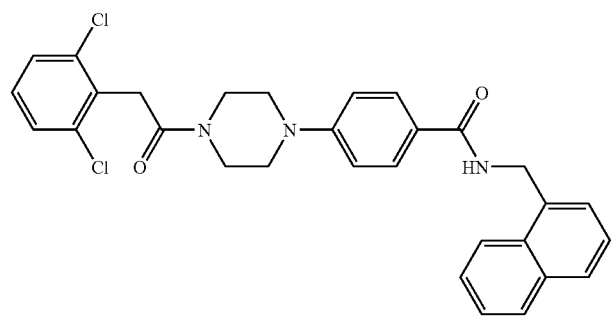
Co. No. 229; Ex. [B21.b]
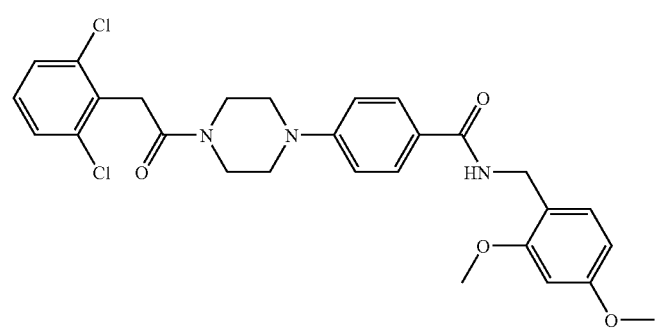
Co. No. 230; Ex. [B21.b]
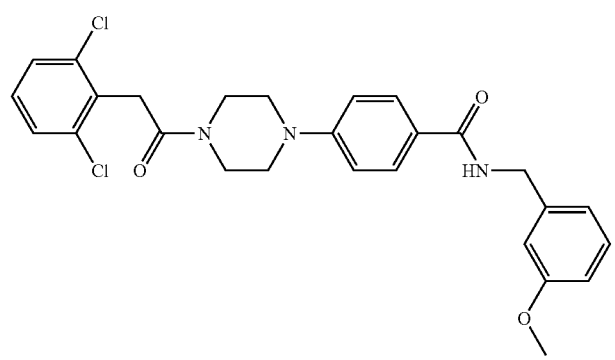
Co. No. 231; Ex. [B21.b]

TABLE 1-continued
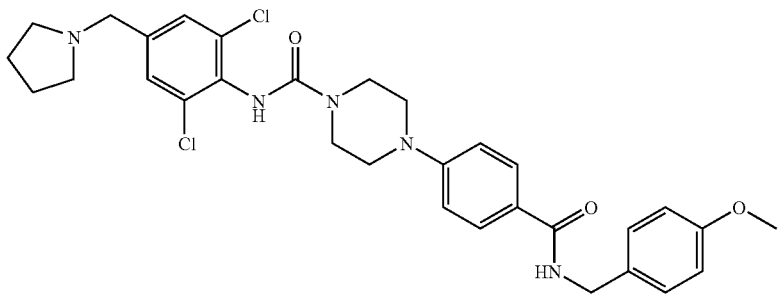
Co. No. 232; Ex. [B21.a]
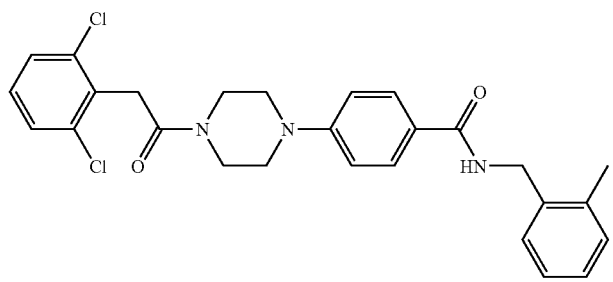
Co. No. 233; Ex. [B21.b]
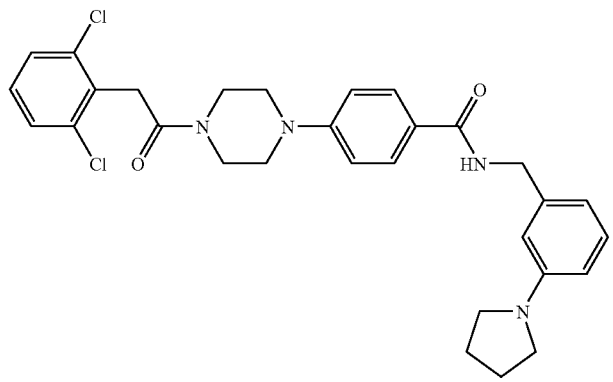
Co. No. 234; Ex. [B21.b]
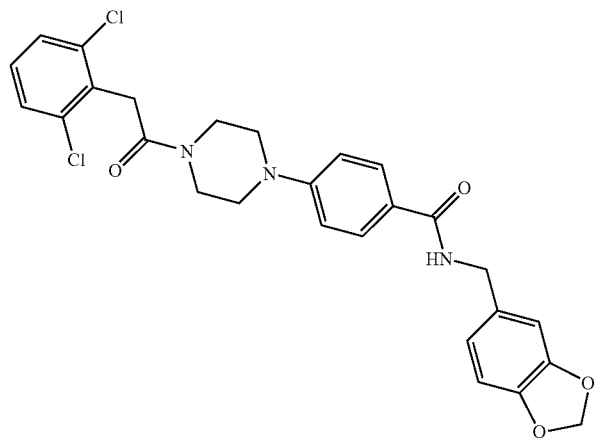
Co. No. 235; Ex. [B21.b]

TABLE 1-continued
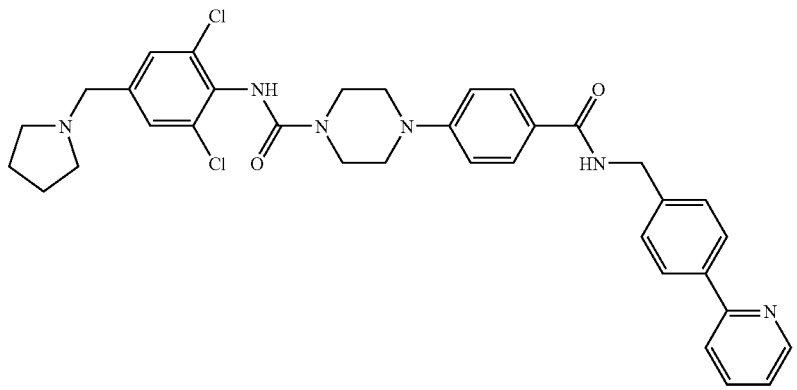
Co. No. 236; Ex. [B21.a]
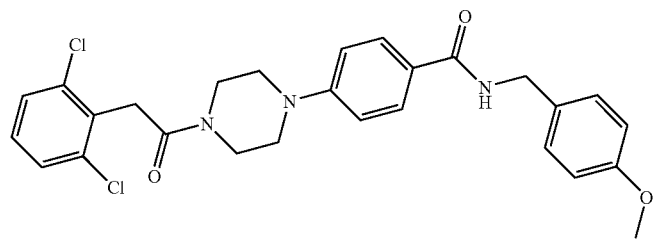
Co. No. 237; Ex. [B21.b]
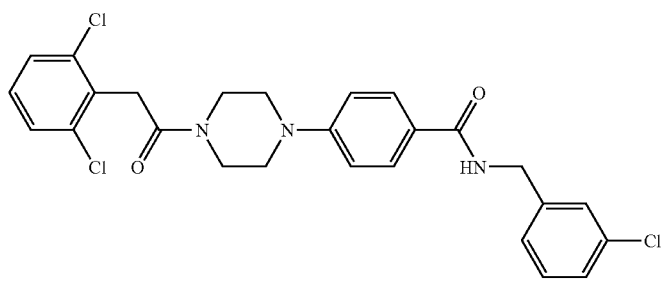
Co. No. 238; Ex. [B21.b]
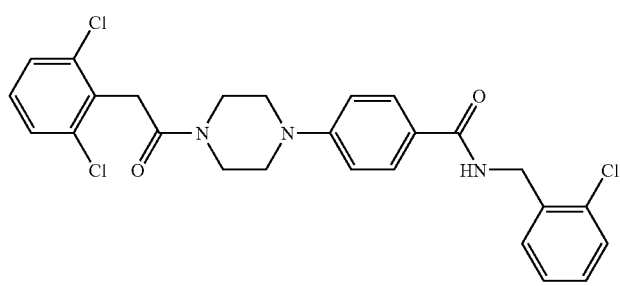
Co. No. 239; Ex. [B21.b]

TABLE 1-continued
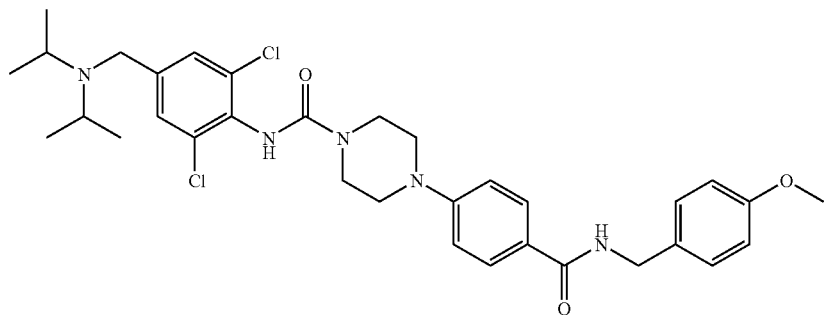
Co. No. 240; Ex. [B21.a]
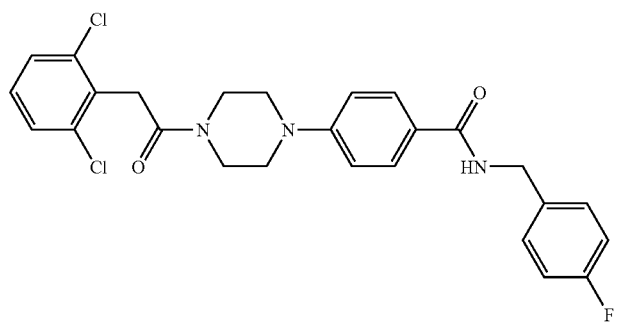
Co. No. 241; Ex. [B21.b]
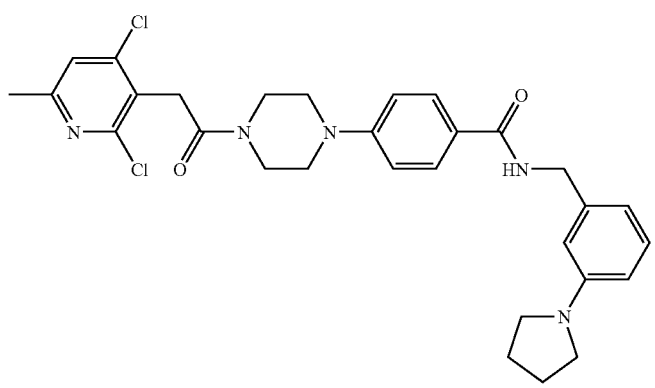
Co. No. 242; Ex. [B21.b]
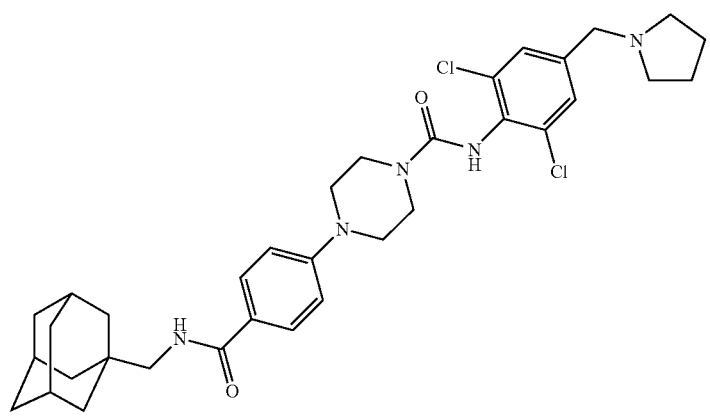
Co. No. 243; Ex. [B21.a]

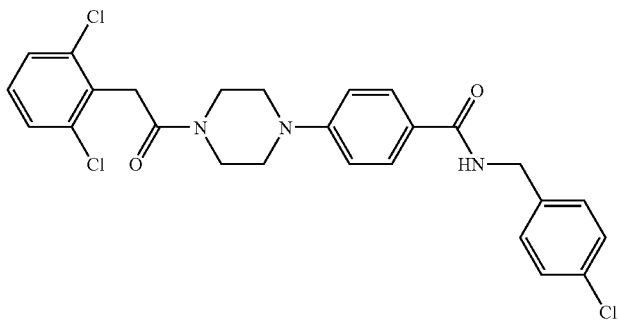
Co. No. 244; Ex. [B21.b]
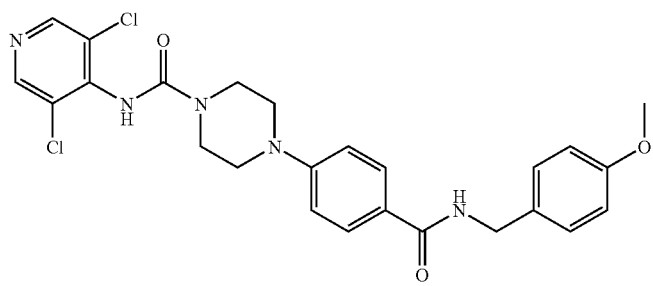
Co. No. 245; Ex. [B21.b]
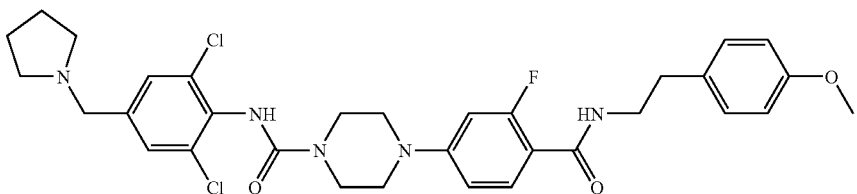
Co. No. 246; Ex. [B21.a]
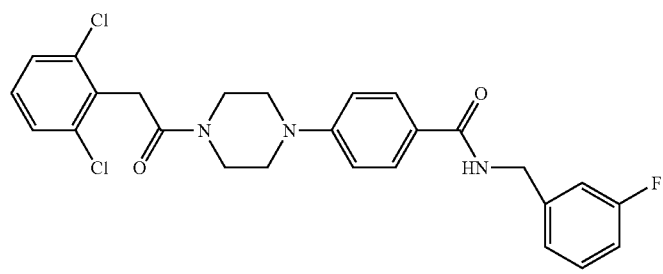
Co. No. 247; Ex. [B21.b]
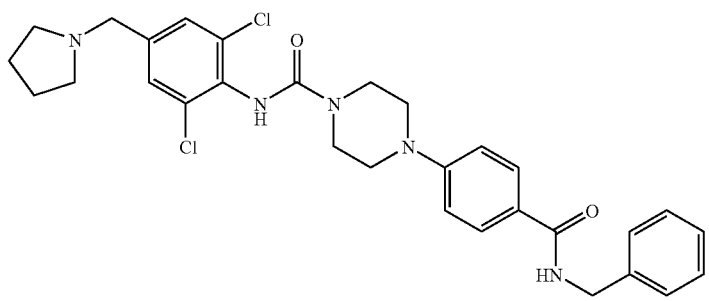
Co. No. 248; Ex. [B21.a]

TABLE 1-continued
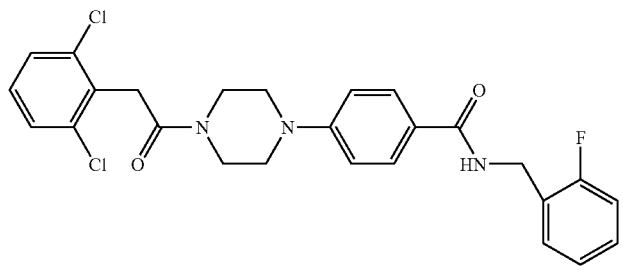
Co. No. 249; Ex. [B21.b]
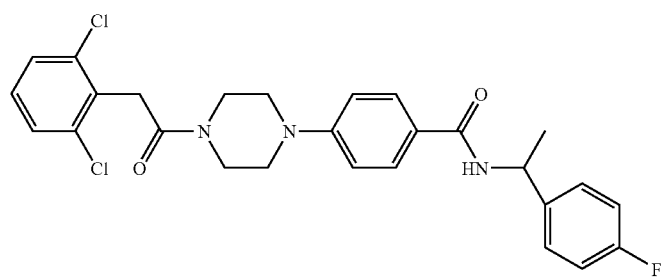
Co. No. 250; Ex. [B21.b]
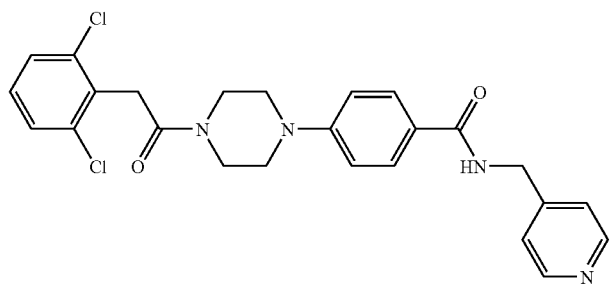
Co. No. 251; Ex. [B21.b]
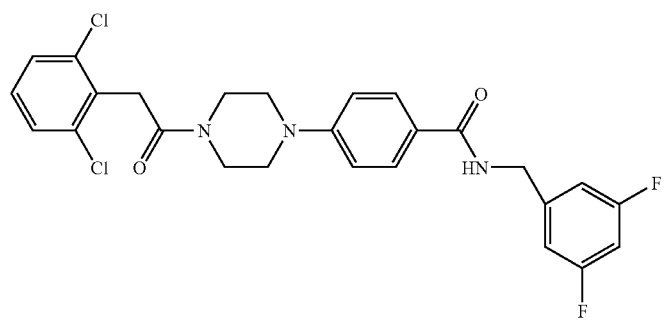
Co. No. 252; Ex. [B21.b]
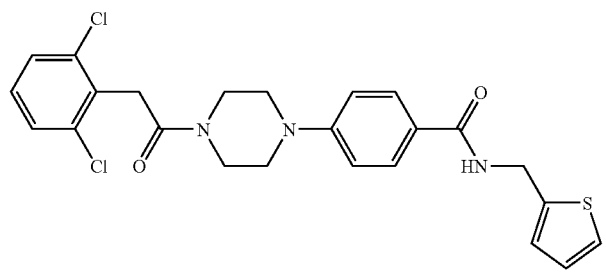
Co. No. 253; Ex. [B21.b]

TABLE 1-continued
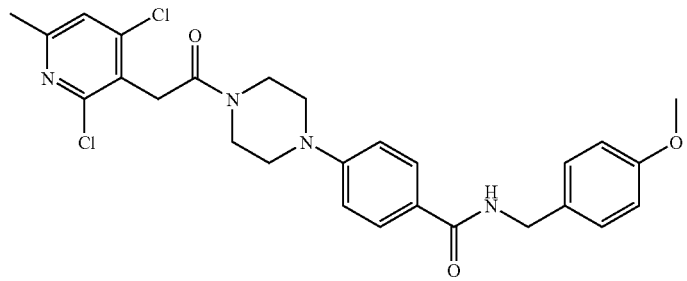
Co. No. 254; Ex. [B21.b]
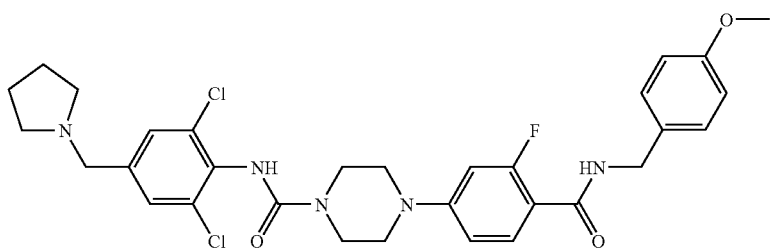
Co. No. 255; Ex. [B21.a]
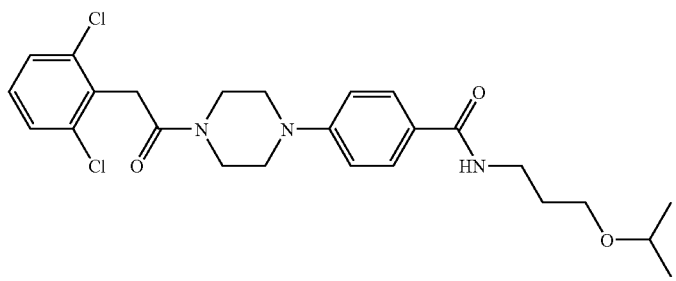
Co. No. 256; Ex. [B21.b]
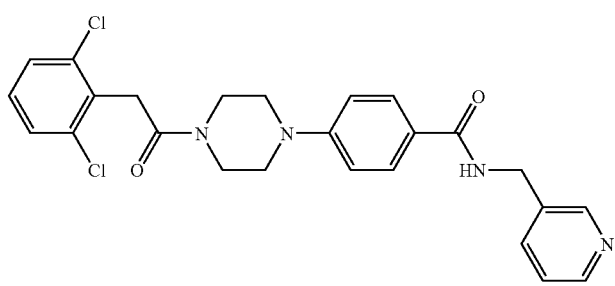
Co. No. 257; Ex. [B21.b]
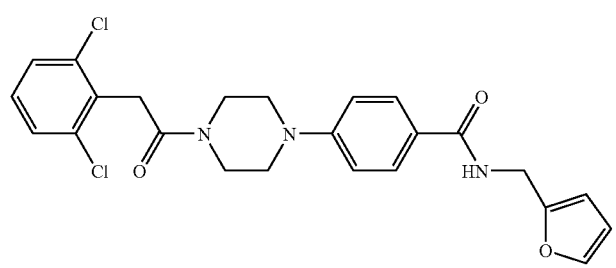
Co. No. 258; Ex. [B21.b]

TABLE 1-continued
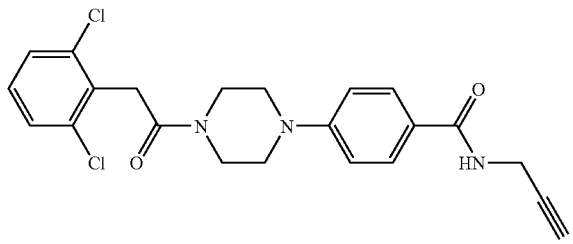
Co. No. 259; Ex. [B21.b]
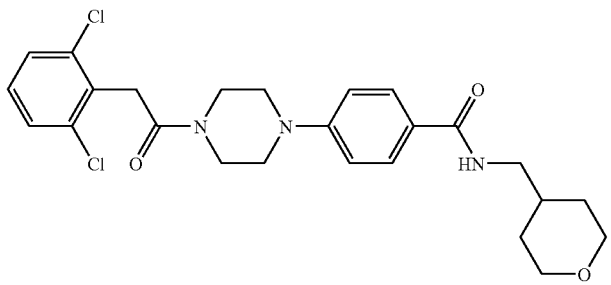
Co. No. 260; Ex. [B21.b]
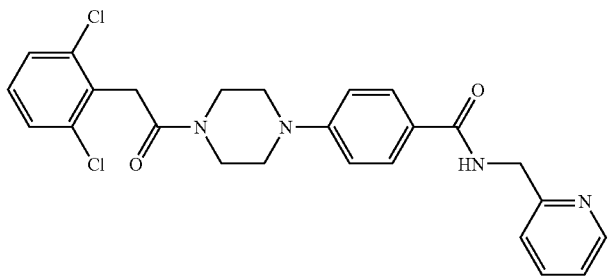
Co. No. 261; Ex. [B21.b]
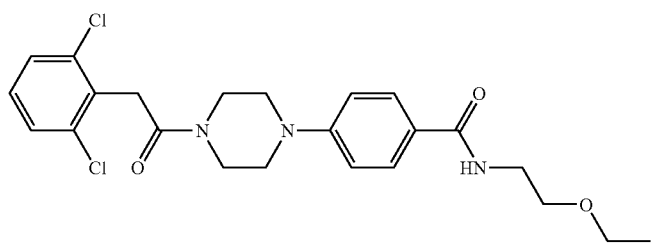
Co. No. 262; Ex. [B21.b]
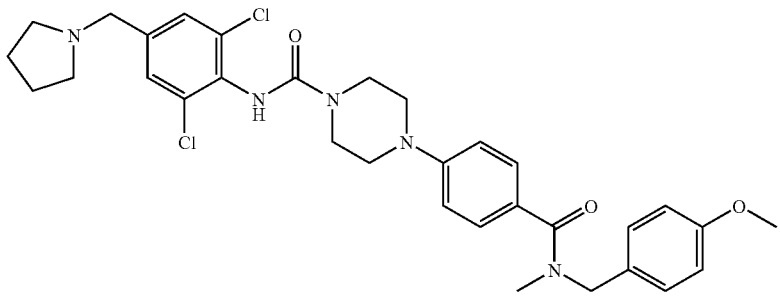
Co. No. 263; Ex. [B21.a]

TABLE 1-continued
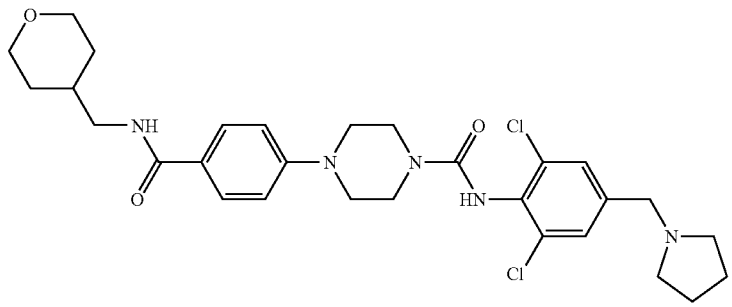
Co. No. 264; Ex. [B21.a]
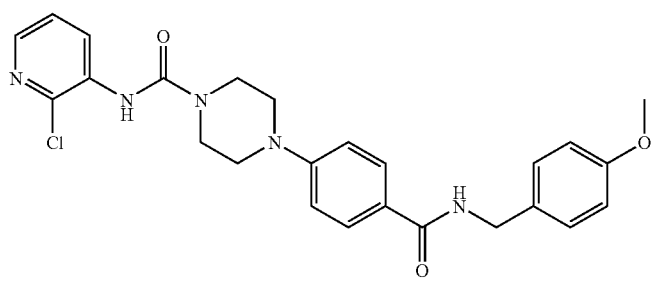
Co. No. 265; Ex. [B21.b]
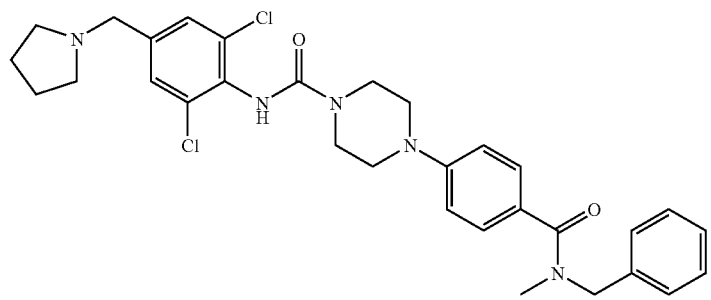
Co. No. 266; Ex. [B21.a]
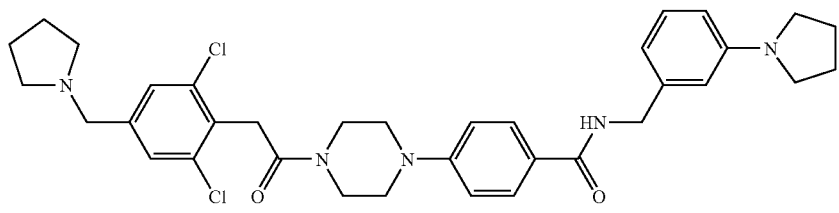
Co. No. 267; Ex. [B22]
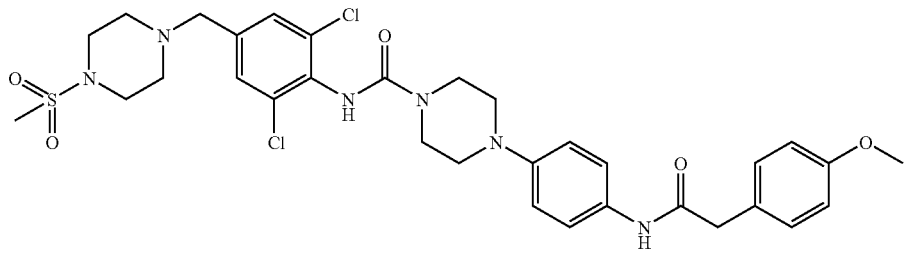
Co. No. 268; Ex. [B6.h]

TABLE 1-continued
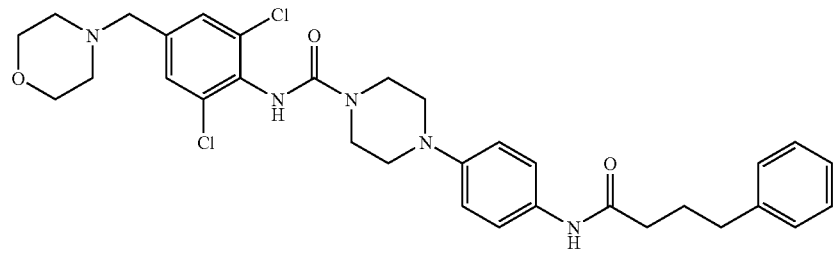
Co. No. 269; Ex. [B6.h]
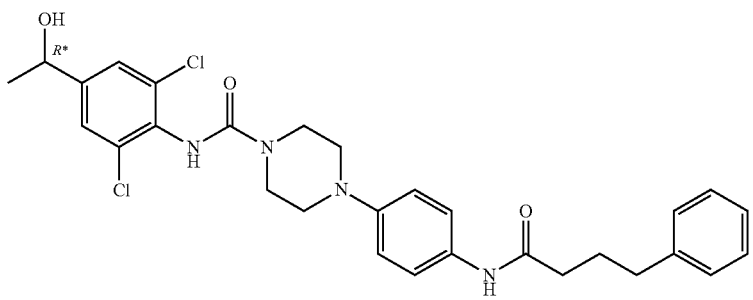
Co. No. 270; Ex. [B23]
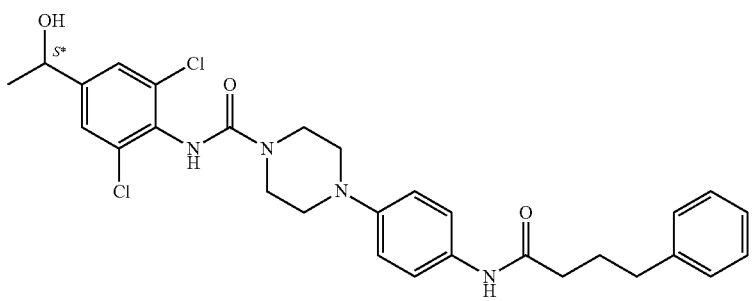
Co. No. 271; Ex. [B23]
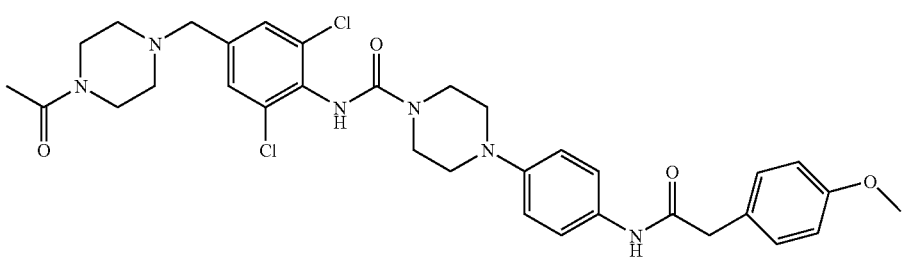
Co. No. 272; Ex. [B6.h]
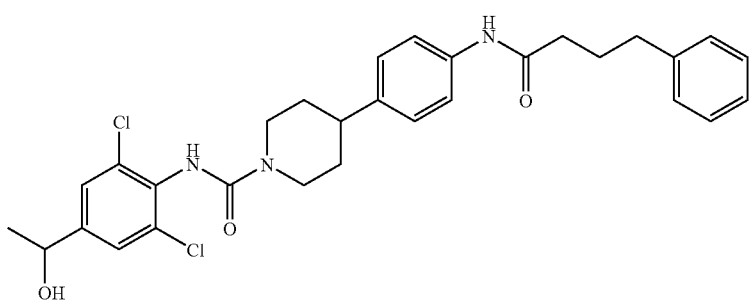
Co. No. 273; Ex. [B23]

TABLE 1-continued
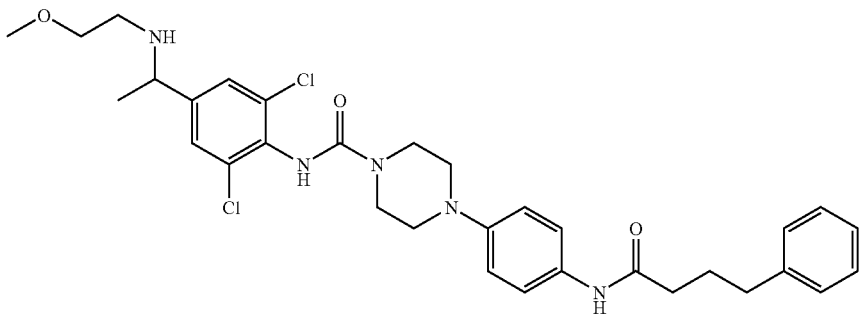
Co. No. 274; Ex. [B13]
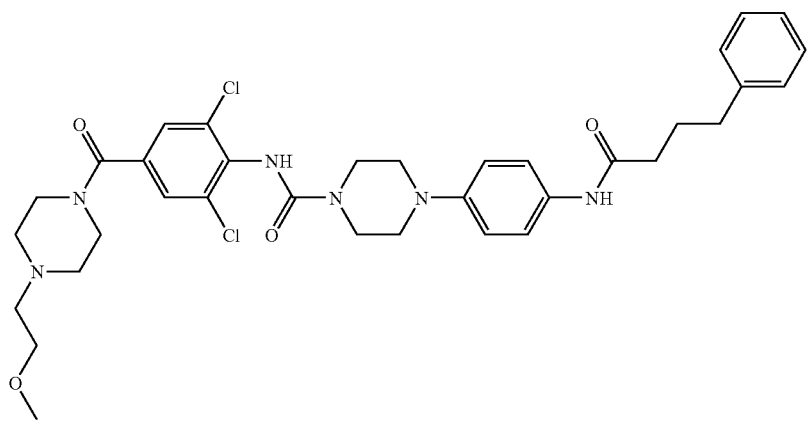
Co. No. 275; Ex. [B24]
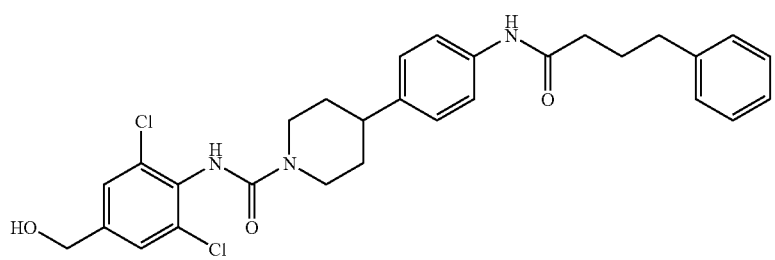
Co. No. 276; Ex. [B24]
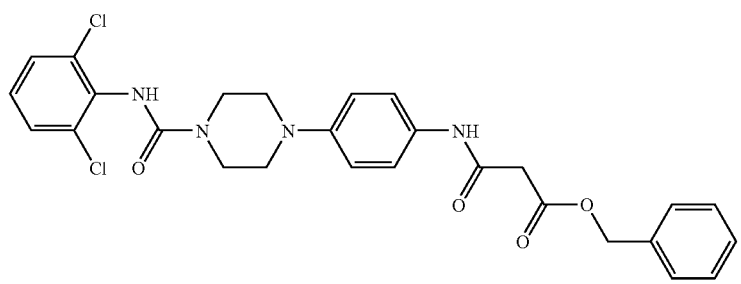
Co. No. 277; Ex. [B1]

TABLE 1-continued
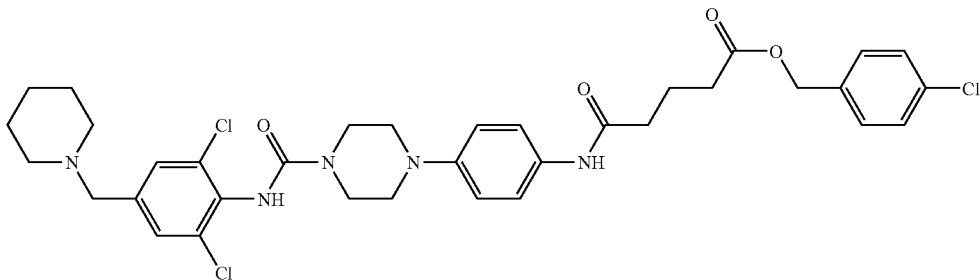
Co. No. 278; Ex. [B6.h]
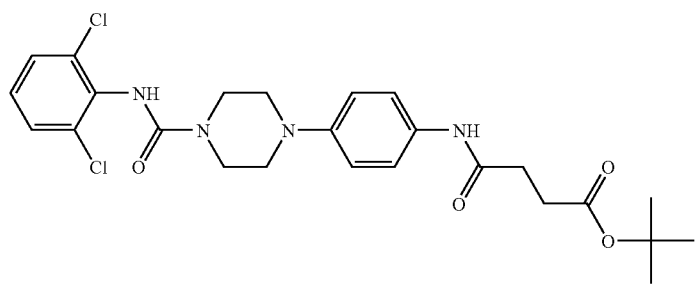
Co. No. 279; Ex. [B1]
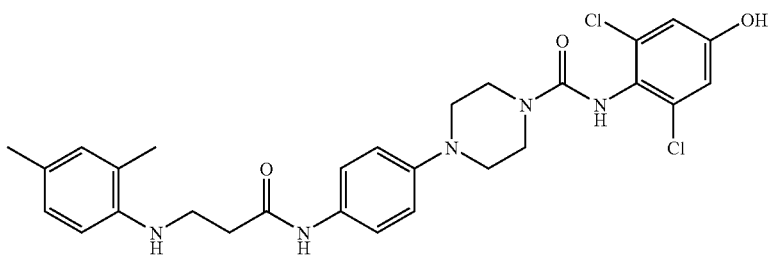
Co. No. 280; Ex. [B11.a]
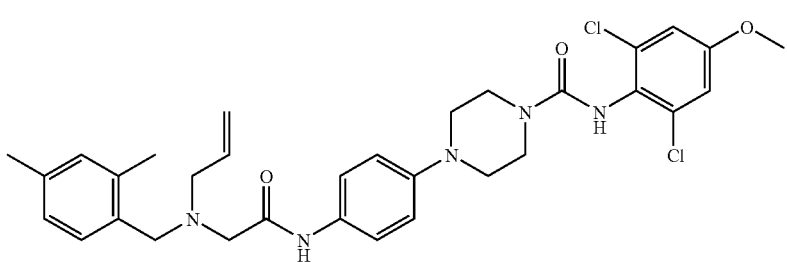
Co. No. 281; Ex. [B11.a]
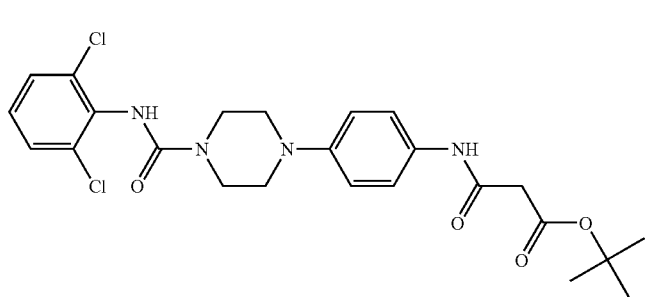
Co. No. 282; Ex. [B1]

TABLE 1-continued
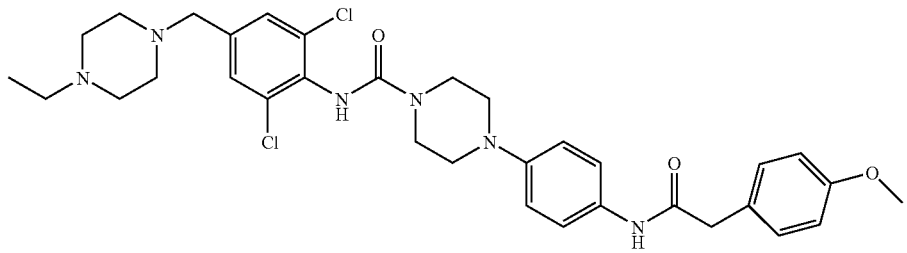
Co. No. 283; Ex. [B6.h]
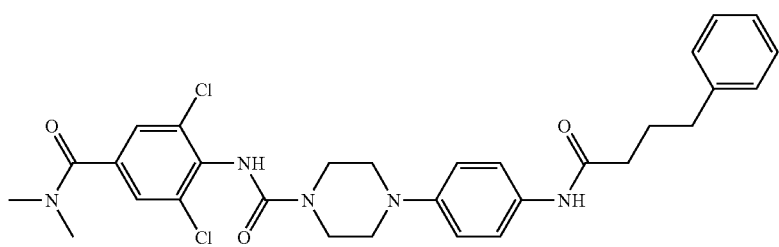
Co. No. 284; Ex. [B6.h]
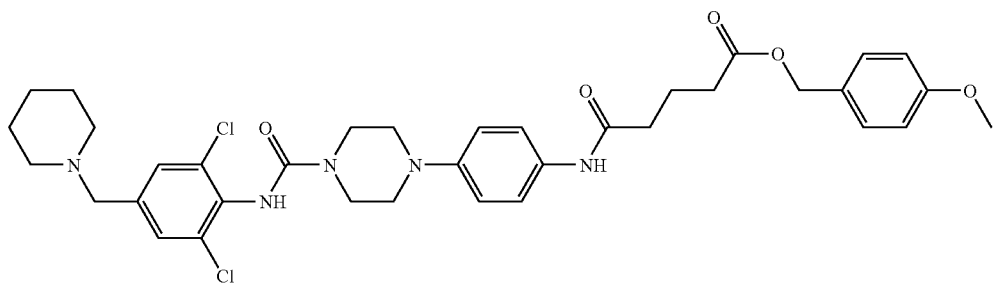
Co. No. 285; Ex. [B6.h]
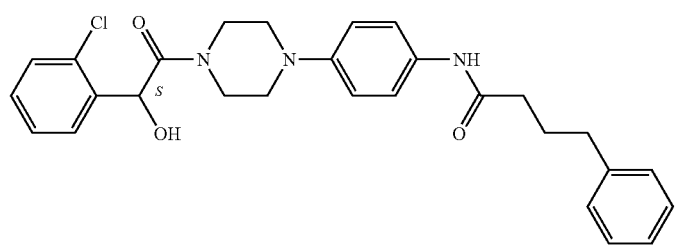
Co. No. 286; Ex. [B10]
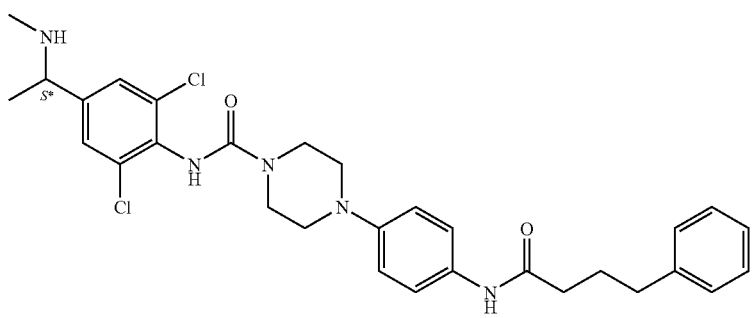
Co. No. 287; Ex. [B13]

TABLE 1-continued
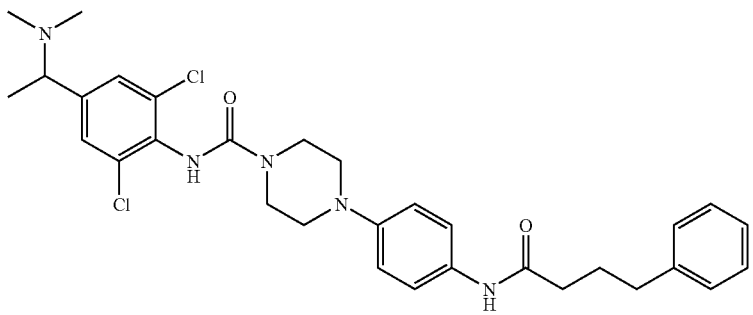
Co. No. 288; Ex. [B13]
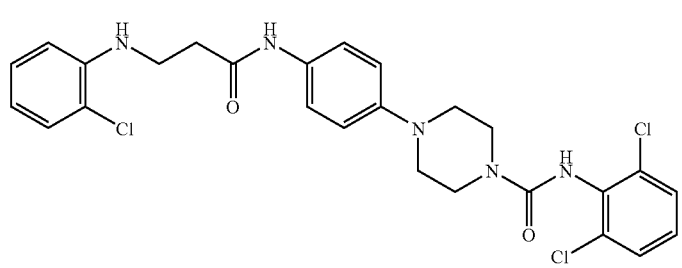
Co. No. 289; Ex. [B11.a]
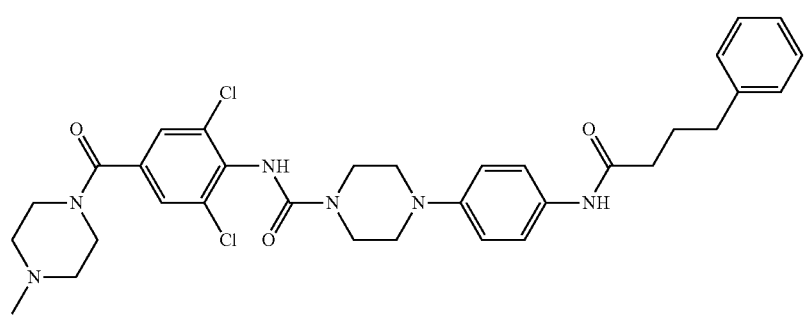
Co. No. 290; Ex. [B6.h]
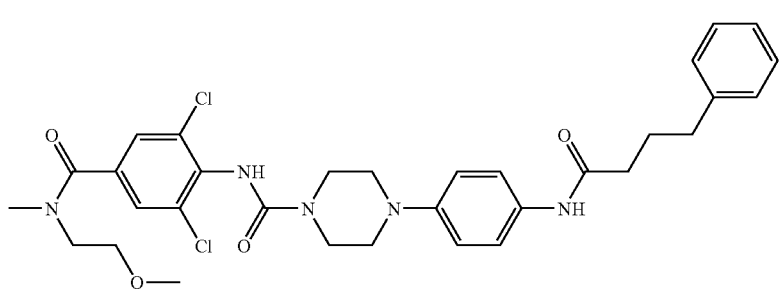
Co. No. 291; Ex. [B6.h]
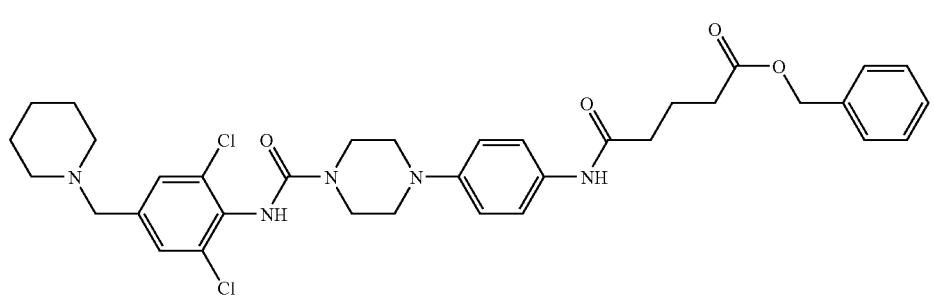
Co. No. 292; Ex. [B31]

TABLE 1-continued
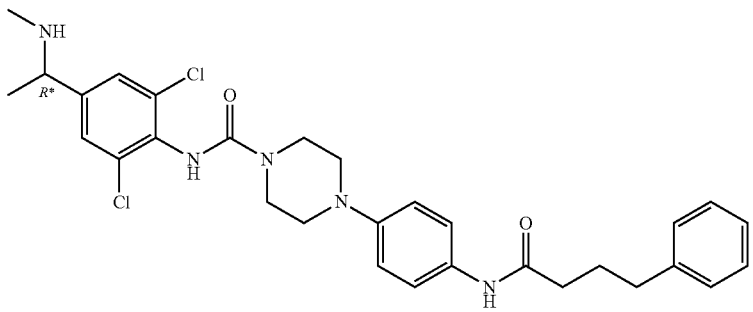
Co. No. 293; Ex. [B13]
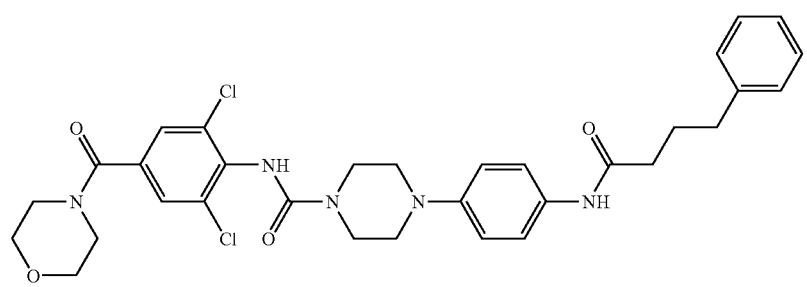
Co. No. 294; Ex. [B6.h]
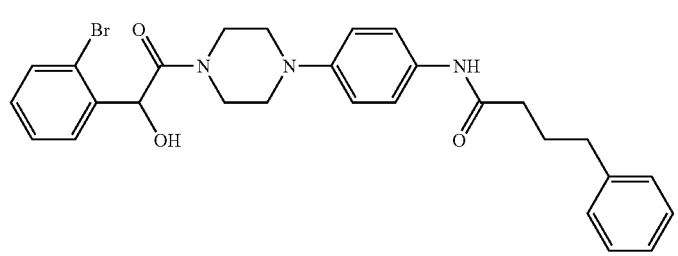
Co. No. 295; Ex. [B10]
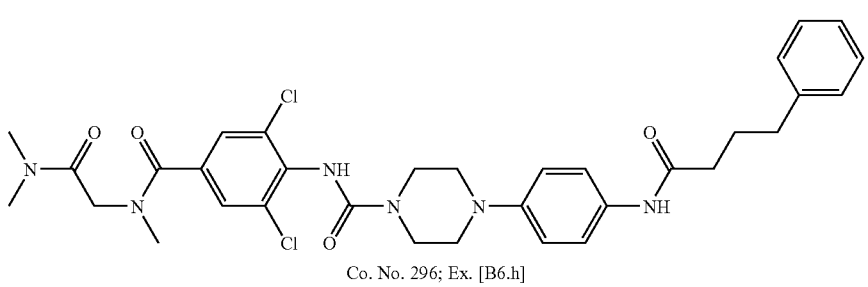 [SMILES: CN(C)C(=O)CN(C)C(=O)c1cc(Cl)c(NC(=O)N2CCN(c3ccc(NC(=O)CCCc4ccccc4)cc3)CC2)c(Cl)c1]
Co. No. 296; Ex. [B6.h]
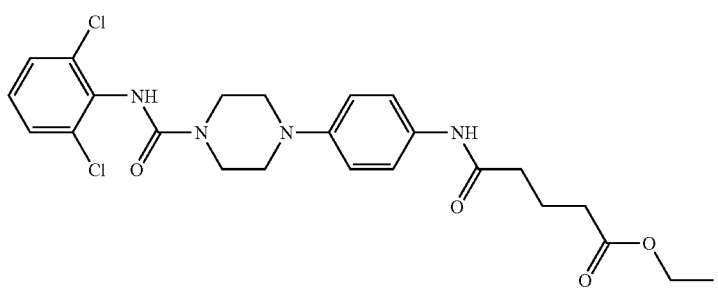
Co. No. 297; Ex. [B1]

TABLE 1-continued
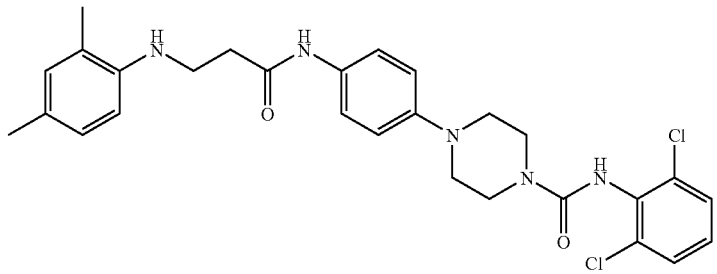
Co. No. 298; Ex. [B1]
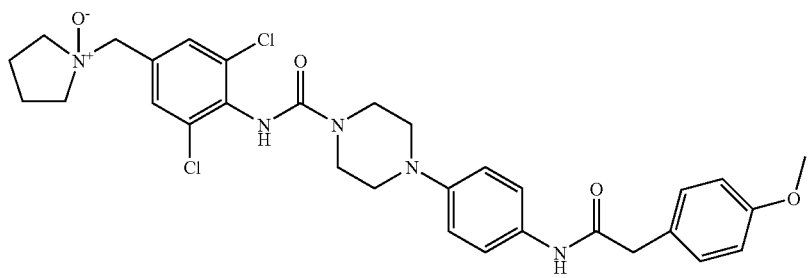
Co. No. 299; Ex. [B25]
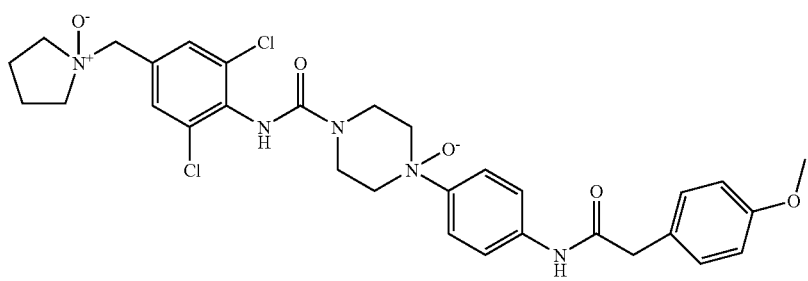
Co. No. 300; Ex. [B25]
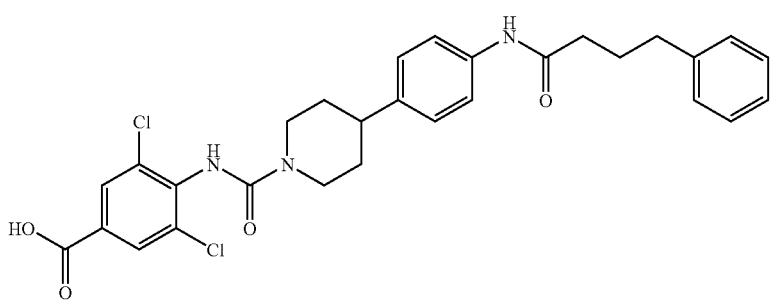
Co. No. 301; Ex. [B15]

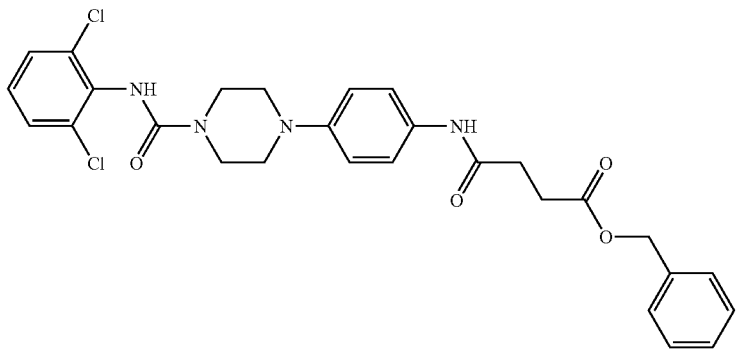
Co. No. 302; Ex. [B1]
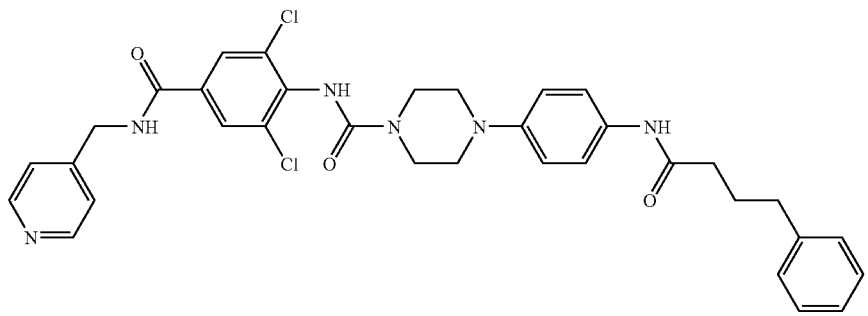
Co. No. 303; Ex. [B6.h]
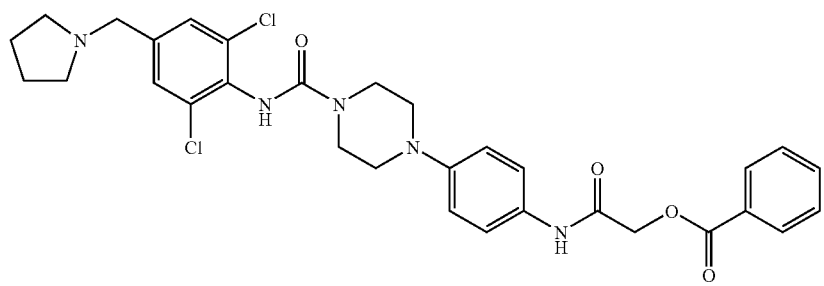
Co. No. 304; Ex. [B21.a]
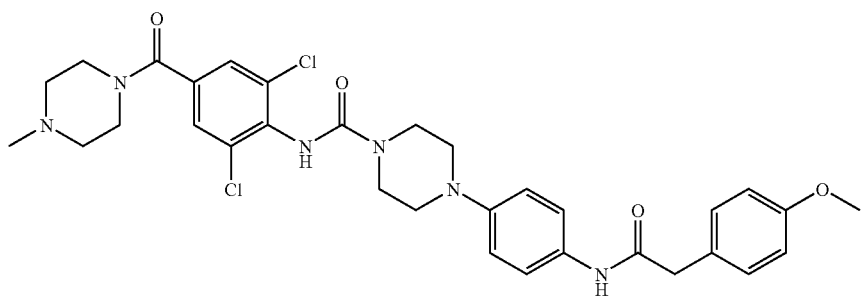
Co. No. 305; Ex. [B6.h]

TABLE 1-continued
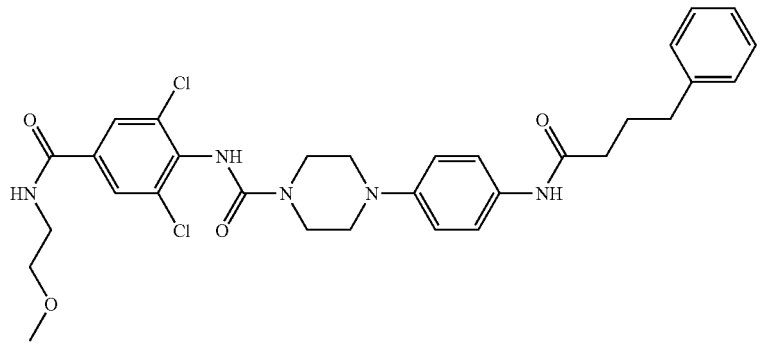
Co. No. 306; Ex. [B6.h]
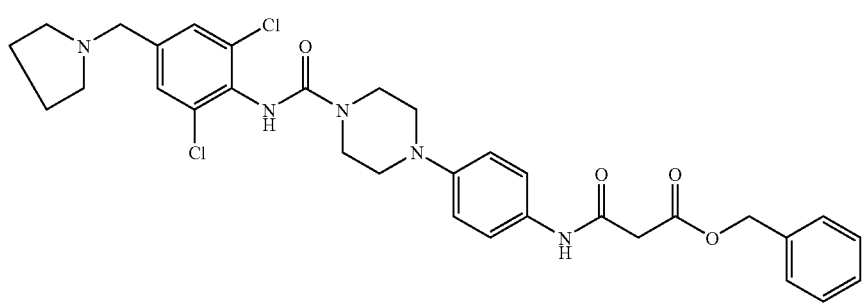
Co. No. 307; Ex. [B21.a]
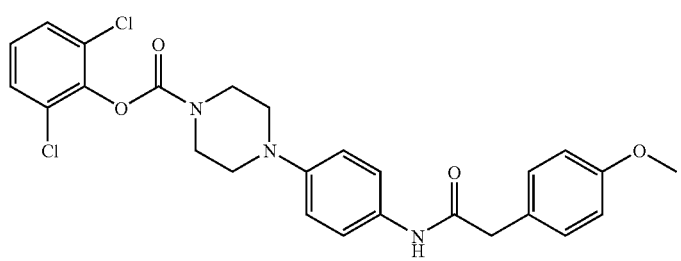
Co. No. 308; Ex. [B26]
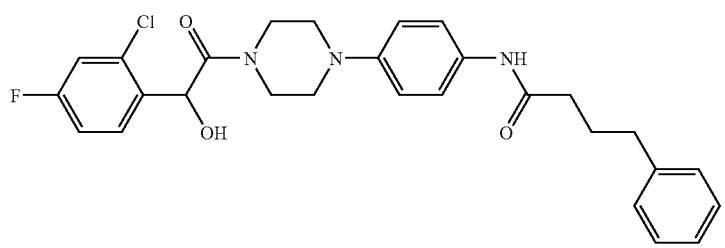
Co. No. 309; Ex. [B10]

TABLE 1-continued
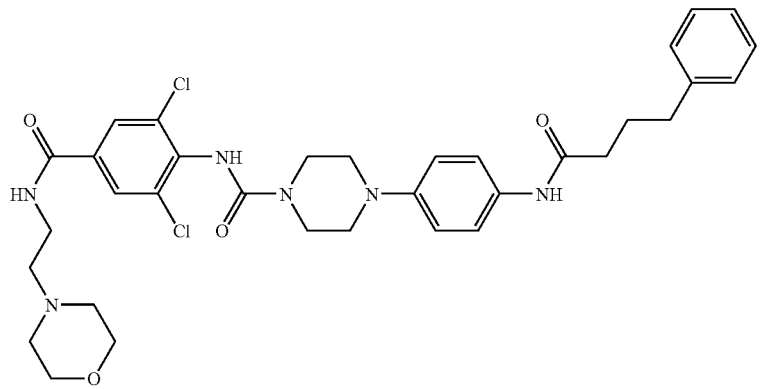
Co. No. 310; Ex. [B6.h]
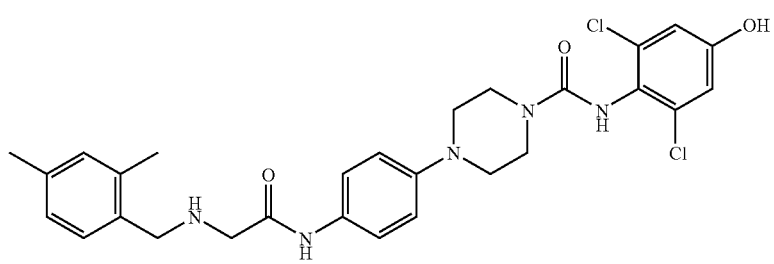
Co. No. 311; Ex. [B1]
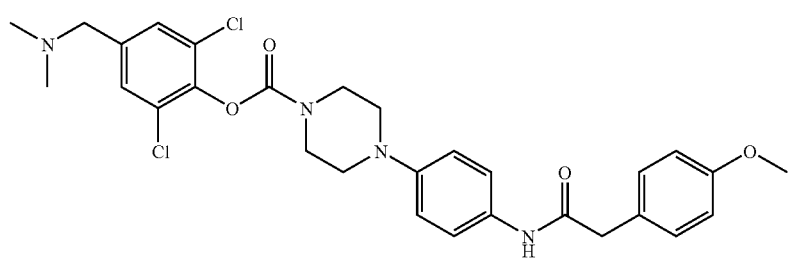
Co. No. 312; Ex. [B21.a]
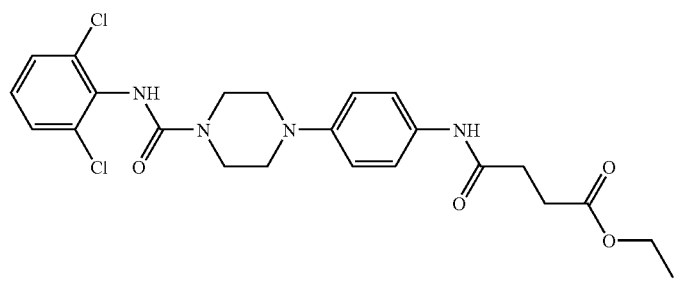
Co. No. 313; Ex. [B1]

TABLE 1-continued
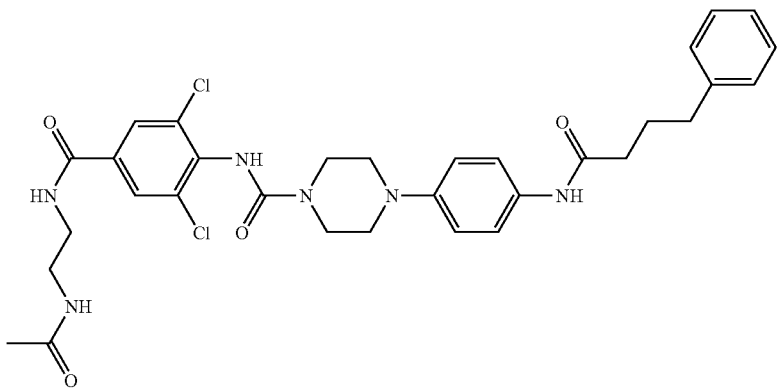
Co. No. 314; Ex. [B6.h]
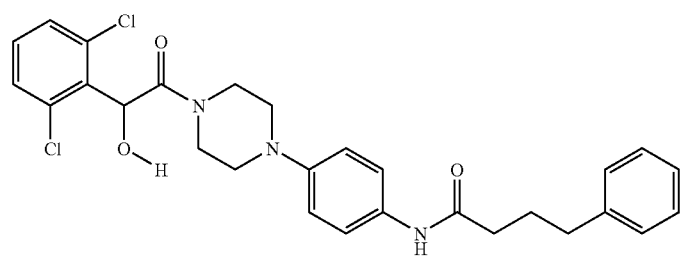
Co. No. 315; Ex. [B10]
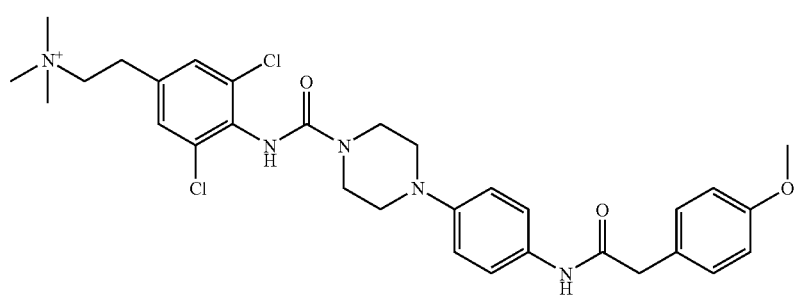
Co. No. 317; Ex. [B6.i]
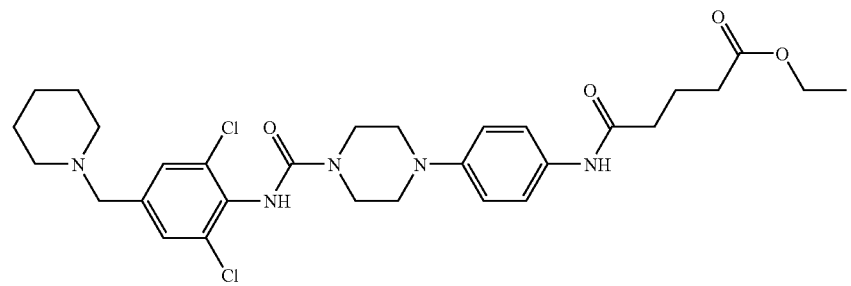
Co. No. 318; Ex. [B21.a]

TABLE 1-continued
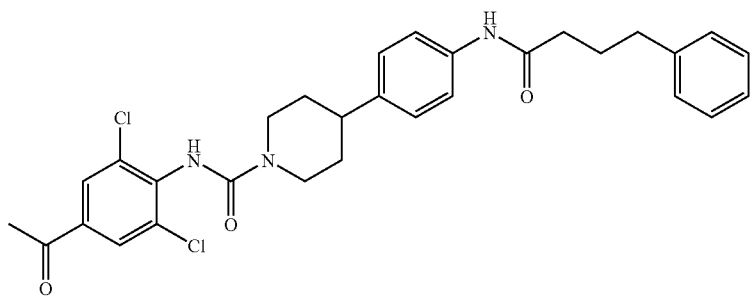
Co. No. 319; Ex. [B6]
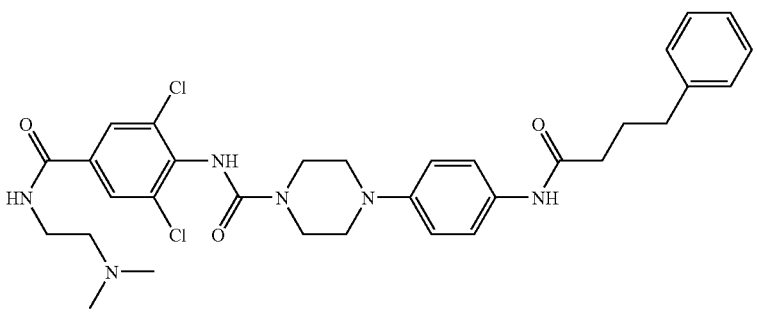
Co. No. 321; Ex. [B6.h]
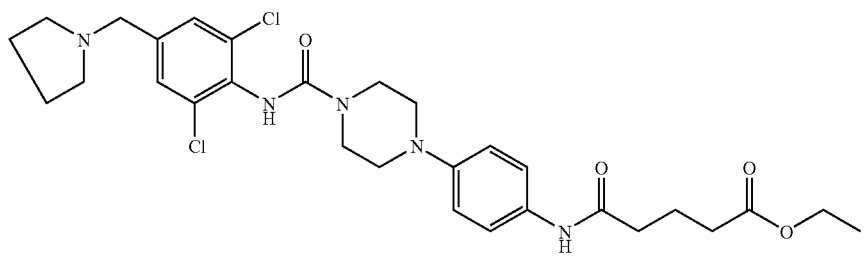
Co. No. 322; Ex. [B21.a]
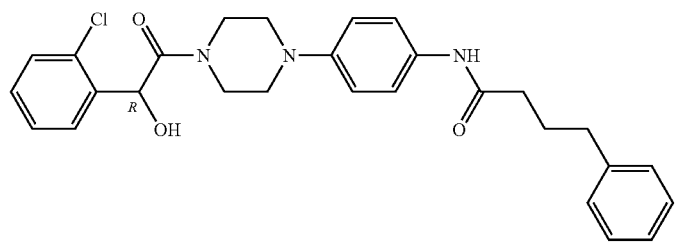
Co. No. 323; Ex. [B10]
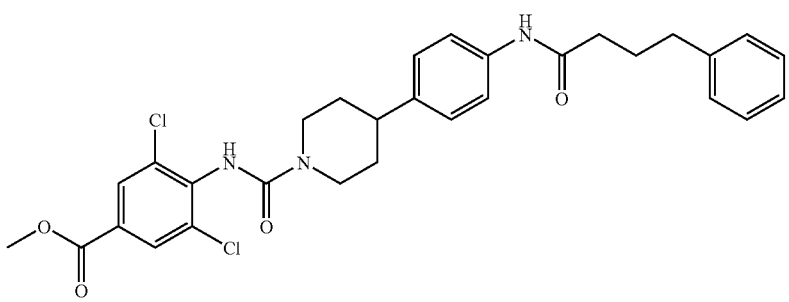
Co. No. 324; Ex. [B6]

TABLE 1-continued
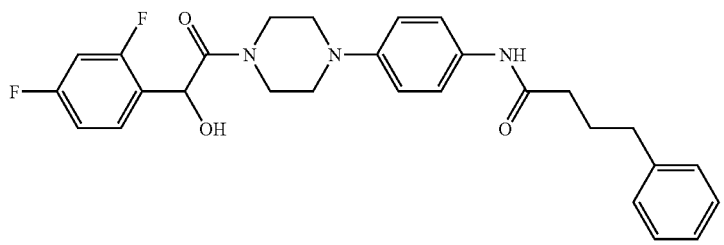
Co. No. 325; Ex. [B10]
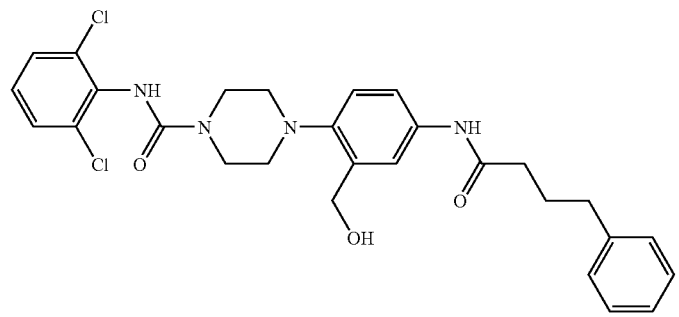
Co. No. 326; Ex. [B27]
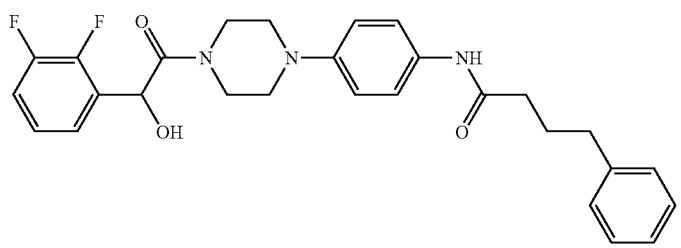
Co. No. 327; Ex. [B10]
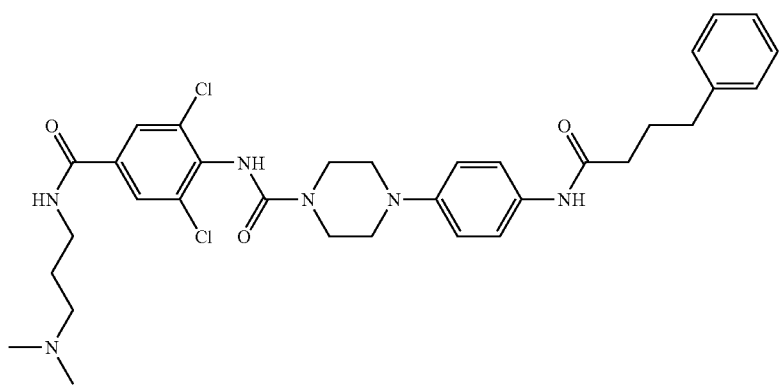
Co. No. 328; Ex. [B6.h]

TABLE 1-continued
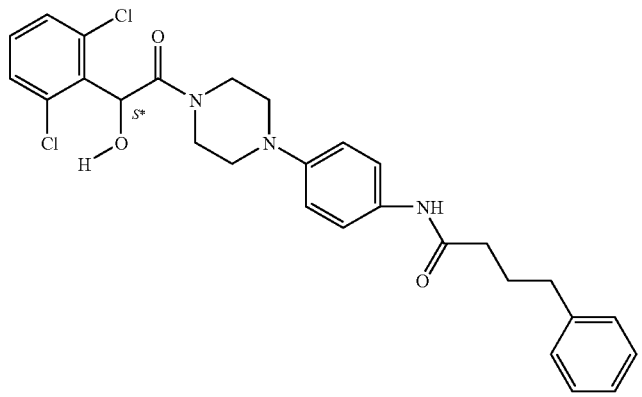
Co. No. 329; Ex. [B10]
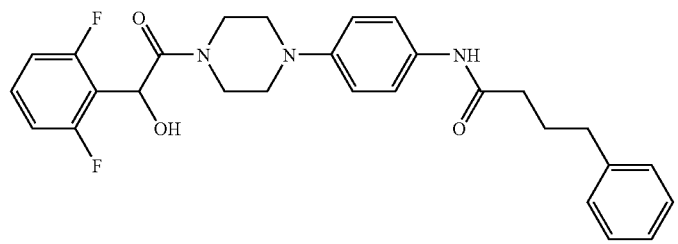
Co. No. 330; Ex. [B10]
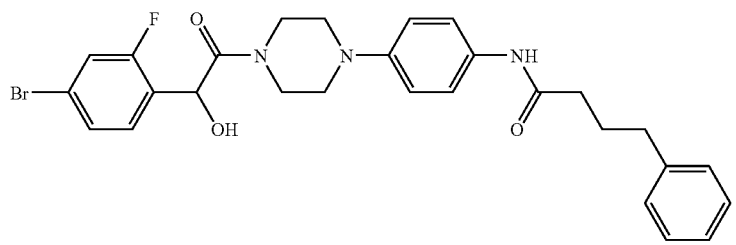
Co. No. 331; Ex. [B10]
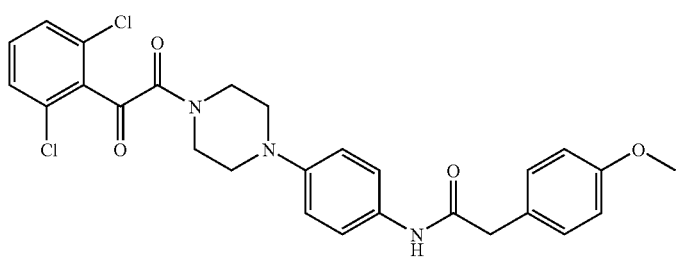
Co. No. 332; Ex. [B10]

TABLE 1-continued
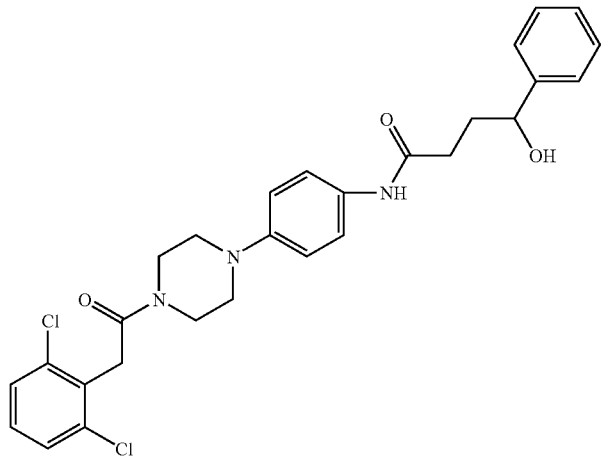
Co. No. 333; Ex. [B28]
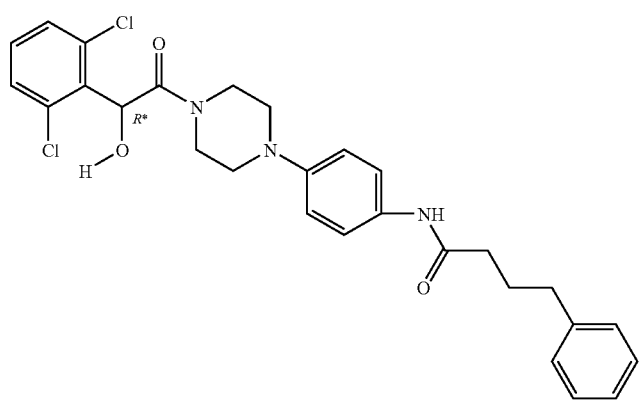
Co. No. 334; Ex. [B10]
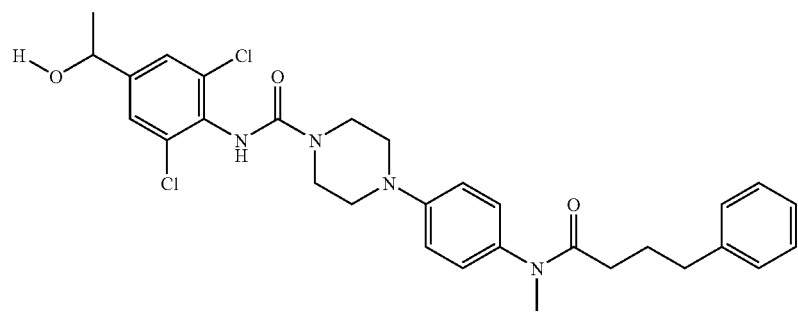
Co. No. 335; Ex. [B21.b]

TABLE 1-continued
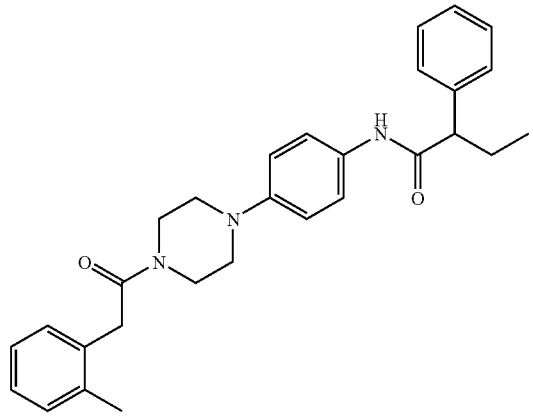
Co. No. 336; Ex. [B28]
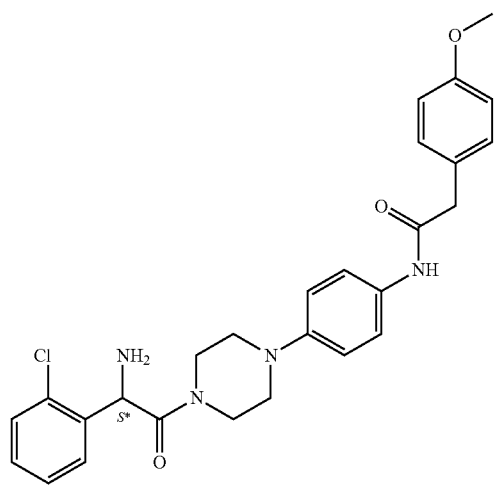
Co. No. 337; Ex. [B29]
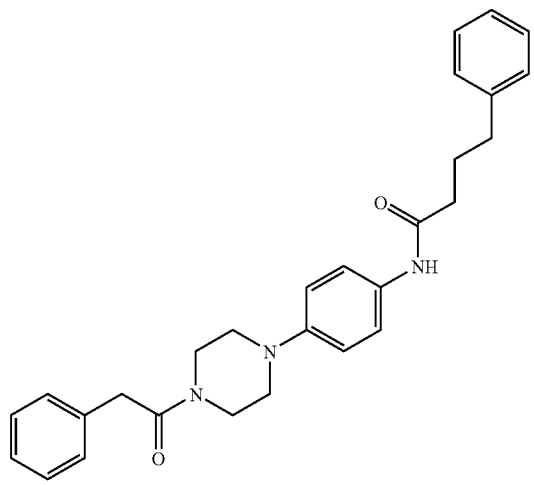
Co. No. 338; Ex. [B28]

TABLE 1-continued
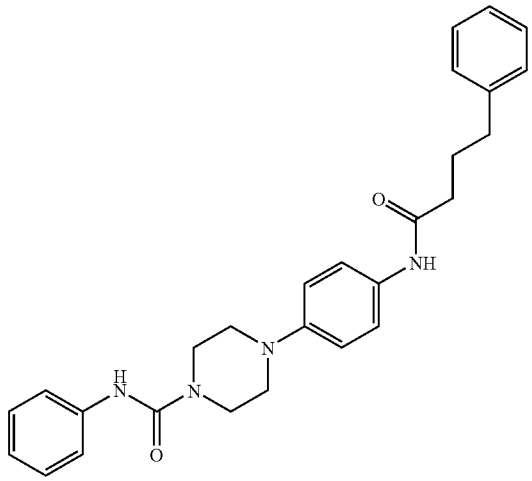
Co. No. 339; Ex. [B1]
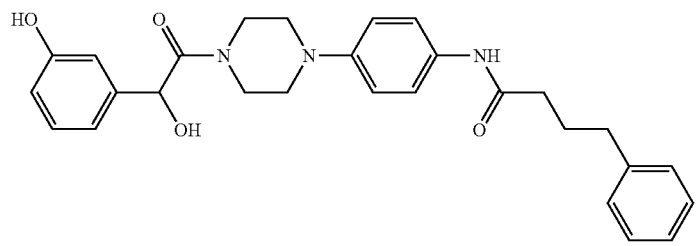
Co. No. 340; Ex. [B10]
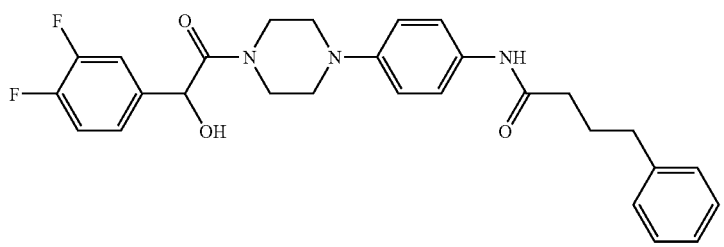
Co. No. 341; Ex. [B10]
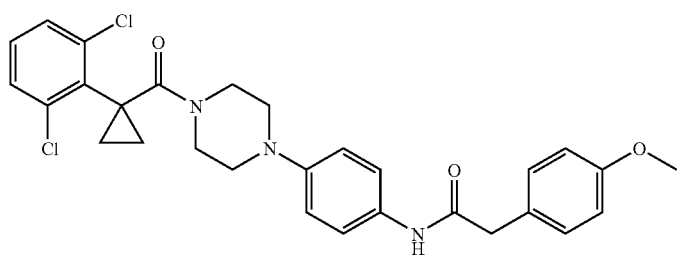
Co. No. 342; Ex. [B28]
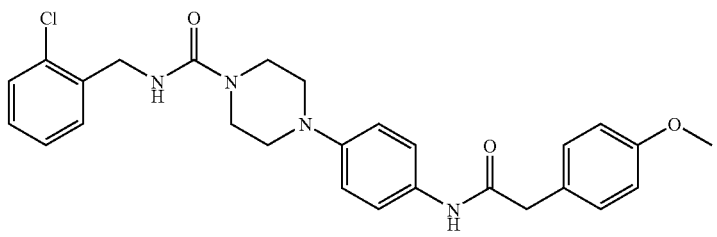
Co. No. 343; Ex. [B1]

TABLE 1-continued
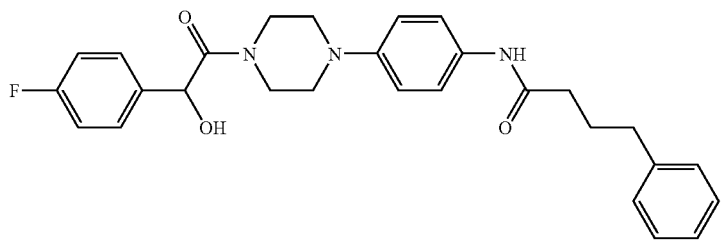
Co. No. 344; Ex. [B10]
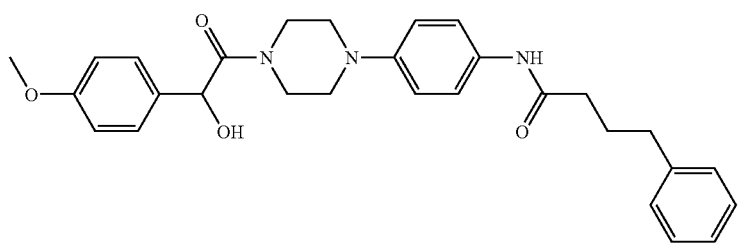
Co. No. 345; Ex. [B10]
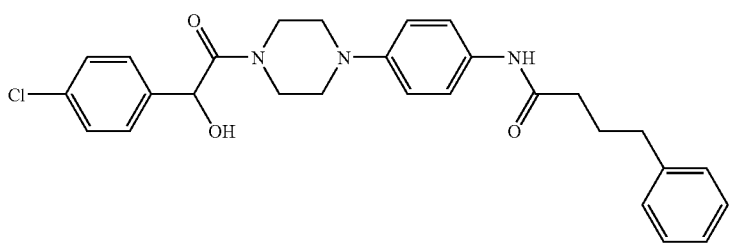
Co. No. 346; Ex. [B10]
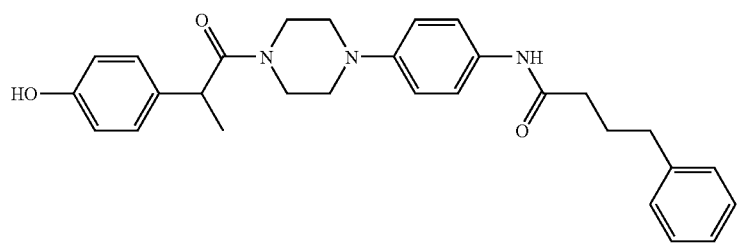
Co. No. 347; Ex. [B10]
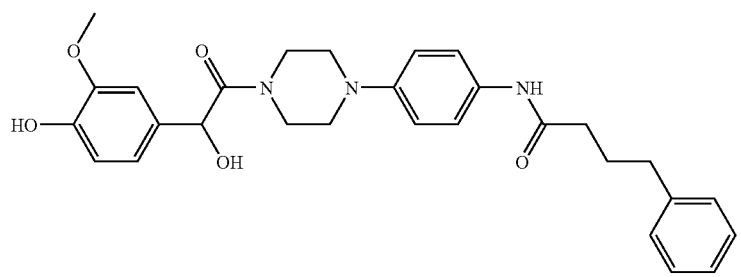
Co. No. 348; Ex. [B10]

TABLE 1-continued
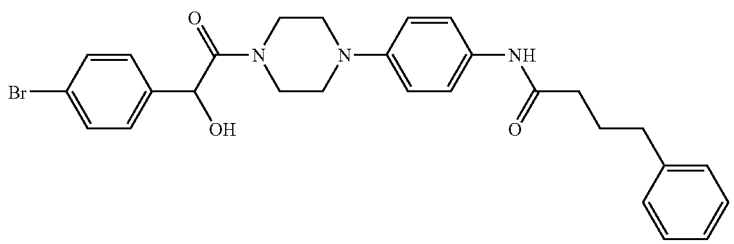
Co. No. 349; Ex. [B10]
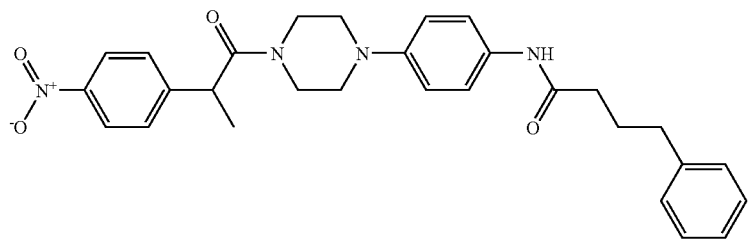
Co. No. 350; Ex. [B10]
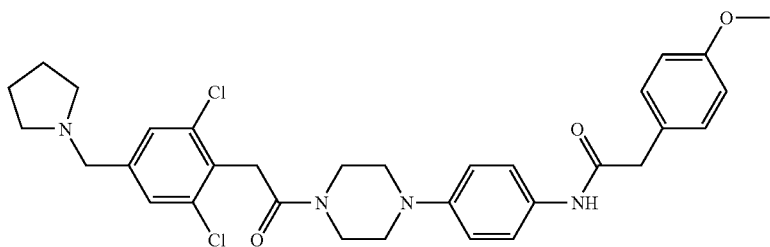
Co. No. 351; Ex. [B30]
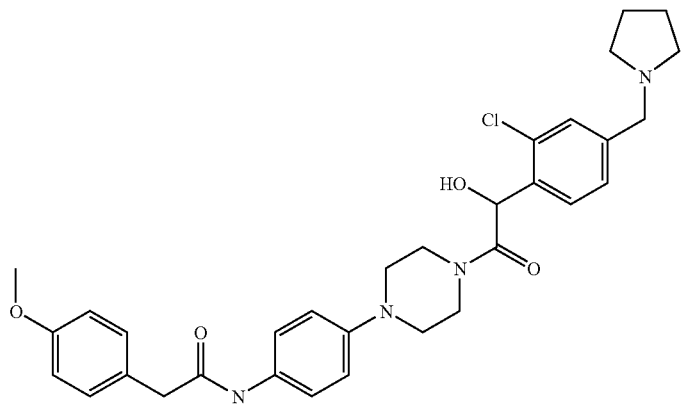
Co. No. 352; Ex. [B10.b]
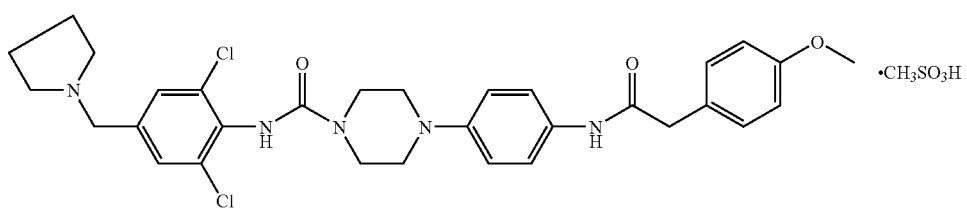
40569321-ABV; Co. No. 223a; Ex. [B6.e]
R*, S* = relative stereochemistry C. Analytical Part For (LC)MS-characterization of the compounds of the present invention, the following methods were used.

General Procedure A

The HPLC measurement was performed using an Alliance HT 2790 (Waters) system comprising a quaternary pump with degasser, an autosampler, a column oven (set at 40° C.), a diode-array detector (DAD) and a column as specified in the respective methods below. Flow from the column was split to a MS detector. The MS detector was configured with an electrospray ionization source. Mass spectra were acquired by scanning from 100 to 1000 in 1 second using a dwell time of 0.1 second. The capillary needle voltage was 3 kV and the source temperature was maintained at 140° C. Nitrogen was used as the nebulizer gas. Data acquisition was performed with a Waters-Micromass MassLynx-Openlynx data system.

General Procedure B

The LC measurement was performed using an Acquity UPLC (Waters) (Ultra Performance Liquid Chromatography) system comprising a binary pump, a sample organizer, a column heater (set at 55° C.), a diode-array detector (DAD) and a column as specified in the respective methods below. Flow from the column was split to a MS detector. The MS detector was configured with an electrospray ionization source. Mass spectra were acquired by scanning from 100 to 1000 in 0.18 seconds using a dwell time of 0.02 seconds. The capillary needle voltage was 3.5 kV and the source temperature was maintained at 140° C. (DSC). Nitrogen was used as the nebulizer gas. Data acquisition was performed with a Waters-Micromass MassLynx-Openlynx data system.

General Procedure C

The LCMS analyses for a number of compounds were done at the Surveyor MSQ™ (Thermo Finnigan, USA) comprising a photo diode array detector (PDA; 190-800 nm) and a column as specified in the respective methods below. Flow from the column was split to a MS spectrometer. The MS detector was configured with APCI (atmospheric pressure chemical ionization, + or – ions). Mass spectra were acquired by scanning from 45 to 1000 (of atomic mass unit) in 0.3 seconds. Typical APCI conditions use a corona discharge current of 10 µA and a cone voltage of 30 V. The APCI probe temperature was 640° C. Nitrogen was used as the nebulizer gas. Data acquisition was performed with an Xcalibur™ data system.

Method 1

In addition to general procedure B: Reversed phase UPLC (Ultra Performance Liquid Chromatography) was carried out on a bridged ethylsiloxane/silica (BEH) C18 column (1.7 µm, 2.1×50 mm) with a flow rate of 0.8 ml/min. Two mobile phases (mobile phase A: 0.1% formic acid in $H_2O$/methanol 95/5; mobile phase B: methanol) were used to run a gradient condition from 95% A and 5% B to 5% A and 95% B in 1.3 minutes and hold for 0.2 minutes. An injection volume of 0.5 µl was used. Cone voltage was 10 V for positive ionization mode and 20 V for negative ionization mode.

Method 2

In addition to general procedure A: Reversed phase HPLC was carried out on an Xterra MS C18 column (3.5 µm, 4.6×100 mm) with a flow rate of 1.6 ml/min. Three mobile phases (mobile phase A: 95% 25 mM ammoniumacetate+5% acetonitrile; mobile phase B: acetonitrile; mobile phase C: methanol) were employed to run a gradient condition from 100% A to 1% A, 49% B and 50% C in 6.5 minutes, to 1% A and 99% B in 1 minute and hold these conditions for 1 minute and reequilibrate with 100% A for 1.5 minutes. An injection volume of 10 µl was used. Cone voltage was 10 V for positive ionization mode and 20 V for negative ionization mode.

Method 3

In addition to general procedure A: Reversed phase HPLC was carried out on a Chromolith (4.6×25 mm) with a flow rate of 3 ml/min. Three mobile phases (mobile phase A: 95% 25 mM ammoniumacetate+5% acetonitrile; mobile phase B: acetonitrile; mobile phase C: methanol) were employed to run a gradient condition from 96% A, 2% B and 2% C, to 49% B and 49% C in 0.9 minutes, to 100% B 0.3 minutes and hold for 0.2 minutes. An injection volume of 2 µl was used. Cone voltage was 10 V for positive ionization mode and 20 V for negative ionization mode.

Method 4 (Only MS)

For a number of compounds only the mass spectra were recorded (no R(t)). The MS detector was configured with an electrospray ionization source. Mass spectra were acquired by scanning from 100 to 1000 in 1 second using a dwell time of 0.1 second. The capillary needle voltage was 3 kV and the source temperature was maintained at 140° C. Nitrogen was used as the nebulizer gas. Data acquisition was performed with a Waters-Micromass MassLynx-Openlynx data system. Cone voltage was 10 V for positive ionization mode and 20 V for negative ionization mode.

Method 5

In addition to general procedure C: Reversed phase HPLC was carried out on a Waters XTerra MS C18 column (3.5 µm, 2.1×30 mm) with a flow rate of 1.0 ml/min. Two mobile phases (mobile phase A: 0.1% aqueous solution of formic acid; mobile phase B: acetonitrile) were used. First, 100% A was hold for 0.1 minutes. Then a gradient was applied to 5% A and 95% B in 3 minutes and hold for 0.8 minutes. The injection volume was 1 µl. The column was at room temperature.

Method 6

In addition to general procedure A: Column heater was set at 60° C. Reversed phase HPLC was carried out on an Xterra MS C18 column (3.5 µm, 4.6×100 mm) with a flow rate of 1.6 ml/min. Three mobile phases (mobile phase A: 95% 25 mM ammoniumacetate+5% acetonitrile; mobile phase B: acetonitrile; mobile phase C: methanol) were employed to run a gradient condition from 100% A to 50% B and 50% C in 6.5 minutes, to 100% B in 0.5 minute and hold these conditions for 1 minute and reequilibrate with 100% A for 1.5 minutes. An injection volume of 10 µl was used. Cone voltage was 10 V for positive ionization mode and 20 V for negative ionization mode.

Method 7

In addition to the general procedure: Column heater was set at 45° C. Reversed phase HPLC was carried out on an Atlantis C18 column (3.5 µm, 4.6×100 mm) with a flow rate of 1.6 ml/min. Two mobile phases (mobile phase A: 70% methanol+ 30% $H_2O$; mobile phase B: 0.1% formic acid in $H_2O$/methanol 95/5) were employed to run a gradient condition from 100% B to 5% B+95% A in 9 minutes and hold these conditions for 3 minutes. An injection volume of 10 µl was used. Cone voltage was 10 V for positive ionization mode and 20 V for negative ionization mode.

Melting Points

Values are either peak values or melt ranges, and are obtained with experimental uncertainties that are commonly associated with this analytical method.

For a number of compounds, melting points were determined with a DSC823e (Mettler-Toledo). Melting points were measured with a temperature gradient of 30° C./minute. Maximum temperature was 300° C. (indicated by DSC in Table 2)

For a number of compounds, melting points were obtained with a Kofler hot bench, consisting of a heated plate with linear temperature gradient, a sliding pointer and a temperature scale in degrees Celsius. (indicated by Kofler in Table 2)

For a number of compounds, melting points were taken on a Sanyo Gallenkamp melting point apparatus. (indicated by Sanyo Gallenkamp in Table 2)

TABLE 2

Analytical data — $R_t$ means retention time (in minutes), $[M + H]^+$ means the protonated mass of the compound, method refers to the method used for (LC)MS.

| Comp. Nr. | $R_t$ | $[M + H]^+$ | Method | Melting Points |
|---|---|---|---|---|
| 130 | 1.22 | 448 | 1 | |
| 131 | 1.26 | 496 | 1 | |
| 129 | 1.11 | 444 | 1 | |
| 128 | 0.87 | 503 | 1 | |
| 132 | 1.20 | 488 | 1 | |
| 133 | 1.20 | 486 | 1 | |
| 127 | 1.06 | 491 | 1 | |
| 43 | 1.02 | 477 | 1 | 209.0° C. (DSC) |
| 134 | 1.21 | 512 | 1 | |
| 135 | 1.31 | 510 | 1 | |
| 126 | 1.13 | 492 | 1 | |
| 125 | 0.83 | 505 | 1 | |
| 124 | 1.33 | 488 | 1 | |
| 123 | — | 472 | 4 | |
| 38 | 1.31 | 493 | 1 | |
| 17 | 1.35 | 478 | 1 | |
| 140 | 1.16 | 449 | 1 | |
| 141 | 1.17 | 498 | 1 | 246.3° C. (DSC) |
| 139 | — | 445 | 4 | |
| 138 | 0.79 | 504 | 1 | 241.1° C. (DSC) |
| 142 | 1.13 | 489 | 1 | |
| 143 | 1.14 | 487 | 1 | |
| 137 | 0.97 | 492 | 1 | |
| 44 | 0.92 | 478 | 1 | |
| 144 | 1.15 | 513 | 1 | |
| 58 | 1.26 | 511 | 1 | 114-124° C. (Kofler) |
| 145 | 1.05 | 493 | 1 | |
| 136 | 0.74 | 506 | 1 | |
| 1 | 1.06 | 489 | 3 | 285.3° C. (DSC) |
| 10 | 1.40 | 491 | 1 | |
| 20 | 0.86 | 461 | 1 | |
| 122 | 0.88 | 463 | 1 | |
| 121 | 0.83 | 474 | 1 | |
| 120 | 0.85 | 479 | 1 | |
| 100 | 1.23 | 497 | 1 | |
| 119 | 0.90 | 501 | 1 | |
| 97 | 1.27 | 511 | 1 | |
| 118 | 0.98 | 529 | 1 | |
| 117 | 0.96 | 511 | 1 | |
| 116 | 0.89 | 475 | 1 | |
| 115 | 1.10 | 519 | 1 | |
| 113 | 0.88 | 477 | 1 | |
| 112 | 0.88 | 489 | 1 | |
| 111 | 0.86 | 491 | 1 | |
| 110 | 0.87 | 493 | 1 | |
| 109 | 0.82 | 449 | 1 | |
| 98 | 0.95 | 519 | 1 | |
| 108 | 0.96 | 517 | 1 | |
| 107 | 1.00 | 525 | 1 | |
| 106 | 1.16 | 594 | 1 | |
| 105 | 1.16 | 594 | 1 | |
| 104 | 1.16 | 594 | 1 | |
| 103 | 1.19 | 634 | 1 | |
| 102 | 0.95 | 291 | 1 | |
| 101 | 1.12 | 652 | 1 | |
| 99 | 1.10 | 533 | 1 | |
| 214 | — | 535 | 4 | |
| 204 | — | 551 | 4 | |
| 206 | — | 535 | 4 | |
| 220 | — | 559 | 4 | |
| 209 | — | 565 | 4 | |
| 219 | — | 549 | 4 | |
| 216 | — | 575 | 4 | |
| 39 | — | 575 | 4 | |
| 213 | — | 577 | 4 | |
| 33 | — | 577 | 4 | |
| 218 | — | 549 | 4 | |
| 217 | — | 549 | 4 | |
| 208 | — | 563 | 4 | |
| 40 | — | 535 | 4 | |
| 205 | — | 549 | 4 | |
| 215 | — | 577 | 4 | |
| 211 | — | 560 | 4 | |
| 210 | — | 581 | 4 | |
| 207 | — | 561 | 4 | |
| 201 | 0.76 | 476 | 1 | 214-216° C. (Sanyo Gallenkamp) |
| 150 | 3.98 | 435 | 2 | |
| 148 | 4.29 | 435 | 2 | |
| 156 | 4.10 | 449 | 2 | |
| 159 | 5.31 | 475 | 2 | |
| 149 | 4.17 | 475 | 2 | |
| 147 | 5.33 | 477 | 2 | |
| 157 | 5.35 | 477 | 2 | |
| 23 | 4.16 | 449 | 2 | |
| 160 | 4.03 | 449 | 2 | |
| 153 | 5.00 | 463 | 2 | |
| 158 | 4.21 | 435 | 2 | |
| 151 | 4.61 | 449 | 2 | |
| 50 | 1.05 | 479 | 1 | 219.9° C. (DSC) |
| 202 | 1.01 | 419 | 1 | 245-246° C. (Sanyo Gallenkamp) |
| 37 | 0.87 | 520 | 1 | 237.1° C. (DSC) |
| 200 | 0.73 | 450 | 1 | 245-246° C. (Sanyo Gallenkamp) |
| 21 | 1.17 | 498 | 1 | 244-246° C. (Sanyo Gallenkamp) |
| 2 | 1.03 | 518 | 1 | |
| 196 | 0.73 | 464 | 1 | 194-196° C. (Sanyo Gallenkamp) |
| 199 | 0.78 | 492 | 1 | 221-222° C. (Sanyo Gallenkamp) |
| 36 | 1.18 | 516 | 1 | 254.2° C. (DSC) |
| 22 | 1.29 | 526 | 1 | 248-249° C. (Sanyo Gallenkamp) |
| 182 | 0.77 | 479 | 1 | 152-154° C. (Sanyo Gallenkamp) |
| 198 | 0.82 | 498 | 1 | 260-261° C. (Sanyo Gallenkamp) |
| 197 | 0.82 | 512 | 1 | 251-252° C. (Sanyo Gallenkamp) |
| 180 | 0.91 | 504 | 1 | 185-187° C. (Sanyo Gallenkamp) |
| 9 | 0.84 | 498 | 1 | 187-188° C. (Sanyo Gallenkamp) |
| 26 | 0.85 | 569 | 1 | 232-234° C. (Sanyo Gallenkamp) |
| 181 | 1.02 | 540 | 1 | 163-165° C. (Sanyo Gallenkamp) |
| 179 | 0.79 | 490 | 1 | 220-222° C. (Sanyo Gallenkamp) |
| 195 | 0.84 | 512 | 1 | |
| 172 | 0.76 | 583 | 1 | 250-252° C. (Sanyo Gallenkamp) |
| 176 | 0.79 | 504 | 1 | 232-233° C. (Sanyo Gallenkamp) |
| 35 | 0.92 | 530 | 1 | 169.9° C. (DSC) |
| 178 | 0.98 | 546 | 1 | 183-184° C. (Sanyo Gallenkamp) |
| 177 | 0.92 | 542 | 1 | 128-129° C. (Sanyo Gallenkamp) |
| 194 | 0.84 | 512 | 1 | 233-234° C. (Sanyo Gallenkamp) |
| 326 | 1.27 | 541 | 1 | |
| 203 | 1.25 | 711 | 1 | |
| 193 | 0.80 | 498 | 1 | 263-264° C. (Sanyo Gallenkamp) |
| 18 | 1.29 | 522 | 1 | 178.2° C. (DSC) |
| 34 | 1.30 | 477 | 1 | 142.1° C. (DSC) |
| 175 | 1.26 | 729 | 1 | 215-216° C. (Sanyo Gallenkamp) |
| 174 | 0.92 | 544 | 1 | 192-193° C. (Sanyo Gallenkamp) |
| 32 | 0.91 | 556 | 1 | 188-189° C. (Sanyo Gallenkamp) |
| 173 | 1.24 | 741 | 1 | 197-199° C. (Sanyo Gallenkamp) |
| 41 | 1.11 | 595 | 1 | 186.1° C. (DSC) |
| 4 | 1.26 | 532 | 1 | 247-249° C. (Sanyo Gallenkamp) |
| 53 | 1.26 | 553 | 1 | |
| 45 | 1.05 | 481 | 1 | 178.7° C. (DSC) |
| 189 | 1.29 | 527 | 1 | 238.7° C. (DSC) |
| 29 | 1.23 | 555 | 1 | 187.3° C. (DSC) |
| 171 | 1.12 | 554 | 1 | 253-255° C. (Sanyo Gallenkamp) |
| 8 | 1.29 | 477 | 1 | 245.1° C. (DSC) |
| 42 | 1.31 | 525 | 1 | 175.2° C. (DSC) |
| 52 | 1.35 | 510 | 1 | |
| 48 | 1.23 | 527 | 1 | 253.4° C. (DSC) |
| 3 | 1.20 | 513 | 1 | 268.2° C. (DSC) |
| 5 | 1.24 | 576 | 1 | 242.6° C. (DSC) |
| 56 | 1.04 | 622 | 1 | 218.0° C. (DSC) |
| 54 | 0.93 | 639 | 1 | 125.4° C. (DSC) |
| 57 | 1.02 | 612 | 1 | |

TABLE 2-continued

Analytical data — $R_t$ means retention time (in minutes), [M + H]⁺ means the protonated mass of the compound, method refers to the method used for (LC)MS.

| Comp. Nr. | $R_t$ | [M + H]⁺ | Method | Melting Points |
|---|---|---|---|---|
| 192 | 1.20 | 675 | 1 | 195-197° C. (Sanyo Gallenkamp) |
| 47 | 1.31 | 569 | 1 | |
| 51 | 5.58 | 570 | 6 | 177.8° C. (DSC) |
| 24 | 1.02 | 568 | 1 | 180.7° C. (DSC) |
| 187 | 1.29 | 745 | 1 | |
| 6 | 1.28 | 745 | 1 | |
| 190 | 1.28 | 541 | 1 | |
| 15 | 1.18 | 543 | 1 | |
| 188 | 1.25 | 537 | 1 | 208-210° C. (Sanyo Gallenkamp) |
| 191 | 1.14 | 539 | 1 | |
| 96 | 1.26 | 457 | 1 | 164.7° C. (DSC) |
| 95 | 1.31 | 521 | 1 | 147.4° C. (DSC) |
| 94 | 1.25 | 461 | 1 | 177.3° C. (DSC) |
| 93 | 1.30 | 471 | 1 | 189.0° C. (DSC) |
| 59 | 1.35 | 545 | 1 | 234.9° C. (DSC) |
| 92 | 1.39 | 501 | 1 | 165.4° C. (DSC) |
| 91 | 1.44 | 515 | 1 | 194.7° C. (DSC) |
| 90 | 1.33 | 485 | 1 | 214.2° C. (DSC) |
| 60 | 1.27 | 491 | 1 | 240.7° C. (DSC) |
| 61 | 1.35 | 549 | 1 | 241.7° C. (DSC) |
| 89 | 1.36 | 499 | 1 | 227.2° C. (DSC) |
| 62 | 1.27 | 545 | 1 | 254.0° C. (DSC) |
| 88 | 1.38 | 579 | 1 | 225.1° C. (DSC) |
| 63 | 1.34 | 617 | 1 | 218.6° C. (DSC) |
| 87 | 1.32 | 533 | 1 | 181.2° C. (DSC) |
| 49 | 1.31 | 557 | 1 | 207.9° C. (DSC) |
| 86 | 1.38 | 499 | 1 | 207.8° C. (DSC) |
| 64 | 1.32 | 505 | 1 | 210.6° C. (DSC) |
| 11 | 1.33 | 549 | 1 | 238.7° C. (DSC) |
| 85 | 1.42 | 479 | 1 | 202.3° C. (DSC) |
| 84 | 1.33 | 527 | 1 | 162.2° C. (DSC) |
| 83 | 1.28 | 502 | 1 | 201.6° C. (DSC) |
| 66 | 1.31 | 471 | 1 | 181.7° C. (DSC) |
| 82 | 1.24 | 497 | 1 | 173.6° C. (DSC) |
| 67 | 1.21 | 479 | 1 | 187.0° C. (DSC) |
| 68 | 1.32 | 485 | 1 | 223.0° C. (DSC) |
| 81 | 1.38 | 545 | 1 | 170.3° C. (DSC) |
| 46 | 1.35 | 597 | 1 | 223.0° C. (DSC) |
| 80 | 1.32 | 488 | 1 | |
| 79 | 1.31 | 489 | 1 | 127.1° C. (DSC) |
| 78 | 1.32 | 569 | 1 | 153.3° C. (DSC) |
| 77 | 1.34 | 485 | 1 | 200.2° C. (DSC) |
| 76 | 1.33 | 487 | 1 | |
| 75 | 1.25 | 503 | 1 | |
| 74 | 1.32 | 518 | 1 | |
| 65 | 1.25 | 487 | 1 | |
| 73 | 1.26 | 479 | 1 | 141.2° C. (DSC) |
| 72 | 1.25 | 515 | 1 | |
| 71 | 1.27 | 487 | 1 | 183.1° C. (DSC) |
| 70 | 1.30 | 511 | 1 | |
| 28 | 1.20 | 541 | 1 | 196.1° C. (DSC) |
| 13 | 1.37 | 595 | 1 | |
| 170 | 0.99 | 492 | 1 | |
| 169 | 1.06 | 506 | 1 | |
| 168 | 1.12 | 520 | 1 | |
| 167 | 1.18 | 534 | 1 | |
| 30 | 1.21 | 527 | 1 | 175.4° C. (DSC) |
| 12 | 1.28 | 519 | 1 | 209.8° C. (DSC) |
| 55 | 1.02 | 554 | 1 | |
| 316 | 1.05 | 506 | 1 | 232-234° C. (Sanyo Gallenkamp) |
| 166 | 1.05 | 506 | 1 | 232-234° C. (Sanyo Gallenkamp) |
| 14 | 1.02 | 521 | 1 | 217-219° C. (Sanyo Gallenkamp) |
| 221 | 2.20 | 596 | 5 | 174-175° C. (Sanyo Gallenkamp) |
| 186 | 1.40 | 592 | 1 | 181-182° C. (Sanyo Gallenkamp) |
| 164 | 0.92 | 478 | 1 | 236-238° C. (Sanyo Gallenkamp) |
| 165 | 1.12 | 535 | 1 | 214-215° C. (Sanyo Gallenkamp) |
| 163 | 0.96 | 552 | 1 | |
| 31 | 1.31 | 556 | 1 | 175-176° C. (Sanyo Gallenkamp) |
| 184 | 1.28 | 552 | 1 | 162-163° C. (Sanyo Gallenkamp) |
| 185 | 1.24 | 542 | 1 | 202-203° C. (Sanyo Gallenkamp) |
| 7 | 1.35 | 586 | 1 | 232-233° C. (Sanyo Gallenkamp) |
| 183 | 1.30 | 580 | 1 | 226-227° C. (Sanyo Gallenkamp) |
| 16 | 1.09 | 529 | 1 | 183-184° C. (Sanyo Gallenkamp) |
| 19 | 1.28 | 492 | 1 | 142.3° C. (DSC) |
| 288 | 1.00 | 582 | 1 | 191.86° C. (DSC) |
| 270 | 1.26 | 555 | 1 | |
| 271 | 1.26 | 555 | 1 | |
| 315 | 1.33 | 526 | 1 | |
| 334 | 1.33 | 526 | 1 | |
| 329 | 1.33 | 526 | 1 | |
| 335 | 1.30 | 569 | 1 | 179.55° C. (DSC) |
| 289 | 1.29 | 546 | 1 | 244-245° C. (Sanyo Gallenkamp) |
| 298 | 1.23 | 540 | 1 | 241-242° C. (Sanyo Gallenkamp) |
| 339 | 1.28 | 443 | 1 | 219.91° C. (DSC) |
| 274 | 1.02 | 612 | 1 | |
| 338 | 1.31 | 442 | 1 | 146.12° C. (DSC) |
| 293 | 1.00 | 568 | 1 | |
| 287 | 1.00 | 568 | 1 | |
| 321 | 1.01 | 625 | 1 | |
| 328 | 1.01 | 639 | 1 | |
| 306 | 1.25 | 612 | 1 | |
| 314 | 1.20 | 639 | 1 | |
| 303 | 1.09 | 645 | 1 | |
| 310 | 1.02 | 667 | 1 | |
| 291 | 1.26 | 626 | 1 | |
| 296 | 1.20 | 653 | 1 | |
| 290 | 0.99 | 637 | 1 | |
| 294 | 1.24 | 624 | 1 | |
| 275 | 1.01 | 681 | 1 | |
| 284 | 1.24 | 582 | 1 | |
| 319 | 1.33 | 552 | 1 | 160-161° C. (Sanyo Gallenkamp) |
| 324 | 1.37 | 568 | 1 | 204-205° C. (Sanyo Gallenkamp) |
| 273 | 1.30 | 554 | 1 | 203-204° C. (Sanyo Gallenkamp) |
| 269 | 1.02 | 610 | 2 | |
| 301 | 1.32 | 554 | 1 | 152-153° C. (Sanyo Gallenkamp) |
| 276 | 1.28 | 540 | 1 | 198-199° C. (Sanyo Gallenkamp) |
| 281 | 1.22 | 610 | 1 | 149-150° C. (Sanyo Gallenkamp) |
| 280 | 1.16 | 556 | 1 | 227-228° C. (Sanyo Gallenkamp) |
| 348 | 1.15 | 504 | 1 | |
| 330 | 1.26 | 494 | 1 | |
| 345 | 1.26 | 488 | 1 | |
| 295 | 1.32 | 536 | 1 | |
| 349 | 1.33 | 536 | 1 | |
| 341 | 1.31 | 494 | 1 | |
| 347 | 1.24 | 472 | 1 | |
| 350 | 1.33 | 501 | 1 | |
| 340 | 1.18 | 474 | 1 | |
| 286 | 1.31 | 492 | 1 | |
| 323 | 1.31 | 492 | 1 | |
| 309 | 1.33 | 510 | 1 | |
| 331 | 1.36 | 554 | 1 | |
| 325 | 1.29 | 494 | 1 | |
| 327 | 1.29 | 494 | 1 | |
| 344 | 1.28 | 476 | 1 | |
| 346 | 1.34 | 492 | 1 | |
| 311 | 0.96 | 556 | 1 | 212-213° C. (Sanyo Gallenkamp) |
| 223 | 4.94 | 596 | 2 | 252.22° C. (DSC) |
| 277 | 1.21 | 541 | 1 | |
| 297 | 1.14 | 507 | 1 | |
| 342 | 1.39 | 538 | 1 | |
| 248 | | | | 252.90° C. (DSC) |
| 232 | 4.92 | 596 | 2 | 222.04° C. (DSC) |
| 313 | 1.10 | 493 | 1 | |
| 302 | 1.19 | 555 | 1 | |
| 279 | 1.22 | 521 | 1 | |
| 282 | 1.19 | 507 | 1 | |
| 318 | 0.86 | 604 | 1 | 211-212° C. (Sanyo Gallenkamp) |
| 292 | 1.00 | 666 | 1 | 180-181° C. (Sanyo Gallenkamp) |
| 278 | 1.07 | 700 | 1 | 172-173° C. (Sanyo Gallenkamp) |
| 285 | 1.00 | 696 | 1 | 178-179° C. (Sanyo Gallenkamp) |
| 266 | 5.46 | 580 | 2 | 161.47° C. (DSC) |
| 263 | 5.43 | 610 | 2 | 132.84° C. (DSC) |
| 308 | 1.36 | 514 | 1 | |
| 305 | 0.88 | 639 | 1 | 253.39° C. (DSC) |
| 224 | 5.71 | 635 | 6 | 229.72° C. (DSC) |
| 337 | 0.90 | 493 | 1 | |

TABLE 2-continued

Analytical data — $R_t$ means retention time (in minutes), $[M + H]^+$ means the protonated mass of the compound, method refers to the method used for (LC)MS.

| Comp. Nr. | $R_t$ | $[M + H]^+$ | Method | Melting Points |
|---|---|---|---|---|
| 272 | 0.91 | 653 | 1 | 234.32° C. (DSC) |
| 283 | 0.92 | 639 | 1 | 218.59° C. (DSC) |
| 333 | 1.28 | 526 | 1 | 200.57° C. (DSC) |
| 322 | 0.84 | 590 | 1 | 208.65° C. (DSC) |
| 268 | 0.97 | 689 | 1 | 224.69° C. (DSC) |
| 307 | 0.93 | 624 | 1 | 206.22° C. (DSC) |
| 300 | 0.7 | 628 | 1 | |
| 299 | 0.89 | 612 | 1 | 168.24° C. (DSC) |
| 304 | 0.92 | 610 | 1 | 243.74° C. (DSC) |
| 317 | 0.87 | 598* | 1 | 248.28° C. (DSC) |
| 226 | 6.23 | 694 | 2 | 180.97° C. (DSC) |
| 312 | 6.67 | 571 | 7 | 182.46° C. (DSC) |
| 332 | 1.32 | 526 | 1 | |
| 236 | 4.97 | 643 | 6 | 217.37° C. (DSC) |
| 245 | 1.12 | 514 | 1 | |
| 237 | | | | 242.60° C. (DSC) |
| 240 | 6.69 | 626 | 2 | 208.87° C. (DSC) |
| 243 | 6.52 | 624 | 2 | |
| 246 | 0.99 | 628 | 1 | 235-237° C. (Sanyo Gallenkamp) |
| 255 | 0.95 | 614 | 1 | 176.5-178° C. (Sanyo Gallenkamp) |
| 264 | 5.39 | 574 | 7 | 223.77° C. (DSC) |
| 228 | 6.11 | 653 | 7 | 220.01° C. (DSC) |
| 259 | 7.26 | 430 | 7 | 247.07° C. (DSC) |
| 256 | 8.11 | 492 | 7 | 180.88° C. (DSC) |
| 262 | 7.64 | 464 | 7 | 175.07° C. (DSC) |
| 260 | | | | 236.30° C. (DSC) |
| 261 | | | | 226.73° C. (DSC) |
| 257 | 6.56 | 483 | 7 | 242.27° C. (DSC) |
| 251 | 6.36 | 483 | 7 | 239.51° C. (DSC) |
| 234 | 8.61 | 551 | 7 | 251.10° C. (DSC) |
| 239 | 8.35 | 517 | 7 | 233.85° C. (DSC) |
| 238 | 8.42 | 517 | 7 | 248.47° C. (DSC) |
| 244 | | | | 266.21° C. (DSC) |
| 241 | | | | 246.03° C. (DSC) |
| 231 | | | | 237.34° C. (DSC) |
| 225 | 8.07 | 542 | 7 | 212.29° C. (DSC) |
| 230 | 8.19 | 542 | 7 | 180.99° C. (DSC) |
| 233 | 8.34 | 496 | 7 | 244.09° C. (DSC) |
| 229 | 8.59 | 532 | 7 | 242.15° C. (DSC) |
| 258 | 7.66 | 472 | 7 | 238.35° C. (DSC) |
| 253 | | | | 246.15° C. (DSC) |
| 242 | 8.20 | 566 | 7 | 172.73° C. (DSC) |
| 254 | 7.55 | 527 | 7 | 216.89° C. (DSC) |
| 235 | 6.01 | 526 | 2 | |
| 343 | 5.10 | 493 | 6 | 238.61° C. (DSC) |
| 227 | 5.55 | 649 | 2 | |
| 250 | 8.20 | 514 | 7 | |
| 252 | 8.23 | 518 | 7 | |
| 247 | 1.28 | 500 | 1 | |
| 249 | 8.02 | 500 | 7 | |
| 352 | 0.85 | 577 | 1 | |
| 336 | 1.34 | 456 | 1 | |
| 351 | 0.93 | 595 | 1 | |

*for compound 317 $[M]^+$ was measured instead of $[M + H]^+$

TABLE 3

Analytical data — $R_t$ means Retention time (in minutes), $[M - H]^-$ means the deprotonated mass of the compound (negative mode), Method refers to the method used for (LC)MS.

| Comp. Nr. | $R_t$ | $[M - H]^-$ | Method | Melting Points |
|---|---|---|---|---|
| 155 | 4.12 | 419 | 2 | |
| 146 | 4.96 | 459 | 2 | |
| 212 | — | 519 | 4 | |
| 27 | 4.67 | 553 | 2 | |
| 162 | 1.50 | 624 | 1 | |
| 114 | 0.92 | 473 | 1 | |
| 154 | 5.06 | 479 | 2 | |
| 161 | 4.66 | 463 | 2 | |
| 152 | 4.86 | 457 | 2 | |

Optical Rotation

For optical rotation measurement of the compounds of the present invention, the following method were used.

The optical rotation was measured using a Perkin Elmer 341 polarimeter. $[\alpha]_D^{20}$ indicates the optical rotation measured with light at the wavelength of the D-line of sodium (589 nm) at a temperature of 20° C. The cell pathlength is 1 dm. Behind the actual value the concentration and solvent of the solution which was used to measure the optical rotation are mentioned. The results are gathered in Table 4.

TABLE 4

Optical rotation

| Comp. No. | $[\alpha]_D^{20}$ | concentration | solvent |
|---|---|---|---|
| 334 | −104.4° | 0.5 w/v % | MeOH |
| 329 | +101.2° | 0.5 w/v % | MeOH |
| 337 | −66.6° | 0.509 w/v % | MeOH |

D. Pharmacological Example

A) Measurement of Inhibition of DGAT1 Activity by the Present Compounds

The inhibiting activity of the present compounds on DGAT1 activity was screened in a single well procedure assay using DGAT1 comprising membrane preparations and DGAT1 substrate comprising micelles and determining formed radio-active triacylglycerol coming in close proximity of a flashplate surface by radio luminescence.

Said assay is described in full detail in WO2006/067071, the content of which is incorporated herein by reference.

By DGAT1 activity is meant the transfer of coenzyme A activated fatty acids to the 3-position of 1,2-diacylglycerols, thus forming a triglyceride molecule, by enzyme DGAT1.

Step 1 of the Assay: Expression of DGAT1 human DGAT1 (NM012079.2) was cloned into the pFastBac vector, containing translation start, a FLAG-tag at the N-terminus as described in literature and a viral Kozak sequence (AAX) preceding the ATG to improve expression in insect cells. Expression was done as described in literature (Cases, S., Smith, S. J., Zheng, Y., Myers H. M., Lear, S. R., Sande, E., Novak, S., Collins, C., Welch, C. B., Lusis, A. J., Erickson, S. K. and Farese, R. V. (1998) *Proc. Natl. Acad. Sci. USA* 95, 13018-13023.) using SF9 cells.

Step 2 of the Assay: Preparation of DGAT1 Membranes 72 h transfected SF9 cells were collected by centrifugation (13000 rpm-15 min-4° C.) and lysed in 2×500 ml lysisbuffer (0.1M Sucrose, 50 mM KCl, 40 mM $KH_2PO_4$, 30 mM EDTA pH 7.2. Cells were homogenized by cell disruptor. After centrifugation 1380 rpm-15 min-4° C. (SN discarded), pellet was resuspended in 500 ml lysisbuffer and total cell membranes collected by ultracentrifugation at 34000 rpm(100 000 g) for 60 min (4° C.). The collected membranes were resuspended in lysis buffer, divided in aliquots and stored with 10% glycerol at −80° C. until use.

Step 3 of the Assay: Preparation of DGAT Substrate Comprising Micelles

Materials a) 1,2-dioleoyl-sn-glycerol, 10 mg/ml (1,2-diacylglycerol (DAG))

Dissolve in acetonitrile; evaporate the acetonitrile solution under nitrogen and reconstitute in chloroform at a final concentration of 10 mg/ml.

b) L-α-phosphatidylcholine, 1 mg/ml (phosphatidylcholine (PC))

Dissolve in chloroform at a final concentration of 1 mg/ml and store at 4° C.

c) L-α-phosphatidyl-L-serine, 1 mg/ml (phophatidylserine (PS))

Dissolve in chloroform at a final concentration of 1 mg/ml and store at 4° C.

Method

Add 1 ml dioleoyl-sn-glycerol (10 mg/ml) to 10 ml of L-α-phosphatidylcholine (1 mg/ml) and 10 ml of L-α-phosphatidyl-L-serine (1 mg/ml) in a thick glass recipient. Evaporate under nitrogen and put on ice for 15 minutes. Reconstitute in 10 ml Tris/HCl (10 mM, pH 7.4) by sonication on ice. The sonification process consists of sonification cycles of 10 seconds in the sonification bath followed by 10 seconds cool down on ice and repeating this sonification cycle till a homogeneous solution is obtained (takes about 15 minutes). The thus obtained micelles are stored at −20° C. till later use and contain DAG at a final concentration of 1.61 mM.

Step 4 of the Assay: DGAT Flashplate™ Assay

Materials a) Assaybuffer 50 mM Tris-HCl (pH 7.4), 150 mM $MgCl_2$, 1 mM EDTA, 0.2% BSA.

b) N-ethylmaleimide, 5M

Dissolve 5 g into a final volume of 8 ml DMSO 100% and store at −20° C. in aliquots till later use.

c) Substrate mix (for 1 384 well plate=3840 μl)

612 μl micelles stock (51 μM final)

16.6 μl oleoylCoA 9.7 mM

23 μl [$^3$H]-oleoylCoA (49 Ci/mmol, 500 μCi/ml)

3188.4 μl Tris pH 7.4, 10 mM d) Enzyme mix (for 1 384 well plate=3520 μl) (5 μg/ml)

Add 11.73 μl of DGAT membrane stock (1500 μg/ml stock) to 3508 μl assay buffer.

e) Stop mix (for 1 384 well plate=7.68 ml) (250 mM)

Add 384 μl of N-ethylmaleimide (5M) to 3.456 ml DMSO 100%, and further dilute 3.84 ml of said solution with 3.84 ml DMSO 10%.

Method

DGAT activity in membrane preparations was assayed in 50 mM Tris-HCl (pH 7.4), 150 mM $MgCl_2$, 1 mM EDTA and 0.2% BSA, containing 50 μM DAG, 32 μg/ml PC/PS and 8.4 μM [$^3$H]-oleoylCoA (at a specific activity of 30 nCi/well) in a final volume of 50 μl in 384-well format using the red shifted Basic Image FlashPlate™ (Perkin Elmer Cat.No. SMP400).

In detail, 10 μl enzyme mix and 10 μl substrate mix were added to 30 μl of assay buffer, optionally in the presence of 1 μl DMSO (blank and controls) or 1 μl of the compound to be tested. This reaction mixture was incubated for 120 minutes at 37° C. and the enzymatic reaction stopped by adding 20 μl of the stop mix. The plates were sealed and the vesicles allowed to settle overnight at room temperature. Plates were centrifuged for 5 minutes at 1500 rpm and measured in Leadseeker.

Experiments with different concentrations of the test compound were performed and curves were calculated and drawn based on % $CTRL_{min}$ (% of normalized control). % $CTRL_{min}$ was calculated according to equation 1, $$\% CTRL_{min} = (sample - LC)/(HC - LC) \quad \text{Equation 1:}$$

where HC (high control) refers to the median of radioluminescence value measured in the wells with enzyme and substrate but without test compound, LC (low control) refers to median background radioluminescence value measured in the wells with substrate without enzyme and without test compound, and sample refers to the radioluminescence value measured in the wells with substrate, enzyme and test compound at a particular concentration.

The calculated % $CTRL_{min}$ values form a sigmoidal dose response descending curve and from this curve $pIC_{50}$ values were calculated (−log$IC_{50}$ where $IC_{50}$ represents the concentration at which the test compound gives 50% inhibition of DGAT1 activity). Table 5 shows the $pIC_{50}$ values for the compounds of formula (I).

In order to determine selectivity of the present compounds for DGAT1 compared to DGAT2, the inhibiting activity of the compounds on DGAT2 was also determined in the above assay, slightly modified to obtain optimal assay conditions for DGAT2. The tested compounds did not show inhibiting activity for DGAT2 (Human DGAT2 (NM032564) was cloned and expressed as described in J. Biolog. Chem. 276(42), pp 38870-38876 (2001)).

TABLE 5

| $pIC_{50}$ values ($IC_{50}$ values expressed in M) | |
|---|---|
| Comp. Nr. | $pIC_{50}$ |
| 1 | 8.35 |
| 2 | 5.54 |
| 3 | 8.12 |
| 4 | 8.57 |
| 5 | 6.82 |
| 6 | 7.33 |
| 7 | 8.07 |
| 8 | 8.05 |
| 9 | 6.26 |
| 10 | 5.96 |
| 11 | 8.21 |
| 12 | 6.74 |
| 13 | 7.53 |
| 14 | 6.50 |
| 15 | 8.34 |
| 16 | 8.33 |
| 17 | 5.65 |
| 18 | 6.92 |
| 19 | 7.51 |
| 20 | 6.24 |
| 21 | 7.14 |
| 22 | 7.83 |
| 23 | 5.59 |
| 24 | 7.80 |
| 26 | 6.16 |
| 27 | 7.47 |
| 28 | 8.71 |
| 29 | 8.40 |
| 30 | 8.35 |
| 31 | 8.35 |
| 32 | 6.46 |
| 33 | 7.45 |
| 34 | 6.84 |
| 35 | 6.62 |
| 36 | 7.06 |
| 37 | 6.89 |
| 38 | 6.31 |
| 39 | 7.77 |
| 40 | 8.11 |
| 41 | 7.11 |
| 42 | 5.16 |
| 43 | 5.30 |

TABLE 5-continued pIC$_{50}$ values (IC$_{50}$ values expressed in M)

| Comp. Nr. | pIC$_{50}$ |
|---|---|
| 44 | 5.29 |
| 45 | 5.63 |
| 46 | 6.48 |
| 47 | 6.87 |
| 48 | 6.83 |
| 49 | 6.92 |
| 50 | 7.02 |
| 51 | 7.74 |
| 52 | 7.45 |
| 53 | 7.33 |
| 54 | 7.63 |
| 55 | 7.99 |
| 56 | 7.79 |
| 57 | 7.97 |
| 58 | 8.27 |
| 59 | 7.89 |
| 60 | 7.90 |
| 61 | 7.42 |
| 62 | 7.79 |
| 63 | 7.51 |
| 64 | 8.15 |
| 65 | 7.64 |
| 66 | 7.57 |
| 67 | 7.22 |
| 68 | 7.91 |
| 70 | 6.86 |
| 71 | 5.97 |
| 72 | 6.31 |
| 73 | 6.34 |
| 74 | 6.76 |
| 75 | 6.22 |
| 76 | 5.25 |
| 77 | 5.78 |
| 78 | 6.90 |
| 79 | 5.84 |
| 80 | 6.23 |
| 81 | 5.48 |
| 82 | 7.12 |
| 83 | 5.75 |
| 84 | 5.83 |
| 85 | 5.71 |
| 86 | 5.77 |
| 87 | 5.48 |
| 88 | 6.32 |
| 89 | 5.66 |
| 90 | 6.23 |
| 91 | 5.26 |
| 92 | 5.13 |
| 93 | 6.62 |
| 94 | 6.53 |
| 95 | 6.90 |
| 96 | 7.12 |
| 97 | 7.31 |
| 98 | 7.30 |
| 99 | 7.59 |
| 100 | 7.06 |
| 101 | 6.86 |
| 102 | 6.28 |
| 103 | 6.40 |
| 104 | 6.90 |
| 105 | 6.77 |
| 106 | 6.64 |
| 107 | 6.74 |
| 108 | 6.60 |
| 109 | 5.63 |
| 110 | 5.85 |
| 111 | 5.92 |
| 112 | 6.10 |
| 113 | 6.13 |
| 114 | 6.25 |
| 115 | 6.69 |
| 116 | 6.24 |
| 117 | 6.67 |
| 118 | 6.46 |
| 119 | 6.41 |
| 120 | 6.08 |
| 121 | 5.42 |
| 122 | 6.25 |
| 123 | 6.06 |
| 124 | 6.78 |
| 125 | 6.19 |
| 126 | 7.17 |
| 127 | 5.40 |
| 128 | 5.68 |
| 129 | 6.61 |
| 130 | 7.42 |
| 131 | 7.59 |
| 132 | 7.35 |
| 133 | 7.42 |
| 134 | 7.81 |
| 135 | 7.68 |
| 136 | 6.41 |
| 137 | 5.47 |
| 138 | 5.88 |
| 139 | 6.92 |
| 140 | 7.72 |
| 141 | 7.82 |
| 142 | 7.86 |
| 143 | 7.74 |
| 144 | 8.24 |
| 145 | 7.26 |
| 146 | 4.98 |
| 147 | 5.06 |
| 148 | 5.15 |
| 149 | 5.14 |
| 150 | 5.16 |
| 151 | 5.16 |
| 152 | 5.17 |
| 153 | 5.42 |
| 154 | 5.26 |
| 155 | 5.29 |
| 156 | 5.36 |
| 157 | 5.25 |
| 158 | 5.46 |
| 159 | 5.49 |
| 160 | 5.50 |
| 161 | 5.54 |
| 162 | 6.95 |
| 163 | 5.85 |
| 164 | 6.44 |
| 165 | 7.19 |
| 166 | 7.20 |
| 167 | 7.65 |
| 168 | 7.51 |
| 169 | 7.27 |
| 170 | 6.61 |
| 171 | 7.55 |
| 172 | 6.22 |
| 173 | 7.46 |
| 174 | 6.46 |
| 175 | 7.62 |
| 176 | 5.21 |
| 177 | 6.61 |
| 178 | 7.12 |
| 179 | 5.97 |
| 180 | 6.39 |
| 181 | 7.12 |
| 182 | 5.49 |
| 183 | 7.90 |
| 184 | 7.72 |
| 185 | 8.43 |
| 186 | 7.86 |
| 187 | 6.72 |
| 188 | 7.13 |
| 189 | 7.92 |
| 190 | 8.21 |
| 191 | 7.35 |
| 192 | 7.68 |
| 193 | 6.47 |
| 194 | 7.47 |
| 195 | 6.91 |
| 196 | 5.17 |

TABLE 5-continued pIC$_{50}$ values (IC$_{50}$ values expressed in M)

| Comp. Nr. | pIC$_{50}$ |
|---|---|
| 197 | 6.91 |
| 198 | 6.64 |
| 199 | 5.20 |
| 200 | 5.44 |
| 201 | 5.71 |
| 202 | 6.97 |
| 203 | 7.64 |
| 204 | 5.72 |
| 205 | 6.40 |
| 206 | 6.57 |
| 207 | 6.68 |
| 208 | 6.72 |
| 209 | 6.78 |
| 210 | 6.81 |
| 211 | 6.90 |
| 212 | 6.94 |
| 213 | 6.97 |
| 214 | 7.01 |
| 215 | 7.23 |
| 216 | 7.46 |
| 217 | 7.58 |
| 218 | 7.64 |
| 219 | 7.71 |
| 220 | 7.72 |
| 223 | 7.70 |
| 223.a | n.d. |
| 224 | 8.08 |
| 225 | 8.02 |
| 226 | 8.01 |
| 227 | 7.93 |
| 228 | 7.72 |
| 229 | 7.51 |
| 230 | 7.37 |
| 231 | 7.37 |
| 232 | 7.33 |
| 233 | 7.30 |
| 234 | 7.30 |
| 235 | 7.27 |
| 236 | 7.22 |
| 237 | 7.20 |
| 238 | 7.20 |
| 239 | 7.13 |
| 240 | 7.09 |
| 241 | 6.93 |
| 242 | 6.89 |
| 243 | 6.89 |
| 244 | 6.88 |
| 245 | 6.84 |
| 246 | 6.82 |
| 247 | 6.81 |
| 248 | 6.80 |
| 249 | 6.79 |
| 250 | 6.76 |
| 251 | 6.72 |
| 252 | 6.63 |
| 253 | 6.57 |
| 254 | 6.50 |
| 255 | 6.47 |
| 256 | 6.38 |
| 257 | 6.18 |
| 258 | 6.12 |
| 259 | 5.87 |
| 260 | 5.81 |
| 261 | 5.65 |
| 262 | 5.49 |
| 263 | 5.43 |
| 264 | 5.40 |
| 265 | 5.33 |
| 266 | 5.21 |
| 267 | 6.97 |
| 268 | 8.77 |
| 269 | 8.69 |
| 270 | 8.67 |
| 271 | 8.49 |
| 272 | 8.46 |
| 273 | 8.43 |
| 274 | 8.40 |
| 275 | 8.38 |
| 276 | 8.37 |
| 277 | 8.34 |
| 278 | 8.31 |
| 279 | 8.17 |
| 280 | 8.17 |
| 281 | 8.14 |
| 282 | 8.11 |
| 283 | 8.10 |
| 284 | 8.09 |
| 285 | 8.04 |
| 286 | 8.02 |
| 287 | 8.00 |
| 288 | 8.00 |
| 289 | 7.99 |
| 290 | 7.98 |
| 291 | 7.98 |
| 292 | 7.97 |
| 293 | 7.91 |
| 294 | 7.91 |
| 295 | 7.86 |
| 296 | 7.83 |
| 297 | 7.82 |
| 298 | 7.76 |
| 299 | 7.72 |
| 300 | 7.70 |
| 301 | 7.68 |
| 302 | 7.68 |
| 303 | 7.67 |
| 304 | 7.66 |
| 305 | 7.61 |
| 306 | 7.58 |
| 307 | 7.53 |
| 308 | 7.50 |
| 309 | 7.45 |
| 310 | 7.43 |
| 311 | 7.36 |
| 312 | 7.35 |
| 313 | 7.34 |
| 314 | 7.29 |
| 315 | 7.23 |
| 316 | 7.20 |
| 317 | 7.20 |
| 318 | 7.19 |
| 319 | 7.18 |
| 320 | 7.13 |
| 321 | 7.04 |
| 322 | 7.04 |
| 323 | 7.01 |
| 324 | 6.97 |
| 325 | 6.94 |
| 326 | 6.90 |
| 327 | 6.89 |
| 328 | 6.88 |
| 329 | 6.86 |
| 330 | 6.70 |
| 331 | 6.62 |
| 332 | 6.51 |
| 333 | 6.45 |
| 334 | 6.33 |
| 335 | 6.32 |
| 336 | 6.16 |
| 337 | 5.61 |
| 338 | 5.59 |
| 339 | 5.51 |
| 340 | 5.45 |
| 341 | 5.43 |
| 342 | 5.40 |
| 343 | 5.39 |
| 344 | 5.39 |
| 345 | 5.36 |
| 346 | 5.33 |
| 347 | 5.30 |
| 348 | 5.28 |
| 349 | 5.22 |

| TABLE 5-continued | |
| --- | --- |
| pIC$_{50}$ values (IC$_{50}$ values expressed in M) | |
| Comp. Nr. | pIC$_{50}$ |
| 350 | 5.12 |
| 351 | 6.61 |
| 352 | 6.47 |

B) In Vivo Study for Effect of Test Compound on GLP-1 Plasma Levels

Elevation of GLP-1 plasma levels by a DGAT inhibitor was studied as follows:

Dogs were deprived from food for a period of 22 hours. At time 0, animals were given a liquid meal, containing 18% fat (w/w), by gavage with a stomach tube. The test compound was given orally together with the meal. Afterwards, a postprandial plasma profile was determined for GLP-1. Therefore, blood was collected at predetermined time intervals in ice-cooled Vacutainers EDTA-plasma tubes and GLP-1 levels were measured in the samples taken at 0 hour (just before the meal) and at 0.5, 1, 2, 4, 6, 8 and 24 hours after dosing. Six dogs (3 males and 3 females) were included per dosage group and the plasma GLP-1 profile was compared with their own GLP-1 profile previously determined in the same conditions but without administration of the test compound.

GLP-1 determinations in plasma were performed with a Glucagon-like peptide-1 (active) ELISA kit 96-well plate of LINCO Research.

Compounds 24, 30 and 223 were tested and were found to increase GLP-1 levels. (see FIG. 1 for compound 223).

In addition to the plasma GLP-1 profile, also the plasma triglyceride profile can be determined and compared with their own triglyceride profile previously determined in the same conditions but without administration of the test compound. After administration of compound 223, triglyceride levels decreased.

E. Composition Examples

"Active ingredient" (a.i.) as used throughout these examples relates to a compound of formula (I), including any stereochemically isomeric form thereof, a N-oxide thereof, a pharmaceutically acceptable salt thereof or a solvate thereof; in particular to any one of the exemplified compounds.

Typical examples of recipes for the formulation of the invention are as follows:

1. Tablets

| Active ingredient | 5 to 50 mg |
| --- | --- |
| Di-calcium phosphate | 20 mg |
| Lactose | 30 mg |
| Talcum | 10 mg |
| Magnesium stearate | 5 mg |
| Potato starch | ad 200 mg |

2. Suspension

An aqueous suspension is prepared for oral administration so that each milliliter contains 1 to 5 mg of active ingredient, 50 mg of sodium carboxymethyl cellulose, 1 mg of sodium benzoate, 500 mg of sorbitol and water ad 1 ml.

3. Injectable

A parenteral composition is prepared by stirring 1.5% (weight/volume) of active ingredient in 0.9% NaCl solution.

4. Ointment

| Active ingredient | 5 to 1000 mg |
| --- | --- |
| Stearyl alcohol | 3 g |
| Lanoline | 5 g |
| White petroleum | 15 g |
| Water | ad 100 g |

The invention claimed is:

1. A compound of formula

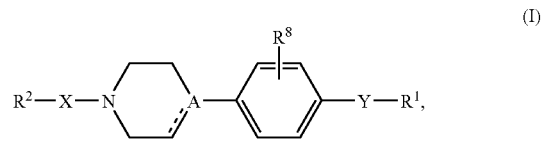

(I)

including any stereochemically isomeric form thereof, wherein

A represents CH or N;

the dotted line represents an optional bond in case A represents a carbon atom;

X represents —C(=O)—C(=O)—; —O—C(=O)—; —NR$^x$—C(=O)—; —Z$^1$—C(=O)—; —Z$^1$—NR$^x$—C(=O)—; —C(=O)—Z$^1$—; —NR$^x$—C(=O)—Z$^1$—; —S(=O)p-; or —NR$^x$—C(=S)—;

Z$^1$ represents a bivalent radical selected from C$_{1-6}$alkanediyl, C$_{2-6}$alkenediyl or C$_{2-6}$alkynediyl; wherein each of said C$_{1-6}$alkanediyl, C$_{2-6}$alkenediyl or C$_{2-6}$alkynediyl may optionally be substituted with hydroxy or amino; and wherein two hydrogen atoms attached to the same carbon atom in C$_{1-6}$alkanediyl may optionally be replaced by C$_{1-6}$alkanediyl;

Y represents -NR$^x$—C(=O)—Z$^2$—; —NR$^x$—C(=O)—Z$^2$—NR$^y$—; —NR$^x$—C(=O)—Z$^2$—NR$^y$—C(=O)—; —NR$^x$—C(=O)—Z$^2$—NR$^y$—C(=O)—O—; —NR$^x$—C(=O)—Z$^2$—O—; —NR$^x$—C(=O)—Z$^2$—O—C(=O)—; —NR$^x$—C(=O)—Z$^2$—C(=O)—O—; —NR$^x$—C(=O)—Z$^2$—C(=O)—NR$^y$—; —NR$^x$—C(=O)—Z$^2$—NR$^y$—C(=O)—NR$^y$—; —C(=O)—Z$^2$—; —C(=O)—NR$^x$—Z$^2$—; or —C(=O)—NR$^x$—Z$^2$—O—;

Z$^2$ represents a bivalent radical selected from C$_{1-6}$alkanediyl, C$_{2-6}$alkenediyl or C$_{2-6}$alkynediyl; wherein each of said C$_{1-6}$alkanediyl, C$_{2-6}$alkenediyl or C$_{2-6}$alkynediyl may optionally be substituted with C$_{1-4}$alkyloxy, C$_{1-4}$alkylthio, hydroxy, cyano or aryl; and wherein two hydrogen atoms attached to the same carbon atom in the definition of Z$^2$ may optionally be replaced by C$_{1-6}$alkanediyl;

R$^x$ represents hydrogen or C$_{1-4}$alkyl;

R$^y$ represents hydrogen; C$_{1-4}$alkyl optionally substituted with C$_{3-6}$cycloalkyl or aryl or Het; C$_{2-4}$alkenyl; or —S(=O)$_p$-aryl;

R$^1$ represents C$_{1-12}$alkyl substituted with C$_{3-6}$cycloalkyl or aryl; C$_{3-6}$cycloalkyl; adamantanyl; aryl$^1$; aryl$^1$C$_{1-6}$alkyl; Het$^1$; or Het$^1$C$_{1-6}$alkyl;

R$^2$ represents R$^3$;

R$^3$ represents phenyl, naphthalenyl, 2,3-dihydrobenzofuranyl or 6-membered aromatic heterocycle containing 1 or 2 N atoms, each of said cycles being optionally substituted with one to five substituents, each substituent independently selected from the group consisting of halo; C$_{1-6}$alkyl optionally substituted with hydroxy; polyhaloC$_{1-6}$alkyl; C$_{1-6}$alkylthio; polyhaloC$_{1-6}$alkyloxy; carboxyl; hydroxy; C$_{1-6}$alkylcarbonyl; C$_{1-6}$alkyloxy; $C_{1-6}$alkyloxycarbonyl; nitro; $R^5R^4N$—C(=O)—; $R^5R^4N$—$C_{1-6}$alkyl; Het$C_{1-4}$alkyl; Het-C(=O)—$C_{1-4}$alkyl; and Het-C(=O)—;

$R^4$ represents hydrogen; $C_{1-4}$alkyl optionally substituted with hydroxy or $C_{1-4}$alkyloxy; $R^7R^6N$—$C_{1-4}$alkyl; $C_{1-4}$alkyloxy; Het; Het-$C_{1-4}$alkyl; aryl; or $R^7R^6N$—C(=O)—$C_{1-4}$alkyl;

$R^5$ represents hydrogen or $C_{1-4}$alkyl;

$R^6$ represents hydrogen; $C_{1-4}$alkyl; or $C_{1-4}$alkylcarbonyl;

$R^7$ represents hydrogen or $C_{1-4}$alkyl; or $R^6$ and $R^7$ may be taken together with the nitrogen to which they are attached to form a saturated monocyclic 5, 6 or 7-membered heterocycle which may further contain one or more heteroatoms each independently selected from the group consisting of O, S, S(=O)$_p$ and N; and which heterocycle may optionally be substituted with $C_{1-4}$alkyl;

$R^8$ represents hydrogen; halo; $C_{1-4}$alkyl; or $C_{1-4}$alkyl substituted with hydroxy;

aryl represents phenyl or phenyl substituted with at least one substituent, each substituent independently being selected from the group consisting of hydroxy; carboxyl; halo; $C_{1-6}$alkyl optionally substituted with $C_{1-4}$alkyloxy, amino or mono- or di($C_{1-4}$alkyl)amino; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxycarbonyl; cyano; aminocarbonyl; mono- or di($C_{1-4}$alkyl)aminocarbonyl; $C_{1-6}$alkylcarbonyl; nitro; amino; mono- or di($C_{1-4}$alkyl)amino; and —S(=O)$_p$—$C_{1-4}$alkyl;

aryl$^1$ represents phenyl, naphthalenyl or fluorenyl; each of said phenyl, naphthalenyl or fluorenyl optionally substituted with at least one substituent, each substituent independently being selected from the group consisting of hydroxy; oxo; carboxyl; halo; $C_{1-6}$alkyl optionally substituted with carboxyl, $C_{1-4}$alkyloxycarbonyl or aryl-C(=O)—; hydroxy$C_{1-6}$alkyl optionally substituted with aryl or aryl-C(=O)—; polyhalo$C_{1-6}$alkyl; $C_{1-6}$alkyloxy optionally substituted with
$C_{1-4}$alkyloxy; $C_{1-6}$alkylthio; polyhalo$C_{1-6}$alkyloxy; $C_{1-6}$alkyloxy-carbonyl wherein $C_{1-6}$alkyl may optionally be substituted with aryl; cyano; aminocarbonyl; mono- or di($C_{1-4}$alkyl)aminocarbonyl; $C_{1-6}$alkylcarbonyl; nitro; amino; mono- or di($C_{1-6}$alkyl)amino; $R^5R^4N$—$C_{1-6}$alkyl; $C_{3-6}$cycloalkyl-NR$^x$—; aryl-NR$^x$—; Het-NR$^x$—; $C_{3-6}$cycloalkyl$C_1C_{1-4}$alkyloxycarbonyl or aryl-C(=O)—; hydroxy$C_{1-6}$alkyl optionally substituted with aryl or aryl-C(=O)—; polyhalo$C_{1-6}$alkyl; $C_{1-6}$alkyloxy optionally substituted with
$C_{1-4}$alkyloxy; $C_{1-6}$alkylthio; polyhalo$C_{1-6}$alkyloxy; $C_{1-6}$alkyloxy-carbonyl wherein $C_{1-6}$alkyl may optionally be substituted with aryl; cyano; aminocarbonyl; mono- or di($C_{1-4}$alkyl)aminocarbonyl; $C_{1-6}$alkylcarbonyl; nitro; amino; mono- or di($C_{1-6}$alkyl)amino$_4$alkyl-NR$^x$—; aryl$C_{1-4}$alkyl-NR$^x$—; Het$C_{1-4}$alkyl-NR$^x$—; —S(=O)$_p$—$C_{1-4}$alkyl; $C_{3-6}$cycloalkyl; $C_{3-6}$cycloalkyl$C_{1-4}$alkyl; $C_{3-6}$cycloalkyl-C(=O)—; aryl; aryloxy; aryl$C_{1-4}$alkyl; aryl-C(=O)—$C_{1-4}$alkyl; aryl-C(=O)—; Het; Het$C_{1-4}$alkyl; Het-C(=O)—$C_{1-4}$alkyl; Het-C(=O)—; and Het-O—;

Het represents a monocyclic non-aromatic or aromatic heterocycle containing at least one heteroatom each independently selected from the group consisting of O, S, S(=O)$_p$ and N; or a bicyclic or tricyclic non-aromatic or aromatic heterocycle containing at least one heteroatom each independently selected from the group consisting of O, S, S(=O)$_p$ and N; said monocyclic heterocycle or said bi- or tricyclic heterocycle optionally being substituted with at least one substituent, each substituent independently being selected from the group consisting of hydroxy; oxo; carboxyl; halo; $C_{1-6}$alkyl optionally substituted with $C_{1-4}$alkyloxy, amino or mono- or di($C_{1-4}$alkyl)amino; polyhalo$C_{1-6}$alkyl; $C_{1-6}$alkyloxy optionally substituted with $C_{1-4}$alkyloxy;
$C_{1-6}$alkylthio; polyhalo$C_{1-6}$alkyloxy; $C_{1-6}$alkyloxycarbonyl; cyano; aminocarbonyl; mono- or di($C_{1-4}$alkyl)aminocarbonyl; $C_{1-6}$alkylcarbonyl; nitro; amino; mono- or di($C_{1-4}$alkyl)amino; and —S(=O)$_p$—$C_{1-4}$alkyl;

Het$^1$ represents a monocyclic non-aromatic or aromatic heterocycle containing at least one heteroatom each independently selected from the group consisting of O, S, S(=O)$_p$ and N; or a bicyclic or tricyclic non-aromatic or aromatic heterocycle containing at least one heteroatom each independently selected from the group consisting of O, S, S(=O)$_p$ and N; said monocyclic heterocycle or said bi- or tricyclic heterocycle optionally being substituted with at least one substituent, each substituent independently being selected from the group consisting of hydroxy; oxo; carboxyl; halo; $C_{1-6}$alkyl optionally substituted with carboxyl, $C_{1-4}$alkyloxycarbonyl or aryl-C(=O)—; hydroxy$C_{1-6}$alkyl optionally substituted with aryl or aryl-C(=O)—; polyhalo$C_{1-6}$alkyl; $C_{1-6}$alkyloxy optionally substituted with $C_{1-4}$alkyloxy; $C_{1-6}$alkylthio;
polyhalo$C_{1-6}$alkyloxy; $C_{1-6}$alkyloxy-carbonyl wherein $C_{1-6}$alkyl may optionally be substituted with aryl; cyano; aminocarbonyl; mono- or di($C_{1-4}$alkyl)aminocarbonyl; $C_{1-6}$alkylcarbonyl; nitro; amino; mono- or di($C_{1-6}$alkyl)amino; $R^5R^4N$—$C_{1-6}$alkyl; $C_{3-6}$cycloalkyl-NR$^x$—; aryl-NR$^x$—; Het-NR$^x$—; $C_{3-6}$cycloalkyl$C_{1-4}$alkyl-NR$^x$—; aryl$C_{1-4}$alkyl-NR$^x$—; Het$C_{1-4}$alkyl-NR$^x$—; —S(=O)$_p$—$C_{1-4}$alkyl; $C_{3-6}$cycloalkyl; $C_{3-6}$cycloalkyl$C_{1-4}$alkyl; $C_{3-6}$cycloalkyl-C(=O)—; aryl; aryloxy; aryl$C_{1-4}$alkyl; aryl-C(=O)—$C_{1-4}$alkyl; aryl-C(=O)—; Het; Het$C_{1-4}$alkyl; Het-C(=O)—$C_{1-4}$alkyl; Het-C(=O)—; and Het-O—;

p represents 1 or 2;

provided that

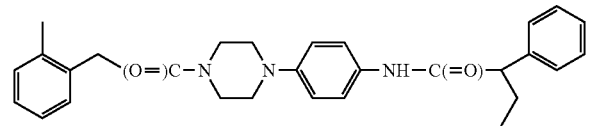

is excluded;

a N-oxide thereof, or a pharmaceutically acceptable salt thereof.

2. The compound according to claim 1 having the following formula

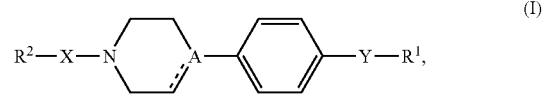

including any stereochemically isomeric form thereof, wherein

A represents CH or N;

the dotted line represents an optional bond in case A represents a carbon atom;

X represents —NR$^x$—C(=O)—; —Z$^1$—C(=O)—; —Z$^1$—NR$^x$—C(=O)—; —C(=O)—Z$^1$—; —NR$^x$—C(=O)—Z$^1$—; —S(=O)$_p$—; or —NR$^x$—C(=S)—;

Z$^1$ represents a bivalent radical selected from C$_{1-6}$alkanediyl, C$_{2-6}$alkenediyl or C$_{2-6}$alkynediyl; wherein each of said C$_{1-6}$alkanediyl, C$_{2-6}$alkenediyl or C$_{2-6}$alkynediyl may optionally be substituted with hydroxy;

Y represents -NR$^x$—C(=O)—Z$^2$—; —NR$^x$—C(=O)—Z$^2$—NR$^y$—; —NR$^x$—C(=O)—Z$^2$—NR$^y$—C(=O)—; —NR$^x$—C(=O)—Z$^2$—NR$^y$—C(=O)—O—; —NR$^x$—C(=O)—Z$^2$—O—; —NR$^x$—C(=O)—Z$^2$—O—C(=O)—; —NR$^x$—C(=O)—Z$^2$—C(=O)—O—; —NR$^x$—C(=O)—Z$^2$—C(=O)—NR$^y$—; —NR$^x$—C(=O)—Z$^2$—NR$^y$—C(=O)—NR$^y$—; —C(=O)—Z$^2$—; —C(=O)—NR$^x$—Z$^2$—; or —C(=O)—NR$^x$—Z$^2$—O—;

Z$^2$ represents a bivalent radical selected from C$_{1-6}$alkanediyl, C$_{2-6}$alkenediyl or C$_{2-6}$alkynediyl; wherein each of said C$_{1-6}$alkanediyl, C$_{2-6}$alkenediyl or C$_{2-6}$alkynediyl may optionally be substituted with C$_{1-4}$alkyloxy, C$_{1-4}$alkylthio, hydroxy, cyano or aryl; and wherein two hydrogen atoms attached to the same carbon atom in the definition of Z$^2$ may optionally be replaced by C$_{1-6}$alkanediyl;

R$^x$ represents hydrogen or C$_{1-4}$alkyl;

R$^y$ represents hydrogen; C$_{1-4}$alkyl optionally substituted with C$_{3-6}$cycloalkyl or aryl or Het; C$_{2-4}$alkenyl; or —S(=O)$_p$-aryl;

R$^1$ represents C$_{1-12}$alkyl substituted with C$_{3-6}$cycloalkyl or aryl; C$_{3-6}$cycloalkyl; aryl$^1$; aryl$^1$C$_{1-6}$alkyl; Het$^1$; or Het$^1$C$_{1-6}$alkyl;

R$^2$ represents R$^3$;

R$^3$ represents phenyl, naphthalenyl, wherein said phenyl, naphthalenyl may optionally be substituted with one to five substituents, each substituent independently selected from the group consisting of hydroxy; carboxyl; halo; C$_{1-6}$alkyl optionally substituted with hydroxy; polyhaloC$_{1-6}$alkyl; C$_{1-6}$alkyloxy; C$_{1-6}$alkylthio; polyhalo-C$_{1-6}$alkyloxy; C$_{1-6}$alkyloxycarbonyl; C$_{1-6}$alkylcarbonyl; nitro; R$^5$R$^4$N—C(=O)—; R$^5$R$^4$N—C$_{1-6}$alkyl; HetC$_{1-4}$alkyl; and Het-C(=O)—;

R$^4$ represents hydrogen; C$_{1-4}$alkyl optionally substituted with hydroxy or C$_{1-4}$alkyloxy; R$^7$R$^6$N—C$_{1-4}$alkyl; C$_{1-4}$alkyloxy; Het; aryl; or R$^7$R$^6$N—C(=O)—C$_{1-4}$alkyl;

R$^5$ represents hydrogen or C$_{1-4}$alkyl;

R$^6$ represents hydrogen; C$_{1-4}$alkyl; or C$_{1-4}$alkylcarbonyl;

R$^7$ represents hydrogen or C$_{1-4}$alkyl; or

R$^6$ and R$^7$ may be taken together with the nitrogen to which they are attached to form a saturated monocyclic 5, 6 or 7-membered heterocycle which may further contain one or more heteroatoms each independently selected from the group consisting of O, S, S(=O)$_p$ and N; and which heterocycle may optionally be substituted with C$_{1-4}$alkyl;

aryl represents phenyl or phenyl substituted with at least one substituent, each substituent independently being selected from the group consisting of hydroxy; carboxyl; halo; C$_{1-6}$alkyl optionally substituted with C$_{1-4}$alkyloxy, amino or mono- or di(C$_{1-4}$alkyl)amino; polyhaloC$_{1-6}$alkyl; C$_{1-6}$alkyloxy optionally substituted with C$_{1-4}$alkyloxy; C$_{1-6}$alkylthio; polyhaloC$_{1-6}$alkyloxy; C$_{1-6}$alkyloxycarbonyl; cyano; aminocarbonyl; mono- or di(C$_{1-4}$-alkyl)aminocarbonyl; C$_{1-6}$alkylcarbonyl; nitro; amino; mono- or di(C$_{1-4}$alkyl)amino; and —S(=O)$_p$—C$_{1-4}$alkyl;

aryl$^1$ represents phenyl, naphthalenyl or fluorenyl; each of said phenyl, naphthalenyl or fluorenyl optionally substituted with at least one substituent, each substituent independently being selected from the group consisting of hydroxy; oxo; carboxyl; halo; C$_{1-6}$alkyl optionally substituted with aryl-C(=O)—; hydroxyC$_{1-6}$alkyl optionally substituted with aryl or aryl-C(=O)—; polyhaloC$_{1-6}$ alkyl; C$_{1-6}$alkyloxy optionally substituted with C$_{1-4}$alkyloxy; C$_{1-6}$alkylthio;

polyhaloC$_{1-6}$alkyloxy; C$_{1-6}$alkyloxy-carbonyl wherein C$_{1-6}$alkyl may optionally be substituted with aryl; cyano; aminocarbonyl; mono- or di(C$_{1-4}$-alkyl)aminocarbonyl; C$_{1-6}$alkylcarbonyl; nitro; amino; mono- or di(C$_{1-6}$alkyl)amino; C$_{3-6}$cycloalkyl-NR$^x$—; aryl-NR$^x$—; Het-NR$^x$—; C$_{3-6}$cycloalkylC$_{1-4}$alkyl-NR$^x$—; arylC$_{1-4}$alkyl-NR$^x$—;

HetC$_{1-4}$alkyl-NR$^x$—; —S(=O)$_p$—C$_{1-4}$alkyl; C$_{3-6}$cycloalkyl; C$_{3-6}$cycloalkylC$_{1-4}$alkyl; C$_{3-6}$cycloalkyl-C(=O)—; aryl; aryloxy; arylC$_{1-4}$alkyl; aryl-C(=O)—; Het; HetC$_{1-4}$alkyl; Het-C(=O)—; and Het-O—;

Het represents a monocyclic non-aromatic or aromatic heterocycle containing at least one heteroatom each independently selected from the group consisting of O, S, S(=O)$_p$ and N; or a bicyclic or tricyclic non-aromatic or aromatic heterocycle containing at least one heteroatom each independently selected from the group consisting of O, S, S(=O)$_p$ and N; said monocyclic heterocycle or said bi- or tricyclic heterocycle optionally being substituted with at least one substituent, each substituent independently being selected from the group consisting of hydroxy; oxo; carboxyl; halo; C$_{1-6}$alkyl optionally substituted with C$_{1-4}$alkyloxy, amino or mono- or di(C$_{1-4}$alkyl)amino; polyhaloC$_{1-6}$alkyl; C$_{1-6}$alkyloxy optionally substituted with C$_{1-4}$alkyloxy;

C$_{1-6}$alkylthio; polyhaloC$_{1-6}$alkyloxy; C$_{1-6}$alkyloxycarbonyl; cyano; aminocarbonyl; mono- or di(C$_{1-4}$alkyl) aminocarbonyl; C$_{1-6}$alkylcarbonyl; nitro; amino; mono- or di(C$_{1-4}$alkyl)amino; and —S(=O)$_p$—C$_{1-4}$alkyl;

Het$^1$ represents a monocyclic non-aromatic or aromatic heterocycle containing at least one heteroatom each independently selected from the group consisting of O, S, S(=O)$_p$ and N; or a bicyclic or tricyclic non-aromatic or aromatic heterocycle containing at least one heteroatom each independently selected from the group consisting of O, S, S(=O)$_p$ and N; said monocyclic heterocycle or said bi- or tricyclic heterocycle optionally being substituted with at least one substituent, each substituent independently being selected from the group consisting of hydroxy; oxo; carboxyl; halo; C$_{1-6}$alkyl optionally substituted with aryl-C(=O)—; hydroxyC$_{1-6}$alkyl optionally substituted with aryl or aryl-C(=O)—; polyhaloC$_{1-6}$alkyl; C$_{1-6}$alkyloxy optionally substituted with C$_{1-4}$alkyloxy; C$_{1-6}$alkylthio;

polyhaloC$_{1-6}$alkyloxy; C$_{1-6}$alkyloxy-carbonyl wherein C$_{1-6}$alkyl may optionally be substituted with aryl; cyano; aminocarbonyl; mono- or di(C$_{1-4}$alkyl)aminocarbonyl; C$_{1-6}$alkylcarbonyl; nitro; amino; mono- or di(C$_{1-6}$alkyl)amino; C$_{3-6}$cycloalkyl-NR$^x$—; aryl-NR$^x$—; Het-NR$^x$—; C$_{3-6}$cycloalkylC$_{1-4}$alkyl-NR$^x$—; arylC$_{1-4}$alkyl-NR$^x$—;

HetC$_{1-4}$alkyl-NR$^x$—; —S(=O)$_p$—C$_{1-4}$alkyl; C$_{3-6}$cycloalkyl; C$_{3-6}$cycloalkylC$_{1-4}$alkyl; C$_{3-6}$cycloalkyl-C(=O)—; aryl; aryloxy; arylC$_{1-4}$alkyl; aryl-C(=O)—; Het; HetC$_{1-4}$alkyl; Het-C(=O)—; and Het-O—;

p represents 1 or 2;

a N-oxide thereof, or a pharmaceutically acceptable salt thereof.

3. The compound according to claim 1 wherein X represents —O—C(=O)—; —C(=O)—C(=O)—; —NR$^x$—C(=O)—; —Z$^1$—C(=O)—; —C(=O)—Z$^1$—; —Z$^1$—NR$^x$—C(=O)—; —NR$^x$—C(=S)— or —S(=O)$_p$—.

4. The compound according to claim 3 wherein X represents —NR$^x$—C(=O)— or —Z$^1$—NR$^x$—C(=O)—.

5. The compound according to claim 4 wherein X represents —NR$^x$—C(=O)—.

6. The compound according to claim 1 wherein A represents N.

7. The compound according to claim 1 wherein R$^1$ represents C$_{3-6}$cycloalkyl; adamantanyl; aryl$^1$; aryl$^1$C$_{1-6}$alkyl; Het$^1$; or Het$^1$C$_{1-6}$alkyl.

8. The compound according to claim 7 wherein R$^1$ represents aryl$^1$ or Het$^1$.

9. The compound according to claim 8 wherein Het$^1$ represents morpholinyl, pyrrolidinyl, piperazinyl, homopiperazinyl, piperidinyl, furanyl, imidazolyl, thienyl, pyridyl, 1,3-benzodioxolyl, or tetrahydropyranyl, each of said heterocycles optionally being substituted with one or two substituents, each substituent independently being selected from the group consisting of halo, C$_{1-6}$alkyl, C$_{1-6}$alkyloxycarbonyl, —S(=O)$_p$—C$_{1-4}$-alkyl, aryl, and arylC$_{1-4}$alkyl.

10. The compound according to claim 8 wherein aryl$^1$ represents phenyl, naphthalenyl or phenyl substituted with one or two substituents, each substituent independently being selected from the group consisting of hydroxy, halo, C$_{1-6}$alkyl, C$_{1-6}$alkyloxy, C$_{1-6}$alkyloxycarbonyl and Het.

11. The compound according to claim 1 wherein R$^1$ represents phenyl substituted with C$_{1-6}$alkyloxy.

12. The compound according to claim 1 wherein R$^3$ represents phenyl, naphthalenyl or 2,3-dihydrobenzofuranyl, each of said cycles being optionally substituted with one to five substituents, each of said substituents being independently selected from the group consisting of halo, C$_{1-6}$alkyl optionally substituted with hydroxy, polyhaloC$_{1-6}$alkyl, C$_{1-6}$alkylthio, polyhaloC$_{1-6}$alkyloxy, carboxyl, hydroxy, C$_{1-6}$alkylcarbonyl, C$_{1-6}$alkyloxy, C$_{1-6}$alkyloxycarbonyl, nitro, R$^5$R$^4$N—C(=O)—, R$^5$R$^4$N—C$_{1-6}$alkyl, HetC$_{1-4}$alkyl, Het-C(=O)—C$_{1-4}$alkyl, and Het-C(=O)—.

13. The compound according to claim 12 wherein R$^3$ represents phenyl substituted with three substituents each independently being selected from halo or HetC$_{1-4}$alkyl.

14. The compound according to claim 1 wherein the compound of formula (I) is a compound of formula (I')

(I')

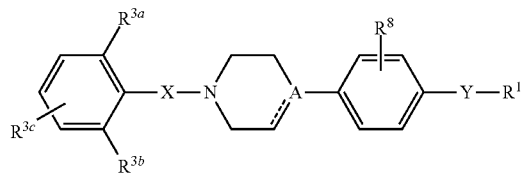

wherein R$^{3a}$ and R$^{3b}$ each independently represent hydrogen; hydroxy; carboxyl; halo; C$_{1-6}$alkyl; polyhaloC$_{1-6}$alkyl; C$_{1-6}$alkyloxy;

C$_{1-6}$alkylthio; polyhaloC$_{1-6}$alkyloxy; C$_{1-6}$alkyloxycarbonyl; aminocarbonyl; mono- or di(C$_{1-4}$alkyl)aminocarbonyl; C$_{1-6}$alkylcarbonyl; nitro; and wherein R$^{3c}$ represents hydrogen; hydroxy; carboxyl; halo; C$_{1-6}$alkyl; polyhaloC$_{1-6}$alkyl; C$_{1-6}$alkyloxy; C$_{1-6}$alkylthio; polyhalo-C$_{1-6}$alkyloxy; C$_{1-6}$alkyloxycarbonyl; C$_{1-6}$alkylcarbonyl; nitro; R$^5$R$^4$N—C(=O)—;
R$^5$R$^4$N—C$_{1-6}$alkyl; HetC$_{1-4}$alkyl; Het-C(=O)—C$_{1-4}$alkyl; or Het-C(=O)—.

15. The compound according to claim 1 wherein the compound of formula (I) is a compound of formula (I")

(I")

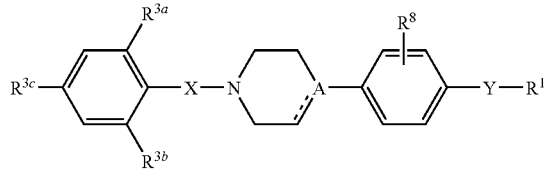

wherein R$^{3a}$ and R$^{3b}$ each independently represent hydrogen; hydroxy; carboxyl; halo; C$_{1-6}$alkyl; polyhaloC$_{1-6}$alkyl; C$_{1-6}$alkyloxy; C$_{1-6}$alkylthio; polyhaloC$_{1-6}$alkyloxy; C$_{1-6}$alkyloxycarbonyl; aminocarbonyl; mono- or di(C$_{1-4}$alkyl)aminocarbonyl; C$_{1-6}$alkylcarbonyl; or nitro; and wherein R$^{3c}$ represents hydrogen; hydroxy; carboxyl; halo; C$_{1-6}$alkyl; polyhaloC$_{1-6}$alkyl; C$_{1-6}$alkyloxy; C$_{1-6}$alkylthio; polyhalo-C$_{1-6}$alkyloxy; C$_{1-6}$alkyloxycarbonyl; C$_{1-6}$alkylcarbonyl; nitro; R$^5$R$^4$N—C(=O)—; R$^5$R$^4$N—C$_{1-6}$alkyl; HetC$_{1-4}$alkyl; Het-C(=O)—C$_{1-4}$alkyl; or Het-C(=O)—.

16. The compound according to claim 14 wherein R$^{3a}$ and R$^{3b}$ each independently represent halo, C$_{1-6}$alkyl or C$_{1-6}$alkyloxy.

17. The compound according to claim 16 wherein R$^{3a}$ and R$^{3b}$ each independently represent halo.

18. The compound according to claim 14 wherein R$^{3c}$ represents R$^5$R$^4$N—C(=O)—; R$^5$R$^4$N—C$_{1-6}$alkyl; Het-C(=O)—, HetC$_{1-4}$alkyl or Het-C(=O)—C$_{1-4}$-alkyl.

19. The compound according to claim 18 wherein R$^{3c}$ represents HetC$_{1-4}$alkyl.

20. The compound according to claim 1 wherein p represents 2.

21. The compound according to claim 1 wherein Z$^2$ represents C$_{1-6}$alkanediyl or C$_{2-6}$alkenediyl.

22. The compound according to claim 1 wherein Y represents —NR$^x$—C(=O)—Z$^2$— and Z$^2$ represents methylene.

23. The compound according to claim 1 wherein R$^x$ represents hydrogen.

24. The compound according to claim 1 wherein R$^y$ represents hydrogen or C$_{1-4}$alkyl or —S(=O)$_p$-aryl.

25. The compound according to claim 1 having the following formula

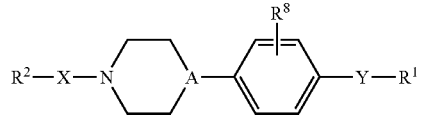

wherein A represents CH or N; X represents —O—C(=O)—; —C(=O)—C(=O)—; —NR$^x$—C(=O)—; —Z$^1$—C(=O)—; —Z$^1$—NR$^x$—C(=O)—; —C(=O)—Z$^1$—; —S(=O)$_p$—; or —NR$^x$—C(=S)—; Z$^1$ represents C$_{1-6}$alkanediyl; wherein said C$_{1-6}$alkanediyl may optionally be substituted with hydroxy or amino; and wherein two hydrogen atoms attached to the same carbon atom in C$_{1-6}$alkanediyl may optionally be replaced by C$_{1-6}$alkanediyl;

Y represents NR$^x$—C(=O)—Z$^2$—; —NR$^x$—C(=O)—Z$^2$—NR$^y$—; —NR$^x$—C(=O)—Z$^2$—NR$^y$—C(=O)—; —NR$^x$—C(=O)—Z$^2$—NR$^y$—C(=O)—O—; —NR$^x$—C(=O)—Z$^2$—NR$^x$—C(=O)—; Z$^2$—O—C(=O)—; —NR$^x$—C(=O)—Z$^2$—C(=O)—O—; —NR$^x$—C(=O)—Z$^2$—C(=O)—NR$^y$—; —NR$^x$—C(=O)—Z$^2$—NR$^y$—C(=O)—NR$^y$—; —C(=O)—Z$^2$—; —C(=O)—NR$^x$—Z$^2$—; or —C(=O)—NR$^x$—Z$^2$—O—;

Z$^2$ represents a bivalent radical selected from C$_{1-6}$alkanediyl, C$_{2-6}$alkenediyl or C$_{2-6}$alkynediyl; wherein each of said C$_{1-6}$alkanediyl, C$_{2-6}$alkenediyl or C$_{2-6}$alkynediyl may optionally be substituted with C$_{1-4}$alkyloxy, C$_{1-4}$alkylthio, hydroxy, cyano or aryl; and wherein two hydrogen atoms attached to the same carbon atom in the definition of Z$^2$ may optionally be replaced by C$_{1-6}$alkanediyl; Rx represents hydrogen or C$_{1-4}$alkyl; R$^y$ represents hydrogen; C$_{1-4}$alkyl; C$_{2-4}$alkenyl; or —S(=O)$_p$-aryl; R$^1$ represents C$_{1-12}$alkyl substituted with C$_{3-6}$cycloalkyl or aryl; C$_{2-6}$alkynyl; C$_{3-6}$cycloalkyl; adamantanyl; aryl$^1$; Het$^1$; or Het$^1$C$_{1-6}$alkyl; R$^2$ represents R$^3$;

R$^3$ represents phenyl, naphthalenyl, 2,3-dihydrobenzofuranyl or a 6-membered aromatic heterocycle containing 1 or 2 N atoms, wherein said phenyl, naphthalenyl, 2,3-dihydrobenzofuranyl or 6-membered aromatic heterocycle containing 1 or 2 N atoms may optionally be substituted with one, two, three, four or five substituents, each substituent independently selected from the group consisting of hydroxy; carboxyl; halo; C$_{1-6}$alkyl optionally substituted with hydroxy; polyhaloC$_{1-6}$alkyl; C$_{1-6}$alkyloxy; C$_{1-6}$alkylthio; polyhalo-C$_{1-6}$alkyloxy; C$_{1-6}$alkyloxycarbonyl; C$_{1-6}$alkylcarbonyl; nitro; R$^5$R$^4$N—C(=O)—; R$^5$R$^4$N—C$_{1-6}$alkyl; HetC$_{1-4}$alkyl; Het-C(=O)—C$_{1-4}$alkyl; and Het-C(=O)—;

R$^4$ represents hydrogen; C$_{1-4}$alkyl optionally substituted with hydroxy or C$_{1-4}$alkyloxy; R$^7$R$^6$N—C$_{1-4}$alkyl; Het-C$_{1-4}$alkyl; or R$^7$R$^6$N—C(=O)—C$_{1-4}$alkyl;

R$^5$ represents hydrogen or C$_{1-4}$alkyl;

R$^6$ represents C$_{1-4}$alkyl or C$_{1-4}$alkylcarbonyl; R$^7$ represents hydrogen or C$_{1-4}$alkyl; or R$^6$ and R$^7$ may be taken together with the nitrogen to which they are attached to form a saturated monocyclic 5, 6 or 7-membered heterocycle which may further contain one or more heteroatoms each independently selected from O or N;

R$^8$ represents hydrogen; halo; or C$_{1-4}$alkyl substituted with hydroxy; aryl represents phenyl or phenyl substituted with one or two substituents, each substituent independently being selected from the group consisting of halo; C$_{1-6}$alkyl; polyhaloC$_{1-6}$alkyl; C$_{1-6}$alkyloxy; and nitro; aryl$^1$ represents phenyl or naphthalenyl; wherein phenyl may optionally be substituted with one or two substituents, each substituent independently being selected from the group consisting of hydroxy; halo; C$_{1-6}$alkyl; C$_{1-6}$alkyloxy; C$_{1-6}$alkyloxy-carbonyl and Het; Het represents a monocyclic non-aromatic or aromatic heterocycle containing at least N atom; said monocyclic heterocycle optionally being substituted with one substituent being selected from C$_{1-6}$alkyl optionally substituted with C$_{1-4}$alkyloxy; C$_{1-6}$alkylcarbonyl; or —S(=O)$_p$—C$_{1-4}$alkyl; Het$^1$ represents a monocyclic non-aromatic or aromatic heterocycle containing at least one heteroatom each independently selected from the group consisting of N, O and S; or a bicyclic non-aromatic heterocycle containing at least O atom; said monocyclic heterocycle or said bicyclic heterocycle optionally being substituted with one or two substituents, each substituent independently being selected from the group consisting of halo; C$_{1-6}$alkyl; C$_{1-6}$alkyloxy-carbonyl; —S(=O)$_p$—C$_{1-4}$alkyl; aryl; and arylC$_{1-4}$alkyl; p represents 2.

26. A compound according to claim 1 wherein the compound is

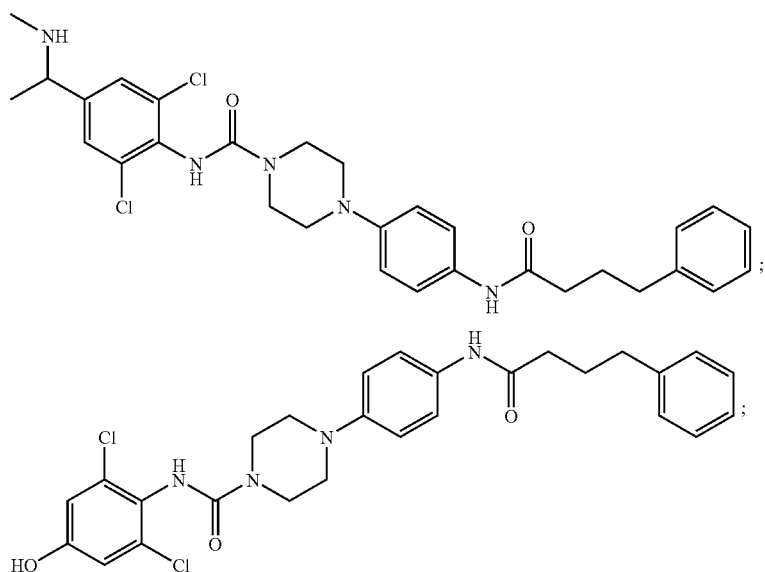

-continued
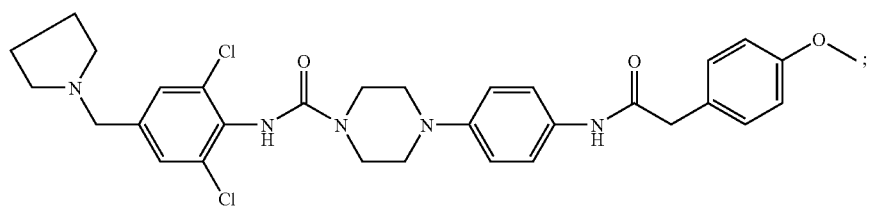
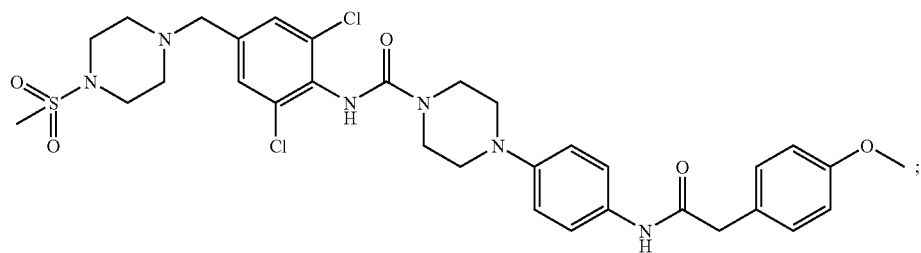
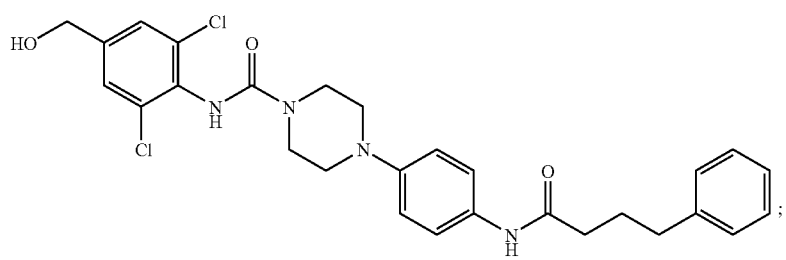
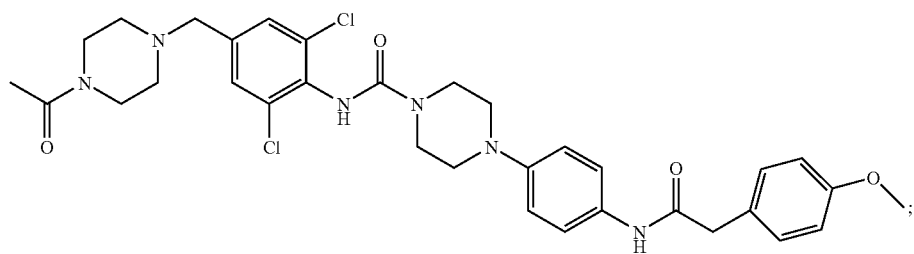
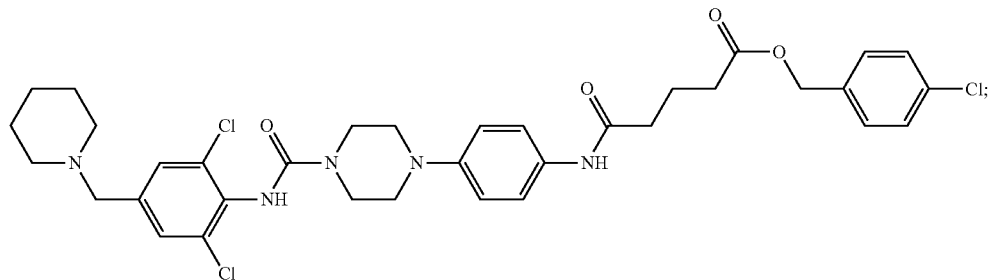
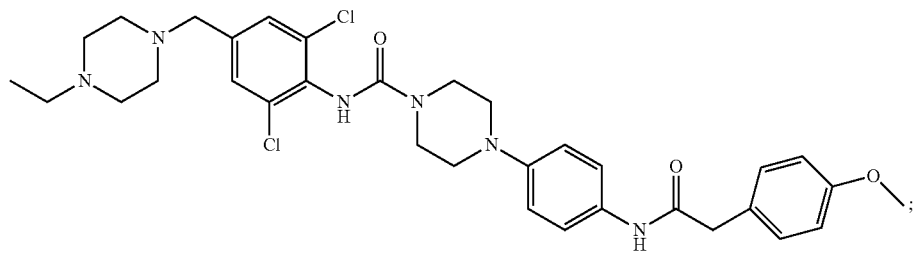

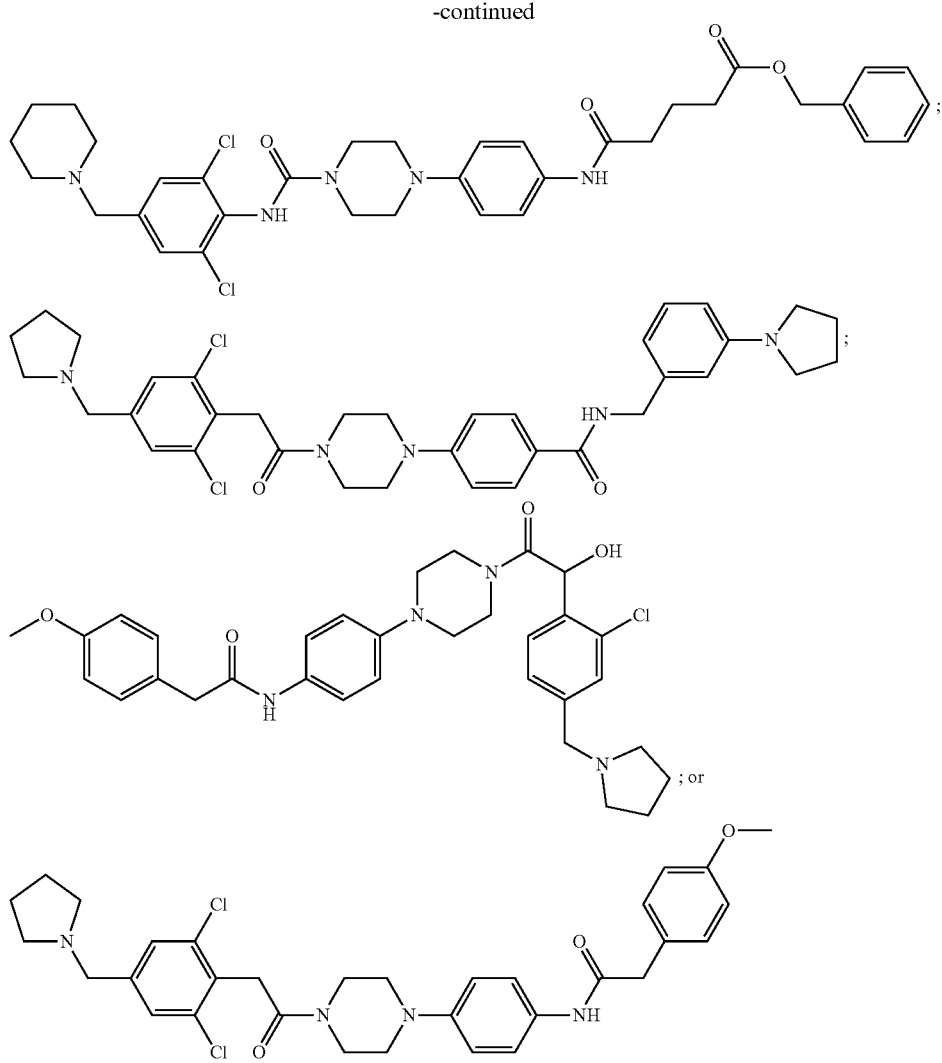
a N-oxide thereof, or a pharmaceutically acceptable salt thereof.
27. A compound wherein the compound is
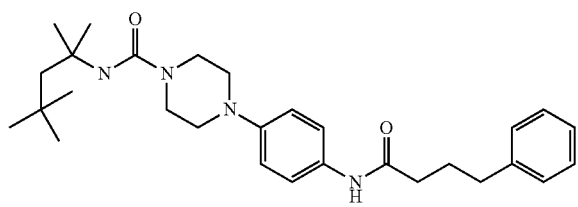 [SMILES: CC(C)(C)CC(C)(C)NC(=O)N1CCN(c2ccc(NC(=O)CCCc3ccccc3)cc2)CC1]
a N-oxide thereof, or a pharmaceutically acceptable salt thereof.
28. A pharmaceutical composition comprising a pharmaceutically acceptable carrier, and as active ingredient a therapeutically effective amount of a compound as claimed in claim 1.
* * * * *